(12) United States Patent
Telfer et al.

(10) Patent No.: US 8,703,153 B2
(45) Date of Patent: Apr. 22, 2014

(54) SALMONELLA VECTORED VACCINES AGAINST CHLAMYDIA AND METHODS OF USE

(75) Inventors: Jonathan Lewis Telfer, Berkshire (GB); Mark Richard Redfern, Berkshire (GB); Michael Joseph Lacy, Gaithersburg, MD (US)

(73) Assignee: Prokarium Ltd.

( * ) Notice: Subject to any disclaimer, the term of this patent is extended or adjusted under 35 U.S.C. 154(b) by 0 days.

(21) Appl. No.: 12/999,246

(22) PCT Filed: Jun. 16, 2009

(86) PCT No.: PCT/US2009/047542
§ 371 (c)(1),
(2), (4) Date: Jul. 20, 2011

(87) PCT Pub. No.: WO2009/158240
PCT Pub. Date: Dec. 30, 2009

(65) Prior Publication Data
US 2011/0268760 A1  Nov. 3, 2011

Related U.S. Application Data

(63) Continuation-in-part of application No. PCT/US2008/007490, filed on Jun. 16, 2008.

(60) Provisional application No. 61/118,204, filed on Nov. 26, 2008.

(51) Int. Cl.
*A61K 39/112* (2006.01)
*A61K 48/00* (2006.01)
*A61K 49/00* (2006.01)

(52) U.S. Cl.
USPC ......... 424/258.1; 424/9.1; 424/9.2; 424/93.2; 424/184.1; 424/234.1

(58) Field of Classification Search
USPC .......... 424/9.1, 9.2, 93.2, 184.1, 234.1, 258.1
See application file for complete search history.

(56) References Cited

U.S. PATENT DOCUMENTS

| | | |
|---|---|---|
| 4,440,859 A | 4/1984 | Rutter |
| 4,530,901 A | 7/1985 | Weissmann |
| 4,550,081 A | 10/1985 | Stocker |
| 4,582,800 A | 4/1986 | Crowl |
| 4,677,063 A | 6/1987 | Mark |
| 4,704,362 A | 11/1987 | Itakura |
| 4,710,463 A | 12/1987 | Murray |
| 4,757,006 A | 7/1988 | Toole |
| 4,766,075 A | 8/1988 | Goeddel et al. |
| 4,810,648 A | 3/1989 | Stalker |
| 4,837,151 A | 6/1989 | Stocker |
| 5,210,035 A | 5/1993 | Stocker |
| 5,356,797 A | 10/1994 | Nielsen |
| 5,397,697 A | 3/1995 | Lam |
| 5,618,666 A | 4/1997 | Popoff et al. |
| 5,643,579 A | 7/1997 | Hung |
| 6,015,669 A | 1/2000 | Holden |
| 6,251,406 B1 | 6/2001 | Haefliger |
| 6,342,215 B1 | 1/2002 | Holden |
| 6,458,368 B1 | 10/2002 | Haeflinger |
| 6,585,975 B1 | 7/2003 | Kleanthous |
| 6,756,042 B1 | 6/2004 | Feldman |
| 6,846,667 B1 | 1/2005 | Crooke |
| 6,936,425 B1 * | 8/2005 | Hensel et al. .................. 435/7.1 |
| 6,951,732 B2 | 10/2005 | Clarke |
| 6,984,490 B1 | 1/2006 | Holden |
| 7,211,264 B2 | 5/2007 | Feldman |
| 7,449,178 B2 | 11/2008 | Crooke |
| 2004/0203039 A1 | 10/2004 | Hensel |
| 2005/0048557 A1 | 3/2005 | Jackson et al. |
| 2006/0216309 A1 | 9/2006 | Holden |
| 2006/0234260 A1 | 10/2006 | Griffais et al. |
| 2008/0075739 A1 | 3/2008 | Hensel et al. |
| 2008/0175866 A1 | 7/2008 | Holdon |

FOREIGN PATENT DOCUMENTS

| | | |
|---|---|---|
| EP | 0889120 | 1/1999 |
| WO | WO 9220805 | 11/1992 |
| WO | WO 9310246 | 5/1993 |
| WO | WO 9611708 | 4/1996 |
| WO | WO 9617951 | 6/1996 |
| WO | WO 9718225 | 5/1997 |
| WO | WO 9806428 | 2/1998 |
| WO | WO 9835562 | 8/1998 |
| WO | WO 9901473 | 1/1999 |
| WO | WO 9945120 | 9/1999 |
| WO | WO00/14240 | 3/2000 |

(Continued)

OTHER PUBLICATIONS

International Search Report, mailed Nov. 13, 2009, and Written Opinion for PCT/US2009/047542, 6 pages.
International Search Report, mailed Dec. 8, 2008, and Written Opinion for PCT/US2008/007490, 9 pages.
Wu et al. "Recombinant enzymes overexpressed in bacteria show broad catalytic specificity of human cytochrome P450 2W1 and limited activity of human cytochrome P450 2S1." *Mol. Pharmacol.* Jun. 2006, 69(6) 2007-2014.
Abaev, et al. (1997) "Stable expresion of heterologous proteins in *Salmonella*: Problems and approaches to their designing," Vestn. Ross Akad Med Nauk 6:48-52 Abstract Only.
Agrawal and Goodchild (1987) "Oligodeoxynucleotide methylphosphonate: synthesis and enzymatic degradation." Tetrahedron Letters, 28:3539-3542.

(Continued)

*Primary Examiner* — Rodney P. Swartz
(74) *Attorney, Agent, or Firm* — Cooley LLP

(57) ABSTRACT

The invention provides an attenuated *Salmonella* vaccine vector comprising one or more heterologous polynucleotides that encode immunogenic Chlamydial peptides. In one embodiment, the attenuated *Salmonella* vaccine vector comprises aroC and ssaV attenuating mutations. The heterologous polynucleotides encoding the immunogenic Chlamydial peptides can be under the control of an inducible promoter such as a *Salmonella* ssaG promoter. In one embodiment of the invention, the immunogenic Chlamydial peptide is a PmpG peptide, for instance, a CT110, CT84 or CT40 peptide.

23 Claims, 58 Drawing Sheets

(56) References Cited

FOREIGN PATENT DOCUMENTS

| WO | WO 0014240 | 3/2000 |
|---|---|---|
| WO | WO 0132697 | 5/2001 |
| WO | WO 0185772 | 11/2001 |
| WO | WO 03044047 | 5/2003 |
| WO | WO2008/156729 | 12/2008 |

OTHER PUBLICATIONS

Agrawal and Tang (1990) "Efficient synthesis of oligoribonucleotide and its phosphorothioate analogue using H-Phosphonate Approach," Tetrahedron Letters, 31:7541-7544.

Agrawal (1998) "Oligodeoxynucleoside phosphoramidates and phosphorothioates as inhibitors of human immunodeficiency virus," PNAS 85:7079-7083.

Agrawal (1990) "Site-specific excision from RNA by RNase H and mixed phosphate-backbone oligodeoxyribonucleotides," PNAS 87:1401-1405.

Agrawal, et al. (1991) "Pharmacokinetics, biodistribution and stability of oligodeoxynucleotide phosphorothioates in mice," PNAS, 88:7595-7599.

Allaoui, et al. (1993) "MxiD, an outer membrane protein necessary for the secretion of *Shigella flexneri* Ipa invasins," Mol. Microbiol., 7:59-68.

Altmeyer, et al. (1993) "Cloning and molecular characterization of gene involved in *Salmonella* adherence and invasion of cultured epithelial cells," Mol. Microbiol., 7:89-98.

Andrews and Maurelli (1992) "MxiA of *Shigella flexneria* 2a, which facilitates export of invasion plasmid antigens encodes a homol of low-calcium-response protein LcrD, of *Yersinia pestis*," Infect. Immun. 60:3287-3295.

Bachman (1990) "Linkage map of *E. coli* K-12," Micro. Rev. 54:10-197.

Bajaj, et al. (1996) "Co-ordinate regulation of *Salmonella typhimurium* invasion genes by environmental and regulatory factor is mediated by control of expression," Mol. Microbiol. 22:703-714.

Bajaj, et al. (1995) "*hilA* is notvel *omp/taxR* family member that activates the expression of *Salmonella typhimurium* invasion genes," Mol. Microbiol, 18:715-727.

Bannwarth (1988) "Solid-phase synthesis of oligodeoxynucleotides containing phosphoramidate internucleotide linkages and their specific chemical cleavage," Helv. Chim. Acta. 71:1517-1527.

Baudry, et al. (1988) "Nucleotide sequence of the invasion plasmid antigen B and C genes (ipaB and ipaC) of *Shigella flexneri*," Microb. Pathog. 4:345-357.

Benson and Goldman (1992) "Rapid mapping in *Salmonella typhimurium* with Mud-P22 prophages," J. Bacteriol. 175:1673-1681.

Boddikcer, et al. (2006) "Signature-tagged mutagenesis of *Klebsiella pneumoniae* to identify genes that influence biofilm formation on extracellular matrix material," Infect. Immun. 74:4590-4597.

Bogdanove, et al. (1996) "Unified nomenclature for broadly conserved hrp genes of phytopathogenic bacteria," Mol. Microbiol. 20:681-683.

Bourgogne, et al. (1998) "*Salmonella abortusivusm* strain RV6, new vaccinal vehicle for small ruminants," Vet. Microbiol. 61:199-213 Abstract Only.

Cardenas, et al. (1994) "Influence of strain viability and antigen done on the use of attenuated mutants of *Salmonella* as vaccine carriers," Vaccine 12:833-840.

Cardenas, et al. (1993) "Stability, immunogenicity and expression of foreign antigens in bacterial vaccine vectors," Vaccine 11:122-125 Abstract Only.

Cardenas, et al. (1992) "Oral administration using live attenuated *Salmonella* spp. as carriers of foreign antigens," Clin. Microbiol. Rev. 5:328-342.

Cattozzo, et al. (1997) "Expression of immunogenicity of V3 loop epitopes of HIV Isolates SC and WMJ2, inserted in *Salmonella flagellin*," J. Biotechnol. 56:191-203 Abstract Only.

Chabalgoity, et al. (1996) "A *Salmonella typhimurium* htrA live vaccine expressing multiple copies of a peptide comprising amino acids 8-23 of herpes simplex virus glycoprotein D as a genetic fusion to tetanus toxin fragment C protects mice from herpes simplex virus infection," Mol. Microbiol. 19:791-801.

Chacon, et al. (1996) "Heterologous expression of the citicular glutathione peroxidase of lymphatic filariae in an attenuated vaccine strain of *Salmonella typhimurium* abrogates H-2 restricton of specific antibody response," Parasite Immunol. 18:307-316 Abstract Only.

Chang, et al. (1978) "Construction and characterization of amplifiable multicopy DNA cloning vehicles derived from the P15A cryptic miniplasmid" J. Bacteriol. 134:114-1156.

Charles, et al. (1990) "Gene expression an the development of live enteric vaccines," Trends Biotechnol. 8:117-121 Abstract Only.

Chatfield, et al (1992) "Construction of a genetically defined *Salmonella typhi* Ty2 aro A, aroC mutain for the engineering of a candidate oral typhoid-tetanus vaccine," Vaccine 10:53-60.

Chatfield, et al. (1994) "The use of live attenuated *Salmonella* for oral vaccination," Dev. Biol. Stand. 82:35-42.

Chatfield, et al. (1993) "The development of oral vaccines based on live attenuated *Salmonella* strains," FEMS Immunol. Med. Microbiol. 7:1-7.

Chatfield, et al. (1995) "The development of oral vaccines against parasitic diseases utilizing live attenuated *Salmonella*," Paristology 110Suppl.:S17-S24.

Chatfield, et al. (1989) "Live *Salmonella* vaccines and carriers of foreign antigenic determinants," Vaccine 7:495-498.

Cirillo, et al. (1995) "Bacterial vaccine vectors and *Bacillus* Calmette-Guerin," Clin. Infect. Dis. 30:1001-1009.

Clemens (1987) "Use of attenuated mutants of *Salmonella* as carriers for delivery of heterologous antigens to the secretory immune system," Pathol. Immunopathol. Res. 6:137-146.

Clements (1990) "Vaccines against enterotoxigenic bacterial pathogens based on hybrid *Salmonella* that express heterologous antigens," Res. Microbiol. 141:981-993. Abstract Only.

Cohen, et al. (1990) "Microbial isopenicillin N synthase genes: structure, function, diversity and evolution," Trends in Biotechnol, 8:105-111.

Collazo, et al. (1995) "Functional analysis of the *Salmonella typhimurium* invasion genes invI and invJ and identification of a target of the protein secretion apparatus encoded in the inv. locus," Mol. Microbiol. 15:25-38.

Cosstick and Vyle (1989) "Solid phase synthesis of oliogonucleotides containing 3'—thioymidase," Tetrahedron Letters, 30:4693:4696.

Covone, et al. (1998) "Levels of expression and immunogenicity of attenuated *Salmonella enterica* servar *typhimurium* strains expression *Escherichia coli* mutant heat-labile enterotoxin," Infect. Immun. 66:224-231.

Coynault, et al. (1992) "Growth phase and SpvR regulation of transcription in *Salmonella typhimurium* spvANC virulence genes," Microb. Pathog. 13:133-143. Abstract Only.

Curtiss, et al. (1990) "Stabilization of recombinant avirulent vaccine strains in vivo," Res. Microbiol. 141:797-805. Abstract Only.

Davidson, et al. (1995) "Lung disease in the cystic fibrosis mouse exposed to bacterial pathogens," Nat. Genet. 9:351-357.

De Lorenzo, et al. (1990) "Mino-Tn5 transposon derivatives for insertion mutagenesis promoter probing, and chromosomal insertion of cloned DNA in gram-negative eubacteria," J. Bacteriol. 172:6568-6572.

De Lorenzo and Timis (1994) "Analysis of stable phenotypes in gram negative bacteria with Tn5 and Tn10-derived minitransposons," Methods Enzymol. 235:386-405.

Degroote, et al (1997) "Periplasmic superoxide dismutase protects *Salmonella* from products of phagocyte NADPH-oxidase and nitric oxide synthase," PNAS 94:13997-14001.

Deiweick, et al. (1999) "Environmental regulation of *Salmonella* pathogenicity island 2 gene expression," Mol. Microbiol. 31:1759-1773.

Diederich, et al. (2000) "In search for specific inhibitors of human 11beta-hydroxysteroid-dehydrogenases (11beta-HSDs): Chenodeoxycholic acid selectivity inhibits 11beta-HSD-1" Eur. J. Endocrinol. 142:200-207.

(56) References Cited

OTHER PUBLICATIONS

Deiwick and Hensel (1999) "Regulation of virulence genes by environmental signal in *Salmonella typhimurium* electrophoresis," 20:813-817. Abstract Only.
Doggett, et al. (1993) "Immune response to *Streptococcus sobrinus* surface protein antigen A expressed by recombinant *Salmonella typhimurium*," Infect. Immun. 61:1859-1866.
Donnenberg, et al. (1991) "Construction of an eae deletion mutant of enterophatic *Escherichia coli* using a positive-selection suicide vector," Infect. Immunol. 59:4310-4317.
Dougan, et al. (1989) "Live bacterial vaccines and their application as carrier for foreign antigen," Adv, in Vet. Sci. and Comp. Med. 33:271-300.
Dougan, et al. (1987) "Live oral *Salmonella* vaccines: potential use of attenuated strains as carriers of heterologous antigens to the immune system," Parasite Immunol. 9:151-160.
Eichelberg, et al. (1994) "Molecular and functional characterization of the *Salmonella typhimurium* invasion genes invB and invC: homology of invC to the FOFI ATPase family of proteins," J. Bacteriol. 176:4501-4510.
Elliot, et al. (1998) "The complete sequence of the locus of enterocyte affeacement (LEE) from enteropathogenic *Escherichia coli* E2348/49," Mol. Microbiol. 28:1-4.
Everst, et al. (1995) "Expression of LacZ from the hrtA, nirB and groE promoters in a *Salmonella* vaccine strain: influence of growth in mammalian cells," FEMS Microbiol. Letters 126:97-101.
Fayole, et al. (1994) Genetic control of antibody responses induced against an antigen delivered by recombinant attenuated *Salmonella typhimurium*,: Infect. Immun. 62:4310-4319.
Fields, et al. (1986) "Mutants of *Salmonella typhimurium* that cannot survive within the macrophage are invirulent," PNAS 83:5189-5193.
Fierer, et al. (1993) "Expression of the *Salmonella* virulence plasmid gene spvB in cultured macrophages and nonphagocytic cells," Infect. Immun. 61:5231-5236.
Filay, et al. (1991) "Cytoskeletal rearrangements accompanying *Salmonella* entry into epithelial cells," 99:283-296.
Finlay (1994) "Molecular and cellular mechanisms of *Salmonella* pathogenesism" Curr. Top. Microbiol. Immunol. 192:163-185.
Foulongne, et al. (2000) "Identification of *Brucella suis* genes affecting intracellular survival in an in vitro human macrophage infection model by signature-tagged transposon mutagenesis," Infect. Immun. 68:1297-1303.
Forsberg, et al. (1994) "Use of transcriptional fusions to monitor gene expression: a cautionary tale," J. Bacteriol. 176:2128-2132.
Fouts, et al. (1995) "Construction and immunogenicity of *Salmonella typhimurium* vaccine vectors that express HIV-1 gp120," Vaccine 13:1697-1705. Abstract Only.
Fouts, et al. (1995) "Construction and characterization of *Salmonella*-typhi based human immunodeficiency virus type 1 vector vaccine," Vaccine 13:561-569. Abstract Only.
Francis et al. (1992) Morphological and cytoskeletal changes in epithelial cells occur immediately upon interaction with *Salmonella typhumurium* grown under low-oxygen conditions, Mol. Microbiol. 6:3077-3087.
Gentschev, et al. (1998) "Delivery of the p67 sporozite antigen *Theileria parva* by using recombinant *Salmonella* dublin: secretion of the product enhances specific antibody responses in cattle," Infect. Immun. 66:2060-2064.
Ginnochio, et al. (1992) "Identification and molecular characterization of a *Salmonella typhimurium* gene involved in triggering the internalization of *Salmonella* into cultured epithelial cells," PNAS 89:5976-5980.
Ginnocchio, et al. (1994) "Contact with epithelial cells induces the formation of surface appendages on *Salmonella typhimurium*," Cell 76:717-724.
Guillobel, et al. (1998) "Immunization against the colonization factor antigen 1 of enterotoxogenic *Escherichia coli* by administration of a bivalent *Salmonella typhimurium* aroA strain," Braz. J. Med. Biol. Res. 31:545-554. Abstract Only.

Gunn and Miller (1996) "PhoP-PhoQ activates transcription of pmrAB, encoding a two-component regulatory system involved in *Salmonella typhimurium* antimicrobiol peptide resistance," J. Bacteriol. 178:6857-6864.
Guy, et al. (2000) "Aggregation of host endosomes by *Salmonella* requires SP12 translocation of SseGF and involves SpvR and the fms-aroE intergenic region," Mol. Microbiol. 37:1417-1435. Abstract Only.
Haddad, et al. (1995) "Surface display compared to periplasmic expression of a malarial antigen in *Salmonella typhimurium* and its implications for immunogencity," FEMS Immunol. Med. Microbiol. 12:175-186. Abstract Only.
Hahn, et al. (1998) A *Salmonella typhimurium* strain genetically engineered to secrete a bioactive human interleukin (hIL)-6 via the *Escherichia coli* hemolysin secretion apparatus, FEMS Immunol. Med. Microbiol. 20:111-119. Abstract Only.
Hakansson, et al. (1996) "The YoB protein of *Yersinia pseudotuberculosis* is essential for the translocation of Yop effector proteins accrsoos the target cell plasma membrane and displays a contact-dependent membrane disrupting activity," EMBO J. 15:5812-5823.
Harokopakis et al. (1997) "Mucosal immunogenicity of a recombinant *Salmonella typhimurium*-cloned heterologous antigen in the absence or presence of co-expressed cholera toxin A2 and B subunits," Infect. Immun. 65:1445-1454.
Hauser, et al. (1998) "Defects in type III secretion correlate with internalization of *Pseudomonas aeruginosa* by epithelial cells," Infect. Immun. 66:1413-1420.
Havaarstein, et al. (1995) "An unmodified heptadecapeptide phermone induces competence for genetic transformation in *Streptococcus pneumoniae*," PNAS 92:11140-11144.
He, et al. (2000) "Function of human brain short chain L-3 hydroxl coenzyme A dehydrogenase in androgen metabolism," Biochemica Er. Biophysica Acta:1484:267-277.
Heithoff, et al. (1999) "An essential role for DNA adenine methylation in bacterial virulence," Science 284:967-970.
Hensel and Holden (1996) "Molecular genetic approaches for the study of viruclence in both pathogenic bacteria and fungi," Microbiol. 142:1049-1058.
Herrero, et al. (1990) "Transposon vectors containing non-antibiotic resistance selection markers for cloning and stable chromosomal insertion of foreign genes in gram negative bacteria," J. Bacteriol. 172:6557-6567.
Hess, et al. (1997) "Protection against murine listerioisis by an attenuated recombinant *Salmonella typhimurium* vaccine strain that secretes the naturally somatic antigen superoxide dismutase," Infect. Immun. 65:1286-1292.
Hess, et al. (1995) "*Listeria* monocytogenes p60 supports host cell invasion by and in vivo survival of attenuated *Salmonella typhimurium*," Infect. Immun. 63:2047-2053.
Hess, et al. (1996) "Superior efficacy of secreted over somatic antigen display in recombinant *Salmonella* vaccine induced protection against listeriosis," PNAS 93:1458-1463.
Hess, et al. (1997) "Modulation of antigen display by attenuated *Salmonella typhimurium* strains and its impact on protective immunity against listeriosis," Behring Inst. Mitt. 160-171.
Hirakata, et al. (1992) "Efficacy of erythromycin lactobionate for treating *Pseudomonas aeuginosa* bacteremia in mice," Antimicrob. Agents Chemother. 36:1198-1203.
Hoffman and Stoffel (1993) "TMbase—a database of membrane spanning protein segments," Biol. Chem. Hoppe-Seyler 347:166.
Hohmann, et al. (1995) "Macrophage-inducile expression of a model antigen in *Salmonella typhimurium* enhances immunogenicity," PNAS 92:2904-2908.
Hohmann, et al. (1996) "Evaluation of phoP/phoQ-deleted aroA-deleted live oral *Salmonella typhi* vaccine strain in human volunteers," Vaccine 14:19-24.
Holden, et al. (1989) "Mutation in heat-regulated hsp70 gene of *Ustilago maydis*," EMBO J. 8:1927-1934.
Holtel, et al. (1992) "Upstream binding sequences of the XylR activator protein and integration host factor in the xylS gene promoter region of the *Pseudomonas* TOL plasmid," Nucl. Acid Res. 20:1755-1762.

(56) References Cited

OTHER PUBLICATIONS

Hone, et al. (1988) "A chromosomal integration system for stabilization of heterologous genes in *Salmonella* based vaccine strains," Microb. Pathog. 5:407-418. Abstract Only.

Hormaeche, et al. (1996) "Protection against oral challenge three months after i.v. immunization of BALB/c mice with live Aro *Salmonella typhimurium* and *Salmonella enteritidis* vaccines is serotype (species)-dependent and only partially determined by the main LPS O antigen," Vaccine 14:251-259. Abstract Only.

Hormaeche, et al. (1991) "Live attenuated *Salmonella* vaccines and their potential as oral combined vaccines carrying heterologous antigens," J. Immunol. 142:113-120. Abstract Only.

Hueck (1998) "Type III protein secretion systems in bacterial pathogens of animals and plants," Microbiol. Mol. Biol. Rev. 62:379-433.

Hueck, et al. (1995) "*Salmonella typhimurium* secreted invasion determinants are homologous to *Shigella* lpa proteins," Mol. Microbiol. 18:479-490.

Jager, et al. (1988) "Oligonucleotide N-alkylphosphoramidates: synthesis and bindings to polynucleotides," Biochemistry 20:7237-7246.

Janssen, et al. (1995) "Induction of the phoE promoter upon invasion of *Salmonella typhimurium* into eukaryotic cells," Microb. Pathog. 19:193-201. Abstract Only.

Jornvall, et al. (1995) "Short chain dehydrogenases/reductases (SDR)" Biochemistry 34:6003-6013.

Jornvall, et al. (1999) "SDR and MDR: Completed genome sequences show these protein families to be large, of old origin and complex nature," FEBS Letters 445:261-264.

Kaniga, et al. (1995) "Homologs of the *Shigella* lpa and lpC invasins are required for *Salmonella typhimurium* entry into cultured epithelial cells," J. Bacteriol. 177:3965-3971.

Kaniga, et al. (1994) "The *Salmonella typhimurium* invasion genes invF and invG encode homologs of the AraC and PulD family of proteins," Mol. Microbiol. 13L555-568.

Karem, et al. (1996) "Cytokine expression in the gut associated lymphoid tissue after oral administration of attenuated *Salmonella* vaccine strains," Vaccine 14:1495-1502. Abstract Only.

Kirsch and Di Domenico (1993) "The discovery of natural products with a therapeutic potential," V.P. Gallo, Ed. Chapter 6, pp. 1770221, Buttersworth, V.K.

Krul, et al. (1996) "Induction of an antibody response in mice against papilloma virus (HPV) type 16 after immunization with HPV recombinant *Salmonella* strains," Cancer Immunol. 43:44-48.

Kuwajiia, et al. (1989) "Export of N-terminal fragment of *Escherichia coli* flagellin by a flagellum-specific pathway," PNAS, 86:4953-4957.

Laemmli (1970) "Cleavage of structural proteins during the assembly of the head of bacteriophage T4," Nature 227:680-685.

Leary, et al. (1997) "Expression of an F1/V fusion protein in attenuated *Salmonella typhimurium* and protection of mice against plague," Microb. Pathog. 23:167-179. Abstract Only.

Lee, et al. (1992) "Identification of a *Salmonella typhimurium* invasion locus by selection for hyperinvasive mutants," PNAS 89:1847-1851.

Leiter, et al. (1990) "Inhibition of influenza virus replication by phosphorothioate oligodeoxynucleotides," PNAS 87:3430-3434.

Lenz, et al. (2000) "Chemical ligands, genomics and drug delivery," Drug Discovery Today 5:145-156.

Levine, et al. (1996) "Attenuated *Salmonella* as live oral vaccines against typhoid fecer and as live vectors." J. Biotechnol. 44(1-3):120-123.

Liljevist, et al. (1996) "A novel expression system for *Salmonella typhimurium*, allowing hight production levels, product secretion and efficient recovery," Biochem. Biophys. Res. Com. 218:356-359. Abstract Only.

Lingberg (1995) "The history of live bacterial vaccines," Dev. Biol. Stand. 84:211-219. Abstract Only.

Li, et al. (1995) "Relationship between evolutionary rate and cellular location among the Inv/Spa invasion proteins of *Salmonella enterica*," PNAS 92:7252-7256.

Lo-Man, et al. (1996) "Control by H-2 genes of the Th1 response induced against foreign antigen expressed by attenuated *Salmonella typhimurium*," Infect. Immun. 64:4424-4432.

Lowe, et al.(1999) "Characterization of candidate live oral *Salmonella typhi* vaccine strains harboring defined mutations in aroA, aroC and htrA" Infect. Imm. 67:700-707.

MacNab (1996) "Flagella and motility in *Escherichia coli* and *Salmonella*: cellular and molecular biology," F.C. Neidardt, et al. (eds.) Washington, D.C.:ASM Press: 123-145.

Maskell, et al. (1987) "*Salmonella typhimurium* aroA mutants as carriers of *Escherichia coli* heat labile enerotoxin B subunit to the murine secretory and systemic immune systems," Microb. Pathog. 2:2211-221. Abstract Only.

Maurer, et al. (1984) "Functional interchangeability of DNA replication genes in *Salmonella typhimurium* and *Escherichia coli* demonstrated by a general complementation procedure," Genetics 108:1-23.

McSorley, et al. (1997) "Vaccine efficacy of *Salmonella* strains expressing glycoprotein 63 with different promoters," Infect. Immun. 65:171-178.

Michiels, et al. (1991) "Analysis of virC, an operon involved in the secretion of Ypo proteins by *Yersinea enterocolitica*," J. Bacteriol. 173:4994-5009.

Milich, et al. (1995) "The hepatitis nucleocapsid as a vaccine carrier moiety," Ann. NY Acad. Sci. 754:187-201. Abstract Only.

Miller and Mekalanos (1998) "A novel suicide vector and its use in construction of inversion mutations: osmoregulation of outer membrane proteins and virulence determinants in *Vibrio cholerae* requires ToxR," J Bacteriol. 170:2575-2583.

Miller et al. (1993) "The PhoP virulence regulon and live oral *Salmonella* vaccines," Vaccine 11:122-125.

Minamino, et al (1999) "Components of the *Salmonella* flagellar export apparatus and classification of export substrates," J. Bacteriol. 181:1388-1394.

Miras, et al. (1995) "Nucleotide sequence of iagA and iagB genes involved in invasion of HeLa cells by *Salmonella enterica* subsp. Enterica Ser. Typhi" Res. Micorbiol. 146:17-20.

Monack, et al. (1996) "*Salmonella typhimurium* invasion induces apoptosis in infected macrophages," PNAS 93:9833-9838.

Newton, et al. (1995) "Studies of the anaerobically induced promoter pairB and the improved expression of bacterial antigens," Res. Microbiol. 146:193-202.

Nielson, et al. (1998) "Synthesis and characterization of dinucleoside phosphorodithoates," Tetrahedron Letters, 29:2911-2914.

Ocallaghan and Charbit (1990) "High efficiency transformation of *Salmonella typhimurium* and *Salmonella typhi* by electroporation," Mol. Gen. Genet. 223:156-158.

Obeysekere et at (1998) "Serines at the active site of 11 beta-hydroxysteroid dehydrogenase type 1 determine the rates of catalysis" Biochem. Biophys. Res. Commun. 250:469-473.

Ohara, et al. (1989) "Direct genomic sequencing of bacterial DNA: the pyruvate kinase I gene of *Escherichia coli*," PNAS 86:6883-6887.

Okahashi, et al. (1996) "Oral immunization of interleukin-4 (IL-4) knockout mice with a recombinant *Salmonell* strain or cholera toxin reveals CD4+ Th2 cells producing IL-6 and IL-10 are associated with mucosal immunoglobulin A responses," Infect. Immun. 64:1516-1525.

Opperman, et al. (1997) "Structure function relationships of SDR hydroxysteroid dehydrogenases," Advances in Exp. Med. and Biol. 414:403-415.

Orr, et al. (1999) "Expression and immunogenicity of a mutant diptheria toxin molecule, CRM197, and its fragments in *Salmonella typhi* vaccine strain CVD 908-htrA" Infect. Immun. 67:4290-4294.

Pallen, et al. (1997) "Coiled-coil domains in proteins secreted by type III secreion systems," Mol. Microbiol. 25:423-425.

Pearce, et al (1993) "Genetic identification of exported proteins in *Streptococcus pneumoniae*," Mol. Microbiol. 9:1037-1050.

Perlman and Freeman (1971) "Experimental endocarditis. II Staphlococcol infection of the aortic valve following placement of polyethylne catheter in the left side of the heart," Yale J. Biol. Med. 44:206-213.

Plano, et al. (1991) "LcrD, a membrane-bound regulator of the *Yersinia pestis* low-calcium response," J. Bacteriol. 173:7293-7303.

(56) References Cited

OTHER PUBLICATIONS

Pozza, et al. (1998) "Construction and characterization of *Salmonella typhimurium* aroA simultaneously expressing the five pertussis toxic subunits," Vaccine 16:522-529. Abstract Only.
Ralph, et al. (1975) "Reticulum cell sarcoma and effector cell in antibody-dependent cell-mediated immunity," J. Immunol. 114:898-905.
Reed and Muench (1938) "A simple method of estimating fifty per cent end points," Am J. Hyg. 27:493-497.
Rhen, et al. (1993) "Transcriptional regulation of *Salmonella enterica* virulence plasmid genes in cultured macrophages," Mol. Microbiol. 10:45-56. Abstract Only.
Ronson, et al. (1987) "Conserved domains in bacterial regulatory proteins that respond to environmental stimuli," Cell 49:579-581.
Roy and Coleman (1994) "Mutations in firA, encoding the second acyltransferase in lippolysaccharide biosynthesis, affect multiple steps in lipopolysaccharide biosynthesis," 176:1639-1646.
Saiki et al. (1988) "Primer directed enzymatic ampliifcation of DNA with a thermostable DNA polymerase," Science 4839:487-491.
Salmond and Reeves (1993) "Membrane traffic wardens and protein secretion in gram negative bacteria," Trends in Bochem. Sci. 18:7-12.
Sanderson, et al. (1995) "Genetic map of *Salmonella typhimurium*,edition VIII," Microbiol. Rev. 59:241-303.
Sanger, et al. (1977) "DNA sequence with chain terminating inhibitors," PNAS 74:5463-5467.
Sarin, et al. (1988) "Inhibition of acquired immunodeficiency syndrome virus by oligodeoxynucleoside methylphosphonates," PNAS 85:7448-7451.
Sasakawa, et al. (1993) "Eigh genes in region 5 that form an operon are essential for invasion of epithelial cells by *Shigella flexneria* 2a," J. Bacteriol. 175:2334-2346.
Schmitt et al. (1996) "The attenuated phenotype of a *Salmonella typhimurium* flgM mutant is related to expression of FliC flagellin," J. Bacteriol. 178:2911-2915.
Schodel, et al. (1990) "Hepatitis B Virus Nucleocapsid/pre-S2 fusion proteins expressed in attenuated *Salmonella* for oral vaccination" J. Immunol. 145:4317-4321.
Schodel (1990) "Oral vaccination using recombinant bacteria," Semin. Immunol. 12:341-349.
Shaw et al. (1991) "Modified deoxyoligonucleotides stable to exonuclease degradation in serum," Nucelic Acids Res. 19:747-750.
Sigwart, et al. (1989) "Effect of purA mutation on efficacy of *Salmonella* live-vaccine vectors," Infect. Immun. 57:1858-1861.
Skorupski and Taylor (1996) "Positive selection vectors for allelic exhange," Gene 169:47-52.
Strugnell et al (1990) "Stable expression of foreign antigens from the chromosome of *Salmonella typhimurium* vaccine strains," Gene 88:57-63. Abstract Only.
Strugnell et al. (1992) "Characterization of a *Salmonella typhimurium* aro vaccine strain expressing the p69 antigen of *Bordella pertussis*," Infect. Immun. 60:3994-4002.
Su et al. (1992) "Extracellular export of Shiga toxin B-subunit haemolysin A (C-terminus) fusion protein expressed in *Salmonella typhimurium* aro-A mutant and stimulation of B-subunit specific antibody responses," Microb. Pathog. 13:465-476. Abstract Only.
Sullivan et al (1993) "Evaluation of the efficacy of ciprofloxacin against *Streptococcus pneumoniae* by using a mouse protection model," Antimicrob. Agents Chemother. 37:234-239.
Tacket at al. (1990) "Safety and immunogenicity, and efficacy against cholera challenge in humans of a typhoid-cholera hybrid vaccine derived from *Salmonella* typhi21a," Infect. Immun. 58:1620-1627.
Tacket et al. (1997) "Safely and immunogenicity in humans of an attenuated *Salmonella typhi* vaccine vector strain expressing plasmid encoded hepatitis B antigens stabilized by the Asd-balanced lethal vector system," Infect. Immun. 65:3381-3385.
Takeuchi (1967) "Electron microscope studies of experimental *Salmonella* infection I. Penetration into the intestinal epithelium by *Salmonella typhimurium*," Am. J. Pathol. 50:109-136.

Tang et al. (1993) "Self-stabilized antisense oligodeoxynucleotide phosphorothioates: properties and anti-HIV activity," Nucleic Acids Res. 21:2729-2735.
Tijhaar et al. (1997) "Induction of feline immunodeficiency virus specific antibodies in cats with an attenuated *Salmonella* strain expressing the Gag protein," Vaccine 15:587-596.
Tijhaar et al. (1997) "*Salmonella typhimurium* aroA recombinants and immune-stimulating complexes as vaccine candidates for feline immunodeficiency virus," J. Gen. Virol. 46:129-138.
Uznanski et al. (1987) "Deoxyribonucleoside 3'-phosphordiamidites as substrates for solid supported synthesis of oligodeoxyribonucleotides," Tetrahedron Letters 78:3265-3275.
Valentine et al. (1996) "Induction of SIV capsid specific CTL and mucosal sIgA in mice immunized with recombinant *S. typhimurium* aroA mutant," Vaccine 14:138-146.
Van Gusegem et al (1993) "Conservation of secretion pathways for pathogenicity determinants of plant and animal bacteria," Trends Microbiol. 1:175-180.
Veber et al. (1993) "Correlation between macrolide lung pharmacokinetics and therapeutic efficacy in a mouse model of pneumococcal pneumonia," J. Antimicrob. Chemother. 32:473-482.
Venkatesan et al. (1992) "Surface presentation of *Shigella flexneri* invasion plasmid antigens requires the products of the spa locus," J. Bacteriol. 174:1990-2001.
Verma et al. (1995) "Induction of a cellular immune response to a defined T cell epitope as an insert in the flagellin of a live vaccine strains of *Salmonella*," Vaccine 13:235-234. Abstract Only.
Villafane et al. (1987) "Replication control genes of plasmid pE194," J. Bacteriol. 169:4822-4829.
Viret et al. (1993) "Molecular cloning and characterization of the genetic determinants that express the complete *Shigella* serotype D (*Shigella sonnei*) lipopolysaccharide in heterologous live attenuated vaccine strains." Mol. Microbiol. 7:239-252. Abstract Only.
Wang et al, (2006) "Application of signature tagged mutagenesis to the study of *Erwina amylovora*" FEMS Microbiol. Lett. 265:164-171.
Wattiau et al. (1994) Individual chaperones required for Yop secretion by Wattiau et al. (1994) "Individual chaperones required for Yop secretion by *Yersinia*" PNAS 91:10493-10497.
Whitman et al (1993) "Antibiotic treatment of experimental endocarditis due to vancomycin- and ampicillin-resistant *Enterococcus faecium*," Antimicrob. Agents Chemother. 37:2069-2073.
Whittle et al. (1997) "Immune response to a Murray Valley encephalitis virus epitope expressed in the flagellin of an attenuated strain of *Salmonella*," J. Med. Microbiol. 46:129-138.
Whittle and Verma (1997) "The immune response to a B-cell epitope delivered by *Salmonella* is enhanced by prior immunological experience," Vaccine 15:1737-1740. Abstract Only.
Wirth et al. (1986) "Highly efficient protoplast transformation system for *Streptococcus faecalis* and a new *Escherichia coli-S. faecalis* shuttle vector," J. Bacteriol. 165:831-836.
Woods et al. (1982) "Contribution of toxin A and elastase to virulence of *Pseudomonas aeruginosa* in chronic lung infections of rats," Infect. Immun. 36:1223-1228.
Yan et al. (1996) "Mixed population approach for vaccination with live recombinant *Salmonella* strains." J. Biotechnol. 44:197-201. Abstract Only.
Yancey (1993) "Recent advances in bovine vaccine technology," J. Dairy Sci. 76:2418-2436.
Yang et al., (1990) "Oral *Salmonella typhimurium* (AroA-) vaccine expressing a major leishmanial surface ptorin (gp63) preferentially induces T helper 1 cells and protective immunity agaist leishmaniasis," J. Immunol. 145:2281-2285. Abstract Only.
Yanisch-Perron et al. (1985) "Improved M13 phage cloning vectors and host strains: nucleotide sequences of the M13mp18 and pUC19 vectors." Gene 33:103-119.
Youderain et al. (1988) "Packaging specific segments of the *Salmonella* chromosome locked-in Mud-P22 prophages," Genetics, 118:581-592.
Young et al (1999) "A new pathway for the secretion of virulence factors by bacteria: the flagellar export apparatus functions as a protein secretion system." PNAS 96:6456-6461.

(56) References Cited

OTHER PUBLICATIONS

Zhu et al. (1993) "Systemic gene expression intravenous DNA delivery into adult mice." Science 261:209-211.
Acharya et al. (1987) "Prevention of typhoid fever in nepal with the vi capsular polysaccharaide of *Salmonella typhi*," NEJM, 317:1101-1104.
Ahmer et al. (1999) "*Salmonella* SirA is a global regulator of genes mediating enteropathogenesis," Mol. Microbiol. 31(3):971-982.
Altare et al. (1998) "Inherited interleukin 12 deficiency in a child with Bacille Calmette-Guerin and *Salmonella enteritidis* disseminated infection," J. Clin. Invest. 102:2035-2040.
Angelakopoulos and Hohmann (2000) "Pilot study of *phoP/phoQ*-deleted *Salmonella enterica* serovar *typhimurium* expressing *Helicobacter pylori* urease in adult volunteers," Infect. Immun., 68:2135-2141.
Aranda et al. (1992) "*Salmonella typhimurium* activates virulence gene transcription within acidified macrophage phagosomes," PNAS, 89:10079-10083.
Arricau et al. (1998) "The ResB-ResC regulatory system of *Salmonella typhi* differentially modulates the expression of invasion proteins, flagellin and Vi antigen in response to osmolarity," Mol. Microbiol. 29:835-850.
Ascon, et al. (1998) "Oral immunization with a *Salmonella typhimurium* vaccine vector expressing recombinant enterotoxigenic *Eschericia coli* K99 fimbrae elicits elevated antibody titers for protective immunity," Infect. Immun. 66:5470-5476.
Attridge (1991) "Oral immunization with *Salmonella typhi* Ty21a-based clones expressing *Vibrio cholerae* O-antigen: serum bactericidal antibody responses in man in relation to pre-immunization antibody levels," Vaccine, 9:877-882.
Bao and Clements (1991) "Prior immunologic experience potentiates the subsequent antibody response when *Salmonella* strains are used as vaccine carriers," Infect. Immun. 59:3841-3845.
Barry et al. (1996) "Expression and Immunogenicity of Pertussis Toxin S1 subunit-tetanus toxin fragment C fusion in *Salmonella typhi* vaccine strain CVD 908," Infect. Immun. 64:4172-4181.
Basso et al. ( 2002) "Characterization of a novel intracellularly activated gene from *Salmonella enterica* serovar *typhi*," Infect. Immun. 70:5404-5411.
Benjamin et al. (1991) "A *hemA* mutation renders *Salmonella typhimurium* avirulent in mice, yet capable of eliciting protection against intravenous infection with *S. typhimurium*," Microb. Pathog. 11:289-295.
Beuzon et al. (1999) "pH-dependant secretion of SseB, a product of the SPI-2 type III secretion system of *Salmonella typhimurium*," Mol. Microbiol. 33:806-816.
Beuzon et al. (2000) "*Salmonella* maintains the integrity of its intracellular vaciole through the action of SifA," EMBO J., 19:3235-3249.
Black, et al. (1983) "Immunogenicity of Ty21a Attenuated *Salmonella typhi* given with sodium bicarbonate or in enteric-coated capsules," Develop. Biol. Stand., 53:9-14.
Bost and Clements (1995) "In vivo induction of interleukin-12 mRNA expression after oral immunization with *Salmonella dublin* or the B subunit of *Escherichia coli* heat-labile enterotoxin," Infect. Immun. 63:1076-1083.
Brennan et al. (1994) "Differences in the immune responses of mice and sheeo ti an aromatic-dependent mutant of *Salmonella typhimurium*," J. Med. Microbiol. 41:20-28.
Brown and Hormaeche (1989) "The antibody response to *salmonellae* in mice and humans studied γ immunoblots and ELISA," Microb. Pathog. 6:445-454.
Brown et al. (1987) "An attenuated *aroA Salmonella typhimurium* vaccine elicits humoral and cellular immunity to cloned β-galactosidase in mice," J. Infect. Dis. 155:86-92.
Browne et al. (2002) "Genetic requirements for *Salmonella*-induced cytopathology in human monocyte-derived macrophages," Infect. Immun. 70:7126-7135.

Buchmeier and Libby (1997) "Dynamics of growth and death within a *Salmonella typhimurium* population during infection of macrophages," Can. J. Microbiol. 43:29-34.
Bumann et al. (2000) "Recombinant live *Salmonella* spp. for human vaccination against heterologous pathogens," FEMS Immunol. Med. Microbiol. 27:357-364.
Bumann et al. (2002) "Safety and immunogenicity of live recombinant *Salmonella enterica* serovar *typhi* Ty21a expressing urease A and B from *Helicobacter pylori* in human volunteers," Vaccine, 20:845-852.
Butler, et al. (1991) "Pattern of morbidity and mortality in typhoid fever dependent on age and gender: review of 552 hospitalized patients with diarrhea," Rev. Infect. Dis. 13:85-90.
Cameron and Fuls (1976) "Immunization of mice and calves agaisnt *Salmonella dublin* with attenuated live and inactivated vaccines," J. Vet. Res. 43:31-37.
Cancellieri and Fara (1985) "Deomonstration of specific IgA in human feces after immunization with live Ty21a *Salmonella typhi* vaccine," J. Infect. Dis. 151:482-484.
Caro, et al. (1999) "Physiological changes of *Salmonella typhimurium* cells under osomotic and starvation conditions by image analysis," FEMS Microbiol. Lett. 179:265-273.
Carrier, et al. (1992) "Expression of Human IL-1β in *Salmonella typhimurium*, a model system for the delivery of recombinant therapeutic proteins in vivo," J. Immunol. 148:1176-1181.
Carter and Collins (1974) "Growth of typhoid and paratyphoid Bacilli in travenously infected mice," Infect. Immun. 10:816-822.
Casadevall (1998) "Antibody-mediated protection against intracellular pathogens," Trends in Microbiol. 6:102-107.
Chabalgoity et al. (1995) "Influence of preimmunization with tetanus toxioid on immune responses to tetanus toxin fragment c-guest antigen fusions in *Salmonella* vaccine carrier," Infect. Immun. 63:2564-2569.
Chabalgoity et al. (1997) "Expression and immunogenicity of an *Echinococcus granulosus* fatty acid-binding protein in live attenuated *Salmonella* vaccine strains," Infect. Immun. 65;2402-2412.
Charles et al. (1990) "Isolation, characterization and nucleotide sequences of the *aroC* genes encoding chorismate synthase from *Salmonella typhi* and *Escherichia coli*," J. Gen. Microbiol. 136:353-358.
Chatfield, et al. (1992) "Use of the *nirB* promoter to direct the stable expression of heterologous antigens in *Salmonella* oral vaccine strains: development of a single-dose oral tetanus vaccine," Biotechnol. 10:888-892.
Chatfield, et al. (1992) "Evaluaton of *Salmonella typhimurium* strains harbouring defined mutations in *htrA* and *aroA* in the murine salmonelloisis model," Microbial Pathog. 12:145-151.
Chatfield, et al. (1994) "Progress in Development of Multivalent Oral Vaccines Based on Live Attenuated *Salmonella*" in *Modern Vaccinology* E. Kurstak, ed., Plenum Medical, New York, NY. 55-85.
Chen and Schifferli (2001) "Enhanced immune responses to viral epitopes by combining macrophage-inducible expression with multimeric display on a *Salmonella* vector," Vaccine, 19:3009-3018.
Chen, et al (1996) "*Salmonella* spp. are cytotoxic for cultured macrophages," Mol. Microbiol. 21:1101-1115.
Chuttani, et al. (1973) "Ineffectiveness of an oral killed typhoid vaccine in a field trial," Bull. Org. Mond. Sante, 48:754-755.
Chuttani, et al. (1977) "Controlled field trial of a high-dose oral killed typhoid vaccine in India," WHO 55:643-644.
Ciacci-Woolwine et al. (1997) "Salmonellae activate tumor necrosis factor apha production in a human promonocytic cell line via a released polypeptide," Infect. Immun. 65:4624-4633.
Cieslak et al. (1993) "Expression of a recombinant *Entamoeba histolytica* antigen in a *Salmonella typhimurium* vaccine strain," Vaccine 11:773-776.
Clairmont et al. (2000) "Biodistribution and genetic stability of the novel antitumor agent VPN20009, a genetically modified strain of *Salmonella typhimurium*" J. Infect. Dis. 181:1996-2002.
Clark, et al. (1996) "Invasion of murine intestinal M cells by *Salmonella typhimurium* inv mutants severely deficient for invasion of cultured cells," Infect. Immun. 64:4363-4368.

(56) References Cited

OTHER PUBLICATIONS

Clark, et al. (1998) "Inoculum composition and *Salmonella* pathogenicity island 1 regulate M-cell invasion and epithelial destruction by *Salmonella typhimurium*," Infect. Immun. 66:724-731.
Clements and El-Morshidy (1984) "Construction of a potential live oral bivalent vaccine for typhoid fever and cholera-*Escherichia coli*-Related diarrheas," Infect. Immun. 46:564-569.
Clements et al. (1986) "Oral immunization of mice with attenuated *Salmonella enteritidis* containing a recombinant plasmid which codes for production of the B subunit of heat-labile *Escherichia coli* enterotoxin," Infect. Immun. 53:685-692.
Cobelens, et al. (2000) "Typhoid fever in groups of travelers: Opporotunity for studying vaccine efficacy," J. Travel Med. 7:19-24.
Collins and Carter (1972) "Comparative immunogenicity of heat-killed and living oral *Salmonella* vaccines," Infect. Immun. 6:451-458.
Collins (1972) "Salmonellosis in orally infected specific pathogen-free C57B1 mice," Infect. Immun. 5:191-198.
Cooper et al. (1992) "Vaccination of chickens with chicken-derived *Salmonella enteritidis* phage type 4 *aroA* live oral *Salmonella* vaccines," Vaccine 10:247-254.
Corbel (1996) "Reasons for instability of bacterial vaccines," Dev. Biol. Stand. 87:113-124.
Coulson et al. (1994) "*Bacillus anthracis* protective antigen, expressed in *Salmonella typhimurium* SL 3261, affords protection against anthrax spore challenge," Vaccine, 12:1395-1401.
Coulson et al. (1994) "Effect of different plasmids on colonization of mouse tissues by the aromatic amino acid dependent *Salmonella typhimurium*, SL 3261," Microbial Pathog. 16:305-311.
Coynault and Noral (1999) "Comparison of the abilities of *Salmonella typhimurium rpoS*, *aroA* and *rpoS aroA* strains to elicit humor immune responses in BALB/c mice to cause lethal infection in athymic BALB/c mice," Microbial Pathog. 26:299-305.
Coynault et al. (1996) "Virulence and vaccine potential of *Salmonella typhimurium* mutants deficient in the expression of the RpoS $\sigma^s$) regulon," Mol. Microbiol. 22:149-160.
Cryz et al. (1989) "Construction and characterization of a Vi-positive variant of the *Salmonella typhi* live oral vaccine strain Ty21a," Infect. Immun. 57:3863-3868.
Cryz et al. (1995) "Safety and immunogenicity of a live oral bivalent typhoid fever (*Salmonella typhi* Ty21a)-cholera (*Vibrio cholerae* CVD 103-HgR) vaccine in healthy adults," Infect. Immun. 63:1336-1339.
Curtiss and Kelly (1987) "*Salmonella typhimurium* deletion mutants lacking adenylate cyclase and cyclic AMP receptor protein are avirulent and immunogenic," Infect. Immun. 55:3035-3043.
Curtiss et al. (1989) "Recombinant avirulent *Salmonella* vaccine strains with stable maintenance and high level expression of cloned genes in vivo," Immunol. Invest. 18:583-596.
D'Amelio et al. (1988) "Comparative analysis of immunological responses to oral (Ty21a) and parenteral (TAB) typhoid vaccines," Infect. Immun.. 56:2731-2735.
De Almeida (1999) "Antibody responses against flagellin in mice orally immunized with attenuated *Salmonella* vaccine strains," Arch. Microbiol. 172:102-108.
Dham and Thompson (1982) "Studies of cellular and humoral immunity in typhoid fever and TAB vaccinated subjects," Clin. Exp. Immunol. 48:389-395.
Dilts, et al. (2000) "Phase I clinical trials of *aroA aroD* and *aroA aroD htrA* attenuated *S. typhi* vaccines; effect of formulation on safety and immunogenicity," Vaccine, 18:1473-1484.
Dima (1981) "Isolation and characterization of two *Salmonella typhosa* mutants for possible use as a live oral attenuated vaccinal strains," Arch. Roum. Path. Exp. Microbiol. 40:33-40.
Depetrillo (2000) "Safety and immunogenicity of *PhoP/PhoQ*-deleted *Salmonella typhi* expressing *Helicobacter pylori* urease in adult volunteers," Vaccine 18:449-459.

Djavani et al. (2001) "Mucosal immuniztion with *Salmonella typhimurium* expressing *Lassa virus* nucleocapsid protein cross-protects mice from lethal challenge with lymphocytic choriomeningitis virus," J. Hum. Virol. 4:103-108.
Dorman et al. (1989) "Characterization of porin and *ompR* mutants of a virulent strain of *Salmonella typhimurium: ompR* mutants are attenuated in vivo," Infect. Immun. 57:2136-2140.
Dorner (1995) "An overview of vaccine vectors," Dev. Biol. Stand. 84:23-32.
Douce, et al. (1991) "Invasion of HEp-2 cells by strains of *Salmonella typhimurium* different virulence in relation to gastroenteritis," J. Med. Microbiol. 35:349-357.
Dougan, et al. (1988) "Construction and characterization of vaccine strains of *Salmonella* harboring mutatons in two different *aro* genes," J. Infect. Dis. 158:1329-1335.
Dragunsky et al. (1990) "In vitro characterization of *Salmonella typhi* mutant strains for live oral vaccines," Vaccine 8:262-268.
Dragunski et al. (1989) "*Salmonella typhi* vaccine strain in vitro; low inefectivity in human cell line U937," J. Biol. Stand. 17:353-360.
Dunstan et al. (1999) "Use of in vivo-regulated promoters to deliver antigens from attenuated *Salmonella enterica* var. *typhimurium*," Infect. Immun. 67:5133-5141.
Dupont et al. (1971) "Studies of immunity in typhoid fever," Bull. Org. Mond. Sante. 44:667-672.
Edwards and Stocker (1988) "Construction of Δ*aroA his* Δ*pur* strains of*Salmonella typhi*," J. Bacteriol. 170:3991-3995.
Eichelberg and Galan (1999) "Differential regulation of *Salmonella typhimurium* type III secreted proteins by pathogenicity island 1 (SP1-1)-encoded transcriptional activators InvF and HilA," Infect. Immun. 67:4099-4105.
Emmerth, et al. (1999) "Genomici subtraction identifies *Salmonella typhimurium* prophages, F-related plasmid sequences, and a novel fimbrial operon, stf, which are absent in *Salmonella typhi*," J. Bacteriol. 181:5652-5661.
Engels, et al. (1998) "Typhoid fever vaccines: a meta-analysis of studies on efficacy and toxicity," BMJ, 316:110-113.
Everest, et al. (1999) "Evaluation of *Salmonella typhimurium* Mutants in a model of a experimental gastroenteritis," Infect. Immun. 67:2815-282.
Fallon, et al. (1991) "Mouse hepatits virus strain UAB infection enhances resistence to *Salmonella typhimurium* in mice by inducing supression of bacterial growth," Infect. Immun. 59:852-856.
Ferricio (1989) "Comparative efficacy of two, three, or four doses of TY21a live oral vaccine in enteric coated capsules: a field trial in an endemic area," J. Infect. Dis. 159:766-769.
Finlay and Falkow (1997) "Common themes in microbial pathogenicity revisited," Microbiol. Mol. Biol. Rev. 61:136-169.
Formal et al. (1981) "Construction of a potential bivalent vaccine strain: introduction of *Shigella sonnei* form 1 antigen genes into the *galE Salmonella typhi* Ty21a typhoid vaccine strain," Infect. Immun. 34:746-750.
Forrest and LaBrooy (1993) "Effect of parenteral immunization on intestinal immune response to *Salmonella typhi* Ty21a as measured using peripheral blood lymphocytes," Vaccine, 11:136-139.
Fu and Galan (1998) "The *Salmonella typhimurium* tyrosine phosphatase SptP is translocated into host cells and disrupts the actin cytoskeleton," Mol. Microbiol. 27:359-368.
Gahring, et al. (1990) "Invasion and replication of *Salmonella typhimurium* in animal cells," Infect. Immun. 58:443-448.
Galan and Colimer (1999) "Type III secretion machines: bacterial devices for protein delivery into host cells," Science, 284:1322-1328.
Galan and Zhou (2000) Striking a balance: modulation of the actin cytoskeleton by *Salmonella*. PNAS, 97:8754-8761.
Galan, et al. (1990) "Cloning and characterization of the *asd* gene of *Salmonella typhimurium*: use in a stable maintenance of recombinant plasmids in *Salmonella* vaccine strains," Gene, 94:29-35.
Galan and Levine (2001) "Can a 'flawless' love vector strain be engineered?" Trends in Microbiol. 9:372-376.
Galan (1996) "Molecular genetic bases of *Salmonella* entry into host cells," Mol. Microbiol. 20:263-271.
Galen et al. (1999) "Optimization of plasmid maintenance in attenuated live vector vaccine strain *Salmonella typhi* CVD 908-*htrA*" Infect. Immun. 67:6424-6433.

(56) References Cited

OTHER PUBLICATIONS

Garcia-Del Portillo, et al. (1993) "*Salmonella* induces the formation of filament structures containing lysosomal membrane glycoproteins in epithelial cells," PNAS, 90:10544-10548.
Garmory et al. (2002) "*Salmonella* vaccines for use in humans: present and future perspectives," FEMS Microbiol. Rev. 26:339-353.
Gautier et al. (1998) "Mouse susceptibility to infection by the *Salmonella abortusovus* vaccine strain Rv6 is controlled by the Ity/Nramp 1 gene and influences the antibody response but not the complement response," Microbial Pathog. 24:47-55.
Gentschev et al. (2000) "Delivery of protein antigens and DNA by virulence attenuated strains of *Salmonella typhimurium* ans *Listeria monocytogenes*," J. Bacteriol. 83:19-26.
Germanier and Furer (1975) "Isolation and characterization of *Gal E* mutant Ty21a of *Salmonella typhi*: a candidate strain for a live oral typhoid vaccine," J. Infect. Dis. 131:553-558.
Germanier and Levine (1986) "The live typhoid vaccine Ty21a: recent field trial results," Bacterial Vaccines and Local Immunity:19-22.
Gewirtz et al (1999) "Orchestration of neutrophil movement by intestinal epithelial cells in response to *Salmonella typhimurium* can be uncoupled from bacterial internalization," Infect. Immun. 67:608-617.
Gilman (1977) "Evaluation of UDP-glucose-4-epineraseless mutant of *Salmonella typhi* as a live oral vaccine," J. Infect. Dis. 130:717-723.
Giron et al. (1995) "Simultaneous expression of CFA/I and CS3 colonization factor antigens of enterotoxifenic *Escherichia coli* by ΔaroC, ΔaroD *Salmonella typhi* vaccine strain CVD 908," Vaccine, 13:939-946.
Gonzales, et al. (1994) "*Salmonella typhi* vaccine strain CVD 908 expressing the circumsporozoite protein of *Plasmodium faliciparum*: Strain construction and safety and immunogenicity in humans," J. Infect. Dis. 169:927-931.
Gonzales et al. (1998) "Immunogenicity of a *Salmonella typhi* CVD 908 candidate vaccine strain expressing the major surface protein gp63 of *Leishmania mexicana mexicana*," Vaccine 16:1043-1052.
Grossman et al. (1995) "Flagellar serotypes of *Salmonella typhi* in Indonesia: Relationships among motility, invasiveness, and clinical illness" J. Infect. Dis. 171:212-216.
Guard-Petter, et al. (1995) "Characterization of lipopolysaccaride heterogeneity in *Salmonella enteritidis* by a improved gel electrophoresis method," Appl. Environ. Microbiol., 61;2845-2851.
Guerrant and Kosek (2001) "Polysaccharide conjugate typhoid vaccine," NEJM, 344:1322-1323.
Guillobel et al. (2000) "Adjuvant activity of a nontoxic mutant *Eschericia coli* heat-labile enterotoxin on systemic and mucosal immune responses elicited against a heterologous antigen carried by a live *Salmonella enterical* serovar *typhimurium* vaccine strain," 68:4349-4353.
Gunn et al. (1995) "Characterization of the *Salmonella typhimurium pagC/pagD* Chromosomal region," J. Bacteriol. 177:5040-5047.
Guo et al. (1997) "Regulation of lipid modifications by *Salmonella typhimurium* virulence genes *phoP-phoQ*," Science, 276:250-253.
Hacket (1993) "Use of *Salmonella* for heterologous gene expression and vaccine delivery systems," Curr. Opin. Biotechnol. 4:611-615.
Hall and Taylor (1970) "*Salmonella dublin*: The relation between a living calf vaccine strain and those isoated from human and other sources," Vet. Rec. 86:534-536.
Harrison et al. (1997) "Correlates of protection induced by live Aro *Salmonella typhimurium* vaccines in the murine typhoid model," Immunol. 90:618-625.
Herrington et al. (1990) "Studies in volunteers to evaluate candidate *Shigella* vaccines: further experience with a bivalent *Salmonella typhi-Shigella sonnei* vaccine and protection conferred by previous *Shigella sonnei* disease," Vaccine, 8:353-357.
Hess et al. (1996) "*Salmonella typhimurium* aroA infection in gene-targeted immunodeficient mice; major role of $CD4^+$ TCR-$\alpha\beta$ cells in IFN-$\gamma$ in bacterial clearance independent of intracellular location," J. Immunol. 156:3321-3326.

Hindle et al. (2002) "Characterization of *Salmonella enterica* derivatives harboring defined *aroC* and *Salmonella* pathogenicity island 2 type III secretion system (*ssaV*) mutations by immunization of healthy volunteers," Infect. Immun. 70:3457-3467.
Hirose et al. (1997) "Survival of Vi-capsulated and Vi-deleted *Salmonella typhi* strains in cultured macrophage expressing different levles of CD14 antigen," FEMS Microbiol. Lett. 147:259-265.
Hohmann and Oletta (1996) "*phoP/phoQ*- deleted *Salmonella typhi* (Ty800) is safe and immunogenic single-dose fever vaccine in volunteers," J. Infect. Dis. 173:1408-1414.
Hoisth and Stocker (1981) "Aromatic-dependent *Salmonella typhimurium* are non-virulent and effective as live vaccines," Nature, 291:238-239.
Holden (2002) "Trafficking of the *Salmonella* vacuole in macrophages," Traffic, 3:1-11.
Holmstrom, et al. (1999) "Physiological states of individual *Salmonella typhimurium* cells monitored by in situreverse transcription PCR," J. Bacteriol. 181:1733-1738.
Hone et al. (1988) "A *galE* via (Vi antigen-negative) mutant *Salmonella typhi* Ty2 retains virulence in humans," Infect. Immun. 56:1326-1333.
Hone et al. (1991) "Construction of genetically defined double aro mutants of *Salmonella typhi*," Vaccine, 9:810-816.
Hone et al. (1992) "Evaluation in volunteers of candidate live oral attenuated *Salmonella typhi* vector vaccine," J. Cline Invest. 90:412-420.
Hone, et al. (1994) "Adaptive acid tolerance response by *Salmonella typhi* and candidate live oral typhoid vaccine strains," Vaccine, 12:895-898.
Hopkins, et al. (1995) "A recombinant *Salmonella typhimurium* vaccine induces local immunity by four different routes of immunization," Infect. Immun. 63:3279-3286.
Hormaeche (1979) "Natural resistance to *Salmonella typhimurium* in different inbred mouse strains," Immunol. 37:311-318.
Hornick (1970) "Typhoid fever: pathogenesis and immunogic control," NEJM, 283: 739-742.
House, et al. (2001) "Typhoid fever: pathogenesis and disease," Curr. Opin. Infect. Dis. 14:573-578.
Humphreys, et al. (1990) The alternative sigma factor, $\sigma^E$ is critically important for the virulence of *Salmonella typhimurium*, Infect. Immun. 67:1560-1568.
Ishibashi and Arai (1995) "*Salmonella typhi* does not inhibit phagosome-lysosome fusion n human monocyte derived macrophages," FEMS Immunol. Med. Microbiol. 12:55-62.
Ivanoff, et al. (1994) "Vaccination against typhoid fever: present status," WHO Bull. DMS, 72:957-971.
Jepson et al. (1996) "Evidence for a rapid, direct effect on epithelial monolayer integrity and transepithelial transport in response to *Salmonella* invasion," Eur. J. Physiol. 432:225-233.
Johnston et al. (1996) "Transcriptional activation of *Salmonella typhimurium* invasion genes by a member of the phosphorylated response-regulator superfamily," Mol. Microbiol. 22:715-727.
Jones et al. (1981) "The invasion of HeLa cells by *Salmonella typhimurium*: Reversible and irreversable bacterial attachment and the role of bacterial motility," J. Gen. Microbiol. 127:351-360.
Kantele, et al. (1991) "Comparision o the human immune response to live oral, killed oral or killed parental *Salmonella typhi* Ty21A vaccines," Microbial Pathog. 10:117-126.
Kantele et al. (1998) "Differences in immune responses induced by oral and rectal immunizations with *Salmonella typhi* TY21a: Evidence for compartmentalization within the common mucosal immune system in humans," Infect. Immun. 66:5630-5635.
Karem, et al. (1995) "Differential induction of carrier antigen-specific immunity by *Salmonella typhimurium* live-vaccine strains after single mucosal or intravenous immunization of Balb/c mice." Infect. Immun. 63:4557-4563.
Karem, et al. (1997) "Protective immunity against herpes simplex (HSV) type 1 following oral administration of recombinant *Salmonella typhimurium* vaccine strains expressing HSV antigens," J. Gen. Virol. 78:427-434.
Kaufman and Hess (1999) "Impact of intracellular location of an antigen display by intracellular bacteria: implications for vaccine development," Immunol. Lett. 65:81-84.

(56) References Cited

OTHER PUBLICATIONS

Kawakami, et al. (1969) "Experimental Salmonellosis immunizing effect of live vaccine prepared from various mutants of *Salmonella* having different cell wall polysaccharides," Japan. J. Microbiol. 13:315-324.

Keddy, et al. (1998) "Efficacy of Vi polysaccharide vaccine against strains of *Salmonella typhi*: reply" Vaccine, 16:871-872.

Kehres, et al. (2000) "The NRAMP proteins of *Salmonella typhimurium* and *Escherichia coli* are selective manganese transporters involved in the response to reactive oxygen," Mol. Microbiol. 36:1085-1100.

Keitel, et al. (1994) "Clinical and serological responses following primary and booster immunizations with *Salmonella typhi* Vi capsular polysaccharicde vaccines," 12:195-199.

Kelly, et al. (1992) "Characterization and protective properties of attenuated mutants of *Salmonella choleraesuis*," Infect. Immun. 60:4881-4890.

Keren, et al. (1978) "The role of peyer's patches in the local immune response of rabbit ileum to live bacteria," J. Immunol. 120:1892-1896.

Khan, et al. (1998) "*Salmonella typhi rpoS* mutant is less cytotoxic than the parent strain but survives inside resting THP-1 macrophages," FEMS Microbiol. Lett. 161:201-208.

Khan et al. (1998) "A lethal role for lipid A in *Salmonella* infections," Mol. Microbiol. 29:571-579.

Khan et al. (2001 "Early responses to *Salmonella typhimurium* infection in mice occur at focal lesions in infected organs," Microbial Pathog. 30:29-38.

Khan et al. (2003) "*Salmonella typhi* and *S. typhimurium* derivatives harbouring deletions in aromatic biosynthesis and *Salmonella* pathogenicity island-2 (SPI-2) genes as vaccines and vectors," Vaccine, 21:538-548.

Khan, et al. (2007) "Ability of SP12 mutant of *S. typhi* to effectively induce antibody responses to the mucosal antigen enterotoxigenic *E. coli* heat labile toxin B subunit after oral delivery to humans," Vaccine, 25:4175-4182.

Kingsley and Baumler (2000) "Host adaptation and the emergency of infectious disase: the *Salmonella* paradigm," 1006-1014.

Kirkpatrick, et al. (2005) "Comparison of the antibodies in lymphocyte supernatant and anti-body-secreting cells assays for measuring intestinal mucosal immune response toa novel oral typhoid vaccine (M01ZH09)" Clin. Diagnostic Lab. Immunol. 12:1127-1129.

Kirkpatrick et al. (2005) "The novel oral typhoic vaccine M01ZH09 is well tolerated and highly immunogenic in 2 vaccine presentations," J. Infect. Dis. 192:360-366.

Kirkpatrick, et al. (2006) "Evaluation of *Salmonella enterica* serovar *typhi* (Ty2 *aroC-ssaV-*) M01ZH09, with a defined mutation in the *Salmonella* pathogenicity island 2, as a live, oral typhoic vaccine in human volunteers," Vaccine, 24:116-123.

Klugman, et al. ( 1987) "Protease activity of Vi capsular polysaccharide vaccine against typhoid fever," Lancet, 1165-1169.

Kohbata, et al. (1986) "Cytopathogenic effect of *Salmonella typhi* GIFU 10007 on M cells of murine ileal peyer's patches in ligated ileal loops: an ultrastructural study," Microbiol. Immunol. 30:1225-1237.

Kohler et al., (2000) "Effect of preexisting immunity to *Salmonella* on the immune response to recombinant *Salmonella enterica* serovar *typhimurium* expressing a *Porphyromonas gingivalis* hemagglutinin," Infect. Immun. 68:3116-3120.

Kollaritsch et al. (1996) "Randomized double-blind placebo-controlled trial to evaluate the safety and immunogenicity of combined *Salmonella typhi* Ty21a and *Vibrio cholerae* CVD 103-HgR live oral vaccines," Infect. Immun. 64:1454-1457.

Kollaritsch et a l. (1997) "Safety and immunogenicity of live oral Cholera and Typhoid vaccines administered alone or in combination with antimalarial drugs, oral polio vaccines, or yellow fever vaccine," J. Infect. Dis. 871-875.

Kollaritsch, et al. (2000) "Local and systemic immune responses to combined *Vibrio cholerae* CVD103-HgR and *Salmonella typhi* Ty21a live oral vaccines after primary immunization and reimmunization," Vaccine 18:3031-3039.

Kotloff, et al. (1996) "Safety, immunogenicity, and transmissibility in humans in CVD 1203 a live oral *Shigella flexneri* 2a vaccine candidate attenuated by deletions in *aroA* and *virG*," Infect. Immun. 64:4542-4548.

Kramer and Vote (2000) "Granulocyte selected live *Salmonella enteritidis* vaccine is species specific," Vaccine, 18:2239-2243.

Lalmanach and Lantier (1999) "Host cytokine response and resistance to *Salmonella* infection," Microbes Infect. 1:719-726.

Lebacq (2001) "Comparative tolerability an immunogenicity of Typherix™ or Typhium Vi™ in healthy adults," Drugs, 15 Suppl. 1:5-12.

Leclerc, et al. (1998) "Environmental regulation of *Salmonella typhi* invasion-defective mutants," Infect. Immun. 66:682-691.

Lee and Schneewind (1999) "Type III secretion machines and the pathogenesis of enteric infections caused by *Yersina* and *Salmonella* spp." Immunol. Rev. 168:241-252.

Lee et al. (2000) "Surface-displayed viral antigens on *Salmonella* carrier vaccine," Nature Biotechnol. 18:645-648.

Lee et al. (2000) "OmpR regulates the two-component system SsrA-SsrB in *Salmonella* pathogenicity island 2," J. Bacteriol 182:771-781.

Lehoux et al. (1999) "Defined oligonucleotide tag pools and PCR screeing in signature-tagged mutagenesis of essential genes from bacteri," BioTechnol 26:473-480.

Leung and Finlay (1991) "Intracellular replication is essential for the virulence of *Salmonella typhimurium*," PNAS 88:11470-11474.

Levine and Sztein (1996) "Human mucosal vaccines for *Salmonella typhi* infections," in *Mucosal Vaccines*, Kiyono, et al., eds. Academic Press, San Diego, pp. 201-211.

Levine, et al. (1985) "The efficacy of attenuated *Salmonella typhi* oral vaccine strain Ty21a evaluated in controlled field trials," Dev. Vaccines and Drugs agains diarrhea, $11^{th}$ nobel Conf. Stockholm, pp. 90-101.

Levine et al. (1987) "Safety, infectivity, immunogenicity, and in vivo stability of two attenuated auxotrophic mutant strains of *Salmonella typhi*, 541Ty and 543Ty, as live oral vaccines in human," J. Clin. Invest. 79:888-902.

Levine (1987) "Large-scale field trial of Ty21a live oral typhoid vaccine in enteric-coated capsule formulation." Lancet, 1049-1052.

Levine et al. (1989) "Progress in vaccines against typhoid fever," Rev. Infect. Dis. 11:S552-S567.

Levine, et al. (1990) "Comparison of enteric-coated capsules and liquid formulation of Ty21a typhoid vaccine in randomised comtrolled field trial," Lancet, 336:891-894.

Levine et al. (1997) "Attenuated *Salmonella typhi* and *Shigella* as love oral vaccines and as live vectors," Behring Inst. Mitt. 98:120-123.

Levine, (1994) "Typhoid Fever Vaccines," in *Vaccines*, Plotkin and Mortimer, eds., W.B. Saunders Company, Philadelphia, 597-633.

Levine, et al. (1999) "Duration of efficacy of Ty21a, attenuated *Salmonella typhi* live oral vaccine," Vaccine, 17:S22-S27.

Levine, et al. (1997) "Attenuated *Salmonella* as a live vector for expression of foreign antigens. Part iii. *Salmonella* expressing protozal antigens," in *New Generation Vaccines* $2^{nd}$ *ed*., Levine, et al., eds. Marcel Dekker, New York. 351-360.

Levine et al. (2001) "Host-*Salmonella* interaction: human trials," Microbes Infect. 3:1271-1279.

Liang-Takasaki, et al. (1982) "Phagocytosis of bacteria by macrophages: Changing the carbohydrate of lipopolysaccharide alters interatction with complement and macrophages," J. Immunol. 128:1229-1235.

Liang-Takasaki et al. (1983) "Complement activation by polysaccharide of lipopolysaccharide: an important virulence determinant of *Salmonellae*," Infect. Immun. 41:563-569.

Liang-Takasaki, et al. (1983) "*Salmonellae* activate complement differentially via the alternative pathway depending on the structure of their lipopolysaccharide O-antigen," J. Immunol. 130:1867-1870.

Libby et al. (1994) "A cytolysin encoded by *Salmonella* is required for survival within macrophages," PNAS, 91:489-493.

Liu, (1988) "Intact motility as *Salmonella typhi* invasion-related factor," Infect. Immun. 56:1967-1973.

(56) References Cited

OTHER PUBLICATIONS

Lodge, et al. (1995) "Biological and genetic characterization of Tn*phoA* mutants of *Salmonella typhimurium* TML in the conext of gastroenteritis," Infect. Immun. 63:762-769.

Londono et al. (1995) "Immunization of mice using *Salmonella typhimurium* expressing human papillomavirus type 16 E7 epitopes inserted into hepatitis B virus core antigen," Vaccine, 14:545-552.

Low, et al. (1999) "Lipid A mutant *Salmonella* with suppressed virulence and TNFα induction retain tumor-targeting in vivo," Nature Biotechnol. 17:37-41.

Lucas, et al. (2000) "Unravelling the mysteries of virulence gene regulation in *Salmonella typhimurium*," Mol. Microbiol. 36:1024-1033.

Lundberg, et al. (1999) "Growth phase-regulated induction of *Salmonella*-induced macrophage apoptosis correlates with transient expression of SPI-1 genes," J. Bacteriol. 181:3433-3437.

Marshall, et al. (2000) "Use of the stationary phase inducible promoters, spv and dps, to drive heterologous antigen expression in *Salmonella* vaccine strains," Vaccine 18: 1298-1306.

Mastroeni, et al. (1998) "Interleukin-12 Is Required for Control of the Growth of Attenuated Aromatic-Compound-Dependent Salmonellae in BALB/c Mice: Role of Gamma Interferon and Macrophage Activation," Infect. Immun. 66: 4767-4776.

Mastroeni, et al. (1995) "Effect of Anti-Tumor Necrosis Factor Alpha Antibodies on Histopathology of Primary *Salmonella* Infections," Infect. Immun. 63: 3674-3682.

Mastroeni, et al. (1992) "Role of T cells, TNFα and IFNγ in recall of immunity to oral challenge with virulent *Salmonellae* in mice vaccinated with live attenuated aro- *Salmonella* vaccines," Microbial Pathogen. 13: 477-491.

Mazurkiewicz, et al. (2006) "Signature-tagged mutagenesis: barcoding mutants for genome-wide screens," Nat. Rev. Genet. 7: 929-939.

McFarland and Stocker (1987) "Effect of different purine auxotrophic mutations on mouse-virulence of a Vi-positive strain of *Salmonella dublin* and of two strains of *Salmonella typhimurium*," Microbial Pathogen. 3: 129-141.

McSorley and Jenkins (2000) "Antibody Is Required for Protection against Virulent bu Not Attenuated *Salmonella enterica* Serovar *typhimurium*," Infect. Immun. 68: 3344-3348.

Medina and Guzman (2001) "Use of live bacterial vaccine vectors for antigen delivery: potential and limitations," Vaccine 19: 1573-1580.

Miao and Miller (2000) "A conserved amino acid sequence directing intracellular type II secretion by *Salmonella typhimurium*," Proc. Natl. Acad. Sci. USA 97:7539-7544.

Mills and Finlay (1994) "Comparison of *Salmonella typhi* and *Salmonella typhimurium* invasion, intracellular growth and localization in cultured human epithelial cells," Microbial. Pathogen. 17:409-423.

Mills, et al. (1998) "Trafficking of Porin-Deficient *Salmonella typhimurium* Mutants inside HeLa Cells: ompR and envZ Mutants Are Defective for the Formation of *Salmonella*-Induced Filaments," Infect. Immun. 66: 1806-1811.

Mintz, et al. (1983) "Effect of Lipopolysaccharide Mutations on the Pathogenesis of Experimental *Salmonella* Gastroenteritis," Infect. Immun. 40: 236-244.

Mittrücker and Kaufmann (2000) "Immune response to injection with *Salmonella typhimurium* in mice," J. Leukoc. Biol. 67: 457-463.

Mittrücker, et al. (2000) "Cutting Edge: Role of B Lymphocytes in Protective Immunity Against *Salmonella typhimurium* Infection," J. Immunol 164: 1648-1652.

Mollenkopf, et al. (2001) "Protective efficacy against tuberculosis of ESAT-6 secreted by a live *Salmonella typhimurium* vaccine carrier strain and expressed by naked DNA," Vaccine 19: 4028-4034.

Mollenkopf, et al. (2001) "Intracellular Bacteria as Targets and Carriers for Vaccination," Biol. Chem. 382: 521-532.

Nardelli-Haefliger, et al. (2001) "Nasal vaccination with attenuated *Salmonella typhimurium* strains expressing the Hepatitis B nucleocapsid: dose response analysis," Vaccine 19: 2854-2861.

Nardelli-Haefliger, et al. (1996) "Oral and Rectal Immunization of Adult Female Volunteers with a Recombinant Attenuated *Salmonella typhi* Vaccine Strain," Infect. Immun. 64: 5219-5224.

Nauciel and Espinasse-Maes (1992) "Role of Gamma Interferon and Tumor Necrosis Factor Alpha in Resistance to *Salmonella typhimurium* infection," Infect. Immun. 60: 450-454.

Nauciel (1990) "Role of CD4+ T Cells and T-Independent Mechanisms in Acquired Resistance to *Salmonella typhimurium* Infection," J. Immunol. 145: 1265-1269.

Nickerson and Curtiss III, et al. (1997) "Role of Sigma Factor RpoS," in Initial Stages of *Salmonella typhimurium* Infection, Infect. Immun. 65: 1814-1823.

Ornellas, et al. (1970) "The Specificity and Importance of Humoral Antibody in the Protection of Mice against Intraperitoneal Challenge with Complement-Sensitive and Complement-Resistant *Salmonella*," J. Infect. Disease 121: 113-123.

Paesold, et al. (2002) "Genes in the *Salmonella* pathogenicity island 2 and the *Salmonella* virulence plasmid are essential for *Salmonella*-induced apoptosis in intestinal epithelial cells," Cell. Microbial. 4: 771-781.

Paglia, et al. (2000) "In vivo correction of genetic defects of monocyte/macrophages using attenuated *Salmonella* as oral vectors for targeted gene delivery," Gene Therapy 7: 1725-1730.

Pang, et al. (1995) "Typhoid fever and other Salmonellosis: a continuing challenge," Trends Microbiol. 3: 253-255.

Pickard, et al. (1994) "Characterization of Defined ompR Mutants of *Salmonella typhi*: ompR Is Involved in the Regulaton of Vi Polysaccharide Expression," Infect. Immun. 62: 3984-3993.

Pickett, et al. (2000) "In Vivo Characterization of the Murine Intranasal Model for Assessing the Immunogenicity of Attenuated *Salmonella enterica* Serovar *typhi* Strains as Live Mucosal Vaccines and as Live Vectors," Infect. Immun. 68: 205-213.

Pie, et al. (1997) "Th1 Response in *Salmonella typhimurium*-Infected Mice with a High or Low Rate of Bacterial Clearance," Infect. Immun. 65: 4509-4514.

Pier, et al. (1998) "*Salmonella typhi* uses CFTR to enter intestinal epithelial cells," Nature 393: 79-82.

Poirer, et al. (1988) "Protective Immunity Evoked by Oral Administration of Attenuated aroA *Salmonella typimurium* Expressing Cloned Streptococcal M Protein," J. Exp. Med. 168: 25-32.

Pulkkinen and Miller (1991) "A *Salmonella typhimurium* Virulence Protein Is Similar to a *Yersinia enterocolitica* Invasion Protein and a Bacteriophage Lambda Outer Membrane Protein," J. Bacteriol. 173: 86-93.

Qian and Pan (2002) "Construction of a tetR-Integrated *Salmonella enterica* Serovar *typhi* CVD908 Strain That Tightly Controls Expression of the Major Merozoite Surface Protein of *Plasmodium falciparum* for Applications in Human Vaccine Production," Infect. Immun. 70: 2029-2038.

Rakeman, et al. (1999) "A HilA-Independent Pathway to *Salmonella typhimurium* Invasion Gene Transcription," J. Bacteriol. 181: 3096-3104.

Richter-Dahfors, et al. (1997) "Murine Salmonollosis Studied by Confocal Microscopy: *Salmonella typhimurium* Resides Intracellularly Inside Macrophages and Exerts a Cytotoxic Effect on Phagocytes In Vivo," J. Exp. Med. 186: 569-579.

Robbe-Saule, et al. (1995) "The live oral typhoid vaccine Ty21a is a rpoS mutant and is susceptible to various environmental stresses," FEMS Microbiol. Lett. 126: 171-176.

Roberts, et al. (2000) "Comparison of Abilities of *Salmonella enterica* Serovar *typhimurium* aroA aroD and aroA htrA Mutants To Act as Live Vectors," Infect. Immun. 68: 6041-6043.

Roberts, et al. (1999) "Prior Immunity to Homologous and Heterologous *Salmonella* Serotypes Suppresses Local and Systemic Anti-Fragment C Antibody Responses and Protection from Tetanus Toxin in Mice Immunized with *Salmonella* Strains Expressing Fragment C," Infect. Immun. 67: 3810-3815.

Roberts, et al. (1998) "Oral Vaccination against Tetanus: Comparison of the Immunogenicities of *Salmonella* Strains Expressing Fragment C from the nirB and htrA Promoters," Infect. Immun. 66: 3080-3087.

Roland, et al. (1999) "Construction and Evaluation of a Δcya Δcrp *Salmonella typhimurium* Strain Expressing Avian Pathogenic

(56) References Cited

OTHER PUBLICATIONS

*Escherichia coli* O78 LPS as a Vaccine to Prevent Airsacculitis in Chickens," Avain Diseases 43: 429-441.

Schödel, et al. (1993) "Avirulent *Salmonella* expressing hybrid hepatitis B virus core/pre-S genes for oral vaccination," Vaccine 11: 143-148.

Schödel, et al. (1994) "Development of Recombinant *Salmonellae* Expressing Hybrid Hepatitis B Virus Core Particles as Candidate Oral Vaccines," Brown F(ed): Recombinant Vectors in Vaccine Development. Dev. Biol. Stand. Basel, Karger 82: 151-158.

Schwan, et al. (2000) "Differential Bacterial Survival, Replication, and Apoptosis-Inducing Ability of *Salmonella* Serovars within Human and Murine Macrophages," Infect. Immun. 68: 1005-1013.

Shata, et al. (2000) "Recent advances with recombinant bacterial vaccine vectors," Mol. Med. Today 6: 66-70.

Sinha, et al. (1997) "*Salmonella typhimurium* aroA, htrA, and aroD htrA Mutants Cause Progressive Infections in Athymic (nu/nu) BALB/c Mice," Infect. Immun. 65: 1566-1569.

Sirard, et al. (1999) "Live attenuated *Salmonella*: a paradigm of mucosal vaccines," Immunol. Rev. 171: 5-26.

Smith, et al. (1984) "Aromatic-dependent *Salmonella dublin* as a parenteral modified live vaccine for calves," Am. J. Vet. Res. 45: 2231-2235.

Smith, et al. (1993) "Vaccination of calves with orally administered aromatic-dependent *Salmonella dublin*," Am. J. Vet. 54: 1249-1255.

Soo, et al. (1998) "Genetic Control of Immune Response to Recombinant Antigens Carried by an Attenuated *Salmonella typhhimurium* Vaccine Strain: Nramp1 Influences T-Helper Subset Responses and Protection against Leishmanial Challenge," Infect. Immun. 66: 1910-1917.

Spreng, et al. (2000) "*Salmonella* vaccines secreting measles virus epitopes induce protective immune responses against measles virus encephalitis," Microbes Infect. 2: 1687-1692.

Stein, et al. (1996) "Identification of a *Salmonella* virulence gene required for formation of filamentous structures containing lysosomal membrane glycoproteins within epithelial cells," Mol. Microbiol. 20: 151-164.

Stocker (2000) "Aromatic-dependent *Salmonella* as anti-bacterial vaccines and a presenters of heterologous antigens or of DNA encoding them," J. Biotechnol. 83: 45-50.

Stocker (1990) "Aromatic-Dependent *Salmonella* as Live Vaccine Presenters of Foreign Epitopes as Inserts in Flagellin," Res. Microbiol. 141: 787-796.

Stocker (1988) "Auxotrophic *Salmonella typhi* as live vaccine," Vaccine 6: 141-145.

Svenson and Lindberg (1983) "Artificial *Salmonella* Vaccines," Prog. Allergy 33: 120-143.

Sydenham, et al. (2000) "*Salmonella enterica* Serovar *typhimurium* surA Mutants Are Attenuated and Effective Live Oral Vaccines," Infect. Immun. 68(3): 1109-1115.

Sztein, et al. (1994) "Cytokine Production Patterns and Lymphoproliferative Responses in Volunteers Orally Immunized with Attenuated Vaccine Strains of *Salmonella tyhpi*," J. Infect. Disease 170: 1508-1517.

Tacket, et al. (2000) "Phase 2 Clinical Trial of Attenuated *Salmonella enterica* Serovar *typhi* Oral Live Vector Vaccine CVD 908-htrA in U.S. Volunteers," Infect. Immun. 68: 1196-1201.

Tacket, et al. (2000) "Safety and Immune Responses to Attenuated *Salmonella enterica* Serovar *typhi* Oral Live Vector Vaccines Expressing Tetanus Toxin Fragment C," Clin. Immunol. 97: 146-153.

Tacket, et al. (1997) "Safety of Live Oral *Salmonella typhi* Vaccine Strains with Deletions in htrA and aroC aroD and Immune Response in Humans," Infect. Immun. 65: 452-456.

Tacket, et al. (1992) "Clinical acceptability and immunogenicity of CVD 908 *Salmonella typhi* vaccine strain," Vaccine 10: 443-446.

Tacket, et al. (1992) "Comparison of the Safety and Immunogenicity of ΔaroC ΔaoD and Δcya Δcrp *Salmonella typhi* Strains in Adult Volunteers," Infect. Immun. 60: 536-541.

Tacket, et al. (1991) "Lack of Immune response to the Vi Component of a Vi-Positive Variant of *Salmonella typhi* Live Oral Vaccine Strain Ty21a in Human Studies," J. Infect. Disease 163: 901-904.

Tacket, et al. (1988) "Persistence of antibody titres three years after vaccination with Vi polysaccharide vaccine against typhoid fever," Vaccine 6: 307-308.

Tacket, et al. (1986) "Safety and Immunogenicity of Two *Salmonella typhi* Vi Capsular Polysaccharide Vaccines," J. Infect. Disease 154: 342-345.

Tagliabue (1989) "Immune Response to Oral *Salmonella* Vaccines," Curr. Topics Microbiol. Immunol. 146: 225-231.

Tang, et al. (2001) "Identification of bacterial genes required for in-vivo survival," J. Pharm. Pharmacol. 53: 1575-1579.

Tite, et al. (1991) "The Involvement of Tumor Necrosis Factor in Immunity to *Salmonella* Infection," J. Immunol. 147: 3161-3164.

Tramont, et al. (1984) "Safety and Antigenicity of Typhoid-*Shigella sonnei* Vaccine (Strain 5076-IC)," J. Infect. Disease 149: 133-136.

Turner, et al. (1993) "*Salmonella typhimurium* ΔaroA ΔaroD Mutants Expressing a Foreign Recombinant Protein Induce Specific Major Histocompatibility Complex Class 1-Restricted Cytotoxic T Lymphocytes in Mice," Infect. Immun. 61: 5374-5380.

Uchiya, et al. (1999) "A *Salmonella* virulence protein that inhibits cellular trafficking," EMBO J. 18: 3924-3933.

Urashima, et al. (2000) "An ordeal CD40 ligand gene therapy against lymhoma using attenuated *Salmonella typhimurium*," Blood 95: 1258-1263.

Valdivia and Falkow (1996) "Bacterial genetics by flow cytometry: rapid isolation of *Salmonella typhimurium* acid-inducible promoters by differential fluorescence induction," Mol. Microbiol. 22: 367-378.

Van Dissel, et al. (1995) "*S. typhi* Vaccine Strain Ty21a Can Cause a Generalized Infection in Whole Body-Irradiated But Not in Hydrocortisone-Treated Mice," Scand. J. Immunol. 41: 457-461.

Van Velkinburgh and Gunn (1999) "PhoP-PhoQ-Regulated Loci Are Required for Enhanced Bile Resistance in *Salmonella* spp.," Infect. Immun. 67: 1614-1622.

Vancott, et al. (1998) "Regulation of host immune responses by modification of *Salmonella* virulence genes," Nat. Med. 4: 1247-1252.

Vancott, et al. (1996) "Regulation of Mucosal and Systemic Antibody Responses by T Helper Cell Subsets, Macrophages, and Derived Cytokines Following Oral Immunization with Live Recombinant *Salmonella*," J. Immunol. 1504: 1514.

Vazquez-Torres, et al. (2000) "*Salmonella* Pathogenicity Island 2-Dependent Evasion of the Phagocyte NADPH Oxidase," Science 287: 1655-1658.

Véscovi, et al. (1996) "MG2+ as an Extracellular Signal: Environmental Regulation of *Salmonella* Virulence," Cell 84: 165-174.

Villarreal, et al. (1992) "Proliferative and T-cell specific interleukin (IL-2/IL-4) production responses in spleen cells from mice vaccinated with aroA live attenuated *Salmonella* vaccines," Microbial Pathogen. 13: 305-315.

Viret, et al. (1999) "Mucosal and Systemic Immune Responses in Humans after Primary and Booster Immunizations with Orally Administered Invasive and Noninvasive Live Attenuated Bacteria," Infect. Immun. 67: 3680-3685.

Virlogeux, et al. (1996) "Characterization of the resA and resB Genes from *Salmonella typhi*: resB through tviA Is Involved in Regulation of Vi Antigen Synthesis," J. Bacteriol. 178: 1691-1698.

Virlogeux, et al. (1995) "Role of the viaB locus in synthesis, transport and expression of *Salmonella typhi* Vi antigen," Microbiol. 141: 3039-3047.

Wahdan, et al. (1982) "A Controlled Field Trial of Live *Salmonella typhi* Strain Ty 21a Oral Vaccine Against Typhoid: Three-Year Results," J. Infect. Dis. 145: 292-295.

Wahdan, et al. (1980) "A controlled field trial of live oral typhoid vaccine Ty21a," Bull. World Health Org. 58: 469-474.

Wallis (2001) "*Salmonella* Pathogenesis and Immunity: We Need Effective Multivalent Vaccines," Vet. J. 161: 104-106.

Wallis and Galyov (2000) "Molecular basis of *Salmonella*-induced enteritis," Mol. Microbiol. 36: 997-1005.

Wang, et al. (2000) "Constitutive Expression of the Vi Polysaccharide Capsular Antigen in Attenuated *Salmonella enterica* Serovar *typhi* Oral Vaccine Strain CVD 909," Infect. Immun 68: 4647-4652.

(56) References Cited

OTHER PUBLICATIONS

Ward, et al. (1999) "Immunogenicity of a *Salmonella typhimurium* aroA aroD Vaccine Expressing a Nontoxic Domain of *Clostridium difficile* Toxic A," Infect. Immun. 67: 2145-2152.
Wedemeyer, et al. (2001) "Oral Immunization With HCV-NS3-Transformed *Salmonella*: Induction of HCV-Specific CTL in a Transgenic Mouse Model," Gastroenterology 121: 1158-1166.
Weinstein, et al. (1998) "Differential Early Interactions between *Salmonella enterica* Serovar *typhi* and Two Other Pathogenic *Salmonella* Serovars with Intestinal Epithelial Calls," Infect. Immun. 66: 2310-2318.
Weinstein, et al. (1997) "*Salmonella typhi* Stimulation of Human Intestinal Epithelial Cells Induces Secretion of Epithelial Cell-Derived Interleukin-6," Infect. Immun. 65: 395-404.
Weintraub, et al. (1997) "Role of $\alpha\beta$ and $\gamma\delta$ T Cells in the Host Response to *Salmonella* Infection as DEmonstrated in T-Cell-Receptor-Deficient Mice of Defined Ity Genotypes," Infect. Immun. 65: 2306-2312.
White, et al. (1999) "High efficiency gene replacement in *Salmonella enteritidis* chimeric fimbrins containing a T-cell epitope from *Leishmania major*," Vaccine 17: 2150-2161.
Wong, et al. (1974) "Vi Antigen from *Salmonella typhosa* and Immunity Against Typhoid Fever," Infect. Immun. 9: 348-353.
Woo, et al. (2001) "Unique immunogenicity of hepatitis B virus DNA vaccine presented by live attenuated *Salmonella typhimurium*," Vaccine 19: 2945-2954.
Wu, et al. (2000) "Construction and immunogenicity in mice of attenuated *Salmonella typhi* expressing *Plasmodium falciparum* merozoite surface protein 1 (MSP-1) fused to tetanus toxin fragment C," J. Biotechnol. 83: 125-135.
Wüthrich, et al. (1985) "Typhusepidemiologie in der Schweiz 1980-1983," Schwiez. med. Wschr. 115: 1714-1720.
Wyant, et al. (1999) "*Salmonella tyohi* Flagella Are Potent Inducers of Proinflammatory Cytokine Secretion by Human Monocytes," Infect. Immun 67: 3619-3624.
Zhang, et al. (1999) "Protection and immune responses induced by attenuated *Salmonella typhimurium* UK-1 strains," Microbial Pathogen. 26: 121-130.
Zhou, et al. (1999) "An invasion-associated *Salmonella* protein modulates the actin-bundling activity of plastin," Proc. Natl. Acad. Sci. USA 96: 10176-10181.
Curtiss, et al. (1994) "Recombinant *Salmonella* vectors in vaccine development" Dev. Biol. Stand. 82:23-33.
Galen et al. (1997) "A murine model of intranasal immunizaiton to asses the immunogenicityy of attenuated *Salmonella typhi* live vector vaccines in stimulating serium antibody responses to expressed foreign antigens," Vaccine, 15:700-707.
Hormaeche, (1979) "Genetics of Natural resistance to salmonellae in mice," Immunology, 37:319-327.
Jones, et al. (1991) "Oral vaccination of calves against experimental salmonellosis using a double aro mutant of *Salmonella typhimurium*," Vaccine, 9:29-34.
Jones-Carson et al. (2007) "Systemic CD8 T cell memory response to a *Salmonella* pathogenicity island 2 effector is restricted to *Salmonella enterica* encountered in the gastrointestinal mucosa," Infect. Immun. 75:2708-2716.
Chenoweth et al. (1990) "Efficacy of ampicilin versus trimethoprim-sulfamethoxazole in a mouse model of lethal enterococcol peritonitis," Antimicrob. Agents Chemother. 34:1800-1802.
Kohler, et al. (1998) "Oral immunization with recombinant *Salmonella typhimurium* expressing a cloned porphyromonas gingivalsi hemaglutinin: effect of bookstin on mucosal systemic and immunoglobulin G subclass response," Oral Microbiol. Immunol. 13:81-88. Abstract Only.
O'Callaghan, et al. (1990) "Immunogenicity of foreign peptide epitopes expressed in bacterial envelope proteins," Res. Microbiol. 141:963-969 Abstract Only.

Schodel, et al. (1996) "Hybrid hepatitis B virus core anigen as a vaccine carrier moiety II. Expression in avirulent *Salmonella* spp. for mucosal immunization," Adv. Exp. Med. Biol. 397:15-21. Abstract Only.
Accession No. A51688, Genbank; "*Salmonella typhimurium*" (1997).
Accession No. A51689, Genbank; "*Salmonella typhimurium*" (1997).
Accession No. AF0208080, EMBL/Genbank; Aug. 7, 1998 Valdiva et al., *Salmonella typhimurium* pathogenicity island 2.
Accession No. AJ224892, Genbank; "*Salmonella typhimurium* ssaE, sseA, sseB, sscA, sseC, sseD, sseE, sscB, sseF, sseG, ssaH, ssaI genes and partial ssaD, ssaJ genes," (1998).
Accession No. AJ224978, Genbank; "*Salmonella typhimurium*" (1999).
Accession No. U51927, Genbank; "*Salmonella typhimurium* SpiR and SpiB genes, partial cds, and SpiC and SpiA genes, complete cds," (1996).
Accession No. X99944, Genbank; "*S. typhimurium* ssA, ssaR, ssaT, and ssaU genes," (1997).
Accession No. Y09357, Genbank; "*S. typhimurium* ssaJ, ssaK, ssaL, ssaM, ssaV, ssaN, ssaO, ssaP, ssaQ genes," (1997).
Accession No. Z95891, EMBL/Genbank; Jan. 8, 1998 *Salmonella typhimurium* ssrA and ssrB genes.
Burgess et al., (1990) "Possible dissociation of the heparin-binding and mitogenic activities of heparin-binding (acidic fibroblast) growth factor-1 from its receptor-binding activities by site-directed mutagenesis of a single lysine residue," J. Cell. Biol. 111:2129-2138.
Coghlan, "Bar codes to tag bad genes,"0 New Scientist p. 18 (Jul. 29, 1995).
Deiwick et al., (1998) "Mutations in *Salmonella* Pathogenicity Island 2 (SP12) Genes Affecting Transcriptional of SP11 Genes and Resistance to Antimicrobial Agents,"J. Bacteriol. 180(18):4775-4780.
Gentschev et al., (1996) "Development of antigen-delivery systems, based on the *Escherichia coli* hemolysin secretion pathway," Gene 179: 133-140. Abstract Only.
Gentschev, et al., (1994) "Synthesis and secretion of bacterial antigens by attenuated *Salmonella* via the *Escherichia coli* hemolysin secretion system," Behring Inst. Mitl. 95: 57-66.
Gentschev, et al., (1997) "The *Escherichia coli* hemolysin secretion apparatus—a versatile antigen delivery system in attenuate *Salmonella*," Behring Inst. Mitl. 98: 103-113. Abstract Only.
Guzman et al., (1991) "Antibody Responses in the Lungs of Mice following Oral Immunization with *Salmonella typhimurium* aroA and Invasive *Escherichia coli* Strains Expressing the Filamentous Hemagglutinin of *Bordetella pertussis*," Inf. Immun. 59:4391-4397.
Guzman et al., (1991) "Direct Expression of *Bordetella pertussis* Filamentous Hemagglutinin in *Escherichia coli* and *Salmonella typhimurium* arpA." Inf.Immun. 39:3787-3795.
Guzman, et al., (1992) "Expression of *Bordetella pertussis* filamentous hemagglutinin in *Escherichia coli* using a two cistron system," Microbiol. Pathogenics 12:383-389.
Guzman, et al., (1993) "Use of *Salmonella* spp carrier strains to delivery *Bordetella pertussis* antigens in mice using the oral route," in Biology of *Salmonella* (Cabello, et al., eds.) Plenum Press: New York, NY.
Hensel, (2000) "*Salmonella* Pathogenicity Island 2," Mol. Microbiol. 36:1015-1023.
Hensel, et al., (1997) "Functional analysis of ssaJ and ssaK/U operon, 13 genes encoding components of the type III secretion apparatus of *Salmonella* pathogenicity island 2," Mol. Microbiol. 24(1): 155-167.
Hensel, et al., (1998) "Genes encoding putative effector proteins of the type III secretion system of *Salmonella* pathogenicity island 2 are required for bacterial virulence and proliferation in macrophages," Mol. Microbiol. 30:163-174.
Hensel, et al., (1999) "Molecular and functional analysis indicates a mosaic structure of *Salmonella* pathogenicity island 2," Mol. Microbiol. 31:489-496.
Hensel et al., (1999) "The genetic basis of tetrathionate respiration in *Salmonella typhimurium*," Mol. Microbiol. 32:275-287.
Holden, "The type III secretion system of *Salmonella* Pathogenicity Island 2," FEBS Advanced Course—Protein Export and Assembly in Bacteria, Lunteren, The Netherlands; Apr. 25-May 1, 1998.

(56) References Cited

OTHER PUBLICATIONS

Lazar et al., "Transforming growth factor alpha: mutation of aspartic acid 47 and leucine 48 results in different biological activities,"Mol. Cell. Biol. 8:1247-1252 (1998).

Lee, (1997) "Type III Secretion systems: machines to deliver bacterial proteins into eukaryotic cells?" Trends Microbiol. 5(4): 148-156.

Levine, et al., eds., (1997) "Attenuated *Salmonella* as a live vector for expression of foreign antigens," in New Generation Vaccines, 2nd ed., Marcell Dekker: New York, Chapter 27, pp. 331-361.

Mecsas & Strauss, (1996) "Molecular mechanisms of bacterial virulence: type III secretion and pathogenicity islands," Emerging Infectious Diseases 2(4): 271-288.

Medina et al., "Pathogenicity island 2 mutants of *S. typhimurium* are efficient carriers for heterologous . . . ", Infection and Immunity, vol. 67, No. 3, Mar. 1999, pp. 1093-1099.

Ochman et al., "Identification of a pathogenicity island required for *Salmonella* . . .", The National Academy of Sciences of USA, vol. 93, Jul. 1996, pp. 7800-7804.

Piatti, et al. "Cloning and Characterization of *S. typhi*," Sociela Italiana di Microbiologia Medica Odontoiatrica e Clinica '93 (Translation), p. 82.

Russman, et al., (1998) "Delivery of epitopes by the *Salmonella* type III secretion system for vaccine development," Science 281:585-568.

Shea, et al., (1996) "Identification of a virulence locus encoding a second type III secretion system in *Salmonella typhimurium*," Proc. Natl. Sci. USA 93:2593-2597.

Staendner, et al., "Identification of *Salmonella typhi* promoters activated by invasion of eukaryotic cells," Mol. Microbiol. 18:891-902 (1995).

Tsolis et al., (1995) "Role of *Salmonella typhimurium* Mn-superoxide dismutase (SodA) in protection against early killing by J774 macrophages," Infect. Immun. 63(5):1739-1744.

Tzschaschel, et al., (1996) "An *Escherichia coli* hemolysin transport system-based vector for the export of polypeptides: export of Shiga-like toxin lleB subunit by *Salmonella tyhphimurium* aroA," Nature Biotechnol. 14: 765-769.

Valdivia & Falkow, (1997) "Fluorescence-based isolation of bacterial genes expressed within host cells," Science 277: 2007-2011.

Walker, et al., "Specific Lung Mucosal and Systemic Immune Responses after Oral Immunization of Mice with *Salmonella typhimurium* aroA, *Salmonella typhi* Ty21a, and invasive *Escherichia coli* expressing Recombinant Pertussis Toxin S1 Subunit," Inf. Immun. 60:4260-4268 (1992).

Bowe, Frances, et al., "Isolation of *Salmonella* mutants defective for intracellular survival," Methods in Enzymology, 1994, vol. 236, pp. 509-526.

Hensel, Michael, et al., "Simulatneous Identification of Bacterial Virulence Genes by Negative Selection," Science, (New York), Jul. 21, 1995, vol. 269, No. 5222, pp. 400-403.

Pascopella, Lisa, "Use of In Vivo Complementation in *Mycobacterium tuberculosis* to Identify a Genomic Fragment Associated with Virulence," Infection and Immunity, Apr. 1994, vol. 62, No. 4, pp. 1313-1319.

Slauch, James M., "In Vivo Expression Technology for Selection of Bacterial Genes Specifically Induced in Host Tissues," Methods in Enzymology, 1994, vol. 235, pp. 481-492.

\* cited by examiner

Figure 1 (SEQ ID NO: 7)

Initial cloning intermediate (using CT84 as an example)

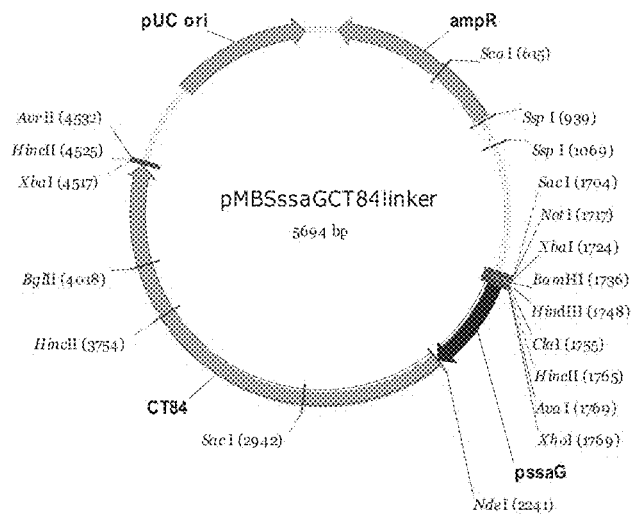

```
  1  AAATTAAAAA TGAAGTTTTA AATCAATCTA AAGTATATAT GAGTAAACTT GGTCTGACAG
 61  TTACCAATGC TTAATCAGTG AGGCACCTAT CTCAGCGATC TGTCTATTTC GTTCATCCAT
                                                                    ampR
121  AGTTGCCTGA CTCCCCGTCG TGTAGATAAC TACGATACGG GAGGGCTTAC CATCTGGCCC
                                                                    ampR
181  CAGTGCTGCA ATGATACCGC GAGACCCACG CTCACCGGCT CCAGATTTAT CAGCAATAAA
                                                                    ampR
241  CCAGCCAGCC GGAAGGGCCG AGCGCAGAAG TGGTCCTGCA ACTTTATCCG CCTCCATCCA
                                                                    ampR
301  GTCTATTAAT TGTTGCCGGG AAGCTAGAGT AAGTAGTTCG CCAGTTAATA GTTTGCGCAA
                                                                    ampR
361  CGTTGTTGCC ATTGCTACAG GCATCGTGGT GTCACGCTCG TCGTTTGGTA TGGCTTCATT
                                                                    ampR
421  CAGCTCCGGT TCCCAACGAT CAAGGCGAGT TACATGATCC CCCATGTTGT GCAAAAAAGC
                                                                    ampR
481  GGTTAGCTCC TTCGGTCCTC CGATCGTTGT CAGAAGTAAG TTGGCCGCAG TGTTATCACT
                                                                    ampR
541  CATGGTTATG GCAGCACTGC ATAATTCTCT TACTGTCATG CCATCCGTAA GATGCTTTTC
                                                                    ampR
                 ScaI
601  TGTGACTGGT GAGTACTCAA CCAAGTCATT CTGAGAATAG TGTATGCGGC GACCGAGTTG
                                                                    ampR
661  CTCTTGCCCG GCGTCAATAC GGGATAATAC CGCGCCACAT AGCAGAACTT TAAAAGTGCT
                                                                    ampR
721  CATCATTGGA AAACGTTCTT CGGGGCGAAA ACTCTCAAGG ATCTTACCGC TGTTGAGATC
                                                                    ampR
781  CAGTTCGATG TAACCCACTC GTGCACCCAA CTGATCTTCA GCATCTTTTA CTTTCACCAG
                                                                    ampR
```

Figure 1 Cont'd

```
 841  CGTTTCTGGG TGAGCAAAAA CAGGAAGGCA AAATGCCGCA AAAAAGGGAA TAAGGGCGAC
                                   ampR
                                               SspI
 901  ACGGAAATGT TGAATACTCA TACTCTTCCT TTTTCAATAT TATTGAAGCA TTTATCAGGG
                ampR
 961  TTATTGTCTC ATGAGCGGAT ACATATTTGA ATGTATTTAG AAAAATAAAC AAATAGGGGT
                                                         SspI
1021  TCCGCGCACA TTTCCCCGAA AAGTGCCACC TAAATTGTAA GCGTTAATAT TTTGTTAAAA
1081  TTCGCGTTAA ATTTTTGTTA AATCAGCTCA TTTTTTAACC AATAGGCCGA AATCGGCAAA
1141  ATCCCTTATA AATCAAAAGA ATAGACCGAG ATAGGGTTGA GTGTTGTTCC AGTTTGGAAC
1201  AAGAGTCCAC TATTAAAGAA CGTGGACTCC AACGTCAAAG GGCGAAAAAC CGTCTATCAG
1261  GGCGATGGCC CACTACGTGA ACCATCACCC TAATCAAGTT TTTTGGGGTC GAGGTGCCGT
1321  AAAGCACTAA ATCGGAACCC TAAAGGGAGC CCCCGATTTA GAGCTTGACG GGGAAAGCCG
1381  GCGAACGTGG CGAGAAAGGA AGGGAAGAAA GCGAAAGGAG CGGGCGCTAG GGCGCTGGCA
1441  AGTGTAGCGG TCACGCTGCG CGTAACCACC ACACCCGCCG CGCTTAATGC GCCGCTACAG
1501  GGCGCGTCCC ATTCGCCATT CAGGCTGCGC AACTGTTGGG AAGGGCGATC GGTGCGGGCC
1561  TCTTCGCTAT TACGCCAGCT GGCGAAAGGG GGATGTGCTG CAAGGCGATT AAGTTGGGTA
1621  ACGCCAGGGT TTTCCCAGTC ACGACGTTGT AAAACGACGG CCAGTGAATT GTAATACGAC
                                                                XbaI
                       SacI                NotI            BamHI
1681  TCACTATAGG GCGAATTGGA GCTCCACCGC GGTGGCGGCC GCTCTAGAAC TAGTGGATCC
          HindIII           HincII
                             XhoI
                  ClaI       AvaI
1741  CCCATCAAGC TTATCGATAC CGTCGACCTC GAGATTGCCA TCGCGGATGT CGCCTGTCTT
1801  ATCTACCATC ATAAACATCA TTTGCCTATG GCTCACGACA GTATAGGCAA TGCCGTTTTT
1861  TATATTGCTA ATTGTTTCGC CAATCAACGC AAAAGTATGG CGATTGCTAA AGCCGTCTCC
1921  CTGGGCGGTA GATTAGCCTT AACCGCGACG GTAATGACTC ATTCATACTG GAGTGGTAGT
1981  TTGGGACTAC AGCCTCATTT ATTAGAGCGT CTTAATGATA TTACCTATGG ACTAATGAGT
2041  TTTACTCGCT TCGGTATGGA TGGGATGGCA ATGACCGGTA TGCAGGTCAG CAGCCCATTA
2101  TATCGTTTGC TGGCTCAGGT AACGCCAGAA CAACGTGCGC CGGAGTAATC GTTTTCAGGT
2161  ATATACCGGA TGTTCATTGC TTTCTAAATT TTGCTATGTT GCCAGTATCC TTACGATGTA
                                                  CT84
                                 NdeI
2221  TTTATTTTAA GGAAAAGCCA TATGGAAATT ATGGTTCCGC AGGGTATCTA CGATGGTGAA
                                                   CT84
2281  ACCCTGACCG TGTCTTTCCC GTATACCGTT ATCGGTGATC CGAGCGGTAC GACCGTTTTC
                                                   CT84
2341  AGCGCCGGTG AACTGACCCT GAAAACCTG GATAATAGCA TTGCGGCGCT GCCGCTGTCT
                                                   CT84
2401  TGCTTCGGTA ACCTGCTGGG TTCTTTCACC GTTCGGGTC GTGGCCATAG CCTGACCTTT
                                                   CT84
2461  GAAAACATTC GTACCAGCAC CAATGGTGCG GCGCTGTCTA TAGCGCGGC GGATGGTCTG
                                                   CT84
2521  TTCACCATTG AAGGTTCAA AGAACTGTCT TTCTCTAACT GCAATAGCCT GCTGGCGGTT
                                                   CT84
2581  CTGCCGGCG CGACCACCAA CAAAGGCAGC CAGACCCCGA CCACCACGAG CACCCCGTCT
                                                   CT84
2641  AACGGCACCA TCTACAGCAA AACCGATCTG CTGCTGCTGA CAACGAAAA ATTCTCTTTT
                                                   CT84
2701  TATAGCAACC TGGTTTCTGG TGATGGTGGT GCGATTGATG CGAAAAGCCT GACCGTTCAG
```

Figure 1 Cont'd

```
                        CT84
        ~~~~~~~~~~~~~~~~~~~~~~~~~~~~~~~~~~~~~~~~~~~~~~~~~~
 2761   GGTATCTCTA AACTGTGCGT TTTCCAGGAA AACACCGCGC AGGCGGATGG CGGTGCGTGC
                        CT84
        ~~~~~~~~~~~~~~~~~~~~~~~~~~~~~~~~~~~~~~~~~~~~~~~~~~
 2821   CAGGTTGTTA CCTCTTTCAG CGCGATGGCC AATGAAGCGC CGATTGCGTT TGTTGCCAAC
                        CT84                                    SacI
        ~~~~~~~~~~~~~~~~~~~~~~~~~~~~~~~~~~~~~~~~~~~~~~~~~~      ~~~~
 2881   GTGGCGGGTG TTCGTGGTGG TGGTATCGCG GCGGTGCAGG ATGGTCAGCA GGGTGTGAGC
                        CT84
  SacI  ~~~~~~~~~~~~~~~~~~~~~~~~~~~~~~~~~~~~~~~~~~~~~~~~~~
  ~~
 2941   TCTTCTACCT CTACCGAAGA TCCGGTGGTG AGCTTCAGCC GTAACACCGC GGTGGAATTT
                        CT84
        ~~~~~~~~~~~~~~~~~~~~~~~~~~~~~~~~~~~~~~~~~~~~~~~~~~
 3001   GATGGTAACG TGGCGCGCGT TGGTGGTGGT ATCTACAGCT ACGGTAACGT GGCGTTCCTG
                        CT84
        ~~~~~~~~~~~~~~~~~~~~~~~~~~~~~~~~~~~~~~~~~~~~~~~~~~
 3061   AACAATGGTA AAACCCTGTT CCTGAATAAC GTTGCGAGCC CGGTGTATAT TGCGGCCAAA
                        CT84
        ~~~~~~~~~~~~~~~~~~~~~~~~~~~~~~~~~~~~~~~~~~~~~~~~~~
 3121   CAGCCGACCT CTGGTCAGGC GTCTAACACC AGCAATAACT ACGGCGATGG TGGCGCCATT
                        CT84
        ~~~~~~~~~~~~~~~~~~~~~~~~~~~~~~~~~~~~~~~~~~~~~~~~~~
 3181   TTCTGCAAAA ACGGTGCGCA GGCGGGCAGC AACAACTCTG GCAGCGTGAG CTTCGATGGC
                        CT84
        ~~~~~~~~~~~~~~~~~~~~~~~~~~~~~~~~~~~~~~~~~~~~~~~~~~
 3241   GAAGGCGTGG TGTTTTTCAG CTCTAATGTG GCGGCGGGTA AAGGCGGCGC GATTTATGCG
                        CT84
        ~~~~~~~~~~~~~~~~~~~~~~~~~~~~~~~~~~~~~~~~~~~~~~~~~~
 3301   AAAAAACTGT CTGTTGCGAA CTGCGGCCCG GTGCAGTTCC TGCGTAACAT TGCGAACGAT
                        CT84
        ~~~~~~~~~~~~~~~~~~~~~~~~~~~~~~~~~~~~~~~~~~~~~~~~~~
 3361   GGTGGTGCGA TCTACCTGGG TGAAAGCGGC GAACTGTCTC TGAGCGCGGA TTATGGCGAT
                        CT84
        ~~~~~~~~~~~~~~~~~~~~~~~~~~~~~~~~~~~~~~~~~~~~~~~~~~
 3421   ATTATCTTCG ATGGTAACAT TAAACGTACC GCGAAAGAAA ACGCGGCGGA TGTGAACGGT
                        CT84
        ~~~~~~~~~~~~~~~~~~~~~~~~~~~~~~~~~~~~~~~~~~~~~~~~~~
 3481   GTGACCGTGT CTTCTCAGGC GATTAGCATG GGTAGCGGCG GCAAAATTAC CACCCTGCGT
                        CT84
        ~~~~~~~~~~~~~~~~~~~~~~~~~~~~~~~~~~~~~~~~~~~~~~~~~~
 3541   GCGAAAGCGG GTCATCAGAT CCTGTTCAAC GATCCGATCG AAATGGCGAA CGGTAATAAC
                        CT84
        ~~~~~~~~~~~~~~~~~~~~~~~~~~~~~~~~~~~~~~~~~~~~~~~~~~
 3601   CAGCCGGCGC AGTCTTCTAA ACTGCTGAAA ATTAACGATG GTGAAGGTTA CACCGGTGAT
                        CT84
        ~~~~~~~~~~~~~~~~~~~~~~~~~~~~~~~~~~~~~~~~~~~~~~~~~~
 3661   ATTGTGTTCG CGAACGGTTC TAGCACCCTG TATCAGAACG TTACCATCGA ACAGGGCCGT
                        CT84                HincII
        ~~~~~~~~~~~~~~~~~~~~~~~~~~~~~~~~~~~~~~~~~~~~~~~~~~
 3721   ATCGTTCTGC GTGAAAAAGC GAAACTGTCT GTTAACAGCC TGAGCCAGAC CGGTGGTAGC
                        CT84
        ~~~~~~~~~~~~~~~~~~~~~~~~~~~~~~~~~~~~~~~~~~~~~~~~~~
 3781   CTGTATATGG AAGCGGGTTC TACCCTGGAT TTCGTTACCC CGCAGCCGCC GCAGCAGCCG
                        CT84
        ~~~~~~~~~~~~~~~~~~~~~~~~~~~~~~~~~~~~~~~~~~~~~~~~~~
 3841   CCGGCGGCGA ATCAGCTGAT CACCCTGAGC AACCTGCATC TGTCTCTGTC TTCTCTGCTG
                        CT84
        ~~~~~~~~~~~~~~~~~~~~~~~~~~~~~~~~~~~~~~~~~~~~~~~~~~
 3901   GCGAACAACG CGGTTACCAA CCCGCCGACC AACCCGCCGG CGCAGGATTC TCATCCGGCG
                        CT84                                    BglII
        ~~~~~~~~~~~~~~~~~~~~~~~~~~~~~~~~~~~~~~~~~~~~~~~~~~      ~~~~~
 3961   GTGATTGGTA GCACCACCGC GGGTAGCGTT ACCATTTCTG GTCCGATTTT CTTTGAAGAT
```

Figure 1 Cont'd

```
                                    CT84
      ~~~~~~~~~~~~~~~~~~~~~~~~~~~~~~~~~~~~~~~~~~~~~~~~~~~~~~~~~~~~
      BglII
      ~~~
4021  CTGGATGATA CCGCGTACGA TCGCTACGAT TGGCTGGGTA GCAACCAGAA AATCAACGTT
                                                    CT84
      ~~~~~~~~~~~~~~~~~~~~~~~~~~~~~~~~~~~~~~~~~~~~~~~~~~~~~~~~~~~~
4081  CTGAAACTGC AACTGGGCAC CAAACCGCCG GCGAACGCGC CGTCTGATCT GACCCTGGGT
                                                    CT84
      ~~~~~~~~~~~~~~~~~~~~~~~~~~~~~~~~~~~~~~~~~~~~~~~~~~~~~~~~~~~~
4141  AACGAAATGC CGAAATATGG CTACCAGGGT TCTTGGAAAC TGGCGTGGGA CCCGAACACC
                                                    CT84
      ~~~~~~~~~~~~~~~~~~~~~~~~~~~~~~~~~~~~~~~~~~~~~~~~~~~~~~~~~~~~
4201  GCGAACAACG GTCCGTACAC CCTGAAAGCG ACCTGGACCA AAACCGGTTA CAATCCGGGC
                                                    CT84
      ~~~~~~~~~~~~~~~~~~~~~~~~~~~~~~~~~~~~~~~~~~~~~~~~~~~~~~~~~~~~
4261  CCGGAACGTG TTGCGTCTCT GGTTCCGAAC TCTCTGTGGG GCAGCATTCT GGATATTCGC
                                                    CT84
      ~~~~~~~~~~~~~~~~~~~~~~~~~~~~~~~~~~~~~~~~~~~~~~~~~~~~~~~~~~~~
4321  AGCGCGCATT CTGCGATCCA GGCGAGCGTG GATGGTCGTA GCTATTGCCG CGGTCTGTGG
                                                    CT84
      ~~~~~~~~~~~~~~~~~~~~~~~~~~~~~~~~~~~~~~~~~~~~~~~~~~~~~~~~~~~~
4381  GTTAGCGGTG TTTCTAACTT CTTCTATCAT GATCGCGATG CGCTGGGCCA GGGCTATCGC
                                                    CT84
      ~~~~~~~~~~~~~~~~~~~~~~~~~~~~~~~~~~~~~~~~~~~~~~~~~~~~~~~~~~~~
4441  TATATTAGCG GTGGTTATAG CCTGGGTGCG AACAGCTATT CGGTAGCAG CATGTTCGGC
          CT84
      ~~~~~~~~~~
               XbaI
               ~~~~~~~~
                        HincII    AvrII
                        ~~~~~~    ~~~~~~
4501  CTGGCGTTCA CCTAATCTAG AGTCGACTAG CCTAGGGGTA CCCAGCTTTT GTTCCCTTTA
4561  GTGAGGGTTA ATTTCGAGCT TGGCGTAATC ATGGTCATAG CTGTTTCCTG TGTGAAATTG
4621  TTATCCGCTC ACAATTCCAC ACAACATACG AGCCGGAAGC ATAAAGTGTA AAGCCTGGGG
4681  TGCCTAATGA GTGAGCTAAC TCACATTAAT TGCGTTGCGC TCACTGCCCG CTTTCCAGTC
4741  GGGAAACCTG TCGTGCCAGC TGCATTAATG AATCGGCCAA CGCGCGGGGA GAGGCGGTTT
4801  GCGTATTGGG CGCTCTTCCG CTTCCTCGCT CACTGACTCG CTGCGCTCGG TCGTTCGGCT
4861  GCGGCGAGCG GTATCAGCTC ACTCAAAGGC GGTAATACGG TTATCCACAG AATCAGGGGA
4921  TAACGCAGGA AAGAACATGT GAGCAAAAGG CCAGCAAAAG GCCAGGAACC GTAAAAAGGC
4981  CGCGTTGCTG GCGTTTTTCC ATAGGCTCCG CCCCCCTGAC GAGCATCACA AAAATCGACG
5041  CTCAAGTCAG AGGTGGCGAA ACCCGACAGG ACTATAAAGA TACCAGGCGT TTCCCCCTGG
5101  AAGCTCCCTC GTGCGCTCTC CTGTTCCGAC CCTGCCGCTT ACCGGATACC TGTCCGCCTT
5161  TCTCCCTTCG GGAAGCGTGG CGCTTTCTCA TAGCTCACGC TGTAGGTATC TCAGTTCGGT
5221  GTAGGTCGTT CGCTCCAAGC TGGGCTGTGT GCACGAACCC CCCGTTCAGC CCGACCGCTG
5281  CGCCTTATCC GGTAACTATC GTCTTGAGTC CAACCCGGTA AGACACGACT TATCGCCACT
5341  GGCAGCAGCC ACTGGTAACA GGATTAGCAG AGCGAGGTAT GTAGGCGGTG CTACAGAGTT
5401  CTTGAAGTGG TGGCCTAACT ACGGCTACAC TAGAAGGACA GTATTTGGTA TCTGCGCTCT
5461  GCTGAAGCCA GTTACCTTCG GAAAAAGAGT TGGTAGCTCT TGATCCGGCA AACAAACCAC
5521  CGCTGGTAGC GGTGGTTTTT TTGTTTGCAA GCAGCAGATT ACGCGCAGAA AAAAAGGATC
5581  TCAAGAAGAT CCTTTGATCT TTTCTACGGG GTCTGACGCT CAGTGGAACG AAAACTCACG
5641  TTAAGGGATT TTGGTCATGA GATTATCAAA AAGGATCTTC ACCTAGATCC TTTT
```

Figure 2 (SEQ ID NO:8)
Suicide Vector

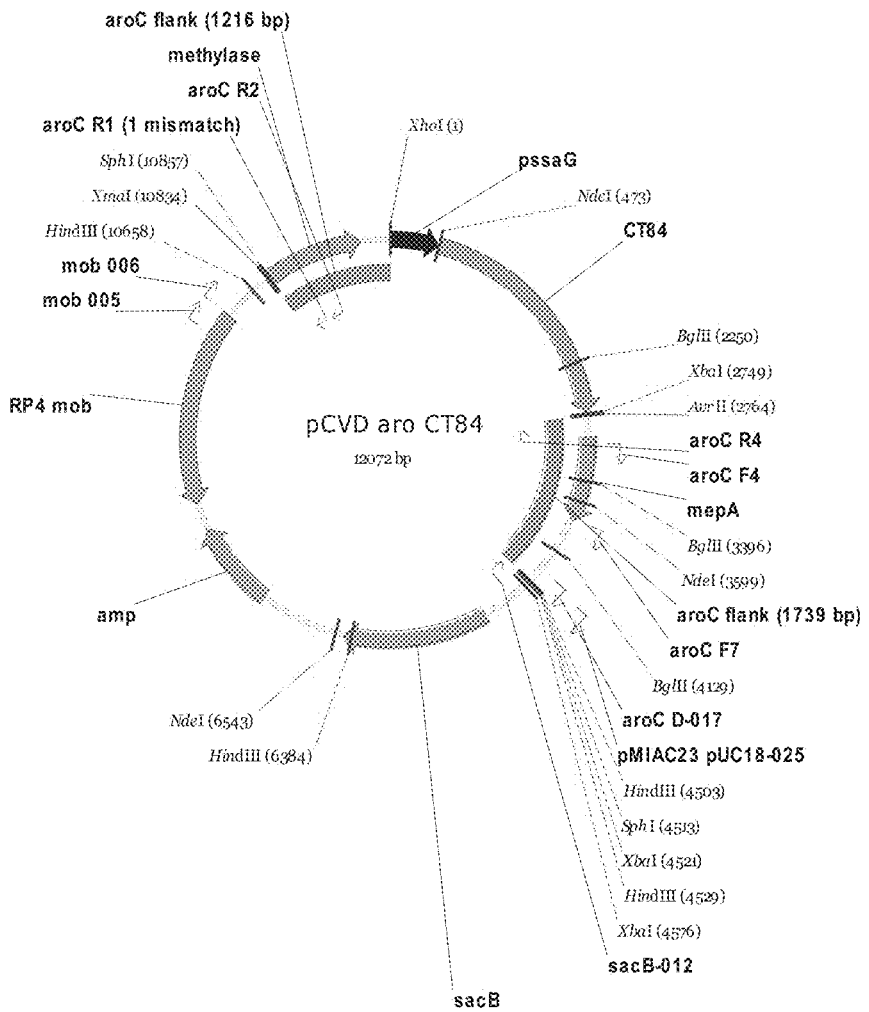

```
       XhoI
   1   TCGAGATTGC CATCGCGGAT GTCGCCTGTC TTATCTACCA TCATAAACAT CATTTGCCTA
       AGCTCTAACG GTAGCGCCTA CAGCGGACAG AATAGATGGT AGTATTTGTA GTAAACGGAT
  61   TGGCTCACGA CAGTATAGGC AATGCCGTTT TTTATATTGC TAATTGTTTC GCCAATCAAC
       ACCGAGTGCT GTCATATCCG TTACGGCAAA AAATATAACG ATTAACAAAG CGGTTAGTTG
 121   GCAAAAGTAT GGCGATTGCT AAAGCCGTCT CCCTGGGCGG TAGATTAGCC TTAACCGCGA
       CGTTTTCATA CCGCTAACGA TTTCGGCAGA GGGACCCGCC ATCTAATCGG AATTGGCGCT
 181   CGGTAATGAC TCATTCATAC TGGAGTGGTA GTTTGGGACT ACAGCCTCAT TTATTAGAGC
       GCCATTACTG AGTAAGTATG ACCTCACCAT CAAACCCTGA TGTCGGAGTA AATAATCTCG
 241   GTCTTAATGA TATTACCTAT GGACTAATGA GTTTTACTCG CTTCGGTATG GATGGGATGG
       CAGAATTACT ATAATGGATA CCTGATTACT CAAAATGAGC GAAGCCATAC CTACCCTACC
 301   CAATGACCGG TATGCAGGTC AGCAGCCCAT TATATCGTTT GCTGGCTCAG GTAACGCCAG
       GTTACTGGCC ATACGTCCAG TCGTCGGGTA ATATAGCAAA CGACCGAGTC CATTGCGGTC
 361   AACAACGTGC GCCGGAGTAA TCGTTTTCAG GTATATACCG GATGTTCATT GCTTTCTAAA
       TTGTTGCACG CGGCCTCATT AGCAAAAGTC CATATATGGC CTACAAGTAA CGAAAGATTT
                                                                    NdeI
 421   TTTTGCTATG TTGCCAGTAT CCTTACGATG TATTTATTTT AAGGAAAAGC CATATGGAAA
       AAAACGATAC AACGGTCATA GGAATGCTAC ATAAATAAAA TTCCTTTTCG GTATACCTTT
 481   TTATGGTTCC GCAGGGTATC TACGATGGTG AAACCCTGAC CGTGTCTTTC CCGTATACCG
       AATACCAAGG CGTCCCATAG ATGCTACCAC TTTGGGACTG GCACAGAAAG GGCATATGGC
```

Figure 2 Cont'd

```
 541  TTATCGGTGA TCCGAGCGGT ACGACCGTTT TCAGCGCCGG TGAACTGACC CTGAAAAACC
      AATAGCCACT AGGCTCGCCA TGCTGGCAAA AGTCGCGGCC ACTTGACTGG GACTTTTTGG
 601  TGGATAATAG CATTGCGGCG CTGCCGCTGT CTTGCTTCGG TAACCTGCTG GGTTCTTTCA
      ACCTATTATC GTAACGCCGC GACGGCGACA GAACGAAGCC ATTGGACGAC CCAAGAAAGT
 661  CCGTTCTGGG TCGTGGCCAT AGCCTGACCT TTGAAAACAT TCGTACCAGC ACCAATGGTG
      GGCAAGACCC AGCACCGGTA TCGGACTGGA AACTTTTGTA AGCATGGTCG TGGTTACCAC
 721  CGGCGCTGTC TAATAGCGCG GCGGATGGTC TGTTCACCAT TGAAGGTTTC AAAGAACTGT
      GCCGCGACAG ATTATCGCGC CGCCTACCAG ACAAGTGGTA ACTTCCAAAG TTTCTTGACA
 781  CTTTCTCTAA CTGCAATAGC CTGCTGGCGG TTCTGCCGGC GGCGACCACC AACAAAGGCA
      GAAAGAGATT GACGTTATCG GACGACCGCC AAGACGGCCG CCGCTGGTGG TTGTTTCCGT
 841  GCCAGACCCC GACCACCACG AGCACCCCGT CTAACGGCAC CATCTACAGC AAAACCGATC
      CGGTCTGGGG CTGGTGGTGC TCGTGGGGCA GATTGCCGTG GTAGATGTCG TTTTGGCTAG
 901  TGCTGCTGCT GAACAACGAA AAATTCTCTT TTTATAGCAA CCTGGTTTCT GGTGATGGTG
      ACGACGACGA CTTGTTGCTT TTTAAGAGAA AAATATCGTT GGACCAAAGA CCACTACCAC
 961  GTGCGATTGA TGCGAAAAGC CTGACCGTTC AGGGTATCTC TAAACTGTGC GTTTTCCAGG
      CACGCTAACT ACGCTTTTCG GACTGGCAAG TCCCATAGAG ATTTGACACG CAAAAGGTCC
1021  AAAACACCGC GCAGGCGGAT GGCGGTGCGT GCCAGGTTGT TACCTCTTTC AGCGCGATGG
      TTTTGTGGCG CGTCCGCCTA CCGCCACGCA CGGTCCAACA ATGGAGAAAG TCGCGCTACC
1081  CCAATGAAGC GCCGATTGCG TTTGTTGCCA ACGTGGCGGG TGTTCGTGGT GGTGGTATCG
      GGTTACTTCG CGGCTAACGC AAACAACGGT TGCACCGCCC ACAAGCACCA CCACCATAGC
1141  CGGCGGTGCA GGATGGTCAG CAGGGTGTGA GCTCTTCTAC CTCTACCGAA GATCCGGTGG
      GCCGCCACGT CCTACCAGTC GTCCCACACT CGAGAAGATG GAGATGGCTT CTAGGCCACC
1201  TGAGCTTCAG CCGTAACACC GCGGTGGAAT TTGATGGTAA CGTGGCGCGC GTTGGTGGTG
      ACTCGAAGTC GGCATTGTGG CGCCACCTTA AACTACCATT GCACCGCGCG CAACCACCAC
1261  GTATCTACAG CTACGGTAAC GTGGCGTTCC TGAACAATGG TAAAACCCTG TTCCTGAATA
      CATAGATGTC GATGCCATTG CACCGCAAGG ACTTGTTACC ATTTTGGGAC AAGGACTTAT
1321  ACGTTGCGAG CCCGGTGTAT ATTGCGGCCA ACAGCCGAC CTCTGGTCAG GCGTCTAACA
      TGCAACGCTC GGGCCACATA TAACGCCGGT TGTCGGCTG GAGACCAGTC CGCAGATTGT
1381  CCAGCAATAA CTACGCGGAT GGTGGCGCCA TTTTCTGCAA AAACGGTGCG CAGGCGGGCA
      GGTCGTTATT GATGCCGCTA CCACCGCGGT AAAAGACGTT TTTGCCACGC GTCCGCCCGT
1441  GCAACAACTC TGGCAGCGTG AGCTTCGATG GCGAAGGCGT GGTGTTTTTC AGCTCTAATG
      CGTTGTTGAG ACCGTCGCAC TCGAAGCTAC CGCTTCCGCA CCACAAAAAG TCGAGATTAC
1501  TGGCGGCGGG TAAAGGCGGC GCGATTTATG CGAAAAAACT GTCTGTTGCG AACTGCGGCC
      ACCGCCGCCC ATTTCCGCCG CGCTAAATAC GCTTTTTTGA CAGACAACGC TTGACGCCGG
1561  CGGTGCAGTT CCTGCGTAAC ATTGCGAACG ATGGTGGTGC GATCTACCTG GGTGAAAGCG
      GCCACGTCAA GGACGCATTG TAACGCTTGC TACCACCACG CTAGATGGAC CCACTTTCGC
1621  GCGAACTGTC TCTGAGCGCG GATTATGCGG ATATTATCTT CGATGGTAAC ATTAAACGTA
      CGCTTGACAG AGACTCGCGC CTAATACCGC TATAATAGAA GCTACCATTG TAATTTGCAT
1681  CCGCGAAAGA AAACGCGGCG GATGTGAACG GTGTGACCGT GTCTTCTCAG GCGATTAGCA
      GGCGCTTTCT TTTGCGCCGC CTACACTTGC CACACGGCA CAGAAGAGTC CGCTAATCGT
1741  TGGGTAGCGG CGGCAAAATT ACCACCCTGC GTGCGAAAGC GGGTCATCAG ATCCTGTTCA
      ACCCATCGCC GCCGTTTTAA TGGTGGGACG CACGCTTTCG CCCAGTAGTC TAGGACAAGT
1801  ACGATCCGAT CGAAATGGCG AACGGTAATA ACCAGCCGGC GCAGTCTTCT AAACTGCTGA
      TGCTAGGCTA GCTTTACCGC TTGCCATTAT TGGTCGGCCG CGTCAGAAGA TTTGACGACT
1861  AAATTAACGA TGGTGAAGGT TACACCGGTG ATATTGTGTT CGCGAACGGT TCTAGCACCC
      TTTAATTGCT ACCACTTCCA ATGTGGCCAC TATAACACAA GCGCTTGCCA AGATCGTGGG
1921  TGTATCAGAA CGTTACCATC GAACAGGGCC GTATCGTTCT GCGTGAAAAA GCGAAACTGT
      ACATAGTCTT GCAATGGTAG CTTGTCCCGG CATAGCAAGA CGCACTTTTT CGCTTTGACA
1981  CTGTTAACAG CCTGAGCCAG ACCGGTGGTA GCCTGTATAT GGAAGCGGGT TCTACCCTGG
      GACAATTGTC GGACTCGGTC TGGCCACCAT CGGACATATA CCTTCGCCCA AGATGGGACC
2041  ATTTCGTTAC CCCGCAGCCG CCGCAGCCGC CGCGGCGGGC GAATCGGTCG ATCAGCCTGA
      TAAAGCAATG GGGCGTCGGC GGCGTCGTCG CGCGCCGCCC GCTTAGTCGAC TAGTGGGACT
2101  GCAACCTGCA TCTGTCTCTG TCTTCTCTGC TGGCGAACAA CGCGGTTACC AACCCGCCGA
      CGTTGGACGT AGACAGAGAC AGAAGAGACG ACCGCTTGTT GCGCCAATGG TTGGGCGGCT
2161  CCAACCCGCC GGCGCAGGAT TCTCATCCGG CGGTGATTGG TAGCACCACC GCGGGTAGCG
      GGTTGGGCGG CCGCGTCCTA AGAGTAGGCC GCCACTAACC ATCGTGGTGG CGCCCATCGC
                                                     BglII
                                                     ~~~~~~
2221  TTACCATTTC TGGTCCGATT TCTTTGAAG ATCTGGATGA TACCGCGTAC GATCGCTACG
      AATGGTAAAG ACCAGGCTAA AGAAACTTC TAGACCTACT ATGGCGCATG CTAGCGATGC
2281  ATTGGCTGGG TAGCAACCAG AAAATCAACG TTCTGAAACT GCAACTGGGC ACCAAACCGC
      TAACCGACCC ATCGTTGGTC TTTTAGTTGC AAGACTTTGA CGTTGACCCG TGGTTTGGCG
2341  CGGCGAACGC GCCGTCTGAT CTGACCCTGG GTAACGAAAT GCCGAAATAT GGCTACCAGG
      GCCGCTTGCG CGGCAGACTA GACTGGGACC CATTGCTTTA CCGGCTTATA CCGATGGTCC
2401  GTCTTGGAAA ACTGGCGTGG GACCCGAACA CCGCGAACAA CGGTCCGTAC ACCCTGAAAG
      CAGAACCTTT TGACCGCACC CTGGGCTTGT GGCGCTTGTT GCCAGGCATG TGGGACTTTC
2461  CGACCTGGAC CAAAAACCGGT TACAATCCGG TACCGTGAAC TGTTGCGTCT CTGGTTCCGA
      GCTGGACCTG GTTTGGCCA ATGTTAGGCC CGGGCCTTGC ACAACGCAGA GACCAAGGCT
2521  ACTCTCTGTG GGGCAGCATT CTGGATATTC GCAGCGCGCA TTCTGCGATC CAGGCGAGCG
      TGAGAGACAC CCCGTCGTAA GACCTATAAG CGTCGCGCGT AAGACGCTAG GTCCGCTCGC
```

Figure 2 Cont'd

```
2581  TGGATGGTCG TAGCTATTGC CGCGGTCTGT GGGTTAGCGG TGTTCTAAC TTCTTCTATC
      ACCTACCAGC ATCGATAACG GCGCCAGACA CCCAATCGCC ACAAAGATTG AAGAAGATAG
2641  ATGATCGCGA TGCGCTGGGC CAGGGCTATC GCTATATTAG CGGTGGTTAT AGCCTGGGTG
      TACTAGCGCT ACGCGACCCG GTCCCGATAG CGATATAATC GCCACCAATA TCGGACCCAC
                                                                  Xba
                                                                  ~~~~~~
2701  CGAACAGCTA TTTCGGTAGC AGCATGTTCG GCCTGGCGTT CACCTAATCT AGAGTCGACT
      GCTTGTCGAT AAAGCCATCG TCGTACAAGC CGGACCGCAA GTGGATTAGA TCTCAGCTGA
      AvrII
      ~~~~~~
2761  AGCCTAGGTC CAGCATTACC GTGCCGGGAC GTACGATCAA CCGGATGGGT GAAGAGGTCG
      TCGGATCCAG GTCGTAATGG CACGGCCCTG CATGCTAGTT GGCCTACCCA CTTCTCCAGC
2821  AGATGATCAC CAAAGGGCGC CACGATCCGT GTGTGGGAT TCGCGCAGTG CCGATCGCAG
      TCTACTAGTG GTTTCCCGCG GTGCTAGGCA CACACCCCTA AGCGCGTCAC GGCTAGCGTC
2881  AAGCCATGCT GGCGATCGTA CTGATGGATC ACCTGCTGCG CCATCGGGCA CAGAATGCGG
      TTCGGTACGA CCGCTAGCAT GACTACCTAG TGGACGACGC GGTAGCCCGT GTCTTACGCC
2941  ATGTAAAGAC AGAGATTCCA CGCTGGTAAG AAATGAAAAA AACCGCGATT GCGCTGCTGG
      TACATTTCTG TCTCTAAGGT GCGACCATTC TTTACTTTT TTGGCGCTAA CGCGACGACC
3001  CATGGTTTGT CAGTAGCGCC AGCCTGGCGG CGACGCCGTG GCAGAAAATA ACCCATCCTG
      GTACCAAACA GTCATCGCGG TCGGACCGCC GCTGCGGCAC CGTCTTTTAT TGGGTAGGAC
3061  TCCCCGGCGC CGCCCAGTCT ATCGGTAGCT TTGCCAACGG ATGCATCATT GGCGCCGACA
      AGGGGCCGCG GCGGGTCAGA TAGCCATCGA AACGGTTGCC TACGTAGTAA CCGCGGCTGT
3121  CGTTGCCGGT ACAGTCCGAT AATTATCAGG TGATGCGCAC CGATCAGCGC CGTTATTTCG
      GCAACGGCCA TGTCAGGCTA TTAATAGTCC ACTACGCGTG GCTAGTCGCG GCAATAAAGC
3181  GCCACCCGGA TCTGGTCATG TTTATCCAGC GGTTGAGTCA TCAGGCGCAG CAACGGGGGC
      CGGTGGGCCT AGACCAGTAC AAATAGGTCG CCAACTCAGT AGTCCGCGTC GTTGCCCCCG
3241  TCGGAACCGT CCTGATAGGC GACATGGGGA TGCCTGCCGG AGGCCCCTTT AATGGCGGAC
      AGCCTTGGCA GGACTATCCG CTGTACCCCT ACGGACGGCC TCCGGCGAAA TTACCGCCTG
3301  ACGCCAGTCA TCAGACCGGG CTTGATGTGG ATATTTTCTT GCAGTTGCCG AAAACGCGCT
      TGCGGTCAGT AGTCTGGCCC GAACTACACC TATAAAAGAA CGTCAACGGC TTTTGCGCGA
                                                    BglII
                                                    ~~~~~~
3361  GGAGCCAGGC GCAGCTATTG CGCCCGCAGG CGTTAGATCT GGTGTCCCGC GACGGTAAAC
      CCTCGGTCCG CGTCGATAAC GCGGGCGTCC GCAATCTAGA CCACAGGGCG CTGCCATTTG
3421  ATGTCGTGCC GTCGCGCTGG TCGTCGGATA TCGCCAGTCT GATCAAACTG GCGGCACAAG
      TACAGCACGG CAGCGCGACC AGCAGCCTAT AGCGGTCAGA CTAGTTTGAC CGCCGTGTTC
3481  ACAATGACGT CACCCGTATT TTCGTCAATC CGGCTATTAA ACAACAGCTT TGCCTCGATG
      TGTTACTGCA GTGGGCATAA AAGCAGTTAG GCCGATAATT TGTTGTCGAA ACGGAGCTAC
                                                                  NdeI
                                                                  ~~~~
3541  CCGGAAGCGA TCGTGACTGG CTACGTAAAG TACGCCCCTG GTTCCAGCAT CGCGCGCATA
      GGCCTTCGCT AGCACTGACC GATGCATTTC ATGCGGGGAC CAAGGTCGTA GCGCGCGTAT
      NdeI
      ~~
3601  TGCACGTGCG TTTACGCTGC CCTGCCGACA GCCTGGAGTG CGAAGATCAA CCTTTACCCC
      ACGTGCACGC AAATGCGACG GGACGGCTGT CGGACCTCAC GCTTCTAGTT GGAAATGGGG
3661  CGCCGGGCGA TGGATGCGGC GCTGAACTGC AAAGCTGGTT CGAACCGCCA AAACCTGGCA
      GCGGCCCGCT ACCTACGCCG CGACTTGACG TTTCGACCAA GCTTGGCGGT TTTGGACCGT
3721  CCACAAAGCC TGAGAAGAAG ACACCGCCGC CGTTGCCGCT TTCCTGCCAG CGCTACTGG
      GGTGTTTCGG ACTCTTCTTC TGTGGCGGCG GCAACGGCGA AAGGACGGTC CGCGATGACC
3781  ATGAGCATGT ACTCTGATGG ACAATTTTTA TGATCTGTTT ATGGTCTCCC CGCTGCTGCT
      TACTCGTACA TGAGACTACC TGTTAAAAAT ACTAGACAAA TACCTAGAGG GCGACGACGA
3841  GGTGGTGCTG TTTTTTTGTCG CCGTACTGGC AGGATTTATC GATTCTATCG CCGGAGGCGG
      CCACCACGAC AAAAAACAGC GGCATGACCG TCCTAAATAG CTAAGATAGC GGCCTCCGCC
3901  AGGGCTGCTC ACTATCCCTG CGCTGATGGC GCCGGGATG TCGCCGGCAA ACGCGTTGGC
      TCCCGACGAG TGATAGGGAC GCGACTACCG CGGCCCTAC AGCGGCCGTT TGCGCAACCG
3961  GACCAATAAA TTACAGGCGT GCGGCGGCTC CCTCTCGTCT TCGCTCTATT TTATTCGCCG
      CTGGTTATTT AATGTCCGCA CGCCGCCGAG GGAGAGCAGA AGCGAGATAA AATAAGCGGC
4021  TAAAGTGGTA AACCTGGCCG AGCAAAAGCT CAATATTCTG ATGACGTTCA TTGGCTCGAT
      ATTTCACCAT TTGGACCGGC TCGTTTTCGA GTTATAAGAC TACTGCAAGT AACCGAGCTA
                                                                  BglII
                                                                  ~~~~~~
4081  GAGCGGCGCG CTGCTGGTGC AGCACGTGCA GGCGGATATT TTGCGCCAGA TCTTGCCCAT
      CTCGCCGCGC GACGACCACG TCGTGCACGT CCGCCTATAA AACGCGGTCT AGAACGGGTA
4141  CCTGGTGATT TTCATCGGCC TCTATTTTT ATTGATGCCG AAGCTGGGCG AGGAAGATCG
      GGACCACTAA AAGTAGCCGG AGATAAAAAA TAACTACGGC TTCGACCCGC TCCTTCTAGC
4201  CCAGCGCCGC CTGTATGGAT TACCGTTCGC GGCTGATAGC GGGGGATGCG TCGGGTTTTA
      GGTCGCGGCG GACATACCTA ATGGCAAGCG CCGACTATCG CCCCCTACGC AGCCCAAAAT
4261  CGACGGCTTT TTCGGGCCTG CCGCAGGGTC GTTTTACGCT CTGGCGTTTG TCACCTTATG
      GCTGCCGAAA AAGCCCGGAC GGCGTCCCAG CAAAATGCGA GACCGCAAAC AGTGGAATAC
4321  TGGCTATAAC CTGGCGAAAT CCACGGCACA TGCCAAAGTG CTTAACGCTA CCTCCAACGT
```

Figure 2 Cont'd

```
         ACCGATATTG GACCGCTTTA GGTGCCGTGT ACGGTTTCAC GAATTGCGAT GGAGGTTGCA
4381     TGGCCGGCCTG CTGTTATTTA TCATCGGCGG CAAAGTGATC TGGGCGACGG GCTTTGTGAT
         ACCGCCGGAC GACAATAAAT AGTAGCCGCC GTTTCACTAG ACCCGCTGCC CGAAACACTA
4441     GCTGGTTGGT CAGTTTTTAG GGGCGCGAAT GGGGTCGCGT CTGGTGTTGA GCAAAGGCCA
         CGACCAACCA GTCAAAAATC CCCGCGCTTA CCCCAGCGCA GACCACAACT CGTTTCCGGT
         HindIII
         ~~~~~~
                 SphI         XbaI       HindIII
                 ~~~~~~~     ~~~~~~~    ~~~~~~~
4501     AAAGCTTGCA TGCGGTACCT CTAGAAGAAG CTTGGGATCC GTCGACCTGC AGATCCGTCG
         TTTCGAACGT ACGCCATGGA GATCTTCTTC GAACCCTAGG CAGCTGGACG TCTAGGCAGC
                                XbaI
                                ~~~~~~
4561     ACCTGCAGGT CGACTCTAGA GGATCGATCC TTTTTAACCC ATCACATATA CCTGCCGTTC
         TGGACGTCCA GCTGAGATCT CCTAGCTAGG AAAAATTGGG TAGTGTATAT GGACGGCAAG
4621     ACTATTATTT AGTGAAATGA GATATTATGA TATTTTCTGA ATTGTGATTA AAAAGGCAAC
         TGATAATAAA TCACTTTACT CTATAATACT ATAAAAGACT TAACACTAAT TTTTCCGTTG
4681     TTTATGCCCA TGCAACAGAA ACTATAAAAA ATACAGAGAA TGAAAAGAAA CAGATAGATT
         AAATACGGGT ACGTTGTCTT TGATATTTTT TATGTCTCTT ACTTTTCTTT GTCTATCTAA
4741     TTTTAGTTCT TTAGGCCCGT AGTCTGCAAA TCCTTTTATG ATTTTCTATC AAACAAAAGA
         AAAATCAAGA AATCCGGGCA TCAGACGTTT AGGAAAATAC TAAAAGATAG TTTGTTTTCT
4801     GGAAAATAGA CCAGTTGCAA TCCAAACGAG AGTCTAATGA AATGAGGTCG AAAAGTAAAT
         CCTTTTATCT GGTCAACGTT AGGTTTGCTC TCAGATTATC TTACTCCAGC TTTTCATTTA
4861     CGCGCGGGTT TGTTACTGAT AAAGCAGGCA AGACCTAAAA TGTGTAAAGG GCAAAGTGTA
         GCGCGCCCAA ACAATGACTA TTTCGTCCGT TCTGGATTTT ACACATTTCC CGTTTCACAT
4921     TACTTTGGCG TCACCCCTTA CATATTTTAG GTCTTTTTTT ATTGTGCGTA ACTAACTTGC
         ATGAAACCGC AGTGGGGAAT GTATAAAATC CAGAAAAAAA TAACACGCAT TGATTGAACG
4981     CATCTTCAAA CAGGAGGGCT GGAAGAAGCA GACCGCTAAC ACAGTACATA AAAAAGGAGA
         GTAGAAGTTT GTCCTCCCGA CCTTCTTCGT CTGGCGATTG TGTCATGTAT TTTTTCCTCT
5041     CATGAACGAT GAACATCAAA AGTTTGCAA AACAAGCAAC AGTATTAACC TTTACTACCG
         GTACTTGCTA CTTGTAGTTT TTCAAACGTT TTGTTCGTTG TCATAATTGG AAATGATGGC
5101     CACTGCTGGC AGGAGGCGCA ACTCAAGCGT TTGCGAAAGA AACGAACCAA AAGCCATATA
         GTGACGACCG TCCTCCGCGT TGAGTTCGCA AACGCTTTCT TTGCTTGGTT TTCGGTATAT
5161     AGGAAACATA CGGCATTTCC CATATTACAC GCCATGATAT GCTGCAAATC CCTGAACAGC
         TCCTTTGTAT GCCGTAAAGG GTATAATGTG CGGTACTATA CGACGTTTAG GGACTTGTCG
5221     AAAAAAATGA AAAATATCAA GTTCCTGAAT TCGATTCGTC CACAATTAAA AATATCTCTT
         TTTTTTTACT TTTTATAGTT CAAGGACTTA AGCTAAGCAG GTGTTAATTT TTATAGAGAA
5281     CTGCAAAAGG CCTGGACGTT TGGGACAGCT GGCCATTACA AAACGCTGAC GGCACTGTCG
         GACGTTTTCC GGACCTGCAA ACCCTGTCGA CCGGTAATGT TTTGCGACTG CCGTGACAGC
5341     CAAACTATCA CGGCTACCAC ATCGTCTTTG CATTAGCCGG AGATCCTAAA AATGCGGATG
         GTTTGATAGT GCCGATGGTG TAGCAGAAAC GTAATCGGCC TCTAGGATTT TTACGCCTAC
5401     ACACATCGAT TTACATGTTC TATCAAAAAG TCGGCGAAAC TTCTATTGAC AGCTGGAAAA
         TGTGTAGCTA AATGTACAAG ATAGTTTTTC AGCCGCTTTG AAGATAACTG TCGACCTTTT
5461     ACGCTGGCCG CGTCTTTAAA GACAGCGACA AATTCGATGC AAATGATTCT ATCCTAAAAG
         TGCGACCGGC GCAGAAATTT CTGTCGCTGT TTAAGCTACG TTTACTAAGA TAGGATTTTC
5521     ACCAAACACA GAATGGTCA GGTTCAGCCA CATTTACATC TGACGGAAAA ATCCGTTTAT
         TGGTTTGTGT CTTACCAGT CCAAGTCGGT GTAAATGTAG ACTGCCTTTT TAGGCAAATA
5581     TCTACACTGA TTTCTCCGGT AAACATTACG GCAAACAAAC ACTGACAACT GCACAAGTTA
         AGATGTGACT AAAGAGGCCA TTTGTAATGC CGTTTGTTTG TGACTGTTGA CGTGTTCAAT
5641     ACGTATCAGC ATCAGACAGC TCTTTGAACA TCAACGGTGT AGAGGATTAT AAATCAATCT
         TGCATAGTCG TAGTCTGTCG AGAAACTTGT AGTTGCCACA TCTCCTAATA TTTAGTTAGA
5701     TTGACGGTGA CGGAAAAACG TATCAAAATG TACAGCAGTT CATCGATGAA GGCAACTACA
         AACTGCCACT GCCTTTTTGC ATAGTTTTAC ATGTCGTCAA GTAGCTACTT CCGTTGATGT
5761     GCTCAGGCGA CAACCATACG CTGAGAGATC AGAAGATAAA GGCCACAAAT
         CGAGTCCGCT GTTGGTATGC GACTCTCTAG GAGTGATGCA TCTTCTATTT CCGGTGTTTA
5821     ACTTAGTATT TGAAGCAAAC ACTGGAACTG AAGATGGCTA CCAAGGCGAA GAATCTTTAT
         TGAATCATAA ACTTCGTTTG TGACCTTGAC TTCTACCGAT GGTTCCGCTT CTTAGAAATA
5881     TTAACAAAGC ATACTATGGC AAAAGCACAT CATTCTTCCG TCAAGAAAGT CAAAAACTTC
         AATTGTTTCG TATGATACCG TTTTCGTGTA GTAAGAAGGC AGTTCTTTCA GTTTTTGAAG
5941     TGCAAAGCGA TAAAAAACGC ACGGCTGAGT TAGCAAACGG CGCTCTCGGT ATGATTGAGC
         ACGTTTCGCT ATTTTTTGCG TGCCGACTCA ATCGTTTGCC GCGAGAGCCA TACTAACTCG
6001     TAAACGATGA TTACACACTG AAAAAGTGA TGAAACCGCT GATTGCATCT AACACAGTAA
         ATTTGCTACT AATGTGTGAC TTTTTCACT ACTTTGGCGA CTAACGTAGA TTGTGTCATT
6061     CAGATGAAAT TGAACGCGCG AACGTCTTTA AAATGAACGG CAAATGGTCT CTGTTCACTG
         GTCTACTTTA ACTTGCGCGC TTGCAGAAAT TTTACTTGCC GTTTACCATG GACAAGTGAC
6121     ACTCCCGCGG ATCAAAAATG ACGATTGACG GCATTACGTC TAACGATATT TACATGCTTG
         TGAGGGCGCC TAGTTTTTAC TGCTAACTGC CGTAATGCAG ATTGCTATAA ATGTACGAAC
6181     GTTATGTTTC TAATTCTTTA ACTGGCCCAT ACAAGCCGCT GAACAAAACT GGCCTTGTGT
         CAATACAAAG ATTAAGAAAT TGACCGGGTA TGTTCGGCGA CTTGTTTTGA CCGGAACACA
```

Figure 2 Cont'd

```
6241  TAAAAATGGA TCTTGATCCT AACGATGTAA CCTTTACTTA CTCACACTTC GCTGTACCTC
      ATTTTTACCT AGAACTAGGA TTGCTACATT GGAAATGAAT GAGTGTGAAG CGACATGGAG
6301  AAGCGAAAGG AAACAATGTC GTGATTACAA GCTATATGAC AAACAGAGGA TTCTACGCAG
      TTCGCTTTCC TTTGTTACAG CACTAATGTT CGATATACTG TTTGTCTCCT AAGATGCGTC
                                       HindIII
                                       ~~~~~~
6361  ACAAACAATC AACGTTTGCG CCAAGCTTCC TGCTGAACAT CAAAGGCAAG AAAACATCTG
      TGTTTGTTAG TTGCAAACGC GGTTCGAAGG ACGACTTGTA GTTTCCGTTC TTTTGTAGAC
6421  TTGTCAAAGA CAGCATCCTT GAACAAGGAC AATTAACAGT TAACAAATAA AAACGCAAAA
      AACAGTTTCT GTCGTAGGAA CTTGTTCCTG TTAATTGTCA ATTGTTTATT TTTGCGTTTT
6481  GAAATGCCG ATATCCTATT GGCATTTTCT TTTATTTCTT ATCAACATAA AGGTGAATCC
      CTTTTACGGC TATAGGATAA CCGTAAAAGA AAATAAAGAA TAGTTGTATT TCCACTTAGG
      NdeI
      ~~~~
6541  CATATGAACT ATATAAAGC AGGCAAATGG CTAACCGTAT TCCTAACCTT TTGGTAATGA
      GTATACTTGA TATATTTCG TCCGTTTACC GATTGGCATA AGGATTGGAA AACCATTACT
6601  CTCCAACTTA TTGATAGTGT TTATGTTCA GATAATGCCC GATGACTTTG TCATGCAGCT
      GAGGTTGAAT AACTATCACA AATACAAGT CTATTACGGG CTACTGAAAC AGTACGTCGA
6661  CCACCGATTT TGAGAACGAC AGCGACTTCC GTCCCAGCCG TGCCAGGTGC TGCCTCAGAT
      GGTGGCTAAA ACTCTTGCTG TCGCTGAAGG CAGGGTCGGC ACGGTCCACG ACGGAGTCTA
6721  TCAGGTTATG CCGCTCAATT CGCTGCGTAT ATCGCTTGCT GATTACGTGC AGCTTTCCCT
      AGTCCAATAC GGCGAGTTAA GCGACGCATA TAGCGAACGA CTAATGCACG TCGAAAGGGA
6781  TCAGGCGGGA TTCATACAGC GGCCAGCCAT CCGTCATCCA TATCACCACG TCAAAGGGTG
      AGTCCGCCCT AAGTATGTCG CCGGTCGGTA GGCAGTAGGT ATAGTGGTGC AGTTTCCCAC
6841  ACAGCAGGCT CATAAGACGC CCCAGCGTCG CCATAGTGCG TTCACCGAAT ACGTGCGCAA
      TGTCGTCCGA GTATTCTGCG GGGTCGCAGC GGTATCACGC AAGTGGCTTA TGCACGCGTT
6901  CAACCGTCTT CGGAGACTG TCATACGCGT AAAACAGCCA GCGCTGCGCG GATTTAGCCC
      GTTGGCAGAA GGCCTCTGAC AGTATGCGCA TTTTGTCGGT CGCGACCGCG CTAAATCGGG
6961  CGACATAGCC CCACTGTTCG TCCATTTCCG CGCAGACGAT GACGTCACTG CCCGGCTGTA
      GCTGTATCGG GGTGACAAGC AGGTAAAGGC GCGTCTGCTA CTGCAGTGAC GGGCCGACAT
7021  TGCGCGAGGT TACCGACTGC GGCCTGAGTT TTTTAAGTGA CGTAAAATCG TGTTGAGGCC
      ACGCGCTCCA ATGGCTGACG CCGGACTCAA AAAATTCACT GCATTTTAGC ACAACTCCGG
7081  AACGCCCATA ATGCGGCTG TTGCCCGGCA TCCAACGCCA TTCATGGCCA TATCAATGAT
      TTGCGGGTAT TACGCCCGAC AACGGGCCGT AAGTACCGGT AGTAGTTACTA
7141  TTTCTGGTGC GTACCGGGTT GAGAAGCCGGT GTAAGTGAAC TGCAGGTGGC ACTTTTCGGG
      AAACACCACG CATGCCCCAA CTCTTCGCCA CATTCACTTG ACGTCCACCG TGAAAAGCCC
7201  GAAATGTGCG CGGAACCCCT ATTTGTTTAT TTTTCTAAAT ACATTCAAAT ATGTATCCGC
      CTTTACACGC GCCTTGGGA TAAACAAATA AAAAGATTTA TGTAAGTTTA TACATAGGCG
7261  TCATGAGACA ATAACCCTGA TAAATGCTTC AATAATATTG AAAAAGGAAG AGTATGAGTA
      AGTACTCTGT TATTGGGACT ATTTACGAAG TTATTATAAC TTTTTCCTTC TCATACTCAT
7321  TTCAACATTT CCGTGTCGCC CTTATTCCCT TTTTTGCGGC ATTTTGCCTT CCTGTTTTTG
      AAGTTGTAAA GGCACAGCGG GAATAAGGGA AAAAACGCCG TAAAACGGAA GGACAAAAAC
7381  CTCACCCAGA AACGCTGGTG AAAGTAAAAG ATGCTGAAGA TCAGTTGGGT GCACGAGTGG
      GAGTGGGTCT TTGCGACCAC TTTCATTTTC TACGACTTCT AGTCAACCCA CGTGCTCACC
7441  GTTACATCGA ACTGGATCTC AACAGCGGTA AGATCCTTGA GAGTTTTCGC CCCGAAGAAC
      CAATGTAGCT TGACCTAGAG TTGTCGCCAT TCTAGGAACT CTCAAAAGCG GGGCTTCTTG
7501  GTTTTCCAAT GATGAGCACT TTTAAAGTTC TGCTATGTGG CGCGGTATTA TCCCGTGTTG
      CAAAAGGTTA CTACTCGTGA AAATTTCAAG ACGATACACC GCGCCATAAT AGGGCACAAC
7561  ACGCCGGGCA AGAGCAACTC GGTCGCCGCA TACACTATTC TCAGAATGAC TTGGTTGAGT
      TGCGGCCCGT TCTCGTTGAG CCAGCGGCGT ATGTGATAAG AGTCTTACTG AACCAACTCA
7621  ACTCACCAGT CACAGAAAAG CATCTTACGG ATGGCATGAC AGTAAGAGAA TTATGCAGTG
      TGAGTGGTCA GTGTCTTTTC GTAGAATGCC TACCGTACTG TCATTCTCTT AATACGTCAC
7681  CTGCCATAAC CATGAGTGAT AACACTGCGG CCAACTTACT TCTGACAACG ATCGGAGGAC
      GACGGTATTG GTACTCACTA TTGTGACGCC GGTTGAATGA AGACTGTTGC TAGCCTCCTG
7741  CGAAGGAGCT AACCGCTTTT TTGCACAACA TGGGGGATCA TGTAACTCGC CTTGATCGTT
      GCTTCCTCGA TTGGCGAAAA AACGTGTTGT ACCCCCTAGT ACATTGAGCG GAACTAGCAA
7801  GGGAACCGGA GCTGAATGAA GCCATACCAA ACGACGAGCG TGACACCACG ATGCCTGCAG
      CCCTTGGCCT CGACTTACTT CGGTATGGTT TGCTGCTCGC ACTGTGGTGC TACGGACGTC
7861  CAATGGCAAC AACGTTGCGC AAACTATTAA CTGGCGAACT ACTTACTCTA GCTTCCCGGC
      GTTACCGTTG TTGCAACGCG TTTGATAATT GACCGCTTGA TGAATGAGAT CGAAGGGCCG
7921  AACAATTAAT AGACTGGATG GAGGCGGATA AAGTTGCAGG ACCACTTCTG CGCTCGGCCC
      TTGTTAATTA TCTGACCTAC CTCCGCCTAT TTCAACGTCC TGGTGAAGAC GCGAGCCGGG
7981  TTCCGGCTGG CTGGTTTATT GCTGATAAAT CTGGAGCCGG TGAGCGTGGG TCTCGCGGTA
      AAGGCCGACC GACCAAATAA CGACTATTTA GACCTCGGCC ACTCGCACCC AGAGCGCCAT
8041  TCATTGCAGC ACTGGGGCCA GATGGTAAGC CCTCCCGTAT CGTAGTTATC TACACGACGG
      AGTAACGTCG TGACCCCGGT CTACCATTCG GGAGGGCATA GCATCAATAG ATGTGCTGCC
8101  GGAGTCAGGC AACTATGGAT GAACGAAATA GACAGATCGC TGAGATAGGT GCCTCACTGA
      CCTCAGTCCG TTGATACCTA CTTGCTTTAT CTGTCTAGCG ACTCTATCCA CGGAGTGACT
8161  TTAAGCATTG GTAACTGTCA GACCAAGTTT ACTCATATAT ACTTTAGATT GATTTATGGT
      AATTCGTAAC CATTGACAGT CTGGTTCAAA TGAGTATATA TGAAATCTAA CTAAATACCA
```

Figure 2 Cont'd

```
8221  GCACTCTCAG TACAATCTGC TCTGATGCCG CATAGTTAAG CCAGTATACA CTCCGCTATC
      CGTGAGAGTC ATGTTAGACG AGACTACGGC GTATCAATTC GGTCATATGT GAGGCGATAG
8281  GCTACGTGAC TGGGTCATGG CTGCGCCCCG ACACCCGCCA ACACCCGCTG ACGCGCCCTG
      CGATGCACTG ACCCAGTACC GACGCGGGGC TGTGGGCGGT TGTGGGCGAC TGCGCGGGAC
8341  ACGGGCTTGT CTGCTCCCGG CATCCGCTTA CAGACAAGCT GTGACCGTCT CCGGGAGCTG
      TGCCCGAACA GACGAGGGCC GTAGGCGAAT GTCTGTTCGA CACTGGCAGA GGCCCTCGAC
8401  CATGTGTCAG AGGTTTTCAC CGTCATCACC GAAACGCGCG AGGCAGCAAG GAGATGGCGC
      GTACACAGTC TCCAAAAGTG GCAGTAGTGG CTTTGCGCGC TCCGTCGTTC CTCTACCGCG
8461  CCAACAGTCC CCCGGCCACG GGGCCTGCCA CCATACCCAC GCCGAAACAA GGGCTCATGA
      GGTTGGTCAGG GGGCCGGTGC CCCGGACGGT GGTATGGGTG CGGCTTTGTT CGCGAGTACT
8521  GCCCGAAGTG GCGAGCCCGA TCTTCCCCAT CGGTGATGTC GGCGATATAG GCGCCAGCAA
      CGGGCTTCAC CGCTCGGGCT AGAAGGGGTA GCCACTACAG CCGCTATATC CGCGGTCGTT
8581  CCGCACCTGT GGCGCCGGTG ATGCCGGCCA CGATGCGTCC GGCGTAGAGG ATCCTTTTTG
      GGCGTGGACA CCGCGGCCAC TACGGCCGGT GCTACGCAGG CCGCATCTCC TAGGAAAAAC
8641  TCCGGTGTTG GGTTGAAGGT GAAGCCGGTC GGGGCGGCAG CGGGGGCGG CTTTTCAGCC
      AGGCCACAAC CCAACTTCCA CTTCGGCCAG CCCCGGCGTC GCCCCGGCC GAAAAGTCGG
8701  TTGCCCCCCT GCTTCGGCCG CCGTGGCTCC GGCGTCTTGG GTGCCGGCGC GGGTTCCGCA
      AACGGGGGGA CGAAGCCGGC GGCACCGAGG CCGCAGAACC CACGGCCGCG CCCAAGGCGT
8761  GCCTTGGCCT GCGGTGCGGG CACATCGGCG GGCTTGGCCT TGATGTGCCG CCTGGCGTGC
      CGGAACCGGA CGCCACGCCC GTGTAGCCGC CCGAACCGGA ACTACACGGC GGACCGCACG
8821  GAGCGGAACG TCTCGTAGGA GAACTTGACC TTCCCCGTTT CCCGCATGTG CTCCCAAATG
      CTCGCCTTGC AGAGCATCCT CTTGAACTGG AAGGGGCAAA GGGCGTACAC GAGGGTTTAC
8881  GTGACGAGCG CATAGCCGGA CGCTAACGCC GCCTCGACAT CCGCCCTCAC CGCCAGGAAC
      CACTGCTCGC GTATCGGCCT GCGATTGCGG CGGAGCTGTA GGCGGGAGTG GCGGTCCTTG
8941  GCAACGGCAG CCTCATCACG CCGGCGCGAA TTGGCCGCGC GGGATTCAAC CCACTCGGCC
      CGTTGGCGTC GGAGTAGTGC GGCCGCGAAG AACCGGCGCG CCCTAAGTTG GGTGAGCCGG
9001  AGCTCGTCGG TGTAGCTCTT TGGCATCGTC TCTCGCCTGT CCCCTCAGTT CAGTAATTTC
      TCGAGCAGCC ACATCGAGAA ACCGTAGCAG AGAGCGGACA GGGGAGTCAA GTCATTAAAG
9061  CTGCATTTGC CTGTTTCCAG TCGGTAGATA TTCCACAAAA CAGCAGGGAA GCAGCGCTTT
      GACGTAAACG GACAAAGGTC AGCCATCTAT AAGGTGTTTT GTCGTCCCTT CGTCGCGAAA
9121  TCCGCTGCAT AACCCTGCTT CGGGGTCATT ATAGCCGATTT TTTCGGTATA TCCATCCTTT
      AGGCGACGTA TTGGGACGAA GCCCCAGTAA TATCGCTAAA AAAGCCATAT AGGTAGGAAA
9181  TTCGCACGAT ATACAGGATT TTGCCAAAGG GTTCGTGTAG ACTTTCCTTG GTGTATCCAA
      AAGCGTGCTA TATGTCCTAA AACGGTTTCC CAAGCACATC TGAAAGGAAC CACATAGGTT
9241  CGGCGTCAGC CGGGCAGGAT AGGTGAAGTA GGCCCACCCG CGAGCGGGTG TTCCTTCTTC
      GCCGCAGTCG GCCCGTCCTA TCCACTTCAT CCGGGTGGGC GCTCGCCCAC AAGGAAGAAG
9301  ACTGTCCCTT ATTCGCACCT GGCGGTGCTC AACGGGAATC CTGCTCTGCG AGGCTGGCCG
      TGACAGGGAA TAAGCGTGGA CCGCCACGAG TTGCCCTTAG GACGAGACGT CCGACCGGC
9361  GCTACCGCCG GCGTAACAGA TGAGGGCAAG CGGATGGCTG ATGAAACCAA GCCAACCAGG
      CGATGGCGGC CGCATTGTCT ACTCCCGTTC GCCTACCGAC TACTTTGGTT CGGTTGGTCC
9421  AAGGGCCAGCC CACCTATCAA GGTGTACTGC CTTCCAGACG AACGAAGAGC GATTGAGGAA
      TTCCCGTCGG GTGGATAGTT CCACATGACG GAAGGTCTGC TTGCTTCTCG CTAACTCCTT
9481  AAGGCGGCGG CGGCCGGCAT GAGCCTGTCG GCCTACCTGC TGGCCGTCGG CCAGGGCTAC
      TTCCGCCGCC GCCGGCCGTA CTCGGACAGC CGGATGGACG ACCGGCAGCC GGTCCCGATG
9541  AAAATCACGG GCGTCGTGGA CTATGAGCAC GTCCGCGAGC TGGCCCGCAT CAATGGCGAC
      TTTTAGTGCC CGCAGCACCT GATACTCGTG CAGGCGCTCG ACCGGGCGTA GTTACCGCTG
9601  CTGGGCCGGCC TGGGCGGCCT GCTGAAACTC TGGCTCACCG ACGACCCGGC CACGGCGCGG
      GACCCGGCGG ACCCGCCGGA CGACTTTGAG ACCGAGTGGC TGCTGGGCGC GTGCCGCGCC
9661  TTCGGTGATG CCACGATCCT CGCCCTGCTG GCGAAGATCG AAGAGAAGCA GGACGAGCTT
      AAGCCACTAC GGTGCTAGGA GCGGACGAC CGCTTCTAGC TTCTCTTCGT CCTGCTCGAA
9721  GGCAAGGTCA TGATGGGCGT GGTCCGCCCG AGGGCAGAGC CATGACTTTT TTAGCCGCTA
      CCGTTCCAGT ACTACCCGCA CCAGGCGGAA TCCCGTCTCG GTACTGAAAA AATCGGCGAT
9781  AAACGGCCGG GGGGTGCGCG TGATTGCCAA GCACGTCCCC ATGCGCTCCA TCAAGAAGAG
      TTTGCCGGCC CCCCACGCGC ACTAACGGTT CGTGCAGGGG TACGCGAGGT AGTTCTTCTC
9841  CGACTTCGCG GAGCTGGTGA AGTACATCAC CGACGAGCAA GGCAAGACGG AGCGCCTGGG
      GCTGAAGCGC CTCGACCACT TCATGTAGTG GCTGCTCGTT CCGTTCTGCC TCGCGGACCC
9901  TCACGTGCGC GTCACGAACT GCGAGGCAAA CACCCTGCCC GCTGTCATGG CCGAGGTGAT
      AGTGCACGCG CAGTGCTTGA CGCTCCGTTT GTGGGACGGG CGACAGTACC GGCTCCACTA
9961  GGCGACCCAG CACGGCAACA CCCGTTCCGA GGCCGACAAG ACCTATCACC TGCTGGTTAG
      CCGCTGGGTC GTGCCGTTGT GGGCAAGGCT CCGGCTGTTC TGGATAGTGG ACGACCAATC
10021 CTTCCGCGCG GGAGAGAAGC CCGACGCGGA GACGTTGCGC GCGATTGAGG ACCGCATCTG
      GAAGGCGCGC CCTCTCTTCG GGCTGCGCCT CTGCAACGCG CGCTAACTCC TGGCGTAGAC
10081 CGCTGGGCTT GGCTTCGCCG AGCATCAGCG CGTCAGTGCC GTGCATCACG ACACCGACAA
      GCGACCCGAA CCGAAGCGGC TCGTAGTCGC GCAGTCACGG CACGTAGTGC TGTGGCTGTT
10141 CCTGCACATC CATATCGCCA TCAACAAGAT TCACCCGACC CGAAACACCA TCCATGAGCC
      GGACGTGTAG GTATAGCGGT AGTTGTTCTA AGTGGGCTGG GCTTTGTGGT AGGTACTCGG
10201 GTATCGGGCC TACCGCGCCC TGCTGACCT CTGCGCGACG CTCGAACGGG ACTACGGGCT
      CATAGCCCGG ATGGCGCGGG AGCGACTGGA GACGCGCTGC GAGCTTGCCC TGATGCCCGA
10261 TGAGCGTGAC AATCACGAAA CGCGGCAGCG CGTTTCCGAG AACGCGCGA ACGACATGGA
      ACTCGCACTG TTAGTGCTTT GCGCCGTCGC GCAAAGGCTC TTGGCGCGCT GCTGTACCT
10321 GCGGCACGCG GCGTGGAAA GCCTGGTCGG CTGGATCCGG CCACGATGCG TCCGGCGTAG
```

Figure 2 Cont'd

```
          CGCCGTGCGC CCGCACCTTT CGGACCAGCC GACCTAGGCC GGTGCTACGC AGGCCGCATC
10381     AGGATCTGAA GATCAGCAGT TCAACCTGTT GATAGTACGT ACTAAGCTCT CATGTTTCAC
          TCCTAGACTT CTAGTCGTCA AGTTGGACAA CTATCATGCA TGATTCGAGA GTACAAAGTG
10441     GTACTAAGCT CTCATGTTTA ACGTACTAAG CTCTCATGTT TAACGAACTA AACCCTCATG
          CATGATTCGA GAGTACAAAT TGCATGATTC GAGAGTACAA ATTGCTTGAT TTGGGAGTAC
10501     GCTAACGTAC TAAGCTCTCA TGGCTAACGT ACTAAGCTCT CATGTTTCAC GTACTAAGCT
          CGATTGCATG ATTCGAGAGT ACCGATTGCA TGATTCGAGA GTACAAAGTG CATGATTCGA
10561     CTCATGTTTG AACAATAAAA TTAATATAAA TCAGCAACTT AAATAGCCTC TAAGGTTTTA
          GAGTACAAAC TTGTTATTTT AATTATATTT AGTCGTTGAA TTTATCGGAG ATTCCAAAAT
                                                        HindIII
                                                        ~~~~~~
10621     AGTTTTATAA GAAAAAAAAG AATATATAAG GCTTTAAAGC TTTTAAGGTT TAACGGTTGT
          TCAAAATATT CTTTTTTTTC TTATATATTC CGAAATTTCG AAAATTCCAA ATTGCCAACA
10681     GGACAACAAG CCAGGGATGT AACGCACTGA GAAGCCCTTA GAGCCTCTCA AAGCAATTTT
          CCTGTTGTTC GGTCCCTACA TTGCGTGACT CTTCGGGAAT CTCGGAGAGT TTCGTTAAAA
10741     GAGTGACACA GGAACACTTA ACGGCTGACA TGGGAATTCC ACATGTGGAA TTCCACATGT
          CTCACTGTGT CCTTGTGAAT TGCCGACTGT ACCCTTAAGG TGTACACCTT AAGGTGTACA
                                                        XmaI                  SphI
                                                        ~~~~~~                ~~~~~~
10801     GGAATTGTGA GCGGATAACA ATTTGTGGAA TTCCCGGGAG AGCTCGATAT CGCATGCCCT
          CCTTAACACT CGCCTATTGT TAAACACCTT AAGGGCCCTC TCGAGCTATA GCGTACGGGA
10861     GGAGGAATAC GTGGATAAAA TTTTCGTCGA TGAAGCAGTA AGTGAACTGC ATACCATTCA
          CCTCCTTATG CACCTATTTT AAAAGCAGCT ACTTCGTCAT TCACTTGACG TATGGTAAGT
10921     GGACATGTTG CGCTGGGCGG TAAGCCGCTT TAGCGCGGCG AATATCTGGT ATGGACACGG
          CCTGTACAAC GCGACCCGCC ATTCGGCGAA ATCGCGCCGC TTATAGACCA TACCTGTGCC
10981     TACCGATAAC CCGTGGGATG AAGCGGTACA ACTGGTGTTG CCGTCTCTTT ATCTGCCGCT
          ATGGCTATTG GGCACCCTAC TTCGCCATGT TGACCACAAC GGCAGAGAAA TAGACGGCGA
11041     GGATATTCCG GAGGATATGC GGACCGCGCG GCTGACGTCC AGCGAAAGAC ACCGCATTGT
          CCTATAAGGC CTCCTATACG CCTGGCGCGC CGACTGCAGG TCGCTTTCTG TGGCGTAACA
11101     CGAGCGAGTG ATTCGTCGCA TTAACGAGCG TATCCGGTA GCCTACCTGA CCAATAAAGC
          GCTCGCTCAC TAAGCAGCGT AATTGCTCGC ATAGGGCCAT CGGATGGACT GGTTATTTCG
11161     CTGGTTCTGC GGCCACGAAT TTTATGTTGA TGAGCGCGTG CTGGTGCCGC GTTCACCGAT
          GACCAAGACG CCGGTGCTTA AAATACAACT ACTCGCGCAC GACCACGGCG CAAGTGGCTA
11221     TGGCGAGCTG ATTAATAACC ACTTCGCTGG CCTTATTAGC CAACAGCCGA AATATATTCT
          ACCGCTCGAC TAATTATTGG TGAAGCGACC GGAATAATCG GTTGTCGGCT TTATATAAGA
11281     GGATATGTGT ACCGGCAGCG GCTGCATCGC CATCGCCGT GCTTATGCTT TCCCGGACGC
          CCTATACACA TGGCCGTCGC CGACGTAGCG GTAGCGGACA CGAATACGAA AGGGCCTGCG
11341     AGAGGTTGAT GCGGTCGATA TTTCGCCGGA TGCGCTGGCT GTCGCCGAGC ATAACATTGA
          TCTCCAACTA CGCCAGCTAT AAAGCGGCCT ACGCGACCGA CAGCGGCTCG TATTGTAACT
11401     AGAACACGGT CTTATCCATC ACGTGACGCC AATCCGTTCC GATCTGTTCC GCGATCTGCC
          TCTTGTGCCA GAATAGGTAG TGCACTGCGG TTAGGCAAGG CTAGACAAGG CGCTAGACGG
11461     GAAAGTTCAG TACGATCTGA TTGTCACTAA CCCGCCTTAT GTCGATGCGG AGGATATGTC
          CTTTCAAGTC ATGCTAGACT AACAGTGATT GGGCGGAATA CAGCTACGCC TCCTATACAG
11521     CGATCTGCCG AACGAATATC GCCACGAACC TGAGCTGGGG CTGGCGTCCG GCACTGACGG
          GCTAGACGGC TTGCTTATAG CGGTGCTTGG ACTCGACCCC GACCGCAGGC CGTGACTGCC
11581     CCTCGAATTG ACCCGCCGTA TCCTGGGAAA TGCGCCGGAT TATCTGTCCG ATGATGCGT
          GGAGTTAAC TGGGCGGCAT AGGACCCTTT ACGCGGCCTA ATAGACAGGC TACTACGCA
11641     TCTGATTTGT GAAGTCGGAA ACAGCATGGT ACATCTGATG GAGCAGTATC GGATGTGCC
          AGACTAAACA CTTCAGCCTT TGTCGTACCA TGTAGACTAC CTCGTCATAG GCCTACACGG
11701     GTTCACCTGG CTGGAGTTTG ACAACGGCGG CGATGGCGTC TTTATGTTGA CCAAAGCGCA
          CAAGTGGACC GACCTCAAAC TGTTGCCGCC GCTACCGCAG AAATACAACT GGTTTCGCGT
11761     GTTGCTCGCG GCCCGTGAAC ATTTCAATAT TTATAAGAT TAAAACACGC AAACGACAAC
          CAACGAGCGC CGGGCACTTG TAAAGTTATA AATATTTCTA ATTTTGTGCG TTTGCTGTTG
11821     AACGATAACG GAGCCGTGAT GGCAGGAAAC ACAATTGGAC AACTCTTTCG CGTAACCACT
          TTGCTATTGC CTCGGCACTA CCGTCCTTTG TGTTAACCTG TTGAGAAAGC GCATTGGTGA
11881     TTCGGCGAAT CACACGGGCT GGCGCTTGGG GGTATCGTCG ATGGCGTGCC GCCCGGCATC
          AAGCCGCTTA GTGTGCCCGA CCGCGACCC CCATAGCAGC TACCGCACGG CGGGCCGTAG
11941     CCGTTGACGG AGGCCGATCT GCAGCACGAT CTCGACAGAC GCCGCCCTGC CACCTCGCGC
          GGCAACTGCC TCCGGCTAGA CGTCGTGCTA GAGCTGTCTG CGGCGGGACG GTGGAGCGCG
12001     TATACTACTC AGCGCCGCGA ACCGGACCAG GTAAAAATTC TCTCCGGCGT GTTTGATGGC
          ATATGATGAG TCGCGGCGCT TGGCCTGGTC CATTTTTAAG AGAGGCCGCA CAAACTACCG
                   XhoI
                   ~~
12061     GTAACGACCG GC
          CATTGCTGGC CG
```

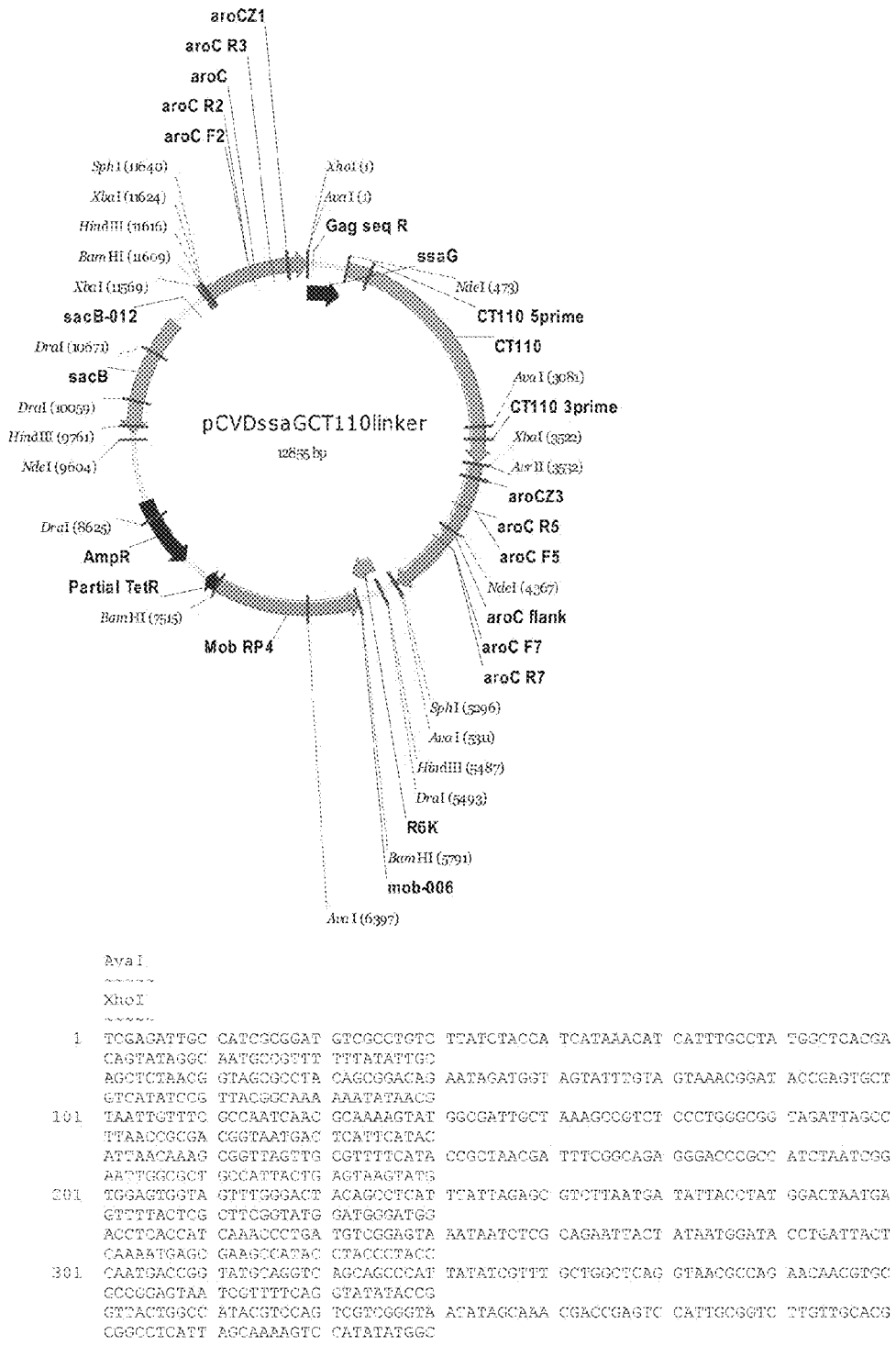
Figure 3 (SEQ ID NO:9)

Figure 3 Cont'd

```
 401  GATGTTCATT GCTTTCTAAA TTTTGCTATG TTGCCAGTAT CCTTACGATG TATTTATTTT AAGGAAAAGC
      CATATGGAAA CCAGCTTCCA TAAATTCTTC
      CTACAACTAA CGAAACATTT AAAACCATAC AACGGTCATA GGAATCCTAC ATAAATAAAA TTCCTTTTCG
      GTATACCTTT GGTCGAAGGT ATTTAAGAAG
 501  CTGTCTATGA TCCTGGCGTA CAGCTGCTGT TCTCTGAACG GTGGTGGTTA TGCGGCGAA ATTATGGTTC
      CGCAGGGTAT CTACGATGGT GAAACCCTGA
      GACAGATACT AGGACCGCAT GTCGACGACA AGAGACTTGC CACCACCAAT ACGCCGCCTT TAATACCAAG
      GCGTCCCATA GATGCTACCA CTTTGGGACT
 601  CCGTGTCTTT CCCGTATACC GTTATCGGTG ATCCGAGCGG TACGACCGTT TTCAGCGCCG GTGAACTGAC
      CCTGAAAAAC CTGGATAATA GCATTGCGGC
      GGCACAGAAA GGGCATATGG CAATAGCCAC TAGGCTCGCC ATGCTGGCAA AAGTCGCGGC CACTTGACTG
      GGACTTTTTG GACCTATTAT CGTAACGCCG
 701  GCTGCCGCTG TCTTGCTTCG GTAACCTGCT GGGTTCTTTC ACCGTTCTGG GTCGTGGCCA TAGCCTGACC
      TTTGAAAACA TTCGTACCAG CACCAATGGT
      CGACGGCGAC AGAACGAAGC CATTGGACGA CCCAAGAAAG TGGCAAGACC CAGCACCGGT ATCGGACTGG
      AAACTTTTGT AAGCATGGTC GTGGTTACCA
 801  GCGGCGCTGT CTAATAGCGC GGCGGATGGT CTGTTCACCA TTGAAGGTTT CAAAGAACTG TCTTTCTCTA
      ACTGCAATAG CCTGCTGGCG GTTCTGCCGG
      CGCCGCGACA GATTATCGCG CCGCCTACCA GACAAGTGGT AACTTCCAAA GTTCTTGAC AGAAAGAGAT
      TGACGTTATC GGACGACCGC CAAGACGGCC
 901  CGGCGACCAC CAACAAAGGC AGCCAGACCC CGACCACCAC GAGCACCCCG TCTAACGGCA CCATCTACAG
      CAAAACCGAT CTGCTGCTGC TGAACAACGA
      GCCGCTGGTG GTTGTTTCCG TCGGTCTGGG GCTGGTGGTG CTCGTGGGGC AGATTGCCGT GGTAGATGTC
      GTTTTGGCTA GACGACGACG ACTTGTTGCT
1001  AAAATTCTCT TTTTATAGCA ACCTGGTTTC TGGTGATGGT GGTGCGATTG ATGCGAAAAG CCTGACCGTT
      CAGGGTATCT CTAAACTGTG CGTTTTCCAG
      TTTTAAGAGA AAAATATCGT TGGACCAAAG ACCACTACCA CCACGCTAAC TACGCTTTTC GGACTGGCAA
      GTCCCATAGA GATTTGACAC GCAAAAGGTC
1101  GAAACACCCG CGCAGGCGGA TGGCGGTGCG TGCCAGGTTG TTACCTCTTT CAGCGCGATG GCCAATGAAG
      CGCCGATTGC GTTTGTTGCC AACGTGGCGG
      CTTTTGTGGC GCGTCCGCCT ACCGCCACGC ACGGTCCAAC AATGGAGAAA GTCGCGCTAC CGGTTACTTC
      GCGGCTAACG CAAACAACGG TTGCACCGCC
1201  GTGTTCGTGG TGGTGGTATC GCGGCCGTGC AGGATGGTCA GCAGGGTGTG AGCTCTTCTA CCTCTACCCA
      AGATCCGGTG GTGAGCTTCA GCCGTAACAC
      CACAAGCACC ACCACCATAG CGCCGGCACG TCCTACCAGT CGTCCCACAC TGGAGAAGAT GGAGATGGCT
      TCTAGGCCAC CACTCGAAGT CGGCATTGTG
1301  CGGCGGTGGAA TTTGATGGTA ACGTGGCGCG CGTTGGTGGT GGTATCTACA GCTACGGTAA CGTGGCGTTC
      CTGAACAATG GTAAAACCCT GTTCCTGAAT
      GCGCCACCTT AAACTACCAT TGCACCGCGC GCAACCACCA CCATAGATGT CGATGCCATT GCACCGCAAG
      GACTTGTTAC CATTTTGGGA CAAGGACTTA
1401  AACGTTGCGA GCCCGGTGTA TATTGCGGCA AAACAGCCGA CCTCTGGTCA GGCGTCTAAC ACCAGCAATA
      ACTACGGCGA TGGTGGCGCC ATTTCTGCA
      TTGCAACGCT CGGGCCACAT ATAACGCCGT TTTGTCGGCT GGAGACCAGT CCGCAGATTG TGGTCGTTAT
      TGATGCCGCT ACCACCGCGG TAAAGACGT
1501  AAAACGGTGC GCAGGCGGGC AGCAACAACT CTGGCAGCGT GAGCTTCGAT GGCGAAGGCG TGGTGTTTTT
      CAGCTCTAAT GTGGCGGCGG GTAAAGGCGG
      TTTTGCCACG CGTCCGCCCG TCGTTGTTGA GACCGTCGCA CTCGAAGCTA CCGCTTCCGC ACCACAAAAA
      GTCGAGATTA CACCGCCGCC CATTTCCGCC
1601  CGCGATTTAT GCGAAAAAAC TGTCTGTTGC GAACTGCGGC CCGGTGCAGT TCCTGCGTAA CATTGCGAAC
      GATGGTGGTG CGATCTACCT GGGTGAAAGC
      GCGCTAAATA CGCTTTTTTG ACAGACAACG CTTGACGCCG GGCCACGTCA AGGACGCATT GTAACGCTTG
      CTACCACCAC GCTAGATGGA CCCACTTTCG
1701  GGCGAACTGT CTCTGACCGC GGATTATGCC GATATTATCT TCGATGGTAA CATTAAACGT ACCGCGAAAG
      AAAACGCGGC GGATGTGAAC GGTGTGACCG
      CCGCTTGACA GAGACTCGCG CCTAATACCG CTATAATAGA AGCTACCATT GTAATTGCA TGGCGCTTTC
      TTTTGCGCCG CCTACACTTG CCACACTGGC
1801  TGTCTTCTCA GGCGATTAGC ATGGGTAGCG GCGGCAAAAT TACCACCCTG CGTGCGAAAG CGGGTCATCA
      GATCCTGTTC AACGATCCGA TCGAAATGGC
      ACAGAAGAGT CCGCTAATCG TACCCATCGC CGCCGTTTTA ATGGTGGGAC GCACGCTTTC GCCCAGTAGT
      CTAGGACAAG TTGCTAGGCT AGCTTTACCG
1901  GAACGGTAAT AACCAGCCGG CGCAGTCTTC TAAACTGCTG AAAATTAACG ATGGTGAAGG TTACACCGGT
      GATATTGTGT TCGCGAACGG TTCTAGCACC
      CTTGCCATTA TTGGTCGGCC GCGTCAGAAG ATTTGACGAC TTTTAATTGC TACCACTTCC AATGTGGCCA
      CTATAACACA AGCGCTTGCC AAGATCGTGG
2001  CTGTATCAGA ACGTTACCAT CGAACAGGGC CGTATCGTTC TGCGTGAAAA AGCGAAACTG TCTGTTAACA
      GCCTGAGCCA GACCGGTGGT AGCCTGTATA
      GACATAGTCT TGCAATGGTA GCTTGTCCCG GCATAGCAAG ACGCACTTTT TCGCTTTGAC AGACAATTGT
      CGGACTCGGT CTGGCCACCA TCGGACATAT
2101  TGGAAGCGGG TTCTACCCTG GATTTCGTTA CCCCGCAGCC GCCGCAGCAG CCGCCGGCGG CGAATCAGCT
      GATCACCCTG AGCAACCTGC ATCTGTCTCT
```

Figure 3 Cont'd

```
          ACCTTCGCCC AAGATGGGAC CTAAAGCAAT GGGGCGTCGG CGGCGTCGTC GGCGGCCGCC GCTTAGTCGA
          CTAGTGGGAC TCGTTGGACG TAGACAGAGA
     2201 GTCTTCTCTG CTGGCGAACA ACGCGGTTAC CAACCCGCCG ACCAACCCGC CGGCGCAGGA TTCTCATCCG
          GCGGTCATTG GTAGCACCAC CGCGGGTAGC
          CAGAAGAGAC GACCGCTTGT TGCGCCAATG GTTGGGCGGC TGGTTGGGCG GCCGCGTCCT AAGAGTAGGC
          CGCCACTAAC CATCGTGGTG GCGCCCATC
     2301 CTTACCATTT CTGCTCCCAT TTTCTTTGAA CATCTCGATG ATACCCCCTA CGATCCGTAC GATTCGGTCG
          GTAGCAACCA GAAAATCAAC GTTCTGAAAC
          CAATGGTAAA GACCAGGCTA AAAGAAACTT CTAGACCTAC TATGGCGCAT GCTAGCGATG CTAACCGACC
          CATCGTTGGT CTTTTAGTTG CAAGACTTTG
     2401 TGCAACTGGG CACCAAACCG CCGGCGAACG CGCCGTCTGA TCTGACCCTG GGTAACGAAA TGCCGAAATA
          TCGTTACCAC GGTTCTTCGA AACTGGGCTC
          ACGTTGACCC GTGGTTTGGC GGCCGCTTGC GCGGCAGACT AGACTGGGAC CCATTGCTTT ACGGCTTTAT
          ACCGATGGTC CCAAGAACCT TTGACCGCAC
     2501 GGACCCGAAC ACCGCGAACA ACGGTCCGTA CACCCTGAAA GCGACCTGGA CCAAAACCGG TTACAATCCG
          GGCCCGGAAC GTGTTGCGTC TCTGGTTCCG
          CCTGGGCTTG TGGCGCTTGT TGCCAGGCAT GTGGGACTTT CGCTGGACCT GGTTTTGGCC AATGTTAGGC
          CCGGGCCTTG CACAACGCAG AGACCAAGGC
     2601 AACTCTCTGT GGGGCAGCAT TCTGGATATT CGCAGCGCGC ATTCTGCGAT CCAGGCGAGC GTGGATGGTC
          GTAGCTATTG CCGCGGTCTG TGGGTTAGCG         CT110
          TTGAGAGACA CCCCGTCGTA AGACCTATAA GCGTCGCGCG TAAGACGCTA GGTCCGCTCG CACCTACCAG
          CATCGATAAC GGCGCCAGAC ACCCAATCGC
     2701 GTGTTCTAA CTTCTTCTAT CATGATCGCG ATGCGCTGGG CCAGGCTAT CGCTATATTA GCGGTGGTTA
          TAGCCTGGGT GCGAACAGCT ATTTCGGTAG
          CACAAAGATT GAAGAAGATA GTACTAGCGC TACGCGACCC GGTCCCGATA GCGATATAAT CGCCACCAAT
          ATCGGACCCA CGCTTGTCGA TAAAGCCATC
     2801 CAGCATGTTC GGCCTGGCGT TCACCGAAGT TTTTGGTCGT TCTAAAGATT ATGTTGTGTG CCGTAGCAAC
          GTCGTACAAG CCGGACCGCA AGTGGCTTCA AAAACCAGCA AGATTCTAA TACAACACAC GGCATCGTTG
          GTAGTACGCA CGTAACCAAG ACAAATAGAC
     2901 AGCACCCAGC AGGCGCTGTG CGGTTCTTAT CTGTTGGGCG ATGCGTTCAT CCGTGCGTCT TATGGTTTCG
          GCAACCAGCA CATGAAAACC AGCTATACCT
          TCGTGGGTCG TCCGCGACAC GCCAAGAATA GACAAACCGC TACGCAAGTA GGCACGCAGA ATACCAAAGC
          CGTTGGTCGT GTACTTTTGG TCGATATGGA

AvaI
          ~~~~~~~
     3001 TTGCGGAAGA AAGCGATGTT CGTTGGGATA CAACTGCCT GGCGGGTGAA ATTGGTGCGG GCCTGCCGAT
          CGTTATCACC CCGAGCAAAC TGTATCTGAA
          AACGCCTTCT TTCGCTACAA GCAACCCTAT TGTTGACGGA CCGCCCACTT TAACCACGCC CGGACGGCTA
          GCAATAGTGG GGCTCGTTTG ACATAGACTT
     3101 CCAACTGCGC CCGTTTGTGC AGGCGGAATT TTCTTACGCC AACCATGAAT CTTTTACCCA AGAACGTCAT
          CAGGCCGGTG CGTTCAAAAG CGGTCATCTG
          GCTTGACGCG GGCAAACACG TCCGCCTTAA AAGAATGCGC TTGGTACTTA GAAAATGGCT TCTTCCACTA
          GTCCGGCCAC GCAAGTTTTC GCCAGTAGAC
     3201 CTGAACCTGA GCGTGCCGGT TGGCGTGAAA TTTGATCGTT GCAGCTCTAC CCATCCGAAC AAATACAGCT
          TTATGGCCGC GTATATCTGT GATGCGTATC
          GACTTCGACT CGCACGGCCA ACCGCACTTT AAACTAGCAA CGTCGAGATG GGTAGGCTTG TTTATGTCGA
          AATACCGGCC CATATAGACA CTACGCATAG
     3301 GTACCATTAG CGGCACCGAA ACCACCCTGC TGAGCCATCA GGGCACCTGG ACCACCGATG CGTTTCATCT
          GGCGCGTCAT GGCGTTGTGG TTCGTGGCAG
          CATGGTAATC GCCGTGGCTT TGGTCGGACG ACTCGGTAGT CCCGTGGACC TGGTGGCTAC GCAAAGTAGA
          CCGCGCAGTA CCGCAACACC AAGCACCGTC
     3401 CATGTATGCG AGCCTGACCA GCAACATTGA AGTGTATGGT CATGGTCGTT ATGAATATCG TGATGCGAGC
          CGTGGTTATG GTCTGAGCGC GGGTAGCCGC
          GTACATACGC TCGGACTGGT CGTTGTAACT TCACATACCA GTACCAGCAA TACTTATAGC ACTACGCTCG
          GCACCAATAC CAGACTCGCG CCCATCGGCG
                                                      XbaI        AvrII
                                                      ~~~~~~      ~~~~~~
     3501 GTTCGTTTTT AATAAGGATC TCTAGACTAG CCTAGGTCCA GCATTACCGT GCCGGGACGT ACGATCAACC
          GGATGGGTGA AGAGGTCGAG ATGATCACCA Linker
          CAAGCAAAAA TTATTCCTAG AGATCTGATC GGATCCAGGT CGTAATGGCA CGGCCCTGCA TGCTAGTTGG
          CCTACCCACT TCTCCAGCTC TACTAGTGGT
     3601 AAGGGCGCCA CGATCCGTGT GTGGGGATTC GCGCAGTGCC GATCGCAGAA GTCATGCTGG CGATCGTACT
          GATGGATCAC CTGCTGCGCC ATCGGGCACA
          TTCCCGCGGT GCTAGGCACA CACCCCTAAG CGCGTCACGG CTAGCGTCTT CAGTACGACC GCTAGCATGA
          CTACCTAGTG GACGACGCGG TAGCCCGTGT
     3701 GAATGCGGAT GTAAAGACAG AGATTCCACG CTGGTAAGAA ATGAAAAAAA CCGCGATTGC GCTGCTGGCA
          TGGTTTGTCA GTAGCGCCAG CCTGGCGGCG
```

Figure 3 Cont'd

```
             CTTACGCCTA CATTTCTGTC TCTAAGGTGC GACCATTCTT TACTTTTTTT GGCGCTAACG CGACGACCGT
             ACCAAACAGT CATCGCGGTC GGACCGCCGC
      3801   ACGTCCTGGC AGAAAATAAC CCATCCTCTC CCCGGCCCCG CCCAGTCTAT CGGTACCTTT GCCAACCCAT
             GCATCCATTGG CGCCGACACG TTGCCGGTAC
             TGCAGCACCG TCTTTTATTG GGTAGGACAG GGGCCGCGGC GGGTCAGATA GCCATCGAAA CGGTTGCCTA
             CGTAGTAACC GCCGCTGTGC AACGGCCATG
      3901   AGTCCCATAA TTATCAGGTC ATGCGCACCG ATCACCGCCC TTATTCGGCC CACCCGCATC TGGTCATGTT
             TCAGGGTATT AATAGTCCAC TACGCGTGGC TAGTCGCGGC AATAAAGCCG GTGGGCCTAG ACCAGTACAA
             ATAGGTCGGC AACTCAGTAG TCCGCGTCGT
      4001   ACGGGGGCTC GGAACCGTCC TGATAGGCGA CATGGGGATG CCTGCCGGAG CCGGCTTTAA TGGCGGACAC
             GGCCAGTCATC AGACCGGGCT TGATGTGGAT
             TGCCCCGAG CCTTGGCAGG ACTATCCGCT GTACCCCTAC GGACGGCCTC CGGCGAAATT ACCGCCTGTG
             CGGTCAGTAG TCTGGCCCGA ACTACACCTA
      4101   ATTTTCTTGC AGTTGCCGAA AACGCGCTGG AGCCAGGCGC AGCTATTGCG CCCGCAGGCG TTAGATCTGG
             TGTCCCGGA CGGTAAACAT GTCGTGCCGT
             TAAAAGAACG TCAACGGCTT TTGCGCGACC TCGGTCCGCG TCGATAACGC GGGCGTCCGC AATCTAGACC
             ACAGGGCGCT GCCATTTGTA CAGCACGGCA
      4201   CGCGCTGGTC GTCGGATATC GCCAGTCTGA TCAAACTGGC GGCACAAGAC AATGACGTCA CCCGTATTTT
             CGTCAATCCG GCTATTAAAC AACAGCTTTG
             GCGCGACCAG CAGCCTATAG CGGTCAGACT AGTTTGACCG CCGTGTTCTG TTACTGCAGT GGGCATAAAA
             GCAGTTAGGC CGATAATTTG TTGTCGAAAC
                                                                              NdeI
                                                                              ~~~~~~~~
      4301   CCTCGATGCC GGAAGCGATC GTGACTGGCT ACGTAAAGTA CGCCCCTGGT TCCAGCATCG CGCGCATATG
             CACGTGCGTT TACGCTGCCC TGCCGACAGC
             GGAGCTACGG CCTTCGCTAG CACTGACCGA TGCATTTCAT GCGGGGACCA AGGTCGTAGC GCGCGTATAC
             GTGCACGCAA ATGCGACGGG ACGGCTGTCG
      4401   CTGGAGTCCG AAGATCAACC TTTACCCCCG CCCGGGCGATG GATGCGGCGC TGAACTGCAA AGCTGGTTCG
             AACCGCCAAA ACCTGGCACC ACAAAGCCTG
             GACCTCAGGC TTCTAGTTGG AAATGGGGGC GGCCCGCTAC CTACGCCGCG ACTTGACGTT TCGACCAAGC
             TTGGCGGTTT TGGACCGTGG TGTTTCGGAC
      4501   AGAAGAAGAC ACCGCCGCCG TTGCCGCTTT CCTGCCAGGC GCTACTGGAT GAGCATGTAC TCTGATGGAC
             AATTTTTATG ATCTGTTTAT GGTCTCCCCG
             TCTTCTTCTG TGGCGGCGGC AACGGCGAAA GGACGGTCCG CGATGACCTA CTCGTACATG AGACTACCTG
             TTAAAAATAC TAGACAAATA CCAGACGGGC
      4601   CTGCTGCTGG TGGTGCTGTT TTTTGTCGCC GTACTGGCAG GATTTATCGA TTCTATCGCC GGAGGCGGAG
             GGCTGCTCAC TATCCCTGCG CTGATGGCCG
             GACGACGACC ACCACGACAA AAAACAGCGG CATGACCGTC CTAAATAGCT AAGATAGCGG CCTCCGCCTC
             CCGACGAGTG ATAGGGACCG GACTACCCGC
      4701   CCGGGATGTC GCCGGCAAAC GCGTTGGCGA CCAATAAATT ACAGGCGTGC GGCGGCTCCC TCTCGTCTTC
             GCTCTATTTT ATTCGCCGTA AAGTGGTAAA
             GGCCCTACAG CGGCCGTTTG CGCAACCGCT GGTTATTTAA TGTCCGCACG CCGCCGAGGG AGAGCAGAAG
             CGAGATAAAA TAAGCGGCAT TTCACCATTT
      4801   CCTGGCCGAG CAAAAGCTCA ATATTCTGAT GACGTTCATT GGCTCGATGA GCGGCGCGCT GCTGGTGCAG
             CACGTGCAGG CGGATATTTT GCGCCAGATC
             GGACCGGCTC GTTTCGAGT TATAAGACTA CTGCAAGTAA CCGAGCTACT CGCCGCGCGA CGACCACGTC
             GTGCACGTCC GCCTATAAAA CGCGGTCTAG
      4901   TTGCCCATCC TGGTGATTTT CATCGGCCTC TATTTTTTAT TGATGCCGAA GCTGGGCGAG GAAGATCGCC
             AGCGCCGCCT GTATGGATTA CCGTTCGCGC
             AACGGGTAGG ACCACTAAAA GTAGCCGGAG ATAAAAAATA ACTACGGCTT CGACCCGCTC CTTCTAGCGG
             TCGCGGCGGA CATACCTAAT GGCAAGCGCG
      5001   TGATAGCCGG GGGATGCGTC GGGTTTTACG ACGGCTTTTT CGGGCCTGCC GCAGGGTCGT TTTACGCTCT
             GCCGTTTGTC ACCTTATGTG CTATAACCCT
             ACTATCGGCC CCCTACGCAG CCCAAAATGC TGCCGAAAAA GCCCGGACGG CGTCCAGCA AAATGCGAGA
             CGGCAAACAG TGGAATACAC CGATATTGGA
      5101   GGCGAAATCC ACGGCACATG CCAAAGTGCT TAACGCTACC TCCAACGTTG GCGGCCTGCT GTTATTTATC
             ATCGGCGGCA AAGTGATCTG GGCGACGGGC
             CCGCTTTAGG TGCCGTGTAC GGTTTCACGA ATTGCGATGG AGGTTGCAAC CGCCGGACGA CAATAAATAG
             TAGCCGCCGT TTCACTAGAC CCGCTGCCCG

SphI
             ~~~~~
      5201   TTTGTGATGC TGGTCGGTCA GTTTTTAGGG GCGCGAATGG GGTCGCGTCT GGTGTTGAGC AAAGGCCAAA
             AGCTGGGAGA GCTCGATATC GCATGCGATA
             AAACACTACG ACCAACCAGT CAAAAATCCC CGCGCTTACC CCAGCGCAGA CCACAACTCG TTTCCGGTTT
             TCGACCCTCT CGAGCTATAG CGTACGCTAT
                       AvaI
                       ~~~~~
```

Figure 3 Cont'd

```
5301   TCGAGCTCTC CCGGGAATTC CACAAATTGT TATCCGCTCA CAATTCCACA TGTGGAATTC CACATGTGGA
       AGTCGAGAG  GGCCCTTAAG GTGTTTAACA ATAGGCGAGT GTTAAGGTGT ACACCTTAAG GTGTACACCT
       AGCTCGAGAG GGCCCTTAAG GTGTTTAACA ATAGGCGAGT GTTAAGGTGT ACACCTTAAG GTGTACACCT
       TAAGGGTACA GTCGGCAATT CACAAGGACA

DraI

~~~~~~~

HindII
       ~~~~~~~
5401   GTCACTCAAA ATTGCTTTGA GAGGCTCTAA GGGCTTCTCA GTGCGTTACA TCCCTGGCTT GTTGTCCACA
       AGCGTTAAAC CTTAAAAGCT TTAAAGCCTT
       CAGTGAGTTT TAACGAAACT CTCCGAGATT CCCGAAGAGT CACGCAATGT AGGGACCGAA CAACAGGTGT
       TGGCAATTTG GAATTTTCGA AATTTCGGAA
5501   ATATATTCTT TTTTTTCCTA TAAAACTTAA AACCTTAGAG GCTATTTAAG TTGCTGATTT ATATTAATTT
       TATTGTTCAA ACATGAGAGC TTAGTACGTG
       TATATAAGAA AAAAAAGAAT ATTTTGAATT TTGGAATCTC CGATAAATTC AACGACTAAA TATAATTAAA
       ATAACAAGTT TGTACTCTCG AATCATGCAC
5601   AAACATGAGA GCTTAGTACG TTAGCCATGA GAGCTTAGTA CGTTAGCCAT GAGGGTTTAG TTCGTTAAAC
       ATGAGAGCTT AGTACGTTAA ACATGAGAGC
       TTTGTACTCT CGAATCATGC AATCGGTACT CTCGAATCAT GCAATCGGTA CTCCCAAATC AAGCAATTTG
       TACTCTCGAA TCATGCAATT TGTACTCTCG BamHI ~~~~~~~
5701   TTAGTACGTG AAACATGAGA GCTTAGTACG TACTATCAAC AGGTTGAACT GCTGATCTTC AGATCCTCTA
       CGCCGGACGC ATCGTGGCCG GATCCAGCCG
       AATCATGCAC TTTGTACTCT CGAATCATGC ATGATAGTTG TCCAACTTGA CGACTAGAAG TCTAGGAGAT
       GCGGCCTGCG TAGCACCGGC CTAGGTCGGC
5801   ACCAGGCTTT CCACGCCCGC GTGCCGCTCC ATGTCGTTCG CGCGGTTCTC GGAAACGCGC TGCCGCGTTT
       CGTGATTGTC ACGCTCAAGC CCGTAGTCCC
       TGGTCCGAAA GGTGCGGGCG CACGGCGAGG TACAGCAAGC GCGCCAAGAG CCTTTGCGCG ACGGCGCAAA
       GCACTAACAG TGCGAGTTCG GGCATCAGGG
5901   GTTCGAGCGT CGCGCAGAGG TCAGCGAGGG CGCGGTAGGC CCGATACGGC TCATGGATGG TGTTTCGGGT
       CGGGTGAATC TTGTTGATGG CGATATGGAT
       CAAGCTCGCA GCGCGTCTCC AGTCGCTCCC GCGCCATCCG GGCTATGCCG AGTACCTACC ACAAAGCCCA
       GCCCACTTAG AACAACTACC GCTATACCTA
6001   GTGCAGGTTC TCGGTGTCGT GATGCACGGC ACTGACGCGC TGATGCTCGG CGAAGCCAAG CCCAGCGCAG
       ATGCGGTCCT CAATCGCGCG CAACGTCTCC
       CACGTCCAAC AGCCACAGCA CTACGTGCCG TGACTGCGCG ACTACGAGCC GCTTCGGTTC GGGTCGCGTC
       TACGCCAGGA GTTAGCGCGC GTTGCAGAGG
6101   GCGTCGGGCT TCTCTCCCGC GCGGAAGCTA ACCAGCAGGT GATAGGTCTT GTCGGCCTCG GAACGGGTGT
       TGCCGTGCTG GGTCGCCATC ACCTCGGCCA
       CGCAGCCCGA AGAGAGGGCG CGCCTTCGAT TGGTCGTCCA CTATCCAGAA CAGCCGGAGC CTTGCCCACA
       ACGGCACGAC CCAGCGGTAG TGGAGCCGGT
6201   TGACAGCGGG CAGGGTGTTT GCCTCGCAGT TCGTGACGCG CACGTGACCC AGGCGCTCGG TCTTGCCTTG
       CTCGTCGGTG ATGTACTTCA CCAGCTCCGC
       ACTGTCGCCC GTCCCACAAA CGGAGCGTCA AGCACTGCGC GTGCACTGGG TCCGCGAGCC AGAACGGAAC
       GAGCAGCCAC TACATGAAGT GGTCGAGGCG AvaI ~~~~~
6301   GAAGTCGCTC TTCTTGATGG AGCGCATGGG GACGTGCTTG GCAATCACGC GCACCCCCCG GCCGTTTTAG
       CGGCTAAAAA AGTCATGGCT CTGCCCTCGG
       CTTCAGCGAG AAGAACTACC TCGCGTACCC CTGCACGAAC CGTTAGTGCG CGTGGGGGGC CGGCAAAATC
       GCCGATTTTT TCAGTACCGA GACGGGAGCC
       AvaI
       ~
6401   GGGGACCACG CCCATCATGA CCTTGCCAAG CTCGTCCTGC TTCTCTTCGA TCTTCGCCAG CAGGGCGAGG
       ATCGTGGCAT CACCGAACCG CGCCGTGCGC
       CGCCTGGTGC GGGTAGTACT GGAACGGTTC GAGCAGGACG AAGAGAAGCT AGAAGCGGTC GTCCCGCTCC
       TAGCACCGTA GTGGCTTGGC GCGGCACGCG
6501   GGGTCGTCGG TGAGCCAGAG TTTCAGCAGG CCGCCCAGGC GGCCCAGGTC GCCATTGATG CGGGCCAGCT
       CGCCGACGTG CTCATAGTCC ACGACGCCCG
       CCCAGCAGCC ACTCGGTCTC AAAGTCGTCC GGCGGGTCCG CCGGGTCCAG CGGTAACTAC GCCCGGTCGA
       GCGGCCTGCAC GAGTATCAGG TGCTGCGGGC
```

Figure 3 Cont'd

```
6601 TGATTTTGTA GCCCTGGCCG ACGGCCAGCA GGTAGGCCGA CAGGCTCATG CCGGCCGCCG CCGCCTTTTC
     CTCAATCGCT CTTCGTTCGT CTGGAAGGCA
     ACTAAAACAT CGGGACCGGC TGCCGGTCGT CCATCCGGCT GTCCGAGTAC GGCCGGCGGC GGCGGAAAAG
     GAGTTAGCGA GAAGCAAGCA GACCTTCCGT
6701 GTACACCTTG ATAGGTGGGC TGCCCTTCCT GGTTGGCTTG GTTCATCAG CCATCCGCTT GCCCTCATCT
     GTTACGCCGG CGGTAGCCGG CCAGCCTCGC
     CATGTGGAAC TATCCACCCG ACGGGAAGGA CCAACCGAAC CAAAGTAGTC GGTAGGCGAA CGGGAGTAGA
     CAATGCGGCC GCCATCGGCC GGTCGGAGCG
6801 AGAGCAGGAT TCCCGTTGAG CACCGCCAGG TGCGAATAAG GGACAGTGAA GAAGGAACAC CCGCTCGCGG
     GTGGGCCTAC TTCACCTATC CTGCCCGGCT
     TCTCGTCCTA AGGGCAACTC GTGGCGGTCC ACGCTTATTC CCTGTCACTT CTTCCTTGTG GGCGAGCGCC
     CACCCGGATG AAGTGGATAG GACGGGCCGA
6901 GACGCCGTTG GATACACCAA GGAAAGTCTA CACGAACCCT TTGGCAAAAT CCTGTATATC GTGCGAAAAA
     GGATGGATAT ACCGAAAAAA TCGCTATAAT
     CTGCGGCAAC CTATGTGGTT CCTTTCAGAT GTGCTTGGGA AACCGTTTTA GGACATATAG CACGCTTTTT
     CCTACCTATA TGGCTTTTTT AGCGATATTA
7001 GACCCCGAAG CAGGGTTATG CAGCGGAAAA GCGCTGCTTC CCTGCTGTTT TGTGGAATAT CTACCGACTG
     GAAACAGGCA AATGCAGGAA ATTACTGAAC
     CTGGGGCTTC GTCCCAATAC GTCGCCTTTT CGCGACGAAG GGACGACAAA ACACCTTATA GATGGCTGAC
     CTTTGTCCGT TTACGTCCTT TAATGACTTG
7101 TGAGGGGACA GGCGAGAGAC GATGCCAAAG AGCTACACCG ACGAGCTGGC CGAGTGGGTT GAATCCCGCG
     CGGCCAAGAA GCGCCGGCGT GATGAGGCTG
     ACTCCCCTGT CCGCTCTCTG CTACGGTTTC TCGATGTGGC TGCTCGACCG GCTCACCCAA CTTAGGGCGC
     GCCGGTTCTT CGCGGCCGCA CTACTCCGAC
7201 CGGTTGCGTT CCTGGCGGTG AGGGCGGATG TCGAGGCGGC GTTAGCGTCC GGCTATGCGC TCGTCACCAT
     TTGGGAGCAC ATGCGGGAAA CGGGGAAGGT
     GCCAACGCAA GGACCGGCAC TCCCGCCTAC AGCTCCGCCG CAATCGCAGG CCGATACGCG AGCAGTGGTA
     AACCCTCGTG TACGCCCTTT GCCCCTTCCA
7301 CAAGTTCTCC TACGAGACGT TCCGCTCGCA CGCCAGGCGG CACATCAAGG CCAAGCCCGC CGATGTGCCC
     GCACCGCAGG CCAAGGCTGC GGAACCCGCG
     GTTCAAGAGG ATGCTCTGCA AGGCGAGCGT GCGGTCCGCC GTGTAGTTCC GGTTCGGGCG GCTACACGGG
     CGTGGCGTCC GGTTCCGACG CCTTGGGCGC
7401 CCGGCACCCA AGACGCCGGA GCCACGGCGG CCGAAGCAGG GGGGCAAGGC TGAAAAGCCG GCCCCCGCTG
     CGGCCCCGAC CGGCTTCACC TTCAACCCAA
     GGCCGTGGGT TCTGCGGCCT CGGTGCCGCC GGCTTCGTCC CCCCGTTCCG ACTTTTCGGC CGGGGGCGAC
     GCCGGGGCTG GCCGAAGTGG AAGTTGGGTT
                         BamHI
                        ~~~~~~
7501 CACCGGACAA AAAGGATCCT CTACGCCGGA CGCATCGTGG CCGGCATCAC CGGCGCCACA GGTGCGGTTG
     CTGGCGCCTA TATCGCCGAC ATCACCGATG
     GTGGCCTGTT TTTCCTAGGA GATGCGGCCT GCGTAGCACC GGCCGTAGTG GCCGCGGTGT CCACGCCAAC
     GACCGCGGAT ATAGCGGCTG TAGTGGCTAC
7601 GGGAAGATCG GGCTCGCCAC TTCGGGCTCA TGAGCGCTTG TTTCGGCGTG GGTATGGTGG CAGGCCCCGT
     GGCCGGGGCA CTGTTGGGCG CCATCTCCTT
     CCCTTCTAGC CCGAGCGGTG AAGCCCGAGT ACTCGCGAAC AAAGCCGCAC CCATACCACC GTCCGGGGCA
     CCGGCCCCCT GACAACCCGC GGTAGAGGAA
7701 GCTGCCTCGC GCGTTTCGGT GATGACGGTG AAAACCTCTG ACACATGCAG CTCCCGGAGA CGGTCACAGC
     TTGTCTGTAA GCGGATGCCG GGAGCAGACA
     CGACGGAGCG CGCAAAGCCA CTACTGCCAC TTTTGGAGAC TGTGTACGTC GAGGGCCTCT GCCAGTGTCG
     AACAGACATT CGCCTACGGC CCTCGTCTGT
7801 AGCCCGTCAG GGCGCGTCAG CGGGTGTTGG CGGGTGTCGG GGCGCAGCCA TGACCCAGTC ACGTAGCGAT
     AGCGGAGTGT ATACTGGCTT AACTATGCGG
     TCGGGCAGTC CCGCGCAGTC GCCCACAACC GCCCACAGCC CCGCGTCGGT ACTGGGTCAG TGCATCGCTA
     TCGCCTCACA TATGACCGAA TTGATACGCC
7901 CATCAGAGCA GATTGTACTG AGAGTGCACC ATAAATCAAT CTAAAGTATA TATGAGTAAA CTTGGTCTGA
     CAGTTACCAA TGCTTAATCA GTGAGGCACC
     GTAGTCTCGT CTAACATGAC TCTCACGTGG TATTTAGTTA GATTTCATAT ATACTCATTT GAACCAGACT
     GTCAATGGTT ACGAATTAGT CACTCCGTGG
8001 TATCTCAGCG ATCTGTCTAT TTCGTTCATC CATAGTTGCC TGACTCCCCG TCGTGTAGAT AACTACGATA
     CGGGAGGGCT TACCATCTGG CCCCAGTGCT
     ATAGAGTCGC TAGACAGATA AAGCAAGTAG GTATCAACGG ACTGAGGGGC AGCACATCTA TTGATGCTAT
     GCCCTCCCGA ATGGTAGACC GGGGTCACGA
8101 GCAATCGATAC CCCCAGACCC ACCCTCACCC GCTCCAGATT TATCAGCAAT AAACCAGCCA GCCGGAAGGG
     CCGAGCGCAG AAGTGGTCCT GCAACTTTAT
     CGTTACTATG GCGCTCTGGG TGCGAGTGGC CGAGGTCTAA ATAGTCGTTA TTTGGTCGGT CGGCCTTCCC
     GGCTCGCGTC TTCACCAGGA CGTTGAAATA
8201 CCGCCTCCAT CCAGTCTATT AATTGTTGCC GGGAAGCTAG AGTAAGTAGT TCGCCAGTTA ATAGTTTGCG
     CAACGTTGTT GCCATTGCTG CAGGCATCGT
     GGCGGAGGTA GGTCAGATAA TTAACAACGG CCCTTCGATC TCATTCATCA AGCGGTCAAT TATCAAACGC
     GTTGCAACAA CGGTAACGAC GTCCGTAGCA
```

Figure 3 Cont'd

```
8301  GGTGTCACGC TCGTCGTTTG GTATGGCTTC ATTCAGCTCC GGTTCCCAAC GATCAAGGCG AGTTACATGA
      TCCCCCATGT TGTGCAAAAA AGCGGTTAGC
      CCACAGTGCG AGCAGCAAAC CATACCGAAG TAAGTCGAGG CCAAGGGTTG CTAGTTCCGC TCAATGTACT
      AGGGGGTACA ACACGTTTTT TGGCCAATCG
8401  TCCTTCGGTC CTCCGATCGT TGTCAGAAGT AAGTTGGCCG CAGTGTTATC ACTCATGGTT ATGGCAGCAC
      TGCATAATTC TCTTACTGTC ATGCCATCCG
      AGGAAGCCAG GAGGCTAGCA ACAGTCTTCA TTCAACCGGC GTCACAATAG TGAGTACCAA TACCGTCGTG
      ACGTATTAAG AGAATGACAG TACGGTAGGC
8501  TAAGATGCTT TTCTGTGACT GGTGAGTACT CAACCAAGTC ATTCTGAGAA TAGTGTATGC GGCGACCGAG
      TTGCTCTTGC CCGGCGTCAA CACGGGATAA
      ATTCTACGAA AAGACACTGA CCACTCATGA GTTGGTTCAG TAAGACTCTT ATCACATACG CCGCTGGCTC
      AACGAGAACG GGCCGCAGTT GTGCCCTATT
                                                                 DraI
                                                                 ~~~~~~
8601  TACCGCGCCA CATAGCAGAA CTTTAAAAGT GCTCATCATT GGAAAACGTT CTTCGGGGCG AAAACTCTCA
      AGGATCTTAC CCCTGTTGAG ATCCAGTTCG
      ATGGCGCGGT GTATCGTCTT GAAATTTTCA CGAGTAGTAA CCTTTTGCAA GAAGCCCCGC TTTTGAGAGT
      TCCTAGAATG GGGACAACTC TAGGTCAAGC
8701  ATGTAACCCA CTCGTGCACC CAACTGATCT TCAGCATCTT TTACTTTCAC CAGCGTTTCT GGGTGAGCAA
      AAACAGGAAG GCAAAATGCC GCAAAAAAGG
      TACATTGGGT GAGCACGTGG GTTGACTAGA AGTCGTAGAA ATGAAAGTG GTCGCAAAGA CCCACTCGTT
      TTTGTCCTTC CGTTTTACGG CGTTTTTTCC
8801  GAATAAGGGC GACACGGAAA TGTTGAATAC TCATACTCTT CCTTTTTCAA TATTATTGAA GCATTTATCA
      GGGTTATTGT CTCATGAGCG GATACATATT
      CTTATTCCCG CTGTGCCTTT ACAACTTATG AGTATGAGAA GGAAAAAGTT ATAATAACTT CGTAAATAGT
      CCCAATAACA GAGTACTCGC CTATGTATAA
8901  TGAATGTATT TAGAAAAATA AACAAATAGG GGTTCCGCGC ACATTTCCCC GAAAAGTGCC ACCTGCAGTT
      CACTTACACC GCTTCTCAAC CCGGTACGCA
      ACTTACATAA ATCTTTTTAT TTGTTTATCC CCAAGGCGCG TGTAAAGGGG CTTTTCACGG TGGACGTCAA
      GTGAATGTGG CGAAGAGTTG GGCCATGCGT
9001  CCAGAAAATC ATTGATATGG CCATGAATGG CGTTGGATGC CGGGCAACAG CCCGCATTAT GGGCGTTGGC
      CTCAACACGA TTTTACGTCA CTTAAAAAAC
      GGTCTTTTAG TAACTATACC GGTACTTACC GCAACCTACG GCCCGTTGTC GGGCGTAATA CCCGCAACCG
      GAGTTGTGCT AAAATGCAGT GAATTCTTTG
9101  TCAGGCCGCA GTCGGTAACC TCGCGCATAC AGCCGGGCAG TGACGTCATC GTCTGCGCGG AAATGGACGA
      ACAGTGGGGC TATGTCGGGG CTAAATCGCG
      AGTCCGGCGT CAGCCATTGG AGCGCGTATG TCGGCCCGTC ACTGCAGTAG CAGACGCGCC TTTACCTGCT
      TGTCACCCCG ATACAGCCCC GATTAGCGC
9201  CCAGCGCTGG CTGTTTTACG CGTATGACAG TCTCCGGAAG ACGGTTGTTG CGCACGTATT CGGTGAACGC
      ACTATGGCGA CGCTGGGGCG TCTTATGAGC
      GGTCGCGACC GACAAAATGC GCATACTGTC AGAGGCCTTC TGCCAACAAC GCGTGCATAA GCCACTTGCG
      TGATACCGCT GCGACCCCGC AGAATACTCG
9301  CTGCTGTCAC CCTTTGACGT GGTGATATGG ATGACGGATG GCTGGCCGCT GTATGAATCC CGCCTGAAGG
      GAAAGCTGCA CGTAATCAGC AAGCGATATA
      GACGACAGTG GGAAACTGCA CCACTATACC TACTGCCTAC CGACCGGCGA CATACTTAGG GCGGACTTCC
      CTTTCGACGT GCATTAGTCG TTCGCTATAT
9401  CGCAGCGAAT TGAGCGGCAT AACCTGAATC TGAGGCAGCA CCTGGCACGG CTGGGACGGA AGTCGCTGTC
      GTTCTCAAAA TCGGTGGAGC TGCATGACAA
      GCGTCGCTTA ACTCGCCGTA TTGGACTTAG ACTCCGTCGT GGACCGTGCC GACCCTGCCT TCAGCGACAG
      CAAGAGTTTT AGCCACCTCG ACGTACTGTT
9501  AGTCATCGGG CATTATCTGA ACATAAAACA CTATCAATAA GTTGGAGTCA TTACCAAAAG GTTAGGAATA
      CGGTTAGCCA TTTGCCTGCT TTTATATAGT
      TCAGTAGCCC GTAATAGACT TGTATTTTGT GATAGTTATT CAACCTCAGT AATGGTTTTC CAATCCTTAT
      GCCAATCGGT AAACGGACGA AAATATATCA
           NdeI
           ~~~~~~
9601  TCATATGGGA TTCACCTTTA TGTTGATAAG AAATAAAAGA AATGCCAAT AGGATATCGG CATTTTCTTT
      TGCGTTTTTA TTTGTTAACT GTTAATTGTC
      AGTATACCCT AAGTGGAAAT ACAACTATTC TTTATTTTCT TTACGGTTA TCCTATAGCC GTAAAAGAAA
      ACGCAAAAAT AAACAATTGA CAATTAACAG
                                                                              HindIII
                                                                              ~~~~~~~~
9701  CTTGTTCAAG GATGCTGTCT TGACAACAG ATGTTTCTT GCCTTTGATG TTCAGCAGGA AGCTTGGCGC
      AAACGTTGAT TGTTTGTCTG CGTAGAATCC
      GAACAAGTTC CTACGACAGA ACTGTTGTC TACAAAAGAA CGGAAACTAC AAGTCGTCCT TCGAACCGCG
      TTTGCAACTA ACAAACAGAC GCATCCTAGG
9801  TCTGTTTGTC ATATAGCTTG TAATCACGAC ATTGTTTCCT TCGCTTGAG GTACAGCGAA GTGTGAGTAA
      GTAAAGGTTA CATCGTTAGG ATCAAGATCC
      AGACAAACAG TATATCGAAC ATTAGTGCTG TAACAAAGGA AGCGAACTC CATGTCGCTT CACACTCATT
      CATTTCCAAT GTAGCAATCC TAGTTCTAGG
```

Figure 3 Cont'd

```
9901   ATTTTTAACA CAAGGCCAGT TTTGTTCAGC GGCTTGTATG GGCCAGTTAA AGAATTAGAA ACATAACCAA
       GCATGTAAAT ATCGTTAGAC GTAATGCCGT
       TAAAAATTGT GTTCCGGTCA AAACAAGTCG CCGAACATAC CCGGTCAATT TCTTAATCTT TGTATTGGTT
       CGTACATTTA TAGCAATCTG CATTACGGCA
                                                                                DraI
                                                                              --------
10001  CAATCGTCAT TTTTGATCCG CGGGAGTCAG TGAACAGGTA CCATTTGCCG TTCATTTTAA AGACGTTCGC
       GCCTTCAATT TCATCTCTTA CTCTGTTACA
       GTTAGCAGTA AAAACTAGGC GCCCTCAGTC ACTTGTCCAT GGTAAACGGC AAGTAAAATT TCTGCAAGCG
       CGCAAGTTAA AGTAGACAAT GACACAATCT
10101  TGCAATCAGC GGTTTCATCA CTTTTTTCAG TGTGTAATCA TCGTTTAGCT CAATCATACC GAGAGCGCCG
       TTTGCTAACT CAGCCGTGCG TTTTTTATCG
       ACGTTAGTCG CCAAAGTAGT GAAAAAAGTC ACACATTAGT AGCAAATCGA GTTAGTATGG CTCTCGCGGC
       AAACGATTGA GTCGGCACGC AAAAAATAGC
10201  CTTTTGCAGAA GTTTTTGACT TTCTTGACGG AAGAATGATG TGCTTTTGCC ATAGTATGCT TTGTTAAATA
       AAGATTCTTC GCCTTGGTAG CCATCTTCAG
       GAAAACGTCTT CAAAAACTGA AAGAACTGCC TTCTTACTAC ACGAAAACGG TATCATACGA AACAATTTAT
       TTCTAAGAAG CGGAACCATC GGTAGAAGTC
10301  TTCCAGTGTT TGCTTCAAAT ACTAAGTATT TGTGGCCTTT ATCTTCTACG TAGTGAGGAT CTCTCAGCGT
       ATGGTGTCG CCTGAGCTGT AGTTGCCTT
       AAGGTCACAA ACGAAGTTTA TGATTCATAA ACACCGGAAA TAGAAGATGC ATCACTCCTA GAGAGTCGCA
       TACCACAGC GGACTCGACA TCAACGGAAG
10401  ATCGATGAAC TGCTGTACAT TTTGATACGT TTTTCCGTCA CCGTCAAAGA TTGATTTATA ATCCTCTACA
       CCGTTGATGT TCAAAGAGCT GTCTGATGCT
       TAGCTACTTG ACGACATGTA AAACTATGCA AAAAGGCAGT GGCAGTTTCT AACTAAATAT TAGGAGATGT
       GGCAACTACA AGTTTCTCGA CAGACTACGA
10501  GATACGTTAA CTTGTGCAGT TGTCAGTGTT TGTTTGCCGT AATGTTTACC GGAGAAATCA GTGTAGAATA
       AACGGATTTT TCCGTCAGAT GTAAATGTGG
       CTATGCAATT GAACACGTCA ACAGTCACAA ACAAACGGCA TTACAAATGG CCTCTTTAGT CACATCTTAT
       TTCCCTAAAA AGGCAGTCTA CATTTACACC
                                                                                DraI
                                                                              --------
10601  CTGAACCTGA CCATTCTTGT GTTTGGTCTT TTAGGATAGA ATCATTTGCA TCGAATTTGT CGCTGTCTTT
       AAAGACGCGG CCAGCGTTTT TCCAGCTGTC
       GACTTGGACT GGTAAGAACA CAAACCAGAA AATCCTATCT TAGTAAACGT AGCTTAAACA GCGACAGAAA
       TTTCTGCGCC GGTCGCAAAA AGGTCGACAG
10701  AATAGAAGTT TCGCCGACTT TTTCGATGAA CATGTAAATC GATGTGTCAT CCGCATTTTT AGGATCTCCG
       GCTAATGCAA AGACGATGTG GTAGCCGTGA
       TTATCTTCAA AGCGGCTGAA AAACTATCCT GTACATTTAG CTACACAGTA GGCGTAAAAA TCCTAGAGGC
       CGATTACGTT TCTGCTACAC CATCGGCACT
10801  TACTTTGCCA CAGTGCCCTC AGCGTTTTGT AATGGCCAGC TCTCCCAAAC GTCCAGGCCT TTTCCACAAC
       AGATATTTTT AATTGTGGAC GAATCGAATT
       ATCAAACGCT GTCACGGCAG TCGCAAAACA TTACCGGTCG ACAGGGTTTG CAGGTCCGGA AAACGTCTTC
       TCTATAAAAA TTAACACCTG CTTAGCTTAA
10901  CAGGAACTTG ATATTTTTCA TTTTTTTGCT GTTCAGGGAT TTGCAGCATA TCATGGCGTG TAATATGGGA
       AATGCCGTAT GTTTCCTTAT ATGGCTTTTG
       GTCCTTGAAC TATAAAAAGT AAAAAAACGA CAAGTCCCTA AACGTCGTAT AGTACCGCAC ATTATACCCT
       TTACGGCATA CAAAGGAATA TACCGAAAAC
11001  GTTCGTTTCT TTCGCAAACG CTTGAGTTGC GCCTCCTGCC AGCAGTGCGG TAGTAAAGGT TAATACTGTT
       GCTTGTTTTG CAAACTTTTT GATGTTCATC
       CAAGCAAAGA AAGCGTTTGC GAACTCAACG CGGAGGACGG TCGTCACGCC ATCATTTCCA ATTATGACAA
       CGAACAAAAC GTTTGAAAAA CTACAAGTAG
11101  GTTCATGTCT CCTTTTTTAT GTACTGTGTT AGCGGTCTGC TTCTTCCAGC CCTCCTGTTT GAAGATGGCA
       AGTTAGTTAC GCACAATAAA AAAGACCTA
       CAAGTACAGA GGAAAAAATA CATGACACAA TCGCCAGACG AAGAAGGTCG GGAGGACAAA CTTCTACCGT
       TCAATCAATG CGTGTTATTT TTTTCTGGAT
11201  AAATATGTAA GGGGTGACGC CAAAGTATAC ACTTTGCCCT TTACACATTT TAGGTCTTGC CTGCTTTATC
       AGTAACAAAC CCGCGCGATT TACTTTTCGA
       TTTATACATT CCCCACTGTG GTTTCATATG TGAAACGGGA AATGTGTAAA ATCCAGAACG GACGAAATAG
       TCATTGTTTG GGCGCGCTAA ATGAAAAGCT
11301  CCTCATTCTA TTTAGACTCTC GTTGGATTG CAACTGGTCT ATTTTCCTCT TTTGTTTGAT AGAAAATCAT
       AAAAGGATTT GCAGACTACG GGCCTAAAGA
       GGAGTAAGAT AATCTGAGAG CAAACCTAAC GTTGACCAGA TAAAAGGAGA AAACAAACTA TCTTTTAGTA
       TTTCCTAAA CGTCTGATGC CCGGATTTCT
11401  ACTAAAAAAT CTATCTGTTT CTTTTCATTC TCTGTATTTT TTATAGTTTC TGTTGCATGG GCATAAAGTT
       GCTTTTTTAA TCACAATTCA GAAATATCA
       TGATTTTTTA GATAGACAAA GAAAAGTAAG AGACATAAAA AATATCAAAG ACAACGTACC CGTATTTCAA
       CGGAAAAATT AGTGTTAAGT CTTTTATAGT
                                                                                XbaI
```

Figure 3 Cont'd

```
11501  TAATATCTCA TTTCACTAAA TAATAGTGAA CGGCAGGTAT ATGTGATGGG TTAAAAGGA TCGATCCTCT
       AGAGTCGACC TGCAGGTCGA CGGATCTGCA
       ATTATAGAGT AAAGTGATTT ATTATCACTT GCCGTCCATA TACACTACCC AATTTTTCCT AGCTAGGAGA
       TCTCAGCTGG ACGTCCAGCT GCCTAGACGT
            BamHI    HindIII    XbaI              SphI
            ~~~~~~~  ~~~~~~~    ~~~~~~            ~~~~~~
11601  GGTCGACGGA TCCCAAGCTT CTTCTAGAGG TACCGCATGC CCTGGAGGAA TACGTGGATA AAATTTCGT
       CCAGCTGCCT AGGGTTCGAA GAAGATCTCC ATGGCGTACG GGACCTCCTT ATGCACCTAT TTTAAAGCA
       CGATGAAGCA GTAAGTGAAC TGCATACCAT
       GCTACTTCGT CATTCACTTG ACGTATGGTA
11701  TCAGGACATG TTGCGCTGGG CGGTAAGCCG CTTTAGCGCG GCGAATATCT GGTATGGACA CGGTACCGAT
       AGTCCTGTAC AACGCGACCC GCCATTCGGC GAAATCGCGC CGCTTATAGA CCATACCTGT GCCATGGCTA
       AACCCGTGGG ATGAAGCGGT ACAACTGGTG
       TTGGGCACCC TACTTCGCCA TGTTGACCAC
11801  TTGCCGTCTC TTTATCTGCC GCTGGATATT CCGGAGGATA TGCGGACCGC GCGGCTGACG TCCAGCGAAA
       AACGGCAGAG AAATAGACGG CGACCTATAA GGCCTCCTAT ACGCCTGGCG CGCCGACTGC AGGTCGCTTT
       GACACCGCAT TGTCGAGCGA GTCATTCGTC
       CTGTGGCGTA ACAGCTCGCT CAGTAAGCAG
11901  GCATTAACGA GCGTATCCCG GTAGCCTACC TGACCAATAA AGCCTGGTTC TGCGGCCACG AATTTTATGT
       CGTAATTGCT CGCATAGGGC CATCGGATGG ACTGGTTATT TCGGACCAAG ACGCCGGTGC TTAAAATACA
       TGATGAGCGC GTGCTGGTGC CGCGTTCACC
       ACTACTCGCG CACGACCACG GCGCAAGTGG
12001  GATTGGCGAG CTGATTAATA ACCACTTCGC TGGCCTTATT AGCCAACAGC CGAAATATAT TCTGGATATG
       CTAACCGCTC GACTAATTAT TGGTGAAGCG ACCGGAATAA TCGGTTGTCG GCTTTATATA AGACCTATAC
       TGTACCGGCG GCGGCTGCAT CGCCATCGCT
       ACATGGCCGC CGCCGACGTA GCGGTAGCGA
12101  TGTGCTTATG CTTTCCCGGA CGCAGAGGTT GATGCGGTCG ATATTCGCC GGATGCGCTG GCTGTCGCCG
       ACACGAATAC GAAAGGGCCT GCGTCTCCAA CTACGCCAGC TATAAGCGG CCTACGCGAC CGACAGCCGC
       AGCATAACAT TGAAGAACAC GGTCTTATCC
       TCGTATTGTA ACTTCTTGTG CCAGAATAGG
12201  ATCACGTGAC GCCAATCCGT TCCGATCTGT TCCGCGATCT GCCGAAAGTT CAGTACGATC TGATTGTCAC
       TAGTGCACTG CGGTTAGGCA AGGCTAGACA AGGCGCTAGA CGGCTTTCAA GTCATGCTAG ACTAACAGTG
       TAACCCGCCT TATGTCGATG CGGAGGATAT
       ATTGGGCGGA ATACAGCTAC GCCTCCTATA
12301  GTCCGATCTG CCGAACGAAT ATCGCCACGA ACCTGAGCTG GGGCTGGCGT CCGGCACTGA CGGCCTCAAA
       CAGGCTAGAC GGCTTGCTTA TAGCGGTGCT TGGACTCGAC CCCGACCGCA GGCCGTGACT GCCGGAGTTT
       TTGACCCGCC GTATCCTGGG AAATGCGCCG
       AACTGGGCGG CATAGGACCC TTTACGCGGC
12401  GATTATCTGT CCGATGATGG CGTTCTGATT TGTGAAGTCG GAAACAGCAT GGTACATCTG ATGGAGCAGT
       CTAATAGACA GGCTACTACC GCAAGACTAA ACACTTCAGC CTTTGTCGTA CCATGTAGAC TACCTCGTCA
       ATCCGGATGT GCCGTTCACC TGGCTGGAGT
       TAGCCCTACA CGGCAAGTGG ACCGACCTCA
12501  TTGACAACGG CGGCGATGGC GTCTTTATGT TGACCAAAGC GCAGTTGCTC GCGGCCCGTG AACATTCAA
       AACTGTTGCC GCCGCTACCG CAGAAATACA ACTGGTTTCG CGTCAACGAG CGCCGGGCAC TTGTAAAGTT
       TATTTATAAA GATTAAAACA CGCAAACGAC
       ATAAATATTT CTAATTTTGT GCGTTTGCTG
12601  AACAACGATA ACGGAGCCGT GATGCAGGA AACACAATTG GACAACTCTT TCCGTAACC ACTTCGGCG
       TTGTTGCTAT TGCCTCGGCA CTACCGTCCT TTGTGTTAAC CTGTTGAGAA AGCGCATTGG TGAAAGCCGC
       AATCACACGG GCTGGCGCTT GGGGGTATCG
       TTAGTGTGCC CGACCGCGAA CCCCCATAGC
12701  TCGATGGCGT GCCGCCCGGC ATCCCGTTGA CGGAGGCCGA TCTGCAGCAC GATCTCGACA GACGCCGCCC
       AGCTACCGCA CGGCGGGCCG TAGGGCAACT GCCTCCGGCT AGACGTCGTG CTAGAGCTGT CTGCGGCGGG
       TGGCACCTCG CGCTATACTA CTCAGCGCCC
       ACCGTGGAGC GCGATATGAT GAGTCGCGGC
                                                                        AvaI
                                                                        ~
                                                                        XhoI
                                                                        ~
12801  CGAACCGGAC CAGGTAAAAA TTCTCTCCGG CGTGTTTGAT GGCGTAACGA CCGGC
       GCTTGGCCTG GTCCATTTTT AAGAGAGGCC GCACAAACTA CCGCATTGCT GGCCG
```

Figure 4 - CT110 E. coli codon optimized sequence (SEQ ID NO: 10)

catatggaaaccagcttccataaattcttcctgtctatgatcctggcgtacagctgctgttctctgaacggtggtggttatgcggcgga
aattatggttccgcagggtatctacgatggtgaaaccctgaccgtgtctttcccgtataccgttatcggtgatccgagcggtacgacc
gttttcagcgccggtgaactgaccctgaaaaacctggataatagcattgcggcgctgccgctgtcttgcttcggtaacctgctgggtt
ctttcaccgttctgggtcgtggccatagcctgaccttgaaaacattcgtaccagcaccaatggtgcggcgctgtctaatagcgcgg
cggatggtctgttcaccattgaaggtttcaaagaactgtctttctctaactgcaatagcctgctggcggttctgccggcggcgaccac
caacaaaggcagccagaccccgaccaccacgagcaccccgtctaacggcaccatctacagcaaaaccgatctgctgctgct
gaacaacgaaaaattctcttttatagcaacctggtttctggtgatggtggtgcgattgatgcgaaaagcctgaccgttcagggtatc
tctaaactgtgcgttttccaggaaaacaccgcgcaggcggatggcggtgcgtgccaggttgttacctctttcagcgcgatggccaa
tgaagcgccgattgcgtttgttgccaacgtggcgggtgttcgtggtggtggtatcgcggcggtgcaggatggtcagcagggtgtga
gctcttctacctctaccgaagatccggtggtgagcttcagccgtaacaccgcggtggaatttgatggtaacgtggcgcgcgttggtg
gtggtatctacagctacggtaacgtggcgttcctgaacaatggtaaaaccctgttcctgaataacgttgcgagcccggtgtatattg
cggccaaacagccgacctctggtcaggcgtctaacaccagcaataactacggcgatggtggcgccattctgcaaaaacggt
gcgcaggcgggcagcaacaactctggcagcgtgagcttcgatggcgaaggcgtggtgttttcagctctaatgtggcggcgggt
aaaggcggcgcgatttatgcgaaaaaactgtctgttgcgaactgcggcccggtgcagttcctgcgtaacattgcgaacgatggtg
gtgcgatctacctgggtgaaagcggcgaactgtctctgagcgcggattatggcgatattatcttcgatggtaacattaaacgtaccg
cgaaagaaaacgcggcggatgtgaacggtgtgaccgtgtcttctcaggcgattagcatgggtagcggcggcaaaattaccacc
ctgcgtgcgaaagcgggtcatcagatcctgttcaacgatccgatcgaaatggcgaacggtaataaccagccggcgcagtcttct
aaactgctgaaaattaacgatggtgaaggttacaccggtgatattgtgttcgcgaacggttctagcaccctgtatcagaacgttacc
atcgaacagggccgtatcgttctgcgtgaaaaagcgaaactgtctgttaacagcctgagccagaccggtggtagcctgtatatgg
aagcgggttctaccctggatttcgttaccccgcagccgccgcagcagccgccggcggcgaatcagctgatcaccctgagcaac
ctgcatctgtctctgtcttctctgctggcgaacaacgcggttaccaacccgccgaccaacccgccggcgcaggattctcatccggc
ggtgattggtagcaccaccgcgggtagcgttaccatttctggtccgattttcttttgaagatctggatgataccgcgtacgatcgctac
gattggctgggtagcaaccagaaaatcaacgttctgaaactgcaactgggcaccaaaccgccggcgaacgcgccgtctgatct
gaccctgggtaacgaaatgccgaaatatggctaccagggttcttggaaactggcgtgggacccgaacaccgcgaacaacggt
ccgtacaccctgaaagcgacctggaccaaaaccggttacaatccgggcccggaacgtgttgcgtctctggttccgaactctctgt
ggggcagcattctggatattcgcagcgcgcattctgcgatccaggcgagcgtggatggtcgtagctattgccgcggtctgtgggtt
agcggtgtttctaacttcttctatcatgatcgcgatgcgctgggccagggctatcgctatattagcggtggttatagcctgggtgcgaa
cagctatttcggtagcagcatgttcggcctggcgttcaccgaagtttttggtcgttctaaagattatgttgtgtgccgtagcaaccatca
tgcgtgcattggttctgtttatctgagcacccagcaggcgctgtgcggttcttatctgtttggcgatgcgttcatccgtgcgtcttatggttt
cggcaaccagcacatgaaaaccagctataccttgcggaagaaagcgatgttcgttgggataacaactgcctggcgggtgaaa
ttggtgcgggcctgccgatcgttatcaccccgagcaaactgtatctgaacgaactgcgcccgtttgtgcaggcggaattttcttacg
cgaaccatgaatcttttaccgaagaaggtgatcaggcgcgtgcgttcaaaagcggtcatctgctgaacctgagcgtgccggttgg
cgtgaaatttgatcgttcagctctacccatccgaacaaatacagctttatggcggcgtatatctgtgatgcgtatcgtaccattagc
ggcaccgaaaccaccctgctgagccatcagggcacctggaccaccgatgcgtttcatctggcgcgtcatggcgttgtggttcgtg
gcagcatgtatgcgagcctgaccagcaacattgaagtgtatggtcatggtcgttatgaatatcgtgatgcgagccgtggttatggtc
tgagcgcgggtagccgcgttcgttttttaataaggatccactagttctagagtcgacctgcag Figure 5 - CT110 E. coli codon optimized coding region (SEQ ID NO:11)

atggaaaccagcttccataaattcttcctgtctatgatcctggcgtacagctgctgttctctgaacggtggtggttatgcggcggaaat
tatggttccgcagggtatctacgatggtgaaaccctgaccgtgtctttcccgtataccgttatcggtgatccgagcggtacgaccgttt
tcagcgccggtgaactgaccctgaaaaacctggataatagcattgcggcgctgccgctgtcttgcttcggtaacctgctgggttcttt
caccgttctgggtcgtggccatagcctgacctttgaaaacattcgtaccagcaccaatggtgcggcgctgtctaatagcgcggcg
gatggtctgttcaccattgaaggtttcaaagaactgtctttctctaactgcaatagcctgctggcggttctgccggcggcgaccacca
acaaaggcagccagaccccgaccaccacgagcaccccgtctaacggcaccatctacagcaaaaccgatctgctgctgctga
acaacgaaaaattctcttttatagcaacctggttctggtgatggtggtgcgattgatgcgaaaagcctgaccgttcagggtatctct
aaactgtgcgttttccaggaaaacaccgcgcaggcggatggcggtgcgtgccaggttgttacctctttcagcgcgatggccaatg
aagcgccgattgcgtttgttgccaacgtggcgggtgttcgtggtggtggtatcgcggcggtgcaggatggtcagcagggtgtgag
ctcttctacctctaccgaagatccggtggtgagcttcagccgtaacaccgcggtggaatttgatggtaacgtggcgcgcgttggtgg
tggtatctacagctacggtaacgtggcgttcctgaacaatggtaaaaccctgttcctgaataacgttgcgagcccggtgtatattgc
ggccaaacagccgacctctggtcaggcgtctaacaccagcaataactacggcgatggtggcgccattttctgcaaaaacggtg
cgcaggcgggcagcaacaactctggcagcgtgagcttcgatgcgaaggcgtggtgttttcagctctaatgtggcggcgggta
aaggcggcgcgatttatgcgaaaaaaactgtctgttgcgaactgcggcccggtgcagttcctgcgtaacattgcgaacgatggtgg
tgcgatctacctgggtgaaagcggcgaactgtctctgagcgcggattatggcgatattatcttcgatggtaacattaaacgtaccgc
gaaagaaaacgcggcggatgtgaacggtgtgaccgtgtcttctcaggcgattagcatgggtagcggcggcaaaattaccaccc
tgcgtgcgaaagcgggtcatcagatcctgttcaacgatccgatcgaaatggcgaacggtaataaccagccggcgcagtcttcta
aactgctgaaaattaacgatggtgaaggttacaccggtgatattgtgttcgcgaacggttctagcaccctgtatcagaacgttacca
tcgaacagggccgtatcgttctgcgtgaaaaagcgaaactgtctgttaacagcctgagccagaccggtggtagcctgtatatgga
agcgggttctaccctggatttcgttaccccgcagccgccgcagcagccgccggcggcgaatcagctgatcaccctgagcaacct
gcatctgtctctgtcttctctgctggcgaacaacgcggttaccaacccgccgaccaacccgccggcgcaggattctcatccggcg
gtgattggtagcaccaccgcgggtagcgttaccatttctggtccgatttctcttttgaagatctggatgataccgcgtacgatcgctacg
attggctgggtagcaaccagaaaatcaacgttctgaaactgcaactgggcaccaaaccgccggcgaacgcgccgtctgatctg
accctgggtaacgaaatgccgaaatatggctaccagggttcttggaaactggcgtgggacccgaacaccgcgaacaacggtc
cgtacaccctgaaagcgacctggaccaaaaccggttacaatccgggcccggaacgtgttgcgtctctggttccgaactctctgtg
gggcagcattctggatattcgcagcgcgcattctgcgatccaggcgagcgtggatggtcgtagctattgccgcggtctgtgggtta
gcggtgttctaacttcttctatcatgatcgcgatgcgctgggccagggctatcgctatattagcggtggttatagcctgggtgcgaac
agctatttcggtagcagcatgttcggcctggcgttcaccgaagttttggtcgttctaaagattatgttgtgtgccgtagcaaccatcat
gcgtgcattggttctgtttatctgagcacccagcaggcgctgtgcgttcttatctgtttggcgatgcgttcatccgtgcgtcttatggtttc
ggcaaccagcacatgaaaaccagctataccctttgcggaagaaagcgatgttcgttgggataacaactgcctggcgggtgaaatt
ggtgcgggcctgccgatcgttatcaccccgagcaaactgtatctgaacgaactgcgcccgtttgtgcaggcggaattttcttacgc
gaaccatgaatcttaccgaagaaggtgatcaggcgcgtgcgttcaaaagcggtcatctgctgaacctgagcgtgccggttggc
gtgaaatttgatcgttgcagctctacccatccgaacaaatacagctttatggcggcgtatatctgtgatgcgtatcgtaccattagcg
gcaccgaaaccaccctgctgagccatcagggcacctggaccaccgatgcgtttcatctggcgcgtcatggcgttgtggttcgtgg
cagcatgtatgcgagcctgaccagcaacattgaagtgtatggtcatggtcgttatgaatatcgtgatgcgagccgtggttatggtct
gagcgcgggtagccgcgttcgtttaa Figure 6 - CT110 polypeptide (SEQ ID NO: 12)

```
METSFHKFFLSMILAYSCCSLNGGGYAAEIMVPQGIYDGETLTVSFPYTVIGDPSGTTVFSA
GELTLKNLDNSIAALPLSCFGNLLGSFTVLGRGHSLTFENIRTSTNGAALSNSAADGLFTIEG
FKELSFSNCNSLLAVLPAATTNKGSQTPTTTSTPSNGTIYSKTDLLLLNNEKFSFYSNLVSGD
GGAIDAKSLTVQGISKLCVFQENTAQADGGACQVVTSFSAMANEAPIAFVANVAGVRGGGI
AAVQDGQQGVSSSTSTEDPVVSFSRNTAVEFDGNVARVGGGIYSYGNVAFLNNGKTLFLN
NVASPVYIAAKQPTSGQASNTSNNYGDGGAIFCKNGAQAGSNNSGSVSFDGEGVVFFSSN
VAAGKGGAIYAKKLSVANCGPVQFLRNIANDGGAIYLGESGELSLSADYGDIIFDGNIKRTAK
ENAADVNGVTVSSQAISMGSGGKITTLRAKAGHQILFNDPIEMANGNNQPAQSSKLLKINDG
EGYTGDIVFANGSSTLYQNVTIEQGRIVLREKAKLSVNSLSQTGGSLYMEAGSTLDFVTPQP
PQQPPAANQLITLSNLHLSLSSLLANNAVTNPPTNPPAQDSHPAVIGSTTAGSVTISGPIFFE
DLDDTAYDRYDWLGSNQKINVLKLQLGTKPPANAPSDLTLGNEMPKYGYQGSWKLAWDP
NTANNGPYTLKATWTKTGYNPGPERVASLVPNSLWGSILDIRSAHSAIQASVDGRSYCRGL
WVSGVSNFFYHDRDALGQGYRYISGGYSLGANSYFGSSMFGLAFTEVFGRSKDYVVCRS
NHHACIGSVYLSTQQALCGSYLFGDAFIRASYGFGNQHMKTSYTFAEESDVRWDNNCLAG
EIGAGLPIVITPSKLYLNELRPFVQAEFSYANHESFTEEGDQARAFKSGHLLNLSVPVGVKFD
RCSSTHPNKYSFMAAYICDAYRTISGTETTLLSHQGTWTTDAFHLARHGVVVRGSMYASLT
SNIEVYGHGRYEYRDASRGYGLSAGSRVRF
```

Figure 7 - CT84 E. coli codon optimized sequence (SEQ ID NO: 13)

catatggaaattatggttccgcagggtatctacgatggtgaaaccctgaccgtgtctttcccgtataccgttatcggtgatccgagcg
gtacgaccgttttcagcgccggtgaactgaccctgaaaaacctggataatagcattgcggcgctgccgctgtcttgcttcggtaac
ctgctgggttctttcaccgttctgggtcgtggccatagcctgacctttgaaaacattcgtaccagcaccaatggtgcggcgctgtcta
atagcgcggcggatggtctgttcaccattgaaggtttcaaagaactgtctttctctaactgcaatagcctgctggcggttctgccggc
ggcgaccaccaacaaaggcagccagaccccgaccaccacgagcaccccgtcaacggcaccatctacagcaaaaccgat
ctgctgctgctgaacaacgaaaaattctctttttatagcaacctggtttctggtgatggtggtgcgattgatgcgaaaagcctgaccgt
tcagggtatctctaaactgtgcgttttccaggaaaacaccgcgcaggcggatggcggtgcgtgccaggttgttacctctttcagcgc
gatggccaatgaagcgccgattgcgtttgttgccaacgtggcgggtgttcgtggtggtggtatcgcggcggtgcaggatggtcagc
agggtgtgagctcttctacctctaccgaagatccggtggtgagcttcagccgtaacaccgcggtggaatttgatggtaacgtggcg
cgcgttggtggtggtatctacagctacggtaacgtggcgttcctgaacaatggtaaaaccctgttcctgaataacgttgcgagccc
ggtgtatattgcggccaaacagccgacctctggtcaggcgtctaacaccagcaataactacggcgatggtggcgccattttctgc
aaaaacggtgcgcaggcgggcagcaacaactctggcagcgtgagcttcgatggcgaaggcgtggtgttttcagctctaatgtg
gcggcgggtaaaggcggcgcgatttatgcgaaaaaactgtctgttgcgaactgcggcccggtgcagttcctgcgtaacattgcg
aacgatggtggtgcgatcacctgggtgaaagcggcgaactgtctctgagcgcggattatggcgatattatcttcgatggtaacatt
aaacgtaccgcgaaagaaaacgcggcggatgtgaacggtgtgaccgtgtcttctcaggcgattagcatgggtagcggcggca
aaattaccaccctgcgtgcgaaagcgggtcatcagatcctgttcaacgatccgatcgaaatggcgaacggtaataaccagccg
gcgcagtcttctaaactgctgaaaattaacgatggtgaaggttacaccggtgatattgtgttcgcgaacggttctagcaccctgtatc
agaacgttaccatcgaacagggccgtatcgttctgcgtgaaaaagcgaaactgtctgttaacagcctgagccagaccggtggta
gcctgtatatggaagcgggttctaccctggatttcgttaccccgcagccgccgcagcagccgccggcggcgaatcagctgatca
ccctgagcaacctgcatctgtctctgtcttctctgctggcgaacaacgcggttaccaacccgccgaccaacccgccggcgcagg
attctcatccggcggtgattggtagcaccaccgcgggtagcgttaccatttctggtccgattttctttgaagatctggatgataccgcgt
acgatcgctacgattggctgggtagcaaccagaaaatcaacgttctgaaactgcaactgggcaccaaaccgccggcgaacgc
gccgtctgatctgaccctgggtaacgaaatgccgaaatatggctaccagggttcttggaaactggcgtgggacccgaacaccgc
gaacaacggtccgtacaccctgaaagcgacctggaccaaaaccggttacaatccgggcccggaacgtgttgcgtctctggttcc
gaactctctgtggggcagcattctggatattcgcagcgcgcattctgcgatccaggcgagcgtggatggtcgtagctattgccgcg
gtctgtggttagcggtgtttctaacttcttctatcatgatcgcgatgcgctgggccagggctatcgctatattagcggtggttatagcct
gggtgcgaacagctatttcggtagcagcatgttcggcctggcgttcacctaatctagagtcgacctgcag Figure 8 - CT84 E. coli codon optimized coding region (SEQ ID NO: 14)

atggaaattatggttccgcagggtatctacgatggtgaaaccctgaccgtgtctttcccgtataccgttatcggtgatccgagcggta
cgaccgttttcagcgccggtgaactgaccctgaaaaacctggataatagcattgcggcgctgccgctgtcttgcttcggtaacctg
ctgggttctttcaccgttctgggtcgtggccatagcctgacctttgaaaacattcgtaccagcaccaatggtgcggcgctgtctaata
gcgcggcggatggtctgttcaccattgaaggtttcaaagaactgtctttctctaactgcaatagcctgctggcggttctgccggcggc
gaccaccaacaaaggcagccagaccccgaccaccacgagcaccccgtctaacggcaccatctacagcaaaaccgatctgc
tgctgctgaacaacgaaaaattctcttttttatagcaacctggtttctggtgatggtggtgcgattgatgcgaaaagcctgaccgttcag
ggtatctctaaactgtgcgttttccaggaaaacaccgcgcaggcggatggcggtgcgtgccaggttgttacctctttcagcgcgatg
gccaatgaagcgccgattgcgtttgttgccaacgtggcgggtgttcgtggtggtggtatcgcggcggtgcaggatggtcagcagg
gtgtgagctcttctacctctaccgaagatccggtggtgagcttcagccgtaacaccgcggtggaatttgatggtaacgtggcgcgc
gttggtggtggtatctacagctacggtaacgtggcgttcctgaacaatggtaaaaccctgttcctgaataacgttgcgagcccggtg
tatattgcggccaaacagccgacctctggtcaggcgtctaacaccagcaataactacggcgatggtggcgccattttctgcaaaa
acggtgcgcaggcgggcagcaacaactctggcagcgtgagcttcgatggcgaaggcgtggtgttttcagctctaatgtggcgg
cgggtaaaggcggcgcgatttatgcgaaaaaactgtctgttgcgaactgcgggcccggtgcagttcctgcgtaacattgcgaacg
atggtggtgcgatctacctgggtgaaagcggcgaactgtctctgagcgcggattatggcgatattatcttcgatggtaacattaaac
gtaccgcgaaagaaaacgcggcggatgtgaacggtgtgaccgtgtcttctcaggcgattagcatgggtagcggcggcaaaatt
accaccctgcgtgcgaaagcgggtcatcagatcctgttcaacgatccgatcgaaatggcgaacggtaataaccagccggcgc
agtcttctaaactgctgaaaattaacgatggtgaaggttacaccggtgatattgtgttcgcgaacggttctagcaccctgtatcagaa
cgttaccatcgaacagggccgtatcgttctgcgtgaaaaagcgaaactgtctgttaacagcctgagccagaccggtggtagcctg
tatatggaagcgggttctaccctggatttcgttaccccgcagccgccgcagcagccgccggcggcgaatcagctgatcaccctg
agcaacctgcatctgtctctgtcttctctgctggcgaacaacgcggttaccaacccgccgaccaacccgccggcgcaggattctc
atccggcggtgattggtagcaccaccgcgggtagcgttaccatttctggtccgattttctttgaagatctggatgataccgcgtacga
tcgctacgattggctgggtagcaaccagaaaatcaacgttctgaaactgcaactgggcaccaaaccgccggcgaacgcgccg
tctgatctgaccctgggtaacgaaatgccgaaatatggctaccagggttcttggaaactggcgtgggacccgaacaccgcgaac
aacggtccgtacaccctgaaagcgacctggaccaaaaccggttacaatccgggcccggaacgtgttgcgtctctggttccgaac
tctctgtggggcagcattctggatattcgcagcgcgcattctgcgatccaggcgagcgtggatggtcgtagctattccgcggtctgt
gggttagcggtgtttctaacttcttctatcatgatcgcgatgcgctgggccagggctatcgctatattagcggtggttatagcctgggtg
cgaacagctatttcggtagcagcatgttcggcctggcgttcacctaa Figure 9 – CT84 Peptide Sequence (SEQ ID NO: 15)

MEIMVPQGIYDGETLTVSFPYTVIGDPSGTTVFSAGELTLKNLDNSIAALP
LSCFGNLLGSFTVLGRGHSLTFENIRTSTNGAALSNSAADGLFTIEGFKEL
SFSNCNSLLAVLPAATTNKGSQTPTTTSTPSNGTIYSKTDLLLLNNEKFSF
YSNLVSGDGGAIDAKSLTVQGISKLCVFQENTAQADGGACQVVTSFSAM
ANEAPIAFVANVAGVRGGGIAAVQDGQQGVSSSTSTEDPVVSFSRNTAVE
FDGNVARVGGGIYSYGNVAFLNNGKTLFLNNVASPVYIAAKQPTSGQAS
NTSNNYGDGGAIFCKNGAQAGSNNSGSVSFDGEGVVFFSSNVAAGKGGA
IYAKKLSVANCGPVQFLRNIANDGGAIYLGESGELSLSADYGDIIFDGNIK
RTAKENAADVNGVTVSSQAISMGSGGKITTLRAKAGHQILFNDPIEMANG
NNQPAQSSKLLKINDGEGYTGDIVFANGSSTLYQNVTIEQGRIVLREKAK
LSVNSLSQTGGSLYMEAGSTLDFVTPQPPQQPPAANQLITLSNLHLSLSSL
LANNAVTNPPTNPPAQDSHPAVIGSTTAGSVTISGPIFFEDLDDTAYDRYD
WLGSNQKINVLKLQLGTKPPANAPSDLTLGNEMPKYGYQGSWKLAWDP
NTANNGPYTLKATWTKTGYNPGPERVASLVPNSLWGSILDIRSAHSAIQA
SVDGRSYCRGLWVSGVSNFFYHDRDALGQGYRYISGGYSLGANSYFGSS
MFGLAFT Stop Figure 10 - PmpG Nucleic Acid Sequence (C. trachomatis serovar L2) (SEQ ID NO:16)

```
gggcaaaact cttccccccg ggatttatat gggaaagggg aaactttggc ccgtattcaa      60
gcgccacggg ttttggggcg gaatgaattt tttcgttccg gaaaaagtaa ttccccggga     120
acgtagggta tcggtttcat aggctcgcca aatgggatat aggtggaaag gtaaaaaaaa     180
ctgagccaag caaaggatag agaagtcttg taatcatcgc aggttaaagg ggggatgtta     240
ttttagcctg caaatagtgt aattattgga tcctgtaaag agaaaaggac gaatgcgctg     300
aagataagaa catttattga tattaaatta ttaatttttt atgaagcgga gtaattaatt     360
      ttatctctca gcttttgtgt g atg caa acg tct ttc cat aag ttc ttt ctt   411
                              Met Gln Thr Ser Phe His Lys Phe Phe Leu
                              1               5                   10
      tca atg att cta gct tat tct tgc tgc tct tta aat ggg ggg gga tat
459
      Ser Met Ile Leu Ala Tyr Ser Cys Cys Ser Leu Asn Gly Gly Gly Tyr
                      15                  20                  25
      gca gca gaa atc atg gtt cct caa gga att tac gat ggg gag acg tta
507
      Ala Ala Glu Ile Met Val Pro Gln Gly Ile Tyr Asp Gly Glu Thr Leu
                  30                  35                  40
      act gta tca ttt ccc tat act gtt ata gga gat ccg agt ggg act act
555
      Thr Val Ser Phe Pro Tyr Thr Val Ile Gly Asp Pro Ser Gly Thr Thr
          45                  50                  55
      gtt ttt tct gca gga gag tta aca tta aaa aat ctt gac aat tct att
603
      Val Phe Ser Ala Gly Glu Leu Thr Leu Lys Asn Leu Asp Asn Ser Ile
          60                  65                  70
      gca gct ttg cct tta agt tgt ttt ggg aac tta tta ggg agt ttt act
651
      Ala Ala Leu Pro Leu Ser Cys Phe Gly Asn Leu Leu Gly Ser Phe Thr
      75                  80                  85                  90
      gtt tta ggg aga gga cac tcg ttg act ttc gag aac ata cgg act tct
699
      Val Leu Gly Arg Gly His Ser Leu Thr Phe Glu Asn Ile Arg Thr Ser
                      95                  100                 105
      aca aat ggg gca gct cta agt aat agc gct gct gat gga ctg ttt act
747
      Thr Asn Gly Ala Ala Leu Ser Asn Ser Ala Ala Asp Gly Leu Phe Thr
                  110                 115                 120
      att gag ggt ttt aaa gaa tta tcc ttt tcc aat tgc aat tca tta ctt
795
      Ile Glu Gly Phe Lys Glu Leu Ser Phe Ser Asn Cys Asn Ser Leu Leu
              125                 130                 135
      gcc gta ctg cct gct gca acg act aat aag ggt agc cag act ccg acg
843
      Ala Val Leu Pro Ala Ala Thr Thr Asn Lys Gly Ser Gln Thr Pro Thr
          140                 145                 150
      aca aca tct aca ccg tct aat ggt act att tat tct aaa aca gat ctt
891
      Thr Thr Ser Thr Pro Ser Asn Gly Thr Ile Tyr Ser Lys Thr Asp Leu
      155                 160                 165                 170
      ttg tta ctc aat aat gag aag ttc tca ttc tat agt aat tta gtc tct
939
      Leu Leu Leu Asn Asn Glu Lys Phe Ser Phe Tyr Ser Asn Leu Val Ser
                      175                 180                 185
      gga gat ggg gga gct ata gat gct aag agc tta acg gtt caa gga att
987
      Gly Asp Gly Gly Ala Ile Asp Ala Lys Ser Leu Thr Val Gln Gly Ile
                  190                 195                 200
      agc aag ctt tgt gtc ttc caa gaa aat act gct caa gct gat ggg gga
1035
```

Figure 10 Cont'd

```
            Ser Lys Leu Cys Val Phe Gln Glu Asn Thr Ala Gln Ala Asp Gly Gly
                205                 210                 215
            gct tgt caa gta gtc acc agt ttc tct gct atg gct aac gag gct cct
1083
            Ala Cys Gln Val Val Thr Ser Phe Ser Ala Met Ala Asn Glu Ala Pro
                220                 225                 230
            att gcc ttt gta gcg aat gtt gca gga gta aga ggg gga ggg att gct
1131
            Ile Ala Phe Val Ala Asn Val Ala Gly Val Arg Gly Gly Gly Ile Ala
            235                 240                 245                 250
            gct gtt cag gat ggg cag cag gga gtg tca tca tct act tca aca gaa
1179
            Ala Val Gln Asp Gly Gln Gln Gly Val Ser Ser Thr Ser Thr Glu
                            255                 260                 265
            gat cca gta gta agt ttt tcc aga aat act gcg gta gag ttt gat ggg
1227
            Asp Pro Val Val Ser Phe Ser Arg Asn Thr Ala Val Glu Phe Asp Gly
                        270                 275                 280
            aac gta gcc cga gta gga gga ggg att tac tcc tac ggg aac gtt gct
1275
            Asn Val Ala Arg Val Gly Gly Gly Ile Tyr Ser Tyr Gly Asn Val Ala
                        285                 290                 295
            ttc ctg aat aat gga aaa acc ttg ttt ctc aac aat gtt gct tct cct
1323
            Phe Leu Asn Asn Gly Lys Thr Leu Phe Leu Asn Asn Val Ala Ser Pro
                        300                 305                 310
            gtt tac att gct gct aag caa cca aca agt gga cag gct tct aat acg
1371
            Val Tyr Ile Ala Ala Lys Gln Pro Thr Ser Gly Gln Ala Ser Asn Thr
            315                 320                 325                 330
            agt aat aat tac gga gat gga gga gct atc ttc tgt aag aat ggt gcg
1419
            Ser Asn Asn Tyr Gly Asp Gly Gly Ala Ile Phe Cys Lys Asn Gly Ala
                            335                 340                 345
            caa gca gga tcc aat aac tct gga tca gtt tcc ttt gat gga gag gga
1467
            Gln Ala Gly Ser Asn Asn Ser Gly Ser Val Ser Phe Asp Gly Glu Gly
                        350                 355                 360
            gta gtt ttc ttt agt agc aat gta gct gct ggg aaa ggg gga gct att
1515
            Val Val Phe Phe Ser Ser Asn Val Ala Ala Gly Lys Gly Gly Ala Ile
                        365                 370                 375
            tat gcc aaa aag ctc tcg gtt gct aac tgt ggc cct gta caa ttt tta
1563
            Tyr Ala Lys Lys Leu Ser Val Ala Asn Cys Gly Pro Val Gln Phe Leu
                        380                 385                 390
            agg aat atc gct aat gat ggt gga gcg att tat tta gga gaa tct gga
1611
            Arg Asn Ile Ala Asn Asp Gly Gly Ala Ile Tyr Leu Gly Glu Ser Gly
            395                 400                 405                 410
            gag ctc agt tta tct gct gat tat gga gat att att ttc gat ggg aat
1659
            Glu Leu Ser Leu Ser Ala Asp Tyr Gly Asp Ile Ile Phe Asp Gly Asn
                            415                 420                 425
            ctt aaa aga aca gcc aaa gag aat gct gcc gat gtt aat ggc gta act
1707
            Leu Lys Arg Thr Ala Lys Glu Asn Ala Ala Asp Val Asn Gly Val Thr
                        430                 435                 440
```

Figure 10 Cont'd

```
      gtg tcc tca caa gcc att tcg atg gga tcg gga ggg aaa ata acg aca
1755
      Val Ser Ser Gln Ala Ile Ser Met Gly Ser Gly Gly Lys Ile Thr Thr
              445                 450                 455
      tta aga gct aaa gca ggg cat cag att ctc ttt aat gat ccc atc gag
1803
      Leu Arg Ala Lys Ala Gly His Gln Ile Leu Phe Asn Asp Pro Ile Glu
              460                 465                 470
      atg gca aac gga aat aac cag cca gcg cag tct tcc aaa ctt cta aaa
1851
      Met Ala Asn Gly Asn Asn Gln Pro Ala Gln Ser Ser Lys Leu Leu Lys
      475                 480                 485                 490
      att aac gat ggt gaa gga tac aca ggg gat att gtt ttt gct aat gga
1899
      Ile Asn Asp Gly Glu Gly Tyr Thr Gly Asp Ile Val Phe Ala Asn Gly
                      495                 500                 505
      agc agt act ttg tac caa aat gtt acg ata gag caa gga agg att gtt
1947
      Ser Ser Thr Leu Tyr Gln Asn Val Thr Ile Glu Gln Gly Arg Ile Val
                  510                 515                 520
      ctt cgt gaa aag gca aaa tta tca gtg aat tct cta agt cag aca ggt
1995
      Leu Arg Glu Lys Ala Lys Leu Ser Val Asn Ser Leu Ser Gln Thr Gly
                  525                 530                 535
      ggg agt ctg tat atg gaa gct ggt agt aca tgg gat ttt gta act cca
2043
      Gly Ser Leu Tyr Met Glu Ala Gly Ser Thr Trp Asp Phe Val Thr Pro
              540                 545                 550
      caa cca cca caa cag cct cct gcc gct aat cag ttg atc acg ctt tcc
2091
      Gln Pro Pro Gln Gln Pro Pro Ala Ala Asn Gln Leu Ile Thr Leu Ser
      555                 560                 565                 570
      aat ctg cat ttg tct ctt tct tct ttg tta gca aac aat gca gtt acg
2139
      Asn Leu His Leu Ser Leu Ser Ser Leu Leu Ala Asn Asn Ala Val Thr
                      575                 580                 585
      aat cct cct acc aat cct cca gcg caa gat tct cat cct gca gtc att
2187
      Asn Pro Pro Thr Asn Pro Pro Ala Gln Asp Ser His Pro Ala Val Ile
                      590                 595                 600
      ggt agc aca act gct ggt tct gtt aca att agt ggg cct atc ttt ttt
2235
      Gly Ser Thr Thr Ala Gly Ser Val Thr Ile Ser Gly Pro Ile Phe Phe
                  605                 610                 615
      gag gat ttg gat gat aca gct tat gat agg tat gat tgg cta ggt tct
2283
      Glu Asp Leu Asp Asp Thr Ala Tyr Asp Arg Tyr Asp Trp Leu Gly Ser
              620                 625                 630
      aat caa aaa atc aat gtc ctg aaa tta cag tta ggg act aag ccc cca
2331
      Asn Gln Lys Ile Asn Val Leu Lys Leu Gln Leu Gly Thr Lys Pro Pro
      635                 640                 645                 650
      gct aat gcc cca tca gat ttg act cta ggg aat gag atg cct aag tat
2379
      Ala Asn Ala Pro Ser Asp Leu Thr Leu Gly Asn Glu Met Pro Lys Tyr
                      655                 660                 665
      ggc tat caa gga agc tgg aag ctt gcg tgg gat cct aat aca gca aat
2427
      Gly Tyr Gln Gly Ser Trp Lys Leu Ala Trp Asp Pro Asn Thr Ala Asn
```

Figure 10 Cont'd

```
                         670                      675                      680
         aat ggt cct tat act ctg aaa gct aca tgg act aaa act ggg tat aat
2475
         Asn Gly Pro Tyr Thr Leu Lys Ala Thr Trp Thr Lys Thr Gly Tyr Asn
                     685                      690                      695
         cct ggg cct gag cga gta gct tct ttg gtt cca aat agt tta tgg gga
2523
         Pro Gly Pro Glu Arg Val Ala Ser Leu Val Pro Asn Ser Leu Trp Gly
             700                      705                      710
         tcc att tta gat ata cga tct gcg cat tca gca att caa gca agt gtg
2571
         Ser Ile Leu Asp Ile Arg Ser Ala His Ser Ala Ile Gln Ala Ser Val
         715                      720                      725                      730
         gat ggg cgc tct tat tgt cga gga tta tgg gtt tct gga gtt tcg aat
2619
         Asp Gly Arg Ser Tyr Cys Arg Gly Leu Trp Val Ser Gly Val Ser Asn
                             735                      740                      745
         ttc ttc tat cat gac cgc gat gct tta ggt cag gga tat cgg tat att
2667
         Phe Phe Tyr His Asp Arg Asp Ala Leu Gly Gln Gly Tyr Arg Tyr Ile
                     750                      755                      760
         agt ggg ggt tat tcc tta gga gca aac tcc tac ttt gga tca tcg atg
2715
         Ser Gly Gly Tyr Ser Leu Gly Ala Asn Ser Tyr Phe Gly Ser Ser Met
                     765                      770                      775
         ttt ggt cta gca ttt acc gaa gta ttt ggt aga tct aaa gat tat gta
2763
         Phe Gly Leu Ala Phe Thr Glu Val Phe Gly Arg Ser Lys Asp Tyr Val
                 780                      785                      790
         gtg tgt cgt tcc aat cat cat gct tgc ata gga tcc gtt tat cta tct
2811
         Val Cys Arg Ser Asn His His Ala Cys Ile Gly Ser Val Tyr Leu Ser
         795                      800                      805                      810
         acc caa caa gct tta tgt gga tcc tat ttg ttc gga gat gcg ttt atc
2859
         Thr Gln Gln Ala Leu Cys Gly Ser Tyr Leu Phe Gly Asp Ala Phe Ile
                             815                      820                      825
         cgt gct agc tac ggg ttt ggg aat cag cat atg aaa acc tca tat aca
2907
         Arg Ala Ser Tyr Gly Phe Gly Asn Gln His Met Lys Thr Ser Tyr Thr
                         830                      835                      840
         ttt gca gag gag agc gat gtt cgt tgg gat aat aac tgt ctg gct gga
2955
         Phe Ala Glu Glu Ser Asp Val Arg Trp Asp Asn Asn Cys Leu Ala Gly
                     845                      850                      855
         gag att gga gcg gga tta ccg att gtg att act cca tct aag ctc tat
3003
         Glu Ile Gly Ala Gly Leu Pro Ile Val Ile Thr Pro Ser Lys Leu Tyr
             860                      865                      870
         ttg aat gag ttg cgt cct ttc gtg caa gct gag ttt tct tat gcc gat
3051
         Leu Asn Glu Leu Arg Pro Phe Val Gln Ala Glu Phe Ser Tyr Ala Asp
         875                      880                      885                      890
         cat gaa tct ttt aca gag gaa ggc gat caa gct cgg gca ttc aag agc
3099
         His Glu Ser Phe Thr Glu Glu Gly Asp Gln Ala Arg Ala Phe Lys Ser
                             895                      900                      905
```

Figure 10 Cont'd

```
       gga cat ctc cta aat cta tca gtt cct gtt gga gtg aag ttt gat cga
3147
       Gly His Leu Leu Asn Leu Ser Val Pro Val Gly Val Lys Phe Asp Arg
                       910             915             920
       tgt tct agt aca cat cct aat aaa tat agc ttt atg gcg gct tat atc
3195
       Cys Ser Ser Thr His Pro Asn Lys Tyr Ser Phe Met Ala Ala Tyr Ile
               925             930             935
       tgt gat gct tat cgc acc atc tct ggt act gag aca acg ctc cta tcc
3243
       Cys Asp Ala Tyr Arg Thr Ile Ser Gly Thr Glu Thr Thr Leu Leu Ser
           940             945             950
       cat caa gag aca tgg aca aca gat gcc ttt cat tta gca aga cat gga
3291
       His Gln Glu Thr Trp Thr Thr Asp Ala Phe His Leu Ala Arg His Gly
       955             960             965             970
       gtt gtg gtt aga gga tct atg tat gct tct cta aca agt aat ata gaa
3339
       Val Val Val Arg Gly Ser Met Tyr Ala Ser Leu Thr Ser Asn Ile Glu
                       975             980             985
       gta tat ggc cat gga aga tat gag tat cga gat gct tct cga  ggc tat
3387
       Val Tyr Gly His Gly Arg Tyr Glu Tyr Arg Asp Ala Ser Arg  Gly Tyr
               990             995              1000
       ggt ttg agt  gca gga agt aga gtc  cgg ttc taaaaatatt ggttagatag
3437
       Gly Leu Ser  Ala Gly Ser Arg Val  Arg Phe
               1005            1010
       ttaagtgtta gcgatgcctt tttctttgag atctacatca ttttgttttt tagcttgttt
3497
       gtgttcctat tcgtatggat tcgcgagctc tcctcaagtg ttaacgccta atgtaaccac
3557
       tcctttttaag ggagacgatg tttacttgaa tggagactgc gcttttgtca atgtctatgc
3617
       aggagctgaa gaaggttcga ttatctcagc taatggcgac aatttaacga ttaccggaca
3677
       aaaccataca ttatcattta cagattctca agggccagtt cttcaaaatt atgccttcat
3737
       ttcagcagga gagacactta ctctgagaga ttttttcgagt ctgatgttct cgaaaaatgt
3797
       ttcttgcgga gaaaagggaa tgatctccgg gaaaaccgtg agtatttccg gagcaggcga
3857
       agtgatttttc tgggataact ccgtgtgggta ttctcctttta tctactgtgc caacctcatc
3917
       atcaactccg cctgctccaa cagttagtga tgctcggaaa gggtctattt tttctgtaga
3977
       gactagtttg gagatctcag gcgtcaaaaa aggggtcatg ttcgataata atgccgggaa
4037
       tttcggaaca gttttttcgag gtaagaataa taataatgct ggtggtggag gcagtgggtt
4097
       ccgctacacc atcaagtacg acttttacag ttaaaaactg taaagggaaa gttttctttca
4157
       cagataacgt agcctcttgc ggaggcggag tggtttataa aggcattgtg cttttcaaag
4217
       acaatgaagg aggcatattc ttccgaggga acacagcata cgatgattta aggattcttg
4277
       ctgctactaa tcaggatcag aatacggaga caggaggcgg tggaggagtt atttgctctc
4337
```

Figure 10 Cont'd

```
       cagatgattc tgtaaagttt gaaggcaata aaggttctat tgtttttgat tacaactttg
4397
       caaaaggcag aggcggaagc atcctaacga aagaattc
4435
```

Figure 11 – PmpG Protein (*C. trachomatis* serovar L2) (SEQ ID NO: 17)

```
Met Gln Thr Ser Phe His Lys Phe Phe Leu Ser Met Ile Leu Ala Tyr
1               5                   10                  15
Ser Cys Cys Ser Leu Asn Gly Gly Gly Tyr Ala Ala Glu Ile Met Val
                20                  25                  30
Pro Gln Gly Ile Tyr Asp Gly Glu Thr Leu Thr Val Ser Phe Pro Tyr
            35                  40                  45
Thr Val Ile Gly Asp Pro Ser Gly Thr Thr Val Phe Ser Ala Gly Glu
        50                  55                  60
Leu Thr Leu Lys Asn Leu Asp Asn Ser Ile Ala Ala Leu Pro Leu Ser
65                  70                  75                  80
Cys Phe Gly Asn Leu Leu Gly Ser Phe Thr Val Leu Gly Arg Gly His
                85                  90                  95
Ser Leu Thr Phe Glu Asn Ile Arg Thr Ser Thr Asn Gly Ala Ala Leu
            100                 105                 110
Ser Asn Ser Ala Ala Asp Gly Leu Phe Thr Ile Glu Gly Phe Lys Glu
        115                 120                 125
Leu Ser Phe Ser Asn Cys Asn Ser Leu Leu Ala Val Leu Pro Ala Ala
    130                 135                 140
Thr Thr Asn Lys Gly Ser Gln Thr Pro Thr Thr Thr Ser Thr Pro Ser
145                 150                 155                 160
Asn Gly Thr Ile Tyr Ser Lys Thr Asp Leu Leu Leu Leu Asn Asn Glu
                165                 170                 175
Lys Phe Ser Phe Tyr Ser Asn Leu Val Ser Gly Asp Gly Gly Ala Ile
            180                 185                 190
Asp Ala Lys Ser Leu Thr Val Gln Gly Ile Ser Lys Leu Cys Val Phe
        195                 200                 205
Gln Glu Asn Thr Ala Gln Ala Asp Gly Gly Ala Cys Gln Val Val Thr
    210                 215                 220
Ser Phe Ser Ala Met Ala Asn Glu Ala Pro Ile Ala Phe Val Ala Asn
225                 230                 235                 240
Val Ala Gly Val Arg Gly Gly Gly Ile Ala Ala Val Gln Asp Gly Gln
                245                 250                 255
Gln Gly Val Ser Ser Ser Thr Ser Thr Glu Asp Pro Val Val Ser Phe
            260                 265                 270
Ser Arg Asn Thr Ala Val Glu Phe Asp Gly Asn Val Ala Arg Val Gly
        275                 280                 285
Gly Gly Ile Tyr Ser Tyr Gly Asn Val Ala Phe Leu Asn Asn Gly Lys
    290                 295                 300
Thr Leu Phe Leu Asn Asn Val Ala Ser Pro Val Tyr Ile Ala Ala Lys
305                 310                 315                 320
Gln Pro Thr Ser Gly Gln Ala Ser Asn Thr Ser Asn Asn Tyr Gly Asp
                325                 330                 335
Gly Gly Ala Ile Phe Cys Lys Asn Gly Ala Gln Ala Gly Ser Asn Asn
            340                 345                 350
Ser Gly Ser Val Ser Phe Asp Gly Glu Gly Val Val Phe Phe Ser Ser
        355                 360                 365
Asn Val Ala Ala Gly Lys Gly Gly Ala Ile Tyr Ala Lys Lys Leu Ser
    370                 375                 380
Val Ala Asn Cys Gly Pro Val Gln Phe Leu Arg Asn Ile Ala Asn Asp
385                 390                 395                 400
Gly Gly Ala Ile Tyr Leu Gly Glu Ser Gly Glu Leu Ser Leu Ser Ala
                405                 410                 415
Asp Tyr Gly Asp Ile Ile Phe Asp Gly Asn Leu Lys Arg Thr Ala Lys
            420                 425                 430
Glu Asn Ala Ala Asp Val Asn Gly Val Thr Val Ser Ser Gln Ala Ile
        435                 440                 445
Ser Met Gly Ser Gly Gly Lys Ile Thr Thr Leu Arg Ala Lys Ala Gly
    450                 455                 460
His Gln Ile Leu Phe Asn Asp Pro Ile Glu Met Ala Asn Gly Asn Asn
```

Figure 11 Cont'd

```
        465                 470                 475                 480
   Gln Pro Ala Gln Ser Ser Lys Leu Leu Lys Ile Asn Asp Gly Glu Gly
                       485                 490             495
   Tyr Thr Gly Asp Ile Val Phe Ala Asn Gly Ser Ser Thr Leu Tyr Gln
                   500                 505                 510
   Asn Val Thr Ile Glu Gln Gly Arg Ile Val Leu Arg Glu Lys Ala Lys
               515                 520                 525
   Leu Ser Val Asn Ser Leu Ser Gln Thr Gly Gly Ser Leu Tyr Met Glu
           530                 535                 540
   Ala Gly Ser Thr Trp Asp Phe Val Thr Pro Gln Pro Pro Gln Gln Pro
   545                 550                 555                 560
   Pro Ala Ala Asn Gln Leu Ile Thr Leu Ser Asn Leu His Leu Ser Leu
                       565                 570                 575
   Ser Ser Leu Leu Ala Asn Asn Ala Val Thr Asn Pro Pro Thr Asn Pro
                   580                 585                 590
   Pro Ala Gln Asp Ser His Pro Ala Val Ile Gly Ser Thr Thr Ala Gly
               595                 600                 605
   Ser Val Thr Ile Ser Gly Pro Ile Phe Phe Glu Asp Leu Asp Asp Thr
           610                 615                 620
   Ala Tyr Asp Arg Tyr Asp Trp Leu Gly Ser Asn Gln Lys Ile Asn Val
   625                 630                 635                 640
   Leu Lys Leu Gln Leu Gly Thr Lys Pro Pro Ala Asn Ala Pro Ser Asp
                       645                 650                 655
   Leu Thr Leu Gly Asn Glu Met Pro Lys Tyr Gly Tyr Gln Gly Ser Trp
                   660                 665                 670
   Lys Leu Ala Trp Asp Pro Asn Thr Ala Asn Asn Gly Pro Tyr Thr Leu
               675                 680                 685
   Lys Ala Thr Trp Thr Lys Thr Gly Tyr Asn Pro Gly Pro Glu Arg Val
           690                 695                 700
   Ala Ser Leu Val Pro Asn Ser Leu Trp Gly Ser Ile Leu Asp Ile Arg
   705                 710                 715                 720
   Ser Ala His Ser Ala Ile Gln Ala Ser Val Asp Gly Arg Ser Tyr Cys
                       725                 730                 735
   Arg Gly Leu Trp Val Ser Gly Val Ser Asn Phe Phe Tyr His Asp Arg
                   740                 745                 750
   Asp Ala Leu Gly Gln Gly Tyr Arg Tyr Ile Ser Gly Gly Tyr Ser Leu
               755                 760                 765
   Gly Ala Asn Ser Tyr Phe Gly Ser Ser Met Phe Gly Leu Ala Phe Thr
           770                 775                 780
   Glu Val Phe Gly Arg Ser Lys Asp Tyr Val Val Cys Arg Ser Asn His
   785                 790                 795                 800
   His Ala Cys Ile Gly Ser Val Tyr Leu Ser Thr Gln Gln Ala Leu Cys
                       805                 810                 815
   Gly Ser Tyr Leu Phe Gly Asp Ala Phe Ile Arg Ala Ser Tyr Gly Phe
                   820                 825                 830
   Gly Asn Gln His Met Lys Thr Ser Tyr Thr Phe Ala Glu Glu Ser Asp
               835                 840                 845
   Val Arg Trp Asp Asn Asn Cys Leu Ala Gly Glu Ile Gly Ala Gly Leu
           850                 855                 860
   Pro Ile Val Ile Thr Pro Ser Lys Leu Tyr Leu Asn Glu Leu Arg Pro
   865                 870                 875                 880
   Phe Val Gln Ala Glu Phe Ser Tyr Ala Asp His Glu Ser Phe Thr Glu
                       885                 890                 895
   Glu Gly Asp Gln Ala Arg Ala Phe Lys Ser Gly His Leu Leu Asn Leu
                   900                 905                 910
   Ser Val Pro Val Gly Val Lys Phe Asp Arg Cys Ser Ser Thr His Pro
               915                 920                 925
   Asn Lys Tyr Ser Phe Met Ala Ala Tyr Ile Cys Asp Ala Tyr Arg Thr
```

Figure 11 Cont'd

```
            930                     935                     940
Ile Ser Gly Thr Glu Thr Thr Leu Leu Ser His Gln Glu Thr Trp Thr
945                     950                     955                     960
Thr Asp Ala Phe His Leu Ala Arg His Gly Val Val Val Arg Gly Ser
                    965                     970                     975
Met Tyr Ala Ser Leu Thr Ser Asn Ile Glu Val Tyr Gly His Gly Arg
                980                     985                     990
Tyr Glu Tyr Arg Asp Ala Ser Arg  Gly Tyr Gly Leu Ser  Ala Gly Ser
            995                     1000                    1005
Arg Val  Arg Phe
    1010
```

Figure 12 – PmpG Nucleic Acid Sequence (*C. trachomatis* serovar B) (SEQ ID NO: 18)

```
atgcaaacgt ctttccataa gttcttcttt tcaatgattc tagcttattc ttgctgctct      60
ttaaatgggg gggggtatgc agaaatcatg gttcctcaag gaatttacga tggggagacg     120
ttaactgtat catttcccta tactgttata ggagatccga gtgggactac tgttttttct     180
gcaggagagt taacgttaaa aaatcttgac aattctattg cagctttgcc tttaagttgt     240
tttgggaact tattagggag ttttactgtt ttagggagag gacactcgtt gactttcgag     300
aacatacgga cttctacaaa tggagctgca ctaagtgaca gcgctaatag cgggttattt     360
actattgagg gttttaaaga attatctttt tccaattgca acccattact tgccgtactg     420
cctgctgcaa cgactaataa tggtagccag actccgtcga caacatctac accgtctaat     480
ggtactattt attctaaaac agatcttttg ttactcaata atgagaagtt ctcattctat     540
agtaattcag tctctggaga tgggggagct atagatgcta agagcttaac ggttcaagga     600
attagcaagc tttgtgtctt ccaagaaaat actgctcaag ctgatggggg agcttgtcaa     660
gtagtcacca gtttctctgc tatggctaac gaggctccta ttgcctttgt agcgaatgtt     720
gcaggagtaa gaggggagg gattgctgct gttcaggatg ggcagcaggg agtgtcatca     780
tctacttcaa cagaagatcc agtagtaagt ttttccagaa atactgcggt agagtttgat     840
gggaacgtag cccgagtagg aggagggatt tactcctacg ggaacgttgc tttcctgaat     900
aatggaaaaa ccttgtttct caacaatgtt gcttctcctg tttacattgc tgctgagcaa     960
ccaacaaatg gacaggcttc taatacgagt gataattacg gagatggagg agctatcttc    1020
tgtaagaatg gtgcgcaagc agcaggatcc aataactctg atcagtttc ctttgatgga    1080
gagggagtag ttttcttag tagcaatgta gctgctggga aaggggggagc tatttatgcc    1140
aaaaagctct cggttgctaa ctgtggccct gtacaactct tagggaatat cgctaatgat    1200
ggtggagcga tttatttagg agaatctgga gagctcagtt tatctgctga ttatgagat     1260
atgatttcg atgggaatct taaagaaca gccaagaga atgctgccga tgttaatgc       1320
gtaactgtgt cctcacaagc catttcgatg ggatcgggag ggaaaataac gacattaaga    1380
gctaaagcag ggcatcagat tctctttaat gatcccatcg agatggcaaa cggaaataac    1440
cagccagcgc agtcttccga acctctaaaa attaacgatg gtgaaggata cacaggggat    1500
attgttttg ctaatggaaa cagtactttg taccaaaatg ttacgataga gcaaggaagg    1560
attgttcttc gtgaaaaggc aaaattatca gtgaattctc taagtcagac aggtgggagt    1620
ctgtatatgg aagctgggag tacattggat tttgtaactc cacaaccacc acaacagcct    1680
cctgccgcta atcagtcgat cacgctttcc aatctgcatt tgtctctttc ttctttgtta    1740
gcaaacaatg cagttacgaa tcctcctacc aatcctccag cgcaagattc tcatcctgca    1800
gtcattggta gcacaactgc tggttctgtt acaattagtg ggcctatctt ttttgaggat    1860
ttggatgata cagcttatga taggtatgat tggctaggtt ctaatcaaaa aatcgatgtc    1920
ctgaaattac agttagggac tcagccccca gctaatgccc catcagattt gactctaggg    1980
aatgagatgc ctaagtatgg ctatcaagga agctggaagc ttgcgtggga tcctaataca    2040
gcaaataatg gtccttatac tctgaaagct acatggacta aaactgggta taatcctggg    2100
cctgagcgag tagcttcttt ggttccaaat agtttatggg gatccatttt agatatacga    2160
tctgcgcatt cagcaattca agcaagtgtg gatgggcgct cttattgtcg aggattatgg    2220
gtttctggag tttcgaattt cttctatcat gaccgcgatg ctttaggtca gggatatcgg    2280
tatattagtg ggggttattc cttaggagca aactcctact ttggatcatc gatgtttggt    2340
ctagcattta ctgaagtatt tggtagatct aaagattatg tagtgtgtcg ttccaatcat    2400
catgcttgca taggatccgt ttatctatct accaaacagg ctttatgtgg atcttatgtg    2460
tttgagatg cgtttattcg tgctagctac gggtttggga atcagcatat gaaaacctca    2520
tatacatttg cagaggagag cgatgtttgt tgggataata actgtctggt tggagagatt    2580
ggagtgggat taccgattgt gattactcca tctaagctct atttgaatga gttgcgtcct    2640
ttcgtgcaag ctgagttttc ttatgccgat catgaatctt ttacagagga aggcgatcaa    2700
gctcgggcat tcaggagtgg acatctcatg aatctatcag ttcctgttgg agtaaaattt    2760
gatcgatgtt ctagtacaca ccctaataaa tatagcttta tggggcttta tatctgtgat    2820
gcttatcgca ccatctctgg gactcagaca acactcctat cccatcaaga gacatggaca    2880
acagatgcct ttcatttggc aagacatgga gtcatagtta gagggtctat gtatgcttct    2940
ctaacaagca atatagaagt atatggccat ggaagatata agtacgaga tacttctcga    3000
ggttatggtt tgagtgcagg aagtaaagtc cggttctaaa aatattggtt agatagttaa    3060
gtgttagcga tgcctttttc tttgagatct acatcatttt gtttttagc ttgtttgtgt     3120
tcctattcgt atggattcgc gagctctcct caagtgttaa cacctaatgt aaccactcct    3180
tttaaggggg acgatgttta cttgaatgga gactgcgctt tgtcaatgt ctatgcaggg      3240
gcagagaacg gctcaattat ctcagctaat ggcgacaatt taacgattac cggacaaaac    3300
catacattat catttacaca ttctcaaggg ccagttcttc aaaattagcc ttca          3354
```

Figure 13 – PmpG Protein (C. trachomatis serovar B) (SEQ ID NO: 19)

```
Met Gln Thr Ser Phe His Lys Phe Phe Leu Ser Met Ile Leu Ala Tyr
 1               5                   10                  15
    Ser Cys Cys Ser Leu Asn Gly Gly Gly Tyr Ala Ala Glu Ile Met Val
                20                  25                  30
    Pro Gln Gly Ile Tyr Asp Gly Glu Thr Leu Thr Val Ser Phe Pro Tyr
                35

Figure 13 Cont'd

```
    465                     470                     475                     480
Asn Gln Pro Ala Gln Ser Ser Glu Pro Leu Lys Ile Asn Asp Gly Glu
                485                     490                     495
Gly Tyr Thr Gly Asp Ile Val Phe Ala Asn Gly Asn Ser Thr Leu Tyr
                500                     505                     510
Gln Asn Val Thr Ile Glu Gln Gly Arg Ile Val Leu Arg Glu Lys Ala
                515                     520                     525
Lys Leu Ser Val Asn Ser Leu Ser Gln Thr Gly Gly Ser Leu Tyr Met
            530                     535                     540
Glu Ala Gly Ser Thr Leu Asp Phe Val Thr Pro Gln Pro Pro Gln Gln
545                     550                     555                     560
Pro Pro Ala Ala Asn Gln Ser Ile Thr Leu Ser Asn Leu His Leu Ser
                565                     570                     575
Leu Ser Ser Leu Leu Ala Asn Asn Ala Val Thr Asn Pro Pro Thr Asn
                580                     585                     590
Pro Pro Ala Gln Asp Ser His Pro Ala Val Ile Gly Ser Thr Thr Ala
                595                     600                     605
Gly Ser Val Thr Ile Ser Gly Pro Ile Phe Phe Glu Asp Leu Asp Asp
            610                     615                     620
Thr Ala Tyr Asp Arg Tyr Asp Trp Leu Gly Ser Asn Gln Lys Ile Asp
625                     630                     635                     640
Val Leu Lys Leu Gln Leu Gly Thr Gln Pro Pro Ala Asn Ala Pro Ser
                645                     650                     655
Asp Leu Thr Leu Gly Asn Glu Met Pro Lys Tyr Gly Tyr Gln Gly Ser
                660                     665                     670
Trp Lys Leu Ala Trp Asp Pro Asn Thr Ala Asn Asn Gly Pro Tyr Thr
                675                     680                     685
Leu Lys Ala Thr Trp Thr Lys Thr Gly Tyr Asn Pro Gly Pro Glu Arg
            690                     695                     700
Val Ala Ser Leu Val Pro Asn Ser Leu Trp Gly Ser Ile Leu Asp Ile
705                     710                     715                     720
Arg Ser Ala His Ser Ala Ile Gln Ala Ser Val Asp Gly Arg Ser Tyr
                725                     730                     735
Cys Arg Gly Leu Trp Val Ser Gly Val Ser Asn Phe Phe Tyr His Asp
                740                     745                     750
Arg Asp Ala Leu Gly Gln Gly Tyr Arg Tyr Ile Ser Gly Gly Tyr Ser
                755                     760                     765
Leu Gly Ala Asn Ser Tyr Phe Gly Ser Ser Met Phe Gly Leu Ala Phe
            770                     775                     780
Thr Glu Val Phe Gly Arg Ser Lys Asp Tyr Val Val Cys Arg Ser Asn
785                     790                     795                     800
His His Ala Cys Ile Gly Ser Val Tyr Leu Ser Thr Lys Gln Ala Leu
                805                     810                     815
Cys Gly Ser Tyr Val Phe Gly Asp Ala Phe Ile Arg Ala Ser Tyr Gly
                820                     825                     830
Phe Gly Asn Gln His Met Lys Thr Ser Tyr Thr Phe Ala Glu Glu Ser
            835                     840                     845
Asp Val Cys Trp Asp Asn Asn Cys Leu Val Gly Glu Ile Gly Val Gly
        850                     855                     860
Leu Pro Ile Val Ile Thr Pro Ser Lys Leu Tyr Leu Asn Glu Leu Arg
865                     870                     875                     880
Pro Phe Val Gln Ala Glu Phe Ser Tyr Ala Asp His Glu Ser Phe Thr
                885                     890                     895
Glu Glu Gly Asp Gln Ala Arg Ala Phe Arg Ser Gly His Leu Met Asn
                900                     905                     910
Leu Ser Val Pro Val Gly Val Lys Phe Asp Arg Cys Ser Ser Thr His
            915                     920                     925
Pro Asn Lys Tyr Ser Phe Met Gly Ala Tyr Ile Cys Asp Ala Tyr Arg
```

Figure 13 Cont'd

```
        930                 935                 940
Thr Ile Ser Gly Thr Gln Thr Thr Leu Leu Ser His Gln Glu Thr Trp
945                 950                 955                 960
Thr Thr Asp Ala Phe His Leu Ala Arg His Gly Val Ile Val Arg Gly
                965                 970                 975
Ser Met Tyr Ala Ser Leu Thr Ser Asn Ile Glu Val Tyr Gly His Gly
                980                 985                 990
Arg Tyr Glu Tyr Arg Asp Thr Ser  Arg Gly Tyr Gly Leu  Ser Ala Gly
            995                 1000                1005
Ser Lys  Val Arg Phe
        1010
```

Figure 14 - PmpG Nucleic Acid Sequence (*C. trachomatis* Serovar F) (SEQ ID NO: 20)

```
atgcaaacgt ctttccataa gttctttctt tcaatgattc tagcttattc ttgctgctct     60
ttaagtgggg gggggtatgc agcagaaatc atgattcctc aaggaattta cgatggggag    120
acgttaactg tatcatttcc ctatactgtt ataggagatc cgagtgggac tactgttttt    180
tctgcaggag agttaacgtt aaaaaatctt gacaattcta ttgcagcttt gcctttaagt    240
tgttttggga acttattagg gagttttact gttttaggga gaggacactc gttgactttc    300
gagaacatac ggacttctac aaatggagct gcactaagtg acagcgctaa tagcgggtta    360
tttactattg agggttttaa agaattatct tttttccaatt gcaactcatt acttgccgta    420
ctgcctgctg caacgactaa taatggtagc cagactccga cgacaacatc tacaccgtct    480
aatggtacta tttattctaa aacagatctt ttgttactca ataatgagaa gttctcattc    540
tatagtaatt tagtctctgg agatggggga actatagatg ctaagagctt aacggttcaa    600
ggaattagca agctttgtgt cttccaagaa aatactgctc aagctgatgg gggagcttgt    660
caagtagtca ccagtttctc tgctatggct aacgaggctc ctattgcctt tatagcgaat    720
gttgcaggag taagaggggg agggattgct gctgttcagg atgggcagca gggagtgtca    780
tcatctactt caacagaaga tccagtagta agtttttcca gaaatactgc ggtagagttt    840
gatgggaacg tagcccgagt aggaggaggg atttactcct acgggaacgt tgctttcctg    900
aataatggaa aaaccttgtt tctcaacaat gttgcttctc ctgtttacat tgctgctgag    960
caaccaacaa atggacaggc ttctaatacg agtgataatt acggagatgg aggagctatc   1020
ttctgtaaga atggtgcgca agcagcagga tccaataact ctggatcagt ttcctttgat   1080
ggagagggag tagttttctt tagtagcaat gtagctgctg ggaaaggggg agctatttat   1140
gccaaaaagc tctcggttgc taactgtggc cctgtacaat tcttagggaa tatcgctaat   1200
gatggtggag cgatttattt aggagaatct ggagagctca gtttatctgc tgattatgga   1260
gatattattt tcgatgggaa tcttaaaaga acagccaaag agaatgctgc cgatgttaat   1320
ggcgtaactg tgtcctcaca agccatttcg atgggatcgg gagggaaaat aacgacatta   1380
agagctaaag cagggcatca gattctcttt aatgatccca tcgagatggc aaacggaaat   1440
aaccagccag cgcagtcttc cgaacctcta aaaattaacg atggtgaagg atacacaggg   1500
gatattgttt ttgctaatgg aaacagtact ttgtaccaaa atgttacgat agagcaagga   1560
aggattgttc ttcgtgaaaa ggcaaaatta tcagtgaatt ctctaagtca gacaggtggg   1620
agtctgtata tggaagctgg gagtacattg gattttgtaa ctccacaacc accacaacag   1680
cctcctgccg ctaatcagtt gatcacgctt tccaatctgc atttgtctct ttcttctttg   1740
ttagcaaaca atgcagttac gaatcctcct accaatcctc cagcgcaaga ttctcatcct   1800
gcagtcattg gtagcacaac tgctggtcct gtcacaatta gtgggccttt ctttttgag   1860
gatttggatg atacagctta tgataggtat gattggctag gttctaatca aaaaatcgat   1920
gtcctgaaat tacagttagg gactcagccc tcagctaatg ccccatcaga tttgactcta   1980
gggaatgaga tgcctaagta tggctatcaa ggaagctgga agcttgcgtg ggatcctaat   2040
acagcaaata atggtcctta tactctgaaa gctacatgga ctaaaactgg gtataatcct   2100
gggcctgagc gagtagcttc tttggttcca aatagtttat ggggatccat tttagatata   2160
cgatctgcgc attcagcaat tcaagcaagt gtggatgggc gctcttattg tcgaggatta   2220
tgggtttctg gagtttcgaa tttctcctat catgaccgcg atgctttagg tcagggatat   2280
cggtatatta gtgggggtta ttccttagga gcaaactcct actttggatc atcgatgttt   2340
ggtctagcat ttaccgaagt atttggtaga tctaaagatt atgtagtgtg tcgttccaat   2400
catcatgctt gcataggatc cgtttatcta tctaccaaac aagctttatg tggatcctat   2460
ttgttcggag atgcgtttat ccgtgctagc tacgggtttg ggaaccagca tatgaaaacc   2520
tcatacacat ttgcagagga gagcgatgtt cgttgggata ataactgtct ggttggagag   2580
attggagtgg gattaccgat tgtgactact ccatctaagc tctatttgaa tgagttgcgt   2640
cctttcgtgc aagctgagtt ttcttatgcc gatcatgaat cttttacaga ggaaggcgat   2700
caagctcggg cattcaggag tggtcatctc atgaatctat cagttcctgt tggagtaaaa   2760
tttgatcgat gttctagtac acaccctaat aaatatagct ttatgggggc ttatatctgt   2820
gatgcttatc gcaccatctc tgggactcag acaacactcc tatcccatca agagacatgg   2880
acaacagatg cctttcattt ggcaagacat ggagtcatag ttagagggtc tatgtatgct   2940
tctctaacaa gcaatataga agtatatggc catggaagat atgagtatcg agatacttct   3000
cgaggttatg gtttgagtgc aggaagtaaa gtccggttct aaaaatattg gttagatagt   3060
taagtgttag cgatgccttt ttctttgaga tctacatcat tttgtttttt agcttgtttg   3120
tgttcctatt cgtatggatt cgcgagctct cctcaagtgt taacacctaa tgtaaccact   3180
ccttttaagg gggacgatgt ttacttgaat ggagactgcg ctttagtcaa tgtctatgca   3240
ggggcagaga acggctcaat tatctcagct aatggcgaca atttaacgat taccggacaa   3300
aaccatgcat tatcatttac agat                                           3324
```

Figure 15 – PmpG Protein (C. trachomatis serovar F)(SEQ ID NO: 21)

```
Met Gln Thr Ser Phe His Lys Phe Phe Leu Ser Met Ile Leu Ala Tyr
1               5                   10                  15
Ser Cys Cys Ser Leu Thr Gly Gly Gly Tyr Ala Ala Glu Ile Met Val
                20                  25                  30
Pro Gln Gly Ile Tyr Asp Gly Glu Thr Leu Thr Val Ser Phe Pro Tyr
                35                  40                  45
Thr Val Ile Gly Asp Pro Ser Gly Thr Thr Val Phe Ser Ala Gly Glu
            50              55                  60
Leu Thr Leu Lys Asn Leu Asp Asn Ser Ile Ala Ala Leu Pro Leu Ser
65                  70                  75                  80
Cys Phe Gly Asn Leu Leu Gly Ser Phe Thr Val Leu Gly Arg Gly His
                85                  90                  95
Ser Leu Thr Phe Glu Asn Ile Arg Thr Ser Thr Asn Gly Ala Ala Leu
                100                 105                 110
Ser Asp Ser Ala Asn Ser Gly Leu Phe Thr Ile Glu Gly Phe Lys Glu
                115                 120                 125
Leu Ser Phe Ser Asn Cys Asn Ser Leu Leu Ala Val Leu Pro Ala Ala
    130                 135                 140
Thr Thr Asn Asn Gly Ser Gln Thr Pro Thr Thr Thr Ser Thr Pro Ser
145                 150                 155                 160
Asn Gly Thr Ile Tyr Ser Lys Thr Asp Leu Leu Leu Asn Asn Glu
                165                 170                 175
Lys Phe Ser Phe Tyr Ser Asn Leu Val Ser Gly Asp Gly Thr Ile
                180                 185                 190
Asp Ala Lys Ser Leu Thr Val Gln Gly Ile Ser Lys Leu Cys Val Phe
                195                 200                 205
Gln Glu Asn Thr Ala Gln Ala Asp Gly Gly Ala Cys Gln Val Val Thr
    210                 215                 220
Ser Phe Ser Ala Met Ala Asn Glu Ala Pro Ile Ala Phe Ile Ala Asn
225                 230                 235                 240
Val Ala Gly Val Arg Gly Gly Gly Ile Ala Ala Val Gln Asp Gly Gln
                245                 250                 255
Gln Gly Val Ser Ser Ser Thr Ser Thr Glu Asp Pro Val Val Ser Phe
                260                 265                 270
Ser Arg Asn Thr Ala Val Glu Phe Asp Gly Asn Val Ala Arg Val Gly
                275                 280                 285
Gly Gly Ile Tyr Ser Tyr Gly Asn Val Ala Phe Leu Asn Asn Gly Lys
                290                 295                 300
Thr Leu Phe Leu Asn Asn Val Ala Ser Pro Val Tyr Ile Ala Ala Glu
305                 310                 315                 320
Gln Pro Thr Asn Gly Gln Ala Ser Asn Thr Ser Asp Asn Tyr Gly Asp
                325                 330                 335
Gly Gly Ala Ile Phe Cys Lys Asn Gly Ala Gln Ala Ala Gly Ser Asn
                340                 345                 350
Asn Ser Gly Ser Val Ser Phe Asp Gly Glu Gly Val Val Phe Phe Ser
                355                 360                 365
Ser Asn Val Ala Ala Gly Lys Gly Ala Ile Tyr Ala Lys Lys Leu
                370                 375                 380
Ser Val Ala Asn Cys Gly Pro Val Gln Phe Leu Gly Asn Ile Ala Asn
385                 390                 395                 400
Asp Gly Gly Ala Ile Tyr Leu Gly Glu Ser Gly Glu Leu Ser Leu Ser
                405                 410                 415
Ala Asp Tyr Gly Asp Ile Ile Phe Asp Gly Asn Leu Lys Arg Thr Ala
                420                 425                 430
Lys Glu Asn Ala Ala Asp Val Asn Gly Val Thr Val Ser Ser Gln Ala
                435                 440                 445
Ile Ser Met Gly Ser Gly Gly Lys Ile Thr Thr Leu Arg Ala Lys Ala
                450                 455                 460
Gly His Gln Ile Leu Phe Asn Asp Pro Ile Glu Met Ala Asn Gly Asn
```

Figure 15 Cont'd

```
465                      470                      475                      480
Asn Gln Pro Ala Gln Ser Ser Glu Pro Leu Lys Ile Asn Asp Gly Glu
                485                      490                      495
Gly Tyr Thr Gly Asp Ile Val Phe Ala Asn Gly Asn Ser Thr Leu Tyr
                500                      505                      510
Gln Asn Val Thr Ile Glu Gln Gly Arg Ile Val Leu Arg Glu Lys Ala
                515                      520                      525
Lys Leu Ser Val Asn Ser Leu Ser Gln Thr Gly Gly Ser Leu Tyr Met
        530                      535                      540
Glu Ala Gly Ser Thr Leu Asp Phe Val Thr Pro Gln Pro Pro Gln Gln
545                      550                      555                      560
Pro Pro Ala Ala Asn Gln Leu Ile Thr Leu Ser Asn Leu His Leu Ser
                565                      570                      575
Leu Ser Ser Leu Leu Ala Asn Asn Ala Val Thr Asn Pro Pro Thr Asn
        580                      585                      590
Pro Pro Ala Gln Asp Ser His Pro Ala Val Ile Gly Ser Thr Thr Ala
        595                      600                      605
Gly Pro Val Thr Ile Ser Gly Pro Phe Phe Phe Glu Asp Leu Asp Asp
610                      615                      620
Thr Ala Tyr Asp Arg Tyr Asp Trp Leu Gly Ser Asn Gln Lys Ile Asp
625                      630                      635                      640
Val Leu Lys Leu Gln Leu Gly Thr Gln Pro Ser Ala Asn Ala Pro Ser
                645                      650                      655
Asp Leu Thr Leu Gly Asn Glu Met Pro Lys Tyr Gly Tyr Gln Gly Ser
                660                      665                      670
Trp Lys Leu Ala Trp Asp Pro Asn Thr Ala Asn Asn Gly Pro Tyr Thr
        675                      680                      685
Leu Lys Ala Thr Trp Thr Lys Thr Gly Tyr Asn Pro Gly Pro Glu Arg
        690                      695                      700
Val Ala Ser Leu Val Pro Asn Ser Leu Trp Gly Ser Ile Leu Asp Ile
705                      710                      715                      720
Arg Ser Ala His Ser Ala Ile Gln Ala Ser Val Asp Gly Arg Ser Tyr
                725                      730                      735
Cys Arg Gly Leu Trp Val Ser Gly Val Ser Asn Phe Ser Tyr His Asp
                740                      745                      750
Arg Asp Ala Leu Gly Gln Gly Tyr Arg Tyr Ile Ser Gly Gly Tyr Ser
        755                      760                      765
Leu Gly Ala Asn Ser Tyr Phe Gly Ser Ser Met Phe Gly Leu Ala Phe
        770                      775                      780
Thr Glu Val Phe Gly Arg Ser Lys Asp Tyr Val Val Cys Arg Ser Asn
785                      790                      795                      800
His His Ala Cys Ile Gly Ser Val Tyr Leu Ser Thr Lys Gln Ala Leu
                805                      810                      815
Cys Gly Ser Tyr Leu Phe Gly Asp Ala Phe Ile Arg Ala Ser Tyr Gly
                820                      825                      830
Phe Gly Asn Gln His Met Lys Thr Ser Tyr Thr Phe Ala Glu Glu Ser
        835                      840                      845
Asp Val Arg Trp Asp Asn Asn Cys Leu Val Gly Glu Ile Gly Val Gly
        850                      855                      860
Leu Pro Ile Val Thr Thr Pro Ser Lys Leu Tyr Leu Asn Glu Leu Arg
865                      870                      875                      880
Pro Phe Val Gln Ala Glu Phe Ser Tyr Ala Asp His Glu Ser Phe Thr
                885                      890                      895
Glu Glu Gly Asp Gln Ala Arg Ala Phe Arg Ser Gly His Leu Met Asn
                900                      905                      910
Leu Ser Val Pro Val Gly Val Lys Phe Asp Arg Cys Ser Ser Thr His
        915                      920                      925
Pro Asn Lys Tyr Ser Phe Met Gly Ala Tyr Ile Cys Asp Ala Tyr Arg
```

Figure 15 Cont'd

```
        930                935                940
Thr Ile Ser Gly Thr Gln Thr Thr Leu Leu Ser His Gln Glu Thr Trp
945                950                955                960
Thr Thr Asp Ala Phe His Leu Ala Arg His Gly Val Ile Val Arg Gly
                965                970                975
Ser Met Tyr Ala Ser Leu Thr Ser Asn Ile Glu Val Tyr Gly His Gly
            980                985                990
Arg Tyr Glu Tyr Arg Asp Thr Ser  Arg Gly Tyr Gly Leu  Ser Ala Gly
        995                1000                1005
Ser Lys  Val Arg Phe
    1010
```

Figure 16 - CT40
Nucleic Acid Sequence (SEQ ID NO: 22)

```
atg att ttc gat ggg aat att aaa aga aca gcc aaa gag aat gct gcc
gat gtt aat ggc gta act gtg tcc tca caa gcc att tcg atg gga tcg
gga ggg aaa ata acg aca tta aga gct aaa gca ggg cat cag att ctc ttt aat
gat ccc atc gag atg gca aac gga aat aac cag cca gcg cag tct tcc aaa ctt cta
aaa att aac gat ggt gaa gga tac aca ggg gat att gtt ttt gct aat gga agc agt
act ttg tac caa aat gtt acg ata gag caa gga agg att gtt ctt cgt gaa aag gca
aaa tta tca gtg aat tct cta agt cag aca ggt ggg agt ctg tat atg gaa gct ggg
agt aca ttg gat ttt gta act cca caa cca cca caa cag cct cct gcc gct aat
cag ttg atc acg ctt tcc aat ctg cat ttg tct ctt tct tct ttg tta gca aac aat
gca gtt acg aat cct cct acc aat cct cca gcg caa gat tct cat cct gca gtc att
ggt agc aca act gct ggt tct gtt aca att agt ggg cct atc ttt ttt gag gat ttg
gat gat aca gct tat gat agg tat gat tgg cta ggt tct aat caa aaa atc aat gtc
ctg aaa tta cag tta ggg act aag ccc cca gct aat gcc cca tca gat ttg act cta
ggg aat gag atg cct aag tat ggc tat caa gga agc tgg aag ctt gcg tgg
gat cct aat aca gca aat aat ggt cct tat act ctg aaa gct aca tgg act aaa act
ggg tat aat cct ggg cct gag cga gta gct tct ttg gtt cca aat agt tta tgg gga
tcc att tta gat ata cga tct gcg cat tca gca att caa gca agt gtg gat ggg cgc
tct tat tgt cga gga tta tgg gtt tct gga gtt tcg aat ttc ttc tat cat gac cgc
gat gct tta ggt cag gga tat cgg tat att agt ggg ggt tat tcc tta gga gca aac
tcc tac ttt gga tca tcg atg ttt ggt cta gca ttt acc taa taa
```

Peptide Sequence (SEQ ID NO: 23)

```
Met Ile Phe Asp Gly Asn Ile Lys Arg Thr Ala Lys Glu Asn Ala Ala
1               5                   10                  15

Asp Val Asn Gly Val Thr Val Ser Ser Gln Ala Ile Ser Met Gly Ser
            20                  25                  30

Gly Gly Lys Ile Thr Thr Leu Arg Ala Lys Ala Gly His Gln Ile Leu
        35                  40                  45

Phe Asn Asp Pro Ile Glu Met Ala Asn Gly Asn Asn Gln Pro Ala Gln
    50                  55                  60

Ser Ser Lys Leu Leu Lys Ile Asn Asp Gly Glu Gly Tyr Thr Gly Asp
65                  70                  75                  80

Ile Val Phe Ala Asn Gly Ser Ser Thr Leu Tyr Gln Asn Val Thr Ile
                85                  90                  95

Glu Gln Gly Arg Ile Val Leu Arg Glu Lys Ala Lys Leu Ser Val Asn
            100                 105                 110

Ser Leu Ser Gln Thr Gly Gly Ser Leu Tyr Met Glu Ala Gly Ser Thr
        115                 120                 125

Leu Asp Phe Val Thr Pro Gln Pro Gln Gln Pro Pro Ala Ala Asn
        130                 135                 140
```

Figure 16 Cont'd

```
Gln Leu Ile Thr Leu Ser Asn Leu His Leu Ser Leu Ser Ser Leu Leu
145                 150                 155                 160

Ala Asn Asn Ala Val Thr Asn Pro Pro Thr Asn Pro Pro Ala Gln Asp
                165                 170                 175

Ser His Pro Ala Val Ile Gly Ser Thr Thr Ala Gly Ser Val Thr Ile
                180                 185                 190

Ser Gly Pro Ile Phe Phe Glu Asp Leu Asp Asp Thr Ala Tyr Asp Arg
                195                 200                 205

Tyr Asp Trp Leu Gly Ser Asn Gln Lys Ile Asn Val Leu Lys Leu Gln
    210                 215                 220

Leu Gly Thr Lys Pro Pro Ala Asn Ala Pro Ser Asp Leu Thr Leu Gly
225                 230                 235                 240

Asn Glu Met Pro Lys Tyr Gly Tyr Gln Gly Ser Trp Lys Leu Ala Trp
                245                 250                 255

Asp Pro Asn Thr Ala Asn Asn Gly Pro Tyr Thr Leu Lys Ala Thr Trp
                260                 265                 270

Thr Lys Thr Gly Tyr Asn Pro Gly Pro Glu Arg Val Ala Ser Leu Val
            275                 280                 285

Pro Asn Ser Leu Trp Gly Ser Ile Leu Asp Ile Arg Ser Ala His Ser
        290                 295                 300

Ala Ile Gln Ala Ser Val Asp Gly Arg Ser Tyr Cys Arg Gly Leu Trp
305                 310                 315                 320

Val Ser Gly Val Ser Asn Phe Phe Tyr His Asp Arg Asp Ala Leu Gly
                325                 330                 335

Gln Gly Tyr Arg Tyr Ile Ser Gly Gly Tyr Ser Leu Gly Ala Asn Ser
            340                 345                 350

Tyr Phe Gly Ser Ser Met Phe Gly Leu Ala Phe Thr
```

Figure 17 - ssaG promoter (SEQ ID NO: 24)

```
gcgcgccgct cgtagccctg gcagggattg gccttgctat tgccatcgcg gatgtcgcct      60
gtcttatcta ccatcataaa catcatttgc ctatggctca cgacagtata ggcaatgccg     120
tttttatat tgctaattgt ttcgccaatc aacgcaaaag tatggcgatt gctaaagccg      180
tctccctggg cggtagatta gccttaaccg cgacggtaat gactcattca tactggagtg    240
gtagtttggg actacagcct catttattag agcgtcttaa tgatattacc tatggactaa    300
tgagttttac tcgcttcggt atggatggga tggcaatgac cggtatgcag gtcagcagcc    360
cattatatcg tttgctggct caggtaacgc cagaacaacg tgcgccggag taatcgtttt    420
caggtatata ccggatgttc attgctttct aaattttgct atgttgccag tatccttacg    480
atgtatttat tttaaggaaa agcatt                                          506
```

Figure 18 – ClyA (SEQ ID NO: 25)

Met Thr Ser Ile Phe Ala Glu Gln Thr Val Glu Val Val Lys Ser Ala
1               5                   10                  15

Ile Glu Thr Ala Asp Gly Ala Leu Asp Leu Tyr Asn Lys Tyr Leu Asp
            20                  25                  30

Gln Val Ile Pro Trp Lys Thr Phe Asp Glu Thr Ile Lys Glu Leu Ser
        35                  40                  45

Arg Phe Lys Gln Glu Tyr Ser Gln Glu Ala Ser Val Leu Val Gly Asp
        50                  55                  60

Ile Lys Val Leu Leu Met Asp Ser Gln Asp Lys Tyr Phe Glu Ala Thr
65                  70                  75                  80

Gln Thr Val Tyr Glu Trp Cys Gly Val Val Thr Gln Leu Leu Ser Ala
            85                  90                  95

Tyr Ile Leu Leu Phe Asp Glu Tyr Asn Glu Lys Lys Ala Ser Ala Gln
            100                 105                 110

Lys Asp Ile Leu Ile Arg Ile Leu Asp Asp Gly Val Lys Lys Leu Asn
        115                 120                 125

Glu Ala Gln Lys Ser Leu Leu Thr Ser Ser Gln Ser Phe Asn Asn Ala
            130                 135                 140

Ser Gly Lys Leu Leu Ala Leu Asp Ser Gln Leu Thr Asn Asp Phe Ser
145                 150                 155                 160

Glu Lys Ser Ser Tyr Phe Gln Ser Gln Val Asp Arg Ile Arg Lys Glu
            165                 170                 175

Ala Tyr Ala Val Ala Ala Ala Gly Ser Val Ser Gly Pro Phe Gly Leu
            180                 185                 190

Figure 18 Cont'd

Ser Ile Ser Tyr Ser Ile Ala Ala Gly Val Ile Glu Gly Lys Leu Ile
    195          200          205

Pro Glu Leu Asn Asn Arg Leu Lys Thr Val Gln Asn Phe Phe Thr Ser
  210          215          220

Leu Ser Ala Thr Val Lys Gln Ala Asn Lys Asp Ile Asp Ala Ala Lys
225          230          235          240

Leu Lys Leu Ala Thr Glu Ile Ala Ala Ile Gly Glu Ile Lys Thr Glu
    245          250          255

Thr Glu Thr Thr Arg Phe Tyr Val Asp Tyr Asp Asp Leu Met Leu Ser
    260          265          270

Leu Leu Lys Gly Ala Ala Lys Lys Met Ile Asn Thr Cys Asn Glu Tyr
    275          280          285

Gln Gln Arg His Ile Ser Gly Lys Lys Thr Leu Phe Glu Val Pro Asp
  290          295          300

Val
305

Figure 19 – CT84-ssaG promoter construct (SEQ ID NOs: 26 and 27)

```
 910 TCGCGGCCCG TGAACATTTC AATATTTATA AAGATTAAAA CACGCAAACG ACAACAACGA
     AGCGCCGGGC ACTTGTAAAG TTATAAATAT TTCTAATTTT GTGCGTTTGC TGTTGTTGCT
 970 TAACGGAGCC GTGATGGCAG GAAACACAAT TGGACAACTC TTTCGCGTAA CCACTTTCGG
     ATTGCCTCGG CACTACCGTC CTTTGTGTTA ACCTGTTGAG AAAGCGCATT GGTGAAAGCC
1030 CGAATCACAC GGGCTGGCGC TTGGGGGTAT CGTCGATGGC GTGCCGCCCG GCATCCCGTT
     GCTTAGTGTG CCCGACCGCG AACCCCATA GCAGCTACCG CACGGCGGGC CGTAGGGCAA
1090 GACGGAGGCC GATCTGCAGC ACGATCTCGA CCTGGCACCT CGCGCTATAC
     CTGCCTCCGG CTAGACGTCG TGCTAGAGCT GTCTGCGGCG GGACCGTGGA GCGCGATATG
1150 TACTCAGCGC CGCGAACCGG ACCAGGTAAA AATTCTCTCC GGCGTGTTTG ATGGCGTAAC
     ATGAGTCGCG GCGCTTGGCC TGGTCCATTT TTAAGAGAGG CCGCACAAAC TACCGCATTG
                XhoI
                ~~~~~~~
1210 GACCGGCTCG AGATTGCCAT CGCGGATGTC GCCTGTCTTA TCTACCATCA TAAACATCAT
     CTGGCCGAGC TCTAACGGTA GCGCCTACAG CGGACAGAAT AGATGGTAGT ATTTGTAGTA
1270 TTGCCTATGG CTCACGACAG TATAGGCAAT GCCGTTTTTT ATATTGCTAA TTGTTTCGCC
     AACGGATACC GAGTGCTGTC ATATCCGTTA CGGCAAAAAA TATAACGATT AACAAAGCGG
1330 AATCAACGCA AAAGTATGGC GATTGCTAAA GCCGTCTCCC TGGGCGGTAG ATTAGCCTTA
     TTAGTTGCGT TTTCATACCG CTAACGATTT CGGCAGAGGG ACCCGCCATC TAATCGGAAT
1390 ACCGCGACGG TAATGACTCA TTCATACTGG AGTGGTAGTT TGGGACTACA GCCTCATTTA
     TGGCGCTGCC ATTACTGAGT AAGTATGACC TCACCATCAA ACCCTGATGT CGGAGTAAAT
1450 TTAGAGCGTC TTAATGATAT TACCTATGGA CTAATGAGTT TTACTCGCTT CGGTATGGAT
     AATCTCGCAG AATTACTATA ATGGATACCT GATTACTCAA AATGAGCGAA GCCATACCTA
1510 GGGATGGCAA TGACCGGTAT GCAGGTCAGC AGCCCATTAT ATCGTTGCT GGCTCAGGTA
     CCCTACCGTT ACTGGCCATA CGTCCAGTCG TCGGGTAATA TAGCAAACGA CCGAGTCCAT
1570 ACGCCAGAAC AACGTGCGCC GGAGTAATCG TTTTCAGGTA TATACCGGAT GTTCATTGCT
     TGCGGTCTTG TTGCACGCGG CCTCATTAGC AAAAGTCCAT ATATGGCCTA CAAGTAACGA
                                                              NdeI
                                                              ~~~
1630 TTCTAAATTT TGCTATGTTG CCAGTATCCT TACGATGTAT TTATTTTAAG GAAAAGCCAT
     AAGATTTAAA ACGATACAAC GGTCATAGGA ATGCTACATA AATAAAATTC CTTTTCGGTA
     NdeI
     ~~~
            M  E  I  M  V  P  Q  G  I  Y  D  G  E  T  L  T  V  S  F  P
1690 ATGGAAATTA TGGTTCCGCA GGGTATCTAC GATGGTGAAA CCCTGACCGT GTCTTTCCCG
     TACCTTTAAT ACCAAGGCGT CCCATAGATG CTACCACTTT GGGACTGGCA CAGAAAGGGC
            Y  T  V  I  G  D  P  S  G  T  V  F  S  A  G  E  L  T  L
1750 TATACCGTTA TCGGTGATCC GAGCGGTACG ACCGTTTTCA GCGCCGGTGA ACTGACCCTG
     ATATGGCAAT AGCCACTAGG CTCGCCATGC TGGCAAAAGT CGCGGCCACT TGACTGGGAC
            K  N  L  D  N  S  I  A  A  L  P  L  S  C  F  G  N  L  L  G
1810 AAAAACCTGG ATAATAGCAT TGCGGCGCTG CCGCTGTCTT GCTTCGGTAA CCTGCTGGGT
     TTTTTGGACC TATTATCGTA ACGCCGCGAC GGCGACAGAA CGAAGCCATT GGACGACCCA
            S  F  T  V  L  G  R  G  H  S  L  T  F  E  N  I  R  T  S  T
1870 TCTTTCACCG TTCTGGGTCG TGGCCATAGC CTGACCTTTG AAAACATTCG TACCAGCACC
     AGAAAGTGGC AAGACCCAGC ACCGGTATCG GACTGGAAAC TTTTGTAAGC ATGGTCGTGG
            N  G  A  A  L  S  N  S  A  A  D  G  L  F  T  I  E  G  F  K
1930 AATGGTGCGG CGCTGTCTAA TAGCGCGGCG GATGGTCTGT TCACCATTGA AGGTTTCAAA
     TTACCACGCC GCGACAGATT ATCGCGCCGC CTACCAGACA AGTGGTAACT TCCAAAGTTT
            E  L  S  F  S  N  C  N  S  L  L  A  V  L  P  A  A  T  T  N
1990 GAACTGTCTT TCTCTAACTG CAATAGCCTG CTGGCGGTTC TGCCGGCGGC GACCACCAAC
     CTTGACAGAA AGAGATTGAC GTTATCGGAC GACCGCCAAG ACGGCCGCCG CTGGTGGTTG
            K  G  S  Q  T  P  T  T  T  S  T  P  S  N  G  T  I  Y  S  K
2050 AAAGGCAGCC AGACCCCGAC CACCACGAGC ACCCCGTCTA ACGGCACCAT CTACAGCAAA
     TTTCCGTCGG TCTGGGGCTG GTGGTGCTCG TGGGGCAGAT TGCCGTGGTA GATGTCGTTT
            T  D  L  L  L  N  E  K  F  S  F  Y  S  N  L  V  S  G
2110 ACCGATCTGC TGCTGCTGAA CAACGAAAAA TTCTCTTTTT ATAGCAACCT GGTTTCTGGT
     TGGCTAGACG ACGACGACTT GTTGCTTTTT AAGAGAAAAA TATCGTTGGA CCAAAGACCA
            D  G  A  I  D  A  K  S  L  T  V  Q  G  I  S  K  L  C  V
2170 GATGGTGGTG CGATTGATGC GAAAAGCCTG ACCGTTCAGG GTATCTCTAA ACTGTGCGTT
```

Figure 19 (Cont'd)

```
       CTACCACCAC GCTAACTACG CTTTTCGGAC TGGCAAGTCC CATAGAGATT TGACACGCAA
        F  Q  E  N   T  A  Q    A  D  G    G  A  C    Q  V  V  T    S  F  S
 2230 TTCCAGGAAA ACACCGCGCA GGCGGATGGC GGTGCGTGCC AGGTTGTTAC CTCTTTCAGC
       AAGGTCCTTT TGTGGCGCGT CCGCCTACCG CCACGCACGG TCCAACAATG GAGAAAGTCG
        A  M  N  E  A  P    I  A  F    V  A  N  V   A  G  V    R  G  G
 2290 GCGATGGCCA ATGAAGCGCC GATTGCGTTT GTTGCCAACG TGGCGGGTGT TCGTGGTGGT
       CGCTACCGGT TACTTCGCGG CTAACGCAAA CAACGGTTGC ACCGCCCACA AGCACCACCA
        G  I  A  A  V  Q  D   G  Q  Q    G  V  S  S   S  T  S    T  E  D
 2350 GGTATCGCGG CGGTGCAGGA TGGTCAGCAG GGTGTGAGCT CTTCTACCTC TACCGAAGAT
       CCATAGCGCC GCCACGTCCT ACCAGTCGTC CCACACTCGA GAAGATGGAG ATGGCTTCTA
        P  V  V  S    F  S  R    N  T  A   V  E  F  D   G  N  V    A  R  V
 2410 CCGGTGGTGA GCTTCAGCCG TAACACCGCG GTGGAATTTG ATGGTAACGT GGCGCGCGTT
       GGCCACCACT CGAAGTCGGC ATTGTGGCGC CACCTTAAAC TACCATTGCA CCGCGCGCAA
        G  G  G  I  Y  S  Y    G  N  V    A  F  L  N    N  G  K    T  L  F
 2470 GGTGGTGGTA TCTACAGCTA CGGTAACGTG GCGTTCCTGA ACAATGGTAA AACCCTGTTC
       CCACCACCAT AGATGTCGAT GCCATTGCAC CGCAAGGACT TGTTACCATT TTGGGACAAG
         L  N  N  V   A  S  P    V  Y  I   A  A  K  Q    P  T  S    G  Q  A
 2530 CTGAATAACG TTGCGAGCCC GGTGTATATT GCGGCCAAAC AGCCGACCTC TGGTCAGGCG
       GACTTATTGC AACGCTCGGG CCACATATAA CGCCGGTTTG TCGGCTGGAG ACCAGTCCGC
         S  N  T  S   N  N  Y    G  D  G    G  A  I  F   C  K  N    G  A  Q
 2590 TCTAACACCA GCAATAACTA CGGCGATGGT GGCGCCATTT TCTGCAAAAA CGGTGCGCAG
       AGATTGTGGT CGTTATTGAT GCCGCTACCA CCGCGGTAAA AGACGTTTTT GCCACGCGTC
        A  G  S  N  N  S  G    S  V  S    F  D  G  E    G  V  V    F  F  S
 2650 GCGGGCAGCA ACAACTCTGG CAGCGTGAGC TTCGATGGCG AAGGCGTGGT GTTTTTCAGC
       CGCCCGTCGT TGTTGAGACC GTCGCACTCG AAGCTACCGC TTCCGCACCA CAAAAAGTCG
         S  N  V  A   G  K  G   G  A  I    Y  A  K  K    L  S  V  A  N
 2710 TCTAATGTGG CGGCGGGTAA AGGCGGCGCG ATTTATGCGA AAAAACTGTC TGTTGCGAAC
       AGATTACACC GCCGCCCATT TCCGCCGCGC TAAATACGCT TTTTTGACAG ACAACGCTTG
        C  G  P  V   Q  F  L   R  N  I    A  N  D  G    A  I  Y  L  G
 2770 TGCGGCCCGG TGCAGTTCCT GCGTAACATT GCGAACGATG GTGGTGCGAT CTACCTGGGT
       ACGCCGGGCC ACGTCAAGGA CGCATTGTAA CGCTTGCTAC CACCACGCTA GATGGACCCA
         E  S  G  E  L  S  L    S  A  D    Y  G  D  I    I  F  D    G  N  I
 2830 GAAAGCGGCG AACTGTCTCT GAGCGCGGAT TATGGCGATA TTATCTTCGA TGGTAACATT
       CTTTCGCCGC TTGACAGAGA CTCGCGCCTA ATACCGCTAT AATAGAAGCT ACCATTGTAA
        K  R  T  A  K  E  N    A  A  D    V  N  G  V   T  V  S    S  Q  A
 2890 AAACGTACCG CGAAAGAAAA CGCGGCGGAT GTGAACGGTG TGACCGTGTC TTCTCAGGCG
       TTTGCATGGC GCTTTCTTTT GCGCCGCCTA CACTTGCCAC ACTGGCACAG AAGAGTCCGC
         I  S  M  G   S  G  G   K  I  T    T  L  R  A    K  A  G    H  Q  I
 2950 ATTAGCATGG GTAGCGGCGG CAAAATTACC ACCCTGCGTG CGAAAGCGGG TCATCAGATC
       TAATCGTACC CATCGCCGCC GTTTTAATGG TGGGACGCAC GCTTTCGCCC AGTAGTCTAG
         L  F  N  D   P  I  E   M  A  N    G  N  N  Q    P  A  Q    S  S  K
 3010 CTGTTCAACG ATCCGATCGA AATGGCGAAC GGTAATAACC AGCCGGCGCA GTCTTCTAAA
       GACAAGTTGC TAGGCTAGCT TTACCGCTTG CCATTATTGG TCGGCCGCGT CAGAAGATTT
         L  L  K  I   N  D  G   E  G  Y    T  G  D  I    V  F  A    N  G  S
 3070 CTGCTGAAAA TTAACGATGG TGAAGGTTAC ACCGGTGATA TTGTGTTCGC GAACGGTTCT
       GACGACTTTT AATTGCTACC ACTTCCAATG TGGCCACTAT AACACAAGCG CTTGCCAAGA
         S  T  L  Y   Q  N  V   T  I  E    Q  G  R  I    V  L  R    E  K  A
 3130 AGCACCCTGT ATCAGAACGT TACCATCGAA CAGGGCCGTA TCGTTCTGCG TGAAAAAGCG
       TCGTGGGACA TAGTCTTGCA ATGGTAGCTT GTCCCGGCAT AGCAAGACGC ACTTTTTCGC
         K  L  S  V   N  S  L    S  Q  T   G  G  S  L    Y  M  E    A  G  S
 3190 AAACTGTCTG TTAACAGCCT GAGCCAGACC GGTGGTAGCC TGTATATGGA AGCGGGTTCT
       TTTGACAGAC AATTGTCGGA CTCGGTCTGG CCACCATCGG ACATATACCT TCGCCCAAGA
         T  L  D  F  V  T  P    Q  P  P    Q  Q  P  P    A  A  N    Q  L  I
 3250 ACCCTGGATT TCGTTACCCC GCAGCCGCCG CAGCAGCCGC CGGCGGCGAA TCAGCTGATC
       TGGGACCTAA AGCAATGGGG CGTCGGCGGC GTCGTCGGCG GCCGCCGCTT AGTCGACTAG
         T  L  S  N  L  H  L    S  L  S    S  L  L  A    N  N  A    V  T  N
 3310 ACCCTGAGCA ACCTGCATCT GTCTCTGTCT TCTCTGCTGG CGAACAACGC GGTTACCAAC
       TGGGACTCGT TGGACGTAGA CAGAGACAGA AGAGACGACC GCTTGTTGCG CCAATGGTTG
         P  P  T  N   P  P  A   Q  D  S    H  P  A  V    I  G  S    T  T  A
```

Figure 19 (Cont'd)

```
3370 CCGCCGACCA ACCCGCCGGC GCAGGATTCT CATCCGGCGG TGATTGGTAG CACCACCGCG
     GGCGGCTGGT TGGGCGGCCG CGTCCTAAGA GTAGGCCGCC ACTAACCATC GTGGTGGCGC
        G  S  V  T     I  S  G     P  I  F     F  E  D  L     D  D  T     A  Y  D
3430 GGTAGCGTTA CCATTTCTGG TCCGATTTTC TTTGAAGATC TGGATGATAC CGCGTACGAT
     CCATCGCAAT GGTAAAGACC AGGCTAAAAG AAACTTCTAG ACCTACTATG GCGCATGCTA
        R  Y  D  W     L  G  S     N  Q  K     I  N  V  L     K  L  Q     L  G  T
3490 CGCTACGATT GGCTGGGTAG CAACCAGAAA ATCAACGTTC TGAAACTGCA ACTGGGCACC
     GCGATGCTAA CCGACCCATC GTTGGTCTTT TAGTTGCAAG ACTTTGACGT TGACCCGTGG
        K  P  P  A  N  P     S  D  L     T  L  G  N     E  M  P     K  Y  G
3550 AAACCGCCGG CGAACGCGCC GTCTGATCTG ACCCTGGGTA ACGAAATGCC GAAATATGGC
     TTTGGCGGCC GCTTGCGCGG CAGACTAGAC TGGGACCCAT TGCTTTACGG CTTTATACCG
        Y  Q  G  S     W  K  L     A  W  D     P  N  T     A  N  N     P  Y  T
3610 TACCAGGGTT CTTGGAAACT GGCGTGGGAC CCGAACACCG CGAACAACGG TCCGTACACC
     ATGGTCCCAA GAACCTTTGA CCGCACCCTG GGCTTGTGGC GCTTGTTGCC AGGCATGTGG
        L  K  A  T     W  T  K     T  G  Y     N  P  G  P     E  R  V     A  S  L
3670 CTGAAAGCGA CCTGGACCAA AACCGGTTAC AATCCGGGCC CGGAACGTGT TGCGTCTCTG
     GACTTTCGCT GGACCTGGTT TTGGCCAATG TTAGGCCCGG GCCTTGCACA ACGCAGAGAC
        V  P  N  S     L  W  G     S  I  L     D  I  R  S     A  H  S     A  I  Q
3730 GTTCCGAACT CTCTGTGGGG CAGCATTCTG GATATTCGCA GCGCGCATTC TGCGATCCAG
     CAAGGCTTGA GAGACACCCC GTCGTAAGAC CTATAAGCGT CGCGCGTAAG ACGCTAGGTC
        A  S  V  D     G  R  S     Y  C  R     G  L  W  V     S  G  V     S  N  F
3790 GCGAGCGTGG ATGGTCGTAG CTATTGCCGC GGTCTGTGGG TTAGCGGTGT TTCTAACTTC
     CGCTCGCACC TACCAGCATC GATAACGGCG CCAGACACCC AATCGCCACA AAGATTGAAG
        F  Y  H  D     R  D  A     L  G  Q     G  Y  R  Y     I  S  G     G  Y  S
3850 TTCTATCATG ATCGCGATGC GCTGGGCCAG GGCTATCGCT ATATTAGCGG TGGTTATAGC
     AAGATAGTAC TAGCGCTACG CGACCCGGTC CCGATAGCGA TATAATCGCC ACCAATATCG
                                                                       XbaI
                                                                       ~~~~~
        L  G  A  N     S  Y  F     G  S  S     M  F  G     L  A  F     T
3910 CTGGGTGCGA ACAGCTATTT CGGTAGCAGC ATGTTCGGCC TGGCGTTCAC CTAATCTAGA
     GACCCACGCT TGTCGATAAA GCCATCGTCG TACAAGCCGG ACCGCAAGTG GATTAGATCT
                 AvrII
                 ~~~~~~~~
3970 GTCGACTAGC CTAGGTCCAG CATTACCGTG CCGGGACGTA CGATCAACCG GATGGGTGAA
     CAGCTGATCG GATCCAGGTC GTAATGGCAC GGCCCTGCAT GCTAGTTGGC CTACCCACTT
4030 GAGGTCGAGA TGATCACCAA AGGGCGCCAC GATCCGTGTG TGGGGATTCG CGCAGTGCCG
     CTCCAGCTCT ACTAGTGGTT TCCCGCGGTG CTAGGCACAC ACCCCTAAGC GCGTCACGGC
4090 ATCGCAGAAG TCATGCTGGC GATCGTACTG ATGGATCACC TGCTGCGCCA TCGGGCACAG
     TAGCGTCTTC AGTACGACCG CTAGCATGAC TACCTAGTGG ACGACGCGGT AGCCCGTGTC
4150 AATGCGGATG TAAAGACAGA GATTCCACGC TGGTAAGAAA TGAAAAAAAC CGCGATTGCG
     TTACGCCTAC ATTTCTGTCT CTAAGGTGCG ACCATTCTTT ACTTTTTTTG GCGCTAACGC
4210 CTGCTGGCAT GGTTTGTCAG TAGCGCCAGC CTGGCGGCGA CGTCGTGGCA GAAAATAACC
     GACGACCGTA CCAAACAGTC ATCGCGGTCG GACCGCCGCT GCAGCACCGT CTTTTATTGG
4270 CATCCTGTCC CCGGCGCCGC CCAGTCTATC GGTAGCTTTG CCAACGGATG
     GTAGGACAGG GGCCGCGGCG GGTCAGATAG CCATCGAAAC GGTTGCCTAC
```

Fragment showing ssaG promoter and CT84
3410 bp

Figure 20 – CT84-ssaG promoter construct (SEQ ID NOs: 28 and 29)

```
1331 AAAGGGGGAT GTGCTGCAAG GCGATTAAGT TGGGTAACGC CAGGGTTTTC CCAGTCACGA
     TTTCCCCCTA CACGACGTTC CGCTAATTCA ACCCATTGCG GTCCCAAAAG GGTCAGTGCT
1391 CGTTGTAAAA CGACGGCCAG TGAATTCTAA TACGACTCAC TATAGGGCGA ATTGGAGCTC
     GCAACATTTT GCTGCCGGTC ACTTAACATT ATGCTGAGTG ATATCCCGCT TAACCTCGAG
                          XbaI
                          ~~~~~~
1451 CACCGCGGTG GCGGCCGCTC TAGAACTAGT GGATCCCCCG GGCTGCAGGA ATTCGATATC
     GTGGCGCCAC CGCCGGCGAG ATCTTGATCA CCTAGGGGGC CCGACGTCCT TAAGCTATAG
                                XhoI
                                ~~~~~~
1511 AAGCTTATCG ATACCGTCGA CCTCGAGATT GCCATCGCGG ATGTCGCCTG TCTTATCTAC
     TTCGAATAGC TATGGCAGCT GGAGCTCTAA CGGTAGCGCC TACAGCGGAC AGAATAGATG
1571 CATCATAAAC ATCATTTGCC TATGGCTCAC GACAGTATAG GCAATGCCGT TTTTTATATT
     GTAGTATTTG TAGTAAACGG ATACCGAGTG CTGTCATATC CGTTACGGCA AAAAATATAA
1631 GCTAATTGTT TCGCCAATCA ACGCAAAAGT ATGGCGATTG CTAAAGCCGT CTCCCTGGGC
     CGATTAACAA AGCGGTTAGT TGCGTTTTCA TACCGCTAAC GATTTCGGCA GAGGGACCCG
1691 GGTAGATTAG CCTTAACCGC GACGGTAATG ACTCATTCAT ACTGGAGTGG TAGTTTGGGA
     CCATCTAATC GGAATTGGCG CTGCCATTAC TGAGTAAGTA TGACCTCACC ATCAAACCCT
1751 CTACAGCCTC ATTTATTAGA GCGTCTTAAT GATATTACCT ATGGACTAAT GAGTTTTACT
     GATGTCGGAG TAAATAATCT CGCAGAATTA CTATAATGGA TACCTGATTA CTCAAAATGA
1811 CGCTTCGGTA TGGATGGGAT GGCAATGACC GGTATGCAGG TCAGCAGCCC ATTATATCGT
     GCGAAGCCAT ACCTACCCTA CCGTTACTGG CCATACGTCC AGTCGTCGGG TAATATAGCA
1871 TTGCTGGCTC AGGTAACGCC AGAACAACGT GCGCCGGAGT AATCGTTTTC AGGTATATAC
     AACGACCGAG TCCATTGCGG TCTTGTTGCA CGCGGCCTCA TTAGCAAAAG TCCATATATG
1931 CGGATGTTCA TTGCTTTCTA AATTTTGCTA TGTTGCCAGT ATCCTTACGA TGTATTTATT
     GCCTACAAGT AACGAAAGAT TTAAAACGAT ACAACGGTCA TAGGAATGCT ACATAAATAA
                                                NdeI
                                                ~~~~~~
                   M  E  T  S  F  H  K  F  F  L  S  M  I  L  A
1991 TTAAGGAAAA GCCATATGGA AACCAGCTTC CATAAATTCT TCCTGTCTAT GATCCTGGCG
     AATTCCTTTT CGGTATACCT TTGGTCGAAG GTATTTAAGA AGGACAGATA CTAGGACCGC
      Y  S  C  C  S  L  N  G  G  Y  A  A  E  I  M  V  P  Q  G
2051 TACAGCTGCT GTTCTCTGAA CGGTGGTGGT TATGCGGCGG AAATTATGGT TCCGCAGGGT
     ATGTCGACGA CAAGAGACTT GCCACCACCA ATACGCCGCC TTTAATACCA AGGCGTCCCA
      I  Y  D  G  E  T  L  T  V  S  F  P  Y  T  V  I  G  D  P  S
2111 ATCTACGATG GTGAAACCCT GACCGTGTCT TTCCCGTATA CCGTTATCGG TGATCCGAGC
     TAGATGCTAC CACTTTGGGA CTGGCACAGA AAGGGCATAT GGCAATAGCC ACTAGGCTCG
      G  T  T  V  F  S  A  G  E  L  T  L  K  N  L  D  N  S  I  A
2171 GGTACGACCG TTTTCAGCGC CGGTGAACTG ACCCTGAAAA ACCTGGATAA TAGCATTGCG
     CCATGCTGGC AAAAGTCGCG GCCACTTGAC TGGGACTTTT TGGACCTATT ATCGTAACGC
      A  L  P  L  S  C  F  G  N  L  G  S  F  T  V  L  G  R  G
2231 GCGCTGCCGC TGTCTTGCTT CGGTAACCTG CTGGGTTCTT TCACCGTTCT GGGTCGTGGC
     CGCGACGGCG ACAGAACGAA GCCATTGGAC GACCCAAGAA AGTGGCAAGA CCCAGCACCG
      H  S  L  T  F  E  N  I  R  T  S  T  N  G  A  A  L  S  N  S
2291 CATAGCCTGA CCTTTGAAAA CATTCGTACC AGCACCAATG GTGCGGCGCT GTCTAATAGC
     GTATCGGACT GGAAACTTTT GTAAGCATGG TCGTGGTTAC CACGCCGCGA CAGATTATCG
      A  A  D  G  L  F  I  I  E  G  F  K  E  L  S  F  S  N  C  N
2351 GCGGCGGATG GTCTGTTCAC CATTGAAGGT TTCAAAGAAC TGTCTTTCTC TAACTGCAAT
     CGCCGCCTAC CAGACAAGTG GTAACTTCCA AAGTTTCTTG ACAGAAAGAG ATTGACGTTA
      S  L  L  A  V  L  P  A  A  T  T  N  K  G  S  Q  T  P  T  T
2411 AGCCTGCTGG CGGTTCTGCC GGCGGCGACC ACCAACAAAG GCAGCCAGAC CCCGACCACC
     TCGGACGACC GCCAAGACGG CCGCCGCTGG TGGTTGTTTC CGTCGGTCTG GGGCTGGTGG
      T  S  T  P  S  N  G  T  I  Y  S  K  T  D  L  L  L  N  N
2471 ACGAGCACCC CGTCTAACGG CACCATCTAC AGCAAAACCG ATCTGCTGCT GCTGAACAAC
     TGCTCGTGGG GCAGATTGCC GTGGTAGATG TCGTTTTGGC TAGACGACGA CGACTTGTTG
      E  K  F  S  F  Y  S  N  L  V  S  G  D  G  A  I  D  A  K
2531 GAAAAATTCT CTTTTTATAG CAACCTGGTT TCTGGTGATG GTGGTGCGAT TGATGCGAAA
     CTTTTTAAGA GAAAAATATC GTTGGACCAA AGACCACTAC CACCACGCTA ACTACGCTTT
```

Figure 20 (Cont'd)

```
            S   L   T   V   Q   G   I   S   K   L   C   V   F   Q   E   N   T   A   Q   A
2591 AGCCTGACCG TTCAGGGTAT CTCTAAACTG TGCGTTTTCC AGGAAAACAC CGCGCAGGCG
     TCGGACTGGC AAGTCCCATA GAGATTTGAC ACGCAAAAGG TCCTTTTGTG GCGCGTCCGC
            D   G   G   A   C   Q   V   V   T   S   F   S   A   M   A   N   E   A   P   I
2651 GATGGCGGTG CGTGCCAGGT TGTTACCTCT TTCAGCGCGA TGGCCAATGA AGCGCCGATT
     CTACCGCCAC GCACGGTCCA ACAATGGAGA AAGTCGCGCT ACCGGTTACT TCGCGGCTAA
            A   F   V   A   N   V   A   G   V   R   G   G   G   I   A   A   V   Q   D   G
2711 GCGTTTGTTG CCAACGTGGC GGGTGTTCGT GGTGGTGGTA TCGCGGCGGT GCAGGATGGT
     CGCAAACAAC GGTTGCACCG CCCACAAGCA CCACCACCAT AGCGCCGCCA CGTCCTACCA
            Q   Q   G   V   S   S   T   S   T   E   D   P   V   S   F   S   R   N
2771 CAGCAGGGTG TGAGCTCTTC TACCTCTACC GAAGATCCGG TGGTGAGCTT CAGCCGTAAC
     GTCGTCCCAC ACTCGAGAAG ATGGAGATGG CTTCTAGGCC ACCACTCGAA GTCGGCATTG
            T   A   V   E   F   D   G   N   V   A   R   V   G   G   I   Y   S   Y   G
2831 ACCGCGGTGG AATTTGATGG TAACGTGGCG CGCGTTGGTG GTGGTATCTA CAGCTACGGT
     TGGCGCCACC TTAAACTACC ATTGCACCGC GCGCAACCAC CACCATAGAT GTCGATGCCA
            N   V   A   F   L   N   N   G   K   T   L   F   L   N   N   V   A   S   P   V
2891 AACGTGGCGT TCCTGAACAA TGGTAAAACC CTGTTCCTGA ATAACGTTGC GAGCCCGGTG
     TTGCACCGCA AGGACTTGTT ACCATTTTGG GACAAGGACT TATTGCAACG CTCGGGCCAC
            Y   I   A   A   K   Q   P   T   S   G   Q   A   S   N   T   S   N   N   Y   G
2951 TATATTGCGG CCAAACAGCC GACCTCTGGT CAGGCGTCTA ACACCAGCAA TAACTACGGC
     ATATAACGCC GGTTTGTCGG CTGGAGACCA GTCCGCAGAT TGTGGTCGTT ATTGATGCCG
            D   G   G   A   I   F   C   K   N   G   A   Q   A   G   S   N   N   S   C   S
3011 GATGGTGGCG CCATTTTCTG CAAAAACGGT GCGCAGGCGG GCAGCAACAA CTCTGGCAGC
     CTACCACCGC GGTAAAAGAC GTTTTTGCCA CGCGTCCGCC CGTCGTTGTT GAGACCGTCG
            V   S   F   D   G   E   G   V   V   F   S   S   N   V   A   A   G   K   G
3071 GTGAGCTTCG ATGGCGAAGG CGTGGTGTTT TCAGCTCTA ATGTGGCGGC GGGTAAAGGC
     CACTCGAAGC TACCGCTTCC GCACCACAAA AAGTCGAGAT TACACCGCCG CCCATTTCCG
            G   A   I   Y   A   K   K   L   S   V   A   N   C   G   P   V   Q   F   L   R
3131 GGCGCGATTT ATGCGAAAAA ACTGTCTGTT GCGAACTGCG GCCCGGTGCA GTTCCTGCGT
     CCGCGCTAAA TACGCTTTTT TGACAGACAA CGCTTGACGC CGGGCCACGT CAAGGACGCA
            N   I   A   N   D   G   G   A   I   Y   L   G   E   S   G   E   L   S   L   S
3191 AACATTGCGA ACGATGGTGG TGCGATCTAC CTGGGTGAAA GCGGCGAACT GTCTCTGAGC
     TTGTAACGCT TGCTACCACC ACGCTAGATG GACCCACTTT CGCCGCTTGA CAGAGACTCG
            A   D   Y   G   D   I   I   F   D   G   N   I   K   R   T   A   K   E   N   A
3251 GCGGATTATG GCGATATTAT CTTCGATGGT AACATTAAAC GTACCGCGAA AGAAAACGCG
     CGCCTAATAC CGCTATAATA GAAGCTACCA TTGTAATTTG CATGGCGCTT TCTTTTGCGC
            A   D   V   N   G   V   T   V   S   S   Q   A   I   S   M   G   S   G   G   K
3311 GCGGATGTGA ACGGTGTGAC CGTGTCTTCT CAGGCGATTA GCATGGGTAG CGGCGGCAAA
     CGCCTACACT TGCCACACTG GCACAGAAGA GTCCGCTAAT CGTACCCATC GCCGCCGTTT
            I   T   T   L   R   A   K   A   G   H   Q   I   L   F   N   D   P   I   E   M
3371 ATTACCACCC TGCGTGCGAA AGCGGGTCAT CAGATCCTGT TCAACGATCC GATCGAAATG
     TAATGGTGGG ACGCACGCTT TCGCCCAGTA GTCTAGGACA AGTTGCTAGG CTAGCTTTAC
            A   N   G   N   N   Q   P   A   Q   S   K   L   L   K   I   N   D   G   E
3431 GCGAACGGTA ATAACCAGCC GGCGCAGTCT TCTAAACTGC TGAAAATTAA CGATGGTGAA
     CGCTTGCCAT TATTGGTCGG CCGCGTCAGA AGATTTGACG ACTTTTAATT GCTACCACTT
            G   Y   T   G   D   I   V   F   A   N   G   S   S   T   L   Y   Q   N   V   T
3491 GCTTACACCG GTGATATTGT GTTCGCCAAC GGTTCTAGCA CCCTGTATCA GAACGTTACC
     CCAATGTGGC CACTATAACA CAAGCGGTTG CCAAGATCGT GGGACATAGT CTTGCAATGG
            I   E   Q   G   R   I   V   L   R   E   K   A   K   L   S   V   N   S   L   S
3551 ATCGAACAGG GCCGTATCGT TCTGCGTGAA AAAGCGAAAC TGTCTGTTAA CAGCCTGAGC
     TAGCTTGTCC CGGCATAGCA AGACGCACTT TTTCGCTTTG ACAGACAATT GTCGGACTCG
            Q   T   G   G   S   L   Y   M   E   A   G   S   T   L   D   F   V   T   F   Q
3611 CAGACCGGTG GTAGCCTGTA TATGGAAGCG GGTTCTACCC TGGATTTCGT TACCCCGCAG
     GTCTGGCCAC CATCGGACAT ATACCTTCGC CCAAGATGGG ACCTAAAGCA ATGGGGCGTC
            P   P   Q   Q   P   P   A   N   Q   L   I   T   L   S   N   L   H   L   S
3671 CCGCCGCAGC AGCCGCCGGC GGCGAATCAG CTGATCACCC TGAGCAACCT GCATCTGTCT
     GGCGGCGTCG TCGGCGGCCG CCGCTTAGTC GACTAGTGGG ACTCGTTGGA CGTAGACAGA
            L   S   S   L   A   N   N   A   V   T   N   P   P   T   N   P   P   A   Q
3731 CTGTCTTCTC TGCTGGCGAA CAACGCGGTT ACCAACCCGC CGACCAACCC GCCGGCGCAG
```

Figure 20 (Cont'd)

```
           GACAGAAGAG ACGACCGCTT GTTGCGCCAA TGGTTGGGCG GCTGGTTGGG CGGCCGCGTC
             D  S  H    P  A  V    I  G  S    T  T  A    G  S  V    T  I  S    G  P
     3791  GATTCTCATC CGGCGGTGAT TGGTAGCACC ACCGCGGGTA GCGTTACCAT TTCTGGTCCG
           CTAAGAGTAG GCCGCCACTA ACCATCGTGG TGGCGCCCAT CGCAATGGTA AAGACCAGGC
             I  F  F    E  D  L    D  D  T    A  Y  D    R  Y  D    W  L  G    S  N
     3851  ATTTTCTTTG AAGATCTGGA TGATACCGCG TACGATCGCT ACGATTGGCT GGGTAGCAAC
           TAAAAGAAAC TTCTAGACCT ACTATGGCGC ATGCTAGCGA TGCTAACCGA CCCATCGTTG
             Q  K  I    N  V  L    K  Q  L    G  T  K    P  P  A    N  A  P    S
     3911  CAGAAAATCA ACGTTCTGAA ACTGCAACTG GGCACCAAAC CGCCGGCGAA CGCGCCGTCT
           GTCTTTTAGT TGCAAGACTT TGACGTTGAC CCGTGGTTTG GCGGCCGCTT GCGCGGCAGA
             D  L  T    L  G  N    E  M  P    K  Y  G    Y  Q  G    S  W  K    L  A
     3971  GATCTGACCC TGGGTAACGA AATGCCGAAA TATGGCTACC AGGGTTCTTG GAAACTGGCG
           CTAGACTGGG ACCCATTGCT TTACGGCTTT ATACCGATGG TCCCAAGAAC CTTTGACCGC
             W  D  P    N  T  A    N  N  G    P  Y  T    L  K  A    T  W  T    K  T
     4031  TGGGACCCGA ACACCGCGAA CAACGGTCCG TACACCCTGA AAGCGACCTG GACCAAAACC
           ACCCTGGGCT TGTGGCGCTT GTTGCCAGGC ATGTGGGACT TTCGCTGGAC CTGGTTTTGG
             G  Y  N    P  G  P    E  R  V    A  S  L    V  P  N    S  L  W    G  S
     4091  GGTTACAATC CGGGCCCGGA ACGTGTTGCG TCTCTGGTTC CGAACTCTCT GTGGGGCAGC
           CCAATGTTAG GCCCGGGCCT TGCACAACGC AGAGACCAAG GCTTGAGAGA CACCCCGTCG
             I  L  D    I  R  S    A  H  S    A  I  Q    A  S  V    D  G  R    S  Y
     4151  ATTCTGGATA TTCGCAGCGC GCATTCTGCG ATCCAGGCGA GCGTGGATGG TCGTAGCTAT
           TAAGACCTAT AAGCGTCGCG CGTAAGACGC TAGGTCCGCT CGCACCTACC AGCATCGATA
             C  R  G    L  W  V    S  G  V    S  N  F    F  Y  H    D  R  A    L
     4211  TGCCGCGGTC TGTGGGTTAG CGGTGTTTCT AACTTCTTCT ATCATGATCG CGATGCGCTG
           ACGGCGCCAG ACACCCAATC GCCACAAAGA TTGAAGAAGA TAGTACTAGC GCTACGCGAC
             G  Q  G    Y  R  Y    I  S  G    G  Y  S    L  G  A    N  Y  F    G
     4271  GGCCAGGGCT ATCGCTATAT TAGCGGTGGT TATAGCCTGG GTGCGAACAG CTATTTCGGT
           CCGGTCCCGA TAGCGATATA ATCGCCACCA ATATCGGACC CACGCTTGTC GATAAAGCCA
             S  S  M    F  G  L    A  F  T    E  V  F    G  R  S    K  D  Y    V  V
     4331  AGCAGCATGT TCGGCCTGGC GTTCACCGAA GTTTTTGGTC GTTCTAAAGA TTATGTTGTG
           TCGTCGTACA AGCCGGACCG CAAGTGGCTT CAAAAACCAG CAAGATTTCT AATACAACAC
             C  R  S    N  H  H    A  C  I    G  S  V    Y  L  S    T  Q  Q    A  L
     4391  TGCCGTAGCA ACCATCATGC GTGCATTGGT TCTGTTTATC TGAGCACCCA GCAGGCGCTG
           ACGGCATCGT TGGTAGTACG CACGTAACCA AGACAAATAG ACTCGTGGGT CGTCCGCGAC
             C  G  S    Y  L  F    G  D  A    F  I  R    A  S  Y    C  F  G    N  Q
     4451  TGCGGTTCTT ATCTGTTTGG CGATGCGTTC ATCCGTGCGT CTTATGGTTT CGGCAACCAG
           ACGCCAAGAA TAGACAAACC GCTACGCAAG TAGGCACGCA GAATACCAAA GCCGTTGGTC
             H  M  K    T  S  Y    T  F  A    E  E  S    D  V  R    W  D  N    N  C
     4511  CACATGAAAA CCAGCTATAC CTTTGCGGAA GAAAGCGATG TTCGTTGGGA TAACAACTGC
           GTGTACTTTT GGTCGATATG GAAACGCCTT CTTTCGCTAC AAGCAACCCT ATTGTTGACG
             L  A  G    E  I  A    G  L  P    I  V  I    T  P  S    K  L  Y    L
     4571  CTGGCGGGTG AAATTGGTGC GGGCCTGCCG ATCGTTATCA CCCCGAGCAA ACTGTATCTG
           GACCGCCCAC TTTAACCACG CCCGGACGGC TAGCAATAGT GGGGCTCGTT TGACATAGAC
             N  E  L    R  P  F    V  Q  A    E  F  S    Y  A  N    H  E  S    F  T
     4631  AACGAACTGC GCCCGTTTGT GCAGGCGGAA TTTTCTTACG CGAACCATGA ATCTTTTACC
           TTGCTTGACG CGGGCAAACA CGTCCGCCTT AAAAGAATGC GCTTGGTACT TAGAAAATGG
             E  E  G    D  Q  A    R  A  F    K  S  G    H  L  L    N  L  S    V  P
     4691  GAAGAAGGTG ATCAGGCGCG TGCGTTCAAA AGCGGTCATC TGCTGAACCT GAGCGTGCCG
           CTTCTTCCAC TAGTCCGCGC ACGCAAGTTT TCGCCAGTAG ACGACTTGGA CTCGCACGGC
             V  G  V    K  F  D    R  C  S    S  T  H    P  N  K    Y  S  F    M  A
     4751  GTTGGCGTGA AATTTGATCG TTGCAGCTCT ACCCATCCGA ACAAATACAG CTTTATGGCG
           CAACCGCACT TTAAACTAGC AACGTCGAGA TGGGTAGGCT TGTTTATGTC GAAATACCGC
             A  Y  I    C  D  A  Y  R  T    I  S  G    T  E  T    T  L  S    H
     4811  GCGTATATCT GTGATGCGTA TCGTACCATT AGCGGCACCG AAACCACCCT GCTGAGCCAT
           CGCATATAGA CACTACGCAT AGCATGGTAA TCGCCGTGGC TTTGGTGGGA CGACTCGGTA
             Q  G  T    W  T  T    D  A  F    H  L  A    R  H  G    V  V  R    G
     4871  CAGGGCACCT GGACCACCGA TGCGTTTCAT CTGGCCCGTC ATGGCGTTGT GGTTCGTGGC
           GTCCCGTGGA CCTGGTGGCT ACGCAAAGTA GACCGGGCAG TACCGCAACA CCAAGCACCG
             S  M  Y    A  S  L    T  S  N    I  E  V    Y  G  H    G  R  Y    E  Y
```

Figure 20 (Cont'd)

```
4931 AGCATGTATG CGAGCCTGAC CAGCAACATT GAAGTGTATG GTCATGGTCG TTATGAATAT
     TCGTACATAC GCTCGGACTG GTCGTTGTAA CTTCACATAC CAGTACCAGC AATACTTATA
      R  D  A  S   R  G  Y   G  L  S   A  G  S   K  V  K  F
4991 CGTGATGCGA GCCGTGGTTA TGGTCTGAGC GCGGGTAGCC GCGTTCGTTT TAATAAGGA
     GCACTACGCT CGGCACCAAT ACCAGACTCG CGCCCATCGG CGCAAGCAAA AATTATTCCT
         XbaI        AvrII
         ~~~~        ~~~~~
5051 TCTCTAGACT AGCCTAGGGG TACCCAGCTT TTGTTCCCTT TAGTGAGGGT TAATTTCGAG
     AGAGATCTGA TCGGATCCCC ATGGGTCGAA AACAAGGGAA ATCACTCCCA ATTAAAGCTC
5111 CTTGGCGTAA TCATGGTCAT AGCTGTTTCC TGTGTGAAAT TGTTATCCGC TCACAATTCC
     GAACCGCATT AGTACCAGTA TCGACAAAGG ACACACTTTA ACAATAGGCG AGTGTTAAGG
5171 ACACAACATA CGAGCCGGAA GCATAAAGTG TAAAGCCTGG GGTGCCTAAT GAGTGAGCTA
     TGTGTTGTAT GCTCGGCCTT CGTATTTCAC ATTTCGGACC CCACGGATTA CTCACTCGAT
5231 ACTCACATTA ATTGCGTTGC GCTCACTGCC CGCT
     TGAGTGTAAT TAACGCAACG CGAGTGACGG GCGA
```

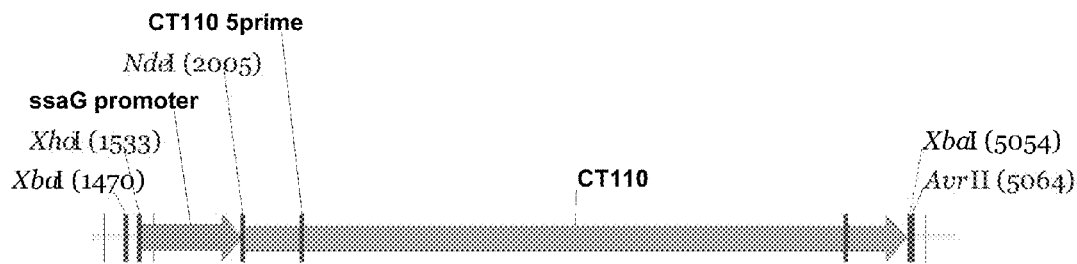

Fragment showing ssaG promoter and CT110

3934 bp

Figure 21 – *C. muridarum* CT110 amino acid sequence (SEQ ID NO:30)

VMQTPFHKFFLLAMLSYSLLQGGHAADISMPPGIYDGTTLTAPFPYTVIGDPRGTKVTSS
GSLELKNLDNSIATLPLSCFGNLLGNFTIAGRGHSLVFENIRTSTNGAALSNHAPSGLFV
IEAFDELSLLNCNSLVSVVPQTGGTTTSVPSNGTIYSRTDLVLRDIKKVSFYSNLVSGDG
GAIDAQSLMVNGIEKLCTFQENVAQSDGGACQVTKTFSAVGNKVPLSFLGNVAGNKGGGV
AAVKDGQGAGGATDLSVNFANNTAVEFEGNSARIGGGIYSDGNISFLGNAKTVFLSNVAS
PIYVDPAAAGGQPPADKDNYGDGGAIFCKNDTNIGEVSFKDEGVVFFSKNIAAGKGGAIY
AKKLTISDCGPVQFLGNVANDGGAIYLVDQGELSLSADRGDIIFDGNLKRMATQGAATVH
DVMVASNAISMATGGQITTLRAKEGRRILFNDPIEMANGQPVIQTLTVNEGEGYTGDIVF
AKGDNVLYSSIELSQGRIILREQTKLLVNSLTQTGGSVHMEGGSTLDFAVTTPPAANSMA
LTNVHFSLASLLKNNGVTNPPTNPPVQVSSPAVIGNTAAGTVTISGPIFFEDLDETAYDN
NQWLGADQTIDVLQLHLGANPPANAPTDLTLGNESSKYGYQGSWTLQWEPDPANPPQNNS
YMLKASWTKTGYNPGPERVASLVSNSLWGSILDVRSAHSAIQASIDGRAYCRGIWISGIS
NFFYHDQDALGQGYRHISGGYSIGANSYFGSSMFGLAFTETFGRSKDYVVCRSNDHTCVG
SVYLSTRQALCGSCLFGDAFVRASYGFGNQHMKTSYTFAEESNVRWDNNCVVGEVGAGLP
IMLAASKLYLNELRPFVQAEFAYAEHESFTERGDQAREFKSGHLMNLSIPVGVKFDRCSS
KHPNKYSFMGAYICDAYRSISGTETTLLSHKETWTTDAFHLARHGVMVRGSMYASLTGNI
EVYGHGKYEYRDASRGYGLSIGSKIRF

Figure 22 – *C. muridarum* CT110 nucleotide sequence (SEQ ID NO:31)

GTGATGCAAACGCCTTTTCATAAGTTCTTTCTTCTAGCAATGCTATCTTACTCTTTATTG
CAAGGAGGGCATGCGGCAGATATTTCCATGCCTCCGGGAATTTATGATGGGACAACATTG
ACGGCGCCATTTCCCTACACTGTGATCGGAGATCCCAGAGGGACAAAGGTTACTTCATCG
GGATCGCTAGAGTTGAAAAACCTGGACAATTCCATTGCGACTTTACCTCTAAGTTGTTTT
GGTAATTTGTTGGGGAATTTCACTATTGCAGGAAGAGGGCATTCGTTAGTATTTGAGAAT
ATACGAACATCTACAAATGGGGCGGCATTGAGTAATCATGCTCCTTCTGGACTGTTTGTA
ATTGAAGCTTTTGATGAACTCTCTCTTTTGAATTGTAATTCATTGGTATCTGTAGTTCCT
CAAACAGGGGGTACGACTACTTCTGTTCCTTCTAATGGGACGATCTATTCTAGAACAGAT
CTTGTTCTAAGAGATATCAAGAAGGTTTCTTTCTATAGTAACTTAGTTTCTGGAGATGGG
GGAGCTATAGATGCACAAAGTTTAATGGTTAACGGAATTGAAAAACTTTGTACCTTCCAA
GAAAATGTAGCGCAGTCCGATGGGGGAGCGTGTCAGGTAACAAAGACCTTCTCTGCTGTG
GGCAATAAGGTTCCTTTGTCTTTTTTAGGCAATGTTGCTGGTAATAAGGGGGGAGGAGTT
GCTGCTGTCAAAGATGGTCAGGGGGCAGGAGGGGCGACTGATCTATCGGTTAATTTTGCC
AATAATACTGCTGTAGAATTTGAGGGAAATAGTGCTCGAATAGGTGGAGGGATCTACTCG
GACGGAAATATTTCCTTTTTAGGGAATGCAAAGACAGTTTTCCTAAGTAACGTAGCTTCG
CCTATTTATGTTGACCCTGCTGCTGCAGGAGGACAGCCCCCTGCAGATAAAGATAACTAT
GGAGATGGAGGAGCCATCTTCTGCAAAAATGATACTAACATAGGTGAAGTCTCTTTCAAA
GACGAGGGTGTTGTTTTCTTTAGTAAAAATATTGCCGCAGGAAAGGGGGGCGCTATTTAT
GCTAAGAAACTGACAATTTCTGACTGTGGTCCGGTCCAGTTTCTTGGTAATGTCGCGAAT
GACGGGGGCGCTATTTATCTAGTAGATCAGGGGGAACTTAGTCTATCTGCTGATCGCGGA
GATATTATTTTTGATGGAAATTTAAAGAGAATGGCTACGCAAGGCGCTGCCACCGTCCAT
GATGTAATGGTTGCATCGAATGCTATCTCTATGGCTACAGGGGGGCAAATCACAACATTA
AGGGCTAAGGAAGGTCGCCGAATTCTTTTTAATGACCCTATTGAAATGGCGAATGGACAA
CCTGTAATACAAACTCTTACAGTAAACGAGGGCGAAGGATATACGGGGGACATTGTTTTT
GCTAAAGGTGATAATGTTTTGTACTCAAGTATTGAGCTGAGTCAGGGAAGAATTATTCTC
CGAGAGCAAACAAAATTATTGGTTAACTCCCTGACTCAGACTGGAGGGAGTGTACATATG
GAAGGGGGGAGTACACTAGACTTTGCAGTAACAACGCCACCAGCTGCTAATTCGATGGCT
CTTACTAATGTACACTTCTCCTTAGCTTCTTTACTAAAAAATAATGGGGTTACAAATCCT
CCAACGAATCCTCCAGTACAGGTTTCTAGTCCAGCTGTAATTGGTAATACAGCTGCTGGT
ACTGTTACGATTTCTGGTCCGATCTTTTTTGAAGATTTAGATGAAACTGCTTACGATAAT
AATCAGTGGTTAGGTGCGGATCAAACTATTGATGTGCTGCAGTTGCATTTAGGAGCGAAT
CCTCCGGCTAACGCTCCAACTGATTTGACTTTAGGGAACGAAAGTTCTAAATATGGGTAT
CAAGGAAGTTGGACACTTCAATGGGAACCAGATCCTGCGAATCCTCCACAGAACAATAGC
TACATGTTGAAGGCAAGCTGGACTAAAACAGGTTATAATCCTGGTCCGGAGCGCGTAGCT
TCTCTGGTCTCTAATAGTCTTTGGGGATCCATTTTAGATGTGCGTTCCGCGCATTCTGCG
ATTCAAGCAAGTATAGATGGACGAGCTTATTGTCGGGGTATTTGGATTTCTGGGATTTCG
AACTTTTTCTATCATGATCAGGATGCTTTAGGACAGGGGTATCGTCATATTAGTGGGGGA
TATTCGATAGGAGCAAACTCTTATTTCGGGTCTTCTATGTTTGGACTTGCTTTTACTGAA
ACTTTTGGTAGGTCCAAAGATTATGTGGTCTGTCGATCTAACGATCACACTTGTGTAGGC
TCTGTTTACTTATCCACTAGACAAGCGTTATGCGGATCCTGTTTATTTGGAGATGCTTTT
GTTCGGGCGAGTTACGGATTTGGAAATCAGCATATGAAGACCTCTTATACATTTGCTGAA
GAGAGTAATGTGCGTTGGGATAATAACTGTGTAGTGGGAGAAGTTGGAGCTGGGCTCCCT
ATCATGCTCGCTGCATCTAAGCTTTATCTAAATGAGTTGCGTCCCTTCGTGCAAGCAGAG
TTTGCTTATGCAGAGCATGAATCTTTTACAGAGAGAGGGGATCAGGCTAGGGAGTTTAAG
AGTGGGCATCTTATGAATCTATCTATTCCAGTTGGGGTGAAGTTTGATCGATGCTCTAGT
AAACATCCTAACAAGTATAGTTTTATGGGAGCTTATATCTGTGATGCTTACCGGTCCATT
TCTGGAACGGAGACAACACTCCTGTCTCATAAAGAGACTTGGACAACAGATGCTTTCCAT
TTAGCAAGGCATGGAGTTATGGTCAGAGGATCTATGTATGCTTCTTTAACAGGTAATATA
GAAGTCTATGGCCATGGAAAATATGAATACAGGGATGCCTCTCGAGGGTATGGTTTAAGT
ATTGGAAGTAAAATCCGATTCTAA

SALMONELLA VECTORED VACCINES AGAINST CHLAMYDIA AND METHODS OF USE

This application is a national stage filing of PCT/US2009/047542 filed Jun. 16, 2009, which claims priority to U.S. Provisional Application No. 61/118,204 filed Nov. 26, 2008, and PCT/US2008/007490 filed Jun. 16, 2008, all of which are herein incorporated by reference in their entireties.

DESCRIPTION OF THE TEXT FILE SUBMITTED ELECTRONICALLY

The contents of the text file submitted electronically herewith are incorporated herein by reference in their entirety: A computer readable format copy of the Sequence Listing (filename: EMER_008_01US_SeqList_ST25.txt, date recorded: Jul. 19, 2011, file size 166 kilobytes).

FIELD OF THE INVENTION

The present invention relates to live *Salmonella* vectors expressing *Chlamydia* antigens for vaccination against *Chlamydia* infection, and methods of vaccination using the same.

BACKGROUND

Chlamydial organisms cause a wide spectrum of diseases in humans, other mammals and birds and have an enormous economic impact on both human and animal health and on agricultural industries worldwide. The two principal pathogens of humans are *Chlamydia trachomatis* and *Chlamydophila pneumoniae*. *Chlamydia trachomatis* is a cause of chronic conjunctivitis and is also the most common cause of sexually transmitted disease in humans. *Chlamydophila pneumoniae* causes acute respiratory disease and is responsible for 5 to 10% of the cases of community-acquired pneumonia, bronchitis and sinusitis. The organism has also been associated with chronic obstructive pulmonary disease, asthma, reactive airway disease, Reiter's syndrome, sarcoidosis and atherosclerosis.

Although antibiotics are available to Chlamydial infections, *C. trachomatis* infection remains asymptomatic in approximately 50% of infected men and approximately 70% of infected women. The major clinical manifestations of genital chlamydial infection in women include mucopurulent cervicitis, endometritis and pelvic inflammatory disease. Genital infection with *C. trachomatis* markedly enhances the risk for reproductive tract sequelae in women, including tubal factor infertility, chronic pain and ectopic pregnancy. Babies born to mothers with infection of their genital tract frequently present with chlamydial eye infection within a week of birth (chlamydial ophthalmia neonatorum), and may subsequently develop pneumonia.

In addition to the complications of genital chlamydia infection, *C. trachomatis* remains the leading cause of preventable blindness worldwide. Chronic ocular infections, referred to as trachoma, predominate in developing countries. It is estimated that 12 million people with trachoma will develop blindness by the year 2020, which has placed trachoma on the WHO priority list for intervention. Since 2001, the WHO has promoted control strategies including, for example, antibiotics, improved hygiene, and environmental measures, with limited success.

*C. trachomatis* infection is also a known co-factor for HIV/AIDS transmission. Epidemiological studies have linked genital chlamydial infection to an increased risk for acquisition of HIV disease. See, for instance, Brunham, R. C. et al., 1996, *J. Infect. Dis.* 173: 950-956 and Ghys, P. D. et al., 1997, *AIDS* 11: F85-F93. Immunosuppression due to HIV may lead to more aggressive chlamydial disease conditions like pelvic inflammatory disease in those who are infected with *C. trachomatis*. See, Thomas, K. et al., 2002, *Hum. Reprod.* 17:1431-1436.

Attempts in the 1950s and 1960s to develop a *C. trachomatis* vaccine capable of preventing infection and disease focused on immunization with crude formalin-killed whole chlamydia elementary body (EB) preparations or detergent extracts of EBs. Overall, the results of these trials demonstrated that a whole cell or detergent extract vaccine, while relatively safe, provided only a marginal benefit that was short-lived.

Following the identification of MOMP as the major protein component (approximately 60%) of the outer membrane in the early 1980s and the discovery that strong antibody responses are raised to that protein in infected animals and humans, vaccine studies focused on this protein. In the early 1990s, attention was turned to the development of recombinant MOMP vaccines. See, Longbottom, D., 2003, *J. Med. Microbiol.* 52:537-540. Although MOMP is highly immunogenic and can elicit a local neutralizing anti-Chlamydia antibody, most MOMP-specific neutralizing epitopes that have been mapped are located within the VD regions and thus give rise only to serovar-specific antibody. Attempts to combine serovar-specific epitopes in various vaccine vectors (e.g., poliovirus) to generate broadly cross-reactive neutralizing antibodies have been only marginally successful. See, for instance, Murdin, A. D. et al., 1993, Infect. Immun., 61:4406-4414 and Murdin, A.D. et al., 1995, Infect. Immun., 63:1116-1121).

Despite efforts to better understand the immune response in Chlamydial infections and efforts to develop an effective Chlamydial vaccine, a *C. trachomatis* vaccine has not been advanced into a Phase I clinical trial in over 40 years. Accordingly, a need exists for an effective vaccine to prevent and/or ameliorate Chlamydial infections and associated conditions such as trachoma.

SUMMARY OF THE INVENTION

The present invention provides attenuated *Salmonella* microorganism comprising: i) an attenuating mutation in a Salmonella Pathogenicity Island 2 (SPI-2) gene; ii) an attenuating mutation in a second gene; and iii) one or more gene expression cassettes, each gene expression cassette comprising a heterologous nucleic acid under the control of an inducible promoter, wherein at least one of said heterologous nucleic acids encodes an immunogenic Chlamydial peptide. In one embodiment, the immunogenic Chlamydial peptide is one or more of a Chlamydial PmpG, Pmpl, PmpE, MOMP, PmpD, PmpH, OmcB, OmpH or HtrA protein (full length or mature) or an immunogenic fragment or variant thereof. For instance, the invention includes an attenuated *Salmonella* capable of expressing PmpG peptides CT110, CT84 or CT40. In one embodiment of the invention, the attenuated *Salmonella* microorganism induces an effective immune response when administered to a human patient. In one embodiment, the effective immune response is to *C. trachomatis* or *C. pneumoniae*.

The attenuated *Salmonella* of the invention comprises at least one attenuating mutation in a SPI-2 gene (e.g., ssa, sse, ssc and/or ssr gene). In one embodiment, the SPI-2 gene is an ssa gene. For instance, the invention includes an attenuated Salmonella with an attenuating mutation in one or more of ssaV, ssaJ, ssaU, ssaK, ssaL, ssaM, ssaO, ssaP, ssaQ, ssaR, ssaS, ssaT, ssaU, ssaD, ssaE, ssaG, ssaI, ssaC (spiA) and ssaH. In one embodiment the attenuating mutation in an ssaV gene or ssaJ gene.

In another embodiment, the SPI-2 is an sse gene. For instance, the invention includes an attenuated Salmonella with an attenuating mutation in one or more of sseA, sseB, sseC, sseD, sseE, sseF, sseG, sseL and spiC (ssaB).

The attenuated Salmonella of the invention comprises an attenuating mutation in a second gene that may or may not be in the SPI-2 region. In one embodiment of the invention, the second gene is outside of the SPI-2 region. In one embodiment of the invention, the second gene is involved in the biosynthesis of aromatic compounds. For instance, the invention includes an attenuating mutation in an aro gene. In one embodiment of the invention, the aro gene is aroA or aroC.

The attenuating mutations in the SPI-2 gene and second gene can be accomplished using methods known in the art. In one embodiment of the invention, the attenuating mutation is the result of a deletion or inactivation of the gene. If the attenuating mutation is a deletion mutation, the mutation results in a deletion site. In one embodiment of the invention, the attenuated Salmonella cell is derived from Salmonella enterica serovar Typhi ZH9 comprising deletion sites in the aroC and ssaV genes.

The attenuated Salmonella of the invention comprises one or more gene expression cassettes. In one embodiment of the invention, the gene expression cassette comprises a heterologous polynucleotide encoding a Chlamydial peptide under the control of an inducible promoter. In one embodiment, the inducible promoter is a prokaryotic promoter. In one embodiment, the inducible promoter is induced under acidic conditions. In another embodiment, the inducible promoter is induced under oxidative conditions. In yet another embodiment, the inducible promoter is induced in macrophages. An in vivo inducible promoter may be used in one embodiment of the invention. For instance, in one embodiment of the invention, the inducible promoter is a Salmonella ssaG promoter.

Although not necessary to induce a cell-mediated immune response, in one embodiment of the invention, the gene expression cassette comprises a secretion signal that acts to secrete the Chlamydial peptide from the cell or display the Chlamydial peptide on the surface of the cell. For instance, a secretion signal such as ClyA secretion signal or E. coli CS3 signal sequence can be used in the construct of the attenuated Salmonella of the invention. By expressing an immunogenic Chlamydial peptide on the surface of the Salmonella cell or exporting a Chlamydial peptide out of the Salmonella cell, a humoral immune response can be elicited.

The invention includes compositions comprising the attenuated microorganism of the invention and a pharmaceutically acceptable carrier and/or diluent. In one embodiment of the invention, the composition comprises a plurality of different attenuated Salmonella cells. For instance, the plurality of Salmonella cells may comprise more than one populations of cells with each population capable of expressing a different Chlamydial antigen(s) (e.g., one population within the plurality may express PmpG peptides such as CT110 and/or CT84 and a second population within the plurality may express HtrA, PmpI, PmpE, PmpD, PmpH, MOMP, OmcB and/or OmpH peptides). The plurality of Salmonella cells may also comprise a population of cells that is capable of exporting the Chlamydial peptides out of the cell and/or are capable of expression the Chlamydial peptides on the cell surface (e.g., population secretes via a secretion signal) and a second population of cells that is not capable of exporting the Chlamydial peptides (e.g., population lacks a secretion signal).

In one embodiment of the invention, the composition comprises an isolated recombinant antigen of the invention and a pharmaceutically acceptable carrier and/or diluent. For instance, the invention includes a composition comprising an isolated recombinant antigen comprising a secretion tag and an immunogenic Chlamydial peptide. In another embodiment, the invention includes a composition comprising an isolated recombinant antigen comprising two or more immunogenic Chlamydial peptides fused together. The recombinant antigens of the invention may further be fused to linker peptides and/or immunostimulatory therapeutic antigens (e.g., cytokine or chemokine).

The compositions of the invention may contain an adjuvant, for instance, a CpG oligodeoxynucleotide adjuvant, aluminium salt (e.g., aluminium hydroxide, aluminum oxide and aluminum phosphate), oil-based adjuvant (e.g., Freund's Complete Adjuvant and Freund's Incomplete Adjuvant), mycolate-based adjuvant (e.g., trehalose dimycolate), bacterial lipopolysaccharide (LPS), peptidoglycan (e.g., murein, mucopeptide or glycoproteins such as N-Opaca, muramyl dipeptide [MDP], or MDP analog), proteoglycan (e.g., extracted from Klebsiella pneumoniae), streptococcal preparation (e.g., OK432), muramyldipeptide, Immune Stimulating Comlex, saponin, DEAE-dextran, neutral oil (e.g., miglyol), vegetable oil (e.g., arachis oil), liposome, polyol, Ribi adjuvant, vitamin E, Carbopol or interleukin.

The invention includes methods for vaccinating a subject against a Chlamydial infection by administering an attenuated microorganism or recombinant antigen to a subject. In one embodiment, the invention includes methods for preventing or ameliorating a condition associated with a Chlamydial infection by administering an attenuated microorganism or recombinant antigen to a subject. For instance, the invention includes a method of preventing or ameliorating a condition associated with C. trachomatis such as urethritis, prostatis, proctitis, epididymitis, cervicitis, salpingitis, endometritis, pelvic inflammatory disease, tubal factor infertility, chronic pelvic pain, cervical dysplasia, ectopic pregnancy, lymphogranuloma venereum (LGV), newborn eye infection, newborn lung infection, trachoma or reactive arthritis. The invention also includes a method of preventing or ameliorating a condition associated with C. pneumoniae such as pneumonia, acute respiratory disease, atherosclerosis, coronary artery disease, myocardial infarction, carotid artery disease, cerebrovascular disease, coronary heart disease, carotid artery stenosis, aortic aneurysm, claudication, stroke, chronic obstructive pulmonary disease, asthma, reactive airway disease, Reiter's syndrome or sarcoidosis. Accordingly the invention is useful as a vaccine and in the treatment of conditions associated with a Chlamydial infection.

The invention further provides methods of eliciting an immune response in a subject by administering an attenuated Salmonella or composition of the invention to a subject. In one embodiment, the immune response is cell-mediated immunity. In another embodiment, the immune response is a mucosal IgA response.

The invention includes antisera and antibodies to the attenuated Salmonella of the invention. In another embodiment, the invention includes antisera and antibodies to a composition of the invention. Antisera and antibodies can be raised by methods known in the art. In one embodiment of the invention, the antibodies are isolated and substantially purified.

DESCRIPTION OF THE FIGURES

FIG. 1 shows a vector map of the pMBS vector map (with CT84 insert) and the nucleic acid sequence around the cloning site.

FIG. 2 shows a vector map of suicide vector pCVD (with CT84 insert) and the nucleic acid sequence around the cloning site.

FIG. 3 shows a vector map of suicide vector pCVD (with CT110 insert) and the nucleic acid sequence around the cloning site.

FIG. 4 is an *E. coli* codon optimized nucleic acid sequence encoding CT110.

FIG. 5 is the coding region of an *E. coli* codon optimized nucleic acid sequence encoding CT110.

FIG. 6 is an immunogenic *Chlamydia* CT110 peptide.

FIG. 7 is an *E. coli* codon optimized nucleic acid sequence encoding CT84.

FIG. 8 is the coding region of an *E. coli* codon optimized nucleic acid sequence encoding CT84.

FIG. 9 is an immunogenic *Chlamydia* CT84 peptide.

FIG. 10 is a nucleic acid sequence encoding *C. trachomatis* serovar L2 PmpG.

FIG. 11 is an immunogenic *C. trachomatis* serovar L2 PmpG protein.

FIG. 12 is a nucleic acid sequence encoding *C. trachomatis* serovar B PmpG.

FIG. 13 is an immunogenic *C. trachomatis* serovar B PmpG protein.

FIG. 14 is a nucleic acid sequence encoding *C. trachomatis* serovar F PmpG.

FIG. 15 is an immunogenic *C. trachomatis* serovar F PmpG protein.

FIG. 16 is a nucleic acid sequence encoding *C. trachomatis* CT40 and the corresponding peptide sequence.

FIG. 17 is a *Salmonella* ssaG promoter nucleic acid sequence.

FIG. 18 is a ClyA secretion signal sequence.

FIG. 20 is a CT110-ssaG promoter construct.

FIG. 21 is an amino acid sequence of *C. muridarum* CT110.

FIG. 22 is a nucleotide sequence of *C. muridarum* CT110.

DETAILED DESCRIPTION OF THE INVENTION

General Description

Figure 19:
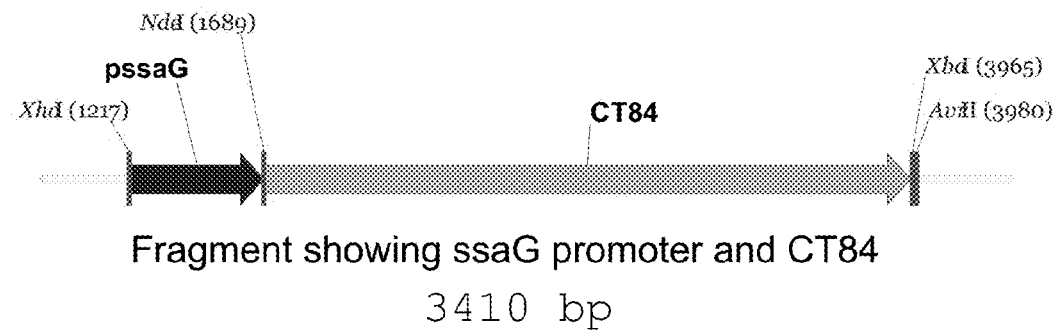
FIG. 19 is a CT84-ssaG promoter construct.

The invention provides live attenuated *Salmonella* microorganisms capable of expressing Chlamydial antigens, vaccine compositions, and methods of preventing and treating Chlamydial infection and related conditions. In particular, the live attenuated *Salmonella* of the invention are capable of expressing Chlamydial PmpG, Pmpl, PmpE, MOMP, PmpD, PmpH, OmcB, OmpH and HtrA proteins or fragments thereof that when administered to a subject, elicit an effective immune response. The vaccine compositions of the present invention are suitable for inducing an effective immune response, e.g., including cellular immune response, against Chlamydial infection such as a *C. trachomatis, C. pneumoniae* or *C. muridarum* infection or a *C. trachomatis* or *C. pneumoniae* related condition.

In one aspect, the invention provides an attenuated *Salmonella* expressing an immunogenic peptide that comprises an immunogenic portion of a *Chlamydia* peptide. The *Salmonella* is capable of presenting the *C. trachomatis* antigen(s) to the host immune system in a manner that generates an effective immune response, e.g., when administered orally to, or to a mucosal surface of, a human or non-human animal patient.

Definitions

As used herein, the term "attenuated" refers to a bacterium that has been genetically modified so as to not cause illness in a human or animal model. The terms "attenuated" and "avirulent" are used interchangeably herein.

As used herein, the term "bacterial vaccine vector" refers to an avirulent bacterium that is used to express a heterologous antigen in a host for the purpose of eliciting a protective immune response to the heterologous antigen. The attenuated microorganisms, including attenuated *Salmonella enterica* serovars, provided herein are suitable bacterial vaccine vectors. Bacterial vaccine vectors and compositions comprising the same disclosed can be administered to a subject to prevent or treat a Chlamydial infection or Chlamydial-related condition. Bacterial vaccine vectors and compositions comprising the same can also be administered to a subject to induce an immune response. In one embodiment, the bacterial vaccine vector is the spi-VEC™ live attenuated bacterial vaccine vector (Emergent Product Development UK Limited, UK).

As used herein, the term "effective immune response" refers to an immune response that confers protective immunity. For instance, an immune response can be considered to be an "effective immune response" if it is sufficient to prevent a subject from developing a Chlamydial infection (e.g., *C. trachomatis* infection, *C. pneumoniae* or *C. muridarum* infection) after administration of a challenge of dose of *C. trachomatis, C. pneumoniae* or *C. muridarum*. An effective immune response may comprise a cell mediated immune response and/or humoral immune response. In one embodiment, an effective immune response is an MHC class II-restricted, CD4+ T-helper type 1 (TH1) response. In one embodiment, the TH1 response is mediated by IFN-gamma or IFN-alpha. In another embodiment, an effective immune response is an MHC class I-restricted cytotoxic CD8+ T cell response. In one embodiment, the effective immune response refers to the ability of the vaccine of the invention to elicit the production of antibodies. An effective immune response may give rise to mucosal immunity. For instance, in one embodiment, an effective immune response is a mucosal IgA response.

As used herein, the term "gene expression cassette" refers to a nucleic acid construct comprising a heterologous nucleic acid under the control of an inducible promoter. In one embodiment, the heterologous nucleic acids encode one or more *C. trachomatis C. pneumoniae* and/or *C. muridarum* peptides. For instance, in one embodiment, the heterologous nucleic acid encodes a PmpG peptide. The Chlamydial peptide may lack an N-terminus (e.g., PmpG peptides CT84 and CT110) and, optionally, may lack a transmembrane domain (e.g., PmpG peptide CT84). In another embodiment, the heterologous nucleic acid encodes one or more of a chemokine and/or cytokine. In one embodiment, the non-*Salmonella* polynucleotide or polynucleotide regions of the gene expression cassette is codon-optimized for expression in a gram negative bacterium such as *Salmonella* or *E. coli*. In one embodiment, the inducible promoter is an in vivo inducible promoter. The gene expressing cassette may additionally comprise, for instance, one or more of a nucleic acid encoding a secretion tag and a nucleic acid encoding a peptide linker. A gene expression cassette may be contained on a plasmid or may be chromosomally integrated, for instance, at a gene deletion site. An attenuated *Salmonella* cell may be constructed to contain more than one gene expression cassette. For instance, a *Salmonella* cell can be constructed to express a first gene expression cassette in an aro gene deletion site (e.g., aroC deletion site) and a second gene expression cassette in a *Salmonella* Pathogenicity Island 2 gene deletion site (e.g., ssaV deletion site).

As used herein, the term "immunogenic peptide" refers to a portion of a Chlamydial protein capable of eliciting an immunogenic response when administered to a subject. An immunogenic peptide can be a full length protein, a mature protein or a protein fragment. The immunogenic peptide can be a recombinant peptide. The invention includes immunogenic peptides comprising at least about 70%, 75%, 80%, 85%, 90%, 95%, 96%, 97%, 98% or 99% identity to Chlamydial PmpG, Pmpl, PmpE, MOMP, PmpD, PmpH, OmcB, OmpH or HtrA peptides and variants and fragments thereof capable of eliciting an immunogenic response. For instance, the invention includes immunogenic *Chlamydia* peptides disclosed in PCT/US08/006656, filed May 23, 2008; PCT/US08/007490, filed Jun. 16, 2008; U.S. Pat. No. 7,731,980, filed Aug. 1, 2003; U.S. Pat. No. 7,803,388, filed Jul. 20, 2007; U.S. Pat. No. 7,851,609, filed Jul. 20, 2007; U.S. Pat. No. 7,537,772, filed Oct. 2, 2000; U.S. Pat. No. 7,459,524, filed Oct. 2, 1997; U.S. Pat. No. 7,534,445, filed Jan. 27, 2004; PCT/US98/20737 (WO 99/17741), filed Oct. 1, 1998; U.S. Pat. No. 6,887,843, filed Apr. 3, 2000; U.S. Pat. No. 6,642,023, filed Jul. 6, 2000; U.S. Pat. No. 7,419,801, filed Nov. 4, 2004; and U.S. Pat. No. 7,655,246, filed Sep. 1, 2004, each of which is herein incorporated by reference in its entirety. In one embodiment of the invention, an immunogenic peptide comprises at least 10, 15, 20, 25, 30, 35, 40, 45 or 50 or more contiguous amino acids of a PmpG, Pmpl, PmpE, MOMP, PmpD, OmcB, OmpH or HtrA peptide.

In one embodiment of the invention, the immunogenic peptide lacks an N-terminus domain. For instance, the invention includes Chlamydial proteins that lack at least about 5, 10, 15, 20, 25, 26, 27, 28, 29, 30, 35, 40, 45, 50, 55, 60, 70, 80, 90, 100, 125, 150, 175, 200, 225, 250, 275 or 300 or more amino acids at the N-terminus. In another embodiment of the invention, the immunogenic peptide lacks a transmembrane region. In yet another embodiment of the invention, the immunogenic peptide lacks at least about 5, 10, 15, 20, 25, 30, 35, 40, 45, 50, 55, 60, 65, 70 80, 90, 100, 125, 150, 175, 200, 225, 250, 275 or 300 or more amino acids at the C-terminus.

In yet another embodiment of the invention, the immunogenic peptide lacks regions greater than 10 amino acids in length that share greater than 90% identity to eukaryotic peptides. For instance, in one embodiment of the invention, the immunogenic peptide is an HtrA peptide that consists essentially of a polypeptide with at least 70% identity to amino acids 1-151 or 1-169 of SEQ ID NOS: 2, 6 or 8 of PCT/US08/006656, filed May 23, 2008, or an immunogenic fragment thereof.

Chlamydial immunogenic peptide and Chlamydial antigen are used interchangeably herein.

The term "pharmaceutically acceptable" means approved by a regulatory agency of the Federal or a state government or listed in the U.S. Pharmacopeia or other generally recognized pharmacopeia for use in animals, and more particularly in humans.

As used herein, the term "promoter" refers to a region of DNA involved in binding RNA polymerase to initiate transcription. In one embodiment of the invention, the promoter is a prokaryotic promoter such as a *Salmonella* ssaG promoter (FIG. 17). In one embodiment of the invention, the promoter is a eukaryotic promoter.

As used herein, the terms "nucleic acid," "nucleic acid molecule," or "polynucleotide" refer to deoxyribonucleotides or ribonucleotides and polymers thereof in either single- or double-stranded form. Unless specifically limited, the terms encompass nucleic acids containing analogues of natural nucleotides that have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions) and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al. (1991) Nucleic Acid Res. 19:5081; Ohtsuka et al. (1985) J. Biol. Chem. 260:2605-2608; Cassol et al. (1992); Rossolini et al. (1994) Mol. Cell. Probes 8:91-98). The term nucleic acid is used interchangeably with gene, cDNA, and mRNA encoded by a gene. As used herein, the terms "nucleic acid," "nucleic acid molecule," or "polynucleotide" are intended to include DNA molecules (e.g., cDNA or genomic DNA), RNA molecules (e.g., mRNA), analogs of the DNA or RNA generated using nucleotide analogs, and derivatives, fragments and homologs thereof.

As used herein, the term "sequence identity" refers to a relationship between two or more polynucleotide sequences or between two or more polypeptide sequences. When a position in one sequence is occupied by the same nucleic acid base or amino acid residue in the corresponding position of the comparator sequence, the sequences are said to be "identical" at that position. The percentage "sequence identity" is calculated by determining the number of positions at which the identical nucleic acid base or amino acid residue occurs in both sequences to yield the number of "identical" positions. The number of "identical" positions is then divided by the total number of positions in the comparison window and multiplied by 100 to yield the percentage of "sequence identity." Percentage of "sequence identity" is determined by comparing two optimally aligned sequences over a comparison window. In order to optimally align sequences for comparison, the portion of a polynucleotide or polypeptide sequence in the comparison window may comprise additions or deletions termed gaps while the reference sequence is kept constant. An optimal alignment is that alignment which, even with gaps, produces the greatest possible number of "identical" positions between the reference and comparator sequences. Percentage "sequence identity" between two sequences can be determined using the version of the program "BLAST 2 Sequences" which was available from the National Center for Biotechnology Information as of Sep. 1, 2004, which program incorporates the programs BLASTN (for nucleotide sequence comparison) and BLASTP (for polypeptide sequence comparison), which programs are based on the algorithm of Karlin and Altschul (*Proc. Natl. Acad. Sci. USA* 90(12):5873-5877, 1993). When utilizing "BLAST 2 Sequences," parameters that were default parameters as of Sep. 1, 2004, can be used for word size (3), open gap penalty (11), extension gap penalty (1), gap dropoff (50), expect value (10) and any other required parameter including but not limited to matrix option.

As used herein, the term "transformation" refers to the transfer of nucleic acid (i.e., a nucleotide polymer) into a cell. As used herein, the term "genetic transformation" refers to the transfer and incorporation of DNA, especially recombinant DNA, into a cell.

"Variants or variant" refers to a nucleic acid or polypeptide differing from a reference nucleic acid or polypeptide, but retaining essential properties thereof. Generally, variants are overall closely similar, and, in many regions, identical to the reference nucleic acid or polypeptide. In one embodiment, "variant" refers to a *C. trachomatis, C. pneumoniae* or *C. muridarum* nucleic acids or peptides. In one embodiment, variants refers to *C. trachomatis* PmpG peptide variants.

In one embodiment of the invention, the immunogenic portions of the Chlamydial peptides, as described below, are presented to the host immune system via a live, attenuated bacterial vaccine vector, such as an attenuated *Salmonella* vaccine vector. In various embodiments, the bacterial vector is an attenuated *Salmonella enterica* serovar, for instance, *S. enterica* serovar Typhi, *S. enterica* serovar Typhimurium, *S. enterica* serovar Paratyphi, *S. enterica* serovar Enteritidis, *S. enterica* serovar Choleraesuis, *S. enterica* serovar Gallinarum, *S. enterica* serovar Dublin, *S. enterica* serovar Hadar, *S. enterica* serovar Infantis and *S. enterica* serovar Pullorum.

Generally, the *Salmonella* vector carries one or more gene deletions or inactivations, rendering the microorganism attenuated. In certain embodiments, the *Salmonella* vector is attenuated by deletion of all or a portion of a gene(s) associated with pathogenicity. The site of the deleted nucleic acids is referred to herein as the deletion site. In one embodiment of the invention, a gene expression cassette is inserted in a deletion site of a mutated gene. For instance, a gene expression cassette comprising nucleic acids encoding one or more of *Chlamydia* proteins PmpG, Pmpl, PmpE, PmpH, MOMP, PmpD, OmcB, OmpH, HtrA or a variant or fragment thereof may be inserted into a deletion site.

Alternatively, the gene(s) may be inactivated, for example, by mutation in an upstream regulatory region or upstream gene so as to disrupt expression of the pathogenesis-associated gene, thereby leading to attenuation. For instance, such a gene may be inactivated by an insertional mutation.

In certain embodiments, the attenuated microorganism may be an attenuated gram negative bacterium as described in U.S. Pat. Nos. 6,342,215 ; 6,756,042 and 6,936,425, each of which is hereby incorporated by reference in its entirety. For example, the microorganism may be an attenuated *Salmonella* spp. (e.g., *S. enterica Typhi, S. enterica Typhimurium* or *S. enterica Enteritidis*) comprising at least one deletion or inactivation in a gene located within the *Salmonella* Pathogenicity Island 2 (SPI2). The present invention includes an attenuated *Salmonella* spp. with more than one deleted or inactivated SPI2 genes.

SPI2 is one of more than two pathogenicity islands located on the *Salmonella* chromosome. SPI2 comprises several genes that encode a type III secretion system involved in transporting virulence-associated proteins, including SPI2 so-called effector proteins, outside of the *Salmonella* bacteria and potentially directly into target host cells such as macrophages. SPI2 apparatus genes encode the secretion apparatus of the type III system. SPI2 is essential for the pathogenesis and virulence of *Salmonella* in the mouse. *S. typhimurium* SPI2 mutants are highly attenuated in mice challenged by the oral, intravenous and intraperitoneal routes of administration.

Infection of macrophages by *Salmonella* activates the SPI2 virulence locus, which allows *Salmonella* to establish a replicative vacuole inside macrophages, referred to as the *Salmonella*-containing vacuole (SCV). SPI2-dependent activities are responsible for SCV maturation along the endosomal pathway to prevent bacterial degradation in phagolysosomes, for interfering with trafficking of NADPH oxidase-containing vesicles to the SCV, and remodeling of host cell microfilaments and microtubule networks. See, for instance, Vazquez-Torres et al., *Science* 287:1655-1658 (2000), Meresse et al., *Cell Microbiol.* 3:567-577 (2001) and Guignot et al., *J. Cell Sci.* 117:1033-1045 (2004), each of which is herein incorporated by reference in its entirety. *Salmonella* SPI2 mutants are attenuated in cultured macrophages (see, for instance, Deiwick et al., *J. Bacteriol.* 180(18):4775-4780 (1998) and Klein and Jones, *Infect. Immun.* 69(2):737-743 (2001), each of which is herein incorporated by reference in its entirety). Specifically, *Salmonella enterica* SPI2 mutants generally have a reduced ability to invade macrophages as well as survive and replicate within macrophages.

The deleted or inactivated SPI2 gene may be, for instance, an apparatus gene (ssa), effector gene (sse), chaperone gene (ssc) or regulatory gene (ssr). In certain embodiments, the attenuated *Salmonella* microorganism is attenuated via a deletion or inactivation of a SPI2 apparatus gene, such as those described in Hensel et al., *Molecular Microbiology* 24(1):155-167 (1997) and U.S. Pat. No. 6,936,425, each of which is herein incorporated by reference in its entirety. In certain embodiments, the attenuated *Salmonella* carries a deletion or inactivation of at least one gene associated with pathogenesis selected from ssaV, ssaJ, ssaU, ssaK, ssaL, ssaM, ssaO, ssaP, ssaQ, ssaR, ssaS, ssaT, ssaU, ssaD, ssaE, ssaG, ssal, ssaC (spiA) and ssaH. For example, the attenuated *Salmonella* may carry a deletion and/or inactivation of the ssaV gene. Alternatively, or in addition, the microorganism carries a mutation within an intergenic region of ssaJ and ssaK. The attenuated *Salmonella* may of course carry additional deletions or inactivations of the foregoing genes, such as two, three, or four genes.

In certain embodiments, the attenuated *Salmonella* microorganism comprises a deletion or inactivation of a SPI2 effector gene. For instance, in certain embodiments, the attenuated *Salmonella* comprises a deletion or inactivation of at least one gene selected from sseA, sseB, sseC, sseD, sseE, sseF, sseG, sseL and spiC (ssaB). SseB is necessary to prevent NADPH oxidase localization and oxyradical formation at the phagosomal membrane of macrophages. SseD is involved in NADPH oxidase assembly. SpiC is an effector protein that is translocated into *Salmonella*-infected macrophages and interferes with normal membrane trafficking, including phagosome-lysosome fusion. See, for instance, Hensel et al., *Mol. Microbiol.*, 30:163-174 (1998); Uchiya et al., EMBO J., 18:3924-3933 (1999); and Klein and Jones, *Infect. Immun.*, 69(2):737-743 (2001), each of which is herein incorporated by reference in its entirety. The attenuated *Salmonella* may of course carry additional deletions or inactivations of the foregoing genes, such as two, three, or four genes.

In certain embodiments, the attenuated *Salmonella* microorganism comprises a deleted or inactivated ssr gene. For instance, in certain embodiments, the attenuated *Salmonella* comprises a deletion or inactivation of at least one gene selected from ssrA (spiR) and ssrB. ssrA encodes a membrane-bound sensor kinase (SsrA), and ssrB encodes a cognate response regulator (SsrB). SsrB is responsible for activating transcription of the SPI2 type III secretion system and effector substrates located outside of SPI2. See, for instance, Coombes et al., *Infect. Immun.*,75(2):574-580 (2007), which is herein incorporated by reference in its entirety.

In other embodiments, the attenuated *Salmonella* comprises an inactivated SPI2 gene encoding a chaperone (ssc). For instance, in certain embodiments, the attenuated *Salmonella* comprises a deletion or inactivation of one or more from sscA and sscB. See, for instance, U.S. Pat. No. 6,936,425, which is herein incorporated by reference in its entirety.

The invention includes an attenuated *Salmonella* comprising a first attenuating mutation in the SPI2 region and a second attenuating mutation outside of SPI2 region. The attenuated *Salmonella* may comprise additional attenuating mutations, for instance, a third, fourth or fifth attenuating mutation.

In one embodiment of the invention, the attenuated *Salmonella* may carry an "auxotrophic mutation," for example, a mutation that is essential to a biosynthetic pathway. The biosynthetic pathway is generally one present in the microorganism, but not present in mammals, such that the mutants cannot depend on metabolites present in the treated patient to circumvent the effect of the mutation. For instance, the present invention includes an attenuated *Salmonella* with a deleted or inactivated gene necessary for the biosynthesis of aromatic amino acids. Exemplary genes for the auxotrophic mutation in *Salmonella*, include an aro gene such as aroA, aroC, aroD and aroE. In one embodiment, the invention comprises a *Salmonella* SPI2 mutant (e.g., *Salmonella* with an attenuating mutation in ssaV, ssaJ, sseB, sseC, etc.) comprising a second attenuating mutation in the aroA gene. In one embodiment of the invention, the invention comprises a *Salmonella* SPI2 mutant (e.g., *Salmonella* with an attenuating mutation in ssaV, ssaJ, sseB, sseC, etc.) and a second attenuating mutation in an aroC gene.

In addition to aro gene mutations, the present invention includes an attenuated *Salmonella* with a deletion or inactivation of a purA, purE, asd, cya and/or crp gene. For instance, the invention includes an attenuated *Salmonella* with a first attenuating mutation in a SPI2 gene (e.g., ssaV, ssaJ, sseB, sseC) and a second mutation in a purA, purE, asd, cya and/or crp gene.

In another embodiment, the attenuated *Salmonella* SPI2 mutant also comprises at least one additional deletion or inactivation of a gene in the *Salmonella* Pathogenicity Island I region (SPI 1). In yet another embodiment, the *Salmonella* SPI2 mutant comprises at least one additional deletion or inactivation of a gene outside of the SPI2 region which reduces the ability of *Salmonella* to invade a host cell and/or survive within macrophages. For instance, the second mutation may be the deletion or inactivation of a rec or sod gene. In yet another embodiment, the *Salmonella* spp. comprises the deletion or inactivation of transcriptional regulator that regulates the expression of one or more virulence genes (including, for instance, genes necessary for surviving and replicating within macrophages). For instance, the *Salmonella* SPI2 mutant may further comprise the deletion or inactivation of one or more genes selected from the group consisting of phoP, phoQ, rpoS and slyA.

In certain embodiments, the attenuated microorganism is a *Salmonella* microorganism having attenuating mutations in a SPI2 gene (e.g., ssa, sse, ssr or ssc gene) and an auxotrophic gene located outside of the SPI2 region. In one embodiment, the attenuated microorganism is a *Salmonella enterica* serovar comprising a deletion or inactivation of an ssa, sse and/or ssr gene and an auxotrophic gene. For instance, the invention includes an attenuated *Salmonella enterica* serovar with deletion or inactivating mutations in the ssaV and aroC genes (for example, a microorganism derived from *Salmonella enterica* Typhi ZH9, as described in U.S. Pat. No. 6,756,042, which description is hereby incorporated by reference) or ssaJ and aroC genes.

In yet another embodiment, the attenuated *Salmonella* is a LPS mutant strain of *Salmonella*.

Where the attenuated microorganism is a *Salmonella* bacterium, the nucleic acids that encode Chlamydial peptides (for instance, PmpG, Pmpl, PmpE, PmpH, MOMP, PmpD, OmcB and OmpH peptides) may be codon-optimized for expression in a gram negative pathogen such as a *Salmonella enterica* serovar. Expression of the antigens may be improved if the G+C content and codon usage are adjusted closer to that of *S. enterica* serovar host. In another embodiment, Chlamydial peptides may be codon-optimized for expression in *E. coli*. Nucleic acids may be codon-optimized by methods known in the art.

In one embodiment of the invention, the Chlamydial peptides are PmpG peptides such as CT110 (FIGS. 6 and 21), CT84 (FIG. 9) or CT40 (FIG. 16). The peptides can be encoded by *E. coli* codon-optimized nucleic acids, see, for instance, FIGS. 4 and 7 which provide codon-optimized nucleic acid sequences for CT110 and CT84, respectively, and FIG. 22 which provides the nucleic acid sequence for *C. muridarum* CT110, which can be expressed by the attenuated *Salmonella* of the invention.

The polynucleotide encoding the immunogenic peptide, e.g., as a recombinant *Chlamydia* peptide under the control of an inducible promoter, may be contained on an extrachromosomal plasmid, or may be integrated into the bacterial chromosome by methods known in the art. In certain embodiments, the microorganism is an attenuated *Salmonella* comprising an integrated gene expression cassette that directs the expression of the immunogenic peptide from an inducible promoter. In one embodiment, the expression of the immunogenic peptide comprising a *C. trachomatis, C. pneumoniae* or *C. muridarum* peptide (e.g., PmpG peptide such as CT110 or CT84), is controlled by a *Salmonella* in vivo promoter (e.g., ssaG promoter) (FIGS. 19 and 20).

In certain embodiments, for example, where the attenuated microorganism is derived from *Salmonella enterica* serovar Typhi ZH9, the gene expression cassette comprising a heterologous antigen is inserted at the aroC and/or ssaV gene deletion site. In one embodiment of the invention, an attenuated *Salmonella enterica* serovar with at least one deletion mutation in a SPI-2 gene (e.g., ssa, sse, ssr or ssc gene) comprises a gene expression cassette in the SPI-2 gene deletion site. In another embodiment, an attenuated *Salmonella enterica* serovar with at least one deletion mutation in a gene involved in the biosynthesis of aromatic compounds comprises a gene expression cassette in the deletion site. In yet another embodiment, the attenuated *Salmonella enterica* serovar with at least one deletion mutation comprises a deletion mutation in a gene involved in the production of lipopolysaccharide and a gene expression cassette inserted in the site of deletion. Attenuated *Salmonella enterica* serovars with one or more attenuating gene deletion mutations (i.e., deletion sites) may comprise one or more gene expression cassettes on extrachromosomal plasmids.

In one embodiment of the invention, the gene expression cassette of the invention, either integrated in a *Salmonella* chromosome or located on a plasmid, comprises at least one heterologous polynucleotide encoding a *Chlamydia* immunogenic peptide. In one embodiment, the gene expression cassette comprises multiple heterologous nucleic acids encoding *Chlamydia* immunogenic peptides. The expressed *Chlamydia* immunogenic peptides may be expressed as a fusion protein. In one embodiment, the expressed *Chlamydia* immunogenic peptides are expressed as a fusion protein comprising one or more linker peptides separating one or more of the *Chlamydia* immunogenic peptides from other peptides (for instance, other *Chlamydia* immunogenic peptides).

In some embodiments, the gene expression cassette comprising the heterologous polynucleotide encoding a *Chlamydia* peptide additionally comprises nucleic acids encoding an export sequence such as a *Salmonella* ClyA (FIG. 18) or *E. coli* CS3 export signal. For instance, in one embodiment, the gene expression cassette comprises, in a 5' to 3' direction, an inducible promoter followed by a nucleic acid encoding the export signal, optionally followed by a nucleic acid encoding a linker peptide, followed by the heterologous nucleic acid encoding one or more Chlamydia peptides. In one embodiment of the invention, the gene expression cassette does not include a nucleic acid encoding an export sequence and/or linker sequence.

The invention also includes a gene expression cassette comprising one or more polynucleotides encoding immunostimulatory therapeutic antigens such as a chemokine or cytokine (e.g., IFN-alpha, IFN-beta, IFN-gamma, IL-2, IL-3, IL-4, IL-5, IL-6, IL-7, IL-8, IL-9, IL-10, IL-11, IL-12, IL-13, IL-14, IL-15 or IL-16). The gene expression cassette comprising the immunostimulatory therapeutic polynucleotide may further comprise a heterologous polynucleotide encoding a *Chlamydia* immunogenic peptide (e.g., PmpG such as CT110, CT84 or CT40). Such a construct may further comprise a nucleic acid encoding a linker peptide to separate an expressed immunostimulatory therapeutic antigen from other antigens (e.g., to separate from other immunostimulatory therapeutic antigens and/or *Chlamydia* immunogenic peptides).

In one embodiment of the invention, the gene expression cassette comprising a polynucleotide encoding one or more immunostimulatory therapeutic antigens does not comprise a heterologous polynucleotide encoding a Chlamydial antigen. In this embodiment, the attenuated bacterial cell comprising the gene expression cassette may be pooled with an attenuated *Salmonella* cell comprising a Chlamydial antigen. In another embodiment, the attenuated *Salmonella* cell of the invention comprises multiple gene expression cassettes such that at least one gene expression cassette may be capable of expressing the immunostimulatory therapeutic antigen or antigens and at least one gene expression cassette may be capable of expression a Chlamydial antigen. In one embodiment of the invention, the multiple gene expression cassettes are located in gene deletion sites within the *Salmonella* genome. For instance, in one embodiment, the gene expression cassettes are located within aroC and ssaV deletion sites. In another embodiment, one or more of the gene expression cassettes are located on extrachromosomal plasmids.

The immunogenic peptide, optionally fused to a secretion tag and/or linker peptide and/or immunostimulatory therapeutic antigen, may be expressed by the live, attenuated bacterial vaccine vector via an inducible promoter, such as a promoter inducible under particular physiological conditions. In certain embodiments, the inducible promoter is a prokaryotic inducible promoter. For instance, the inducible promoter of the invention includes a gram negative bacterium promoter, including, but not limited to, a *Salmonella* promoter. In certain embodiments, the inducible promoter is an in vivo inducible promoter. In certain embodiments, the inducible promoter directs expression of an immunogenic peptide and, optionally, a fused secretion tag and/or linker peptide and/or immunostimulatory therapeutic antigen, within the gastrointestinal tract of the host. In certain embodiments, the inducible promoter directs expression of the immunogenic peptide and, optionally, fused secretion tag and/or linker peptide and/or immunostimulatory therapeutic antigen, within the gastrointestinal tract and immune cells (for instance, macrophages) of the host.

In certain embodiments, the inducible promoter directs expression of an immunogenic peptide (optionally, fused to a secretion tag and/or linker peptide and/or immunostimulatory therapeutic antigen) under acidic conditions. For instance, in certain embodiments, the inducible promoter directs expression of an immunogenic peptide at a pH of less than or about pH 7, including, for instance, at a pH of less than or about pH 6, pH 5, pH 4, pH 3 or pH 2.

The promoter of the invention can also be induced under conditions of low phosphate concentrations. In one embodiment, the promoter is induced in the presence of low pH and low phosphate concentration such as the conditions that exist within macrophages. In certain embodiments, the promoter of the invention is induced under highly oxidative conditions such as those associated with macrophages.

The promoter of the invention can be a *Salmonella* SPI2 promoter. In one embodiment, the microorganism is engineered such that the SPI2 promoter that directs expression of the immunogenic peptide is located in a gene cassette outside of the SPI2 region or within a SPI2 region that is different from the normal location of the specified SPI2 promoter. Examples of SPI2 promoters include the ssaG promoter, ssrA promoter, sseA promoter and promoters disclosed, for instance, in U.S. Pat. No. 6,936,425.

In certain embodiments, the promoter directs the expression of the immunogenic peptide under conditions and/or locations in the host so as to induce systemic and/or mucosal immunity against the antigen, including the ssaG, ssrA, sseA, pagC, nirB and katG promoters of *Salmonella*. The in vivo inducible promoter may be as described in WO 02/072845, which is hereby incorporated by reference in its entirety.

In certain embodiments, the expression of the immunogenic peptide and, optionally, fused secretion tag and/or linker peptide and/or immunostimulatory therapeutic antigen, by the attenuated microorganism may be controlled by a *Salmonella* ssaG promoter. The ssaG promoter is normally located upstream of the start codon for the ssaG gene, and may comprise the nucleotide sequence of FIG. 17. In this context, the term "ssaG promoter" includes promoters having similar or modified sequences, and similar or substantially identical promoter activity, as the wild-type ssaG promoter, and particularly with respect to its ability to induce expression in vivo. Similar or modified sequences may include nucleotide sequences with high identity to the nucleic acid sequence of FIG. 17 such as nucleic acid sequences having at least about 70%, 80%, 85%, 90%, 95%, 96%, 97%, 98% or 99% identity to the nucleic acid sequence of FIG. 17, as well as functional fragments, including functional fragments with high identity to corresponding functional fragments of the nucleic acid sequence of FIG. 17. In certain embodiments, the functional ssaG promoter fragment comprises at least about 30 nucleotides, at least about 40 nucleotides, or at least about 60 nucleotides.

Levels of identity between coding or promoter sequences may be calculated using known methods. Publicly available computer-based methods for determining identity include the BLASTP, BLASTN and FASTA (Atschul et al., *J. Molec. Biol.*,215: 403-410, (1990)), the BLASTX programme available from NCBI, and the Gap programme from Genetics Computer Group (Madison Wis.). Levels of identity may be obtained using the Gap programme, with a Gap penalty of 50 and a Gap length penalty of 3 for the polynucleotide sequence comparisons.

Thus, the present invention provides vaccines, and particularly, live attenuated bacterial vectors, capable of expressing immunogenic portions of one or more Chlamydial antigens. In one embodiment of the invention, one or more Chlamydial antigens expressed by the attenuated *Salmonella* of the invention are *Chlamydia* outer surface membrane proteins or immunogenic fragments thereof. In another embodiment of the invention, the one or more Chlamydial peptides (i.e., antigens) are selected from the group consisting of PmpG, Pmpl, PmpE, MOMP, PmpD, PmpH, OmcB, OmpH and HtrA. In one embodiment of the invention, the Chlamydial antigens are mature antigens (i.e., lacking a signal sequence).

The invention includes one or more Chlamydial antigens lacking 5, 10, 15, 20, 25, 26, 27, 28, 29 or 30 or more amino acids from the N-terminus. In another embodiment of the invention, the invention includes Chlamydial antigens lacking a transmembrane domain.

The invention further includes a Chlamydial antigen that is protease resistant. In one embodiment of the invention the Chlamydial antigen is modified to express reduced or no protease activity.

In one embodiment of the invention, the Chlamydial antigen is a PmpG protein or fragment thereof. The PmpG protein can be full length or mature. In one embodiment of the invention, the PmpG protein is missing at least about 5 amino acids at the N-termus. In one embodiment of the invention, the PmpG peptide lacks about 5, 10, 15, 20, 25, 26, 27, 28, 29 or 30 or more amino acids at the N-terminus. In one embodiment, the PmpG peptide lacks one or more amino acids in the transmembrane domain. In one embodiment of the invention, the PmpG peptide lacks a transmembrane domain. In one embodiment of the invention, the PmpG peptide comprises a heparin binding domain. In one embodiment of the invention, the PmpG peptide comprises a porin-like domain.

PmpG peptides included in the invention are CT110, CT84 and CT40. The present invention includes PmpG peptides from all *C. trachomatis* serovars, *C. pneumoniae* serovars or *C. muridarum*. In one embodiment of the invention, the PmpG peptides are capable of eliciting an immune response across *C. trachomatis* serovars. *C. trachomatis* PmpG peptides of the invention include peptides with at least about 70%, 75%, 80%, 85%, 90%, 95%, 96%, 97%, 98% or 99% identity to peptides comprising or consisting essentially of SEQ ID NO: 2 (serovar $L_{2B}$), SEQ ID NO: 15 (serovar B) and SEQ ID NO: 16 (serovar F) of U.S. Pat. Nos. 7,459,524; 7,419,807; 6,887,843; and 6,642,023, each of which is herein incorporated by reference in its entirety. These peptides are reproduced in FIGS. 11, 13 and 15 herein. The invention includes PmpG proteins encoded by nucleic acids with at least about 70%, 75%, 80%, 85%, 90%, 95%, 96%, 97%, 98% or 99% identity to nucleic acids comprising or consisting essentially of SEQ ID NOS: 1 (serovar $L_{2B}$), 23 (serovar B) and 24 (serovar F) of U.S. Pat. Nos. 7,459,524; 7,419,807; 6,887,843; and 6,642,023. These nucleic acid sequences are reproduced as FIGS. 12, 14 and 16 herein. The invention includes polynucleotides that encode PmpG that are codon-optimized for expression in *Salmonella* or *E. coli*.

CT110 peptide is a PmpG fragment that corresponds to methionine plus amino acids 29 to 1012 of SEQ ID NO: 2 and methionine plus amino acids 29 to 1013 of SEQ ID NOS: 15 and 16 of U.S. Pat. Nos. 7,459,524; 7,419,807; 6,887,843; and 6,642,023. In one embodiment of the invention, the CT110 peptide consists essentially of a peptide with at least about 70%, 75%, 80%, 85%, 90%, 95%, 96%, 97%, 98% or 99% identity to the peptide of FIG. 6. In another embodiment of the invention, the CT110 peptide consists essentially of a peptide with at least about 70%, 75%, 80%, 85%, 90%, 95%, 96%, 97%, 98% or 99% identity to the peptide of FIG. 21. The invention includes CT110 encoded by a polynucleotide with at least about 70%, 75%, 80%, 85%, 90%, 95%, 96%, 97%, 98% or 99% identity to the polynucleotide comprising the sequence of FIG. 4 or 5. In another embodiment the invention includes CT110 encoded by a polynucleotide with at least about 70%, 75%, 80%, 85%, 90%, 95%, 96%, 97%, 98% or 99% identity to the polynucleotide comprising the sequence of FIG. 22. In one embodiment of the invention, CT110 is encoded by a polynucleotide codon-optimized for expression in *E. coli* or *Salmonella* comprising the nucleic acid sequence of FIG. 4.

CT84 peptide is a PmpG fragment that lacks both an N-terminus and a transmembrane domain. In one embodiment of the invention, CT84 consists essentially of a peptide with at least about 70%, 75%, 80%, 85%, 90%, 95%, 96%, 97%, 98% or 99% identity to the peptide of FIG. 9. The invention includes CT84 encoded by a polynucleotide with at least about 70%, 75%, 80%, 85%, 90%, 95%, 96%, 97%, 98% or 99% identity to the polynucleotide comprising the nucleic acid of FIG. 7 or 8. In one embodiment of the invention, CT110 is encoded by a polynucleotide codon-optimized for expression in *E. coli* or *Salmonella* comprising the nucleic acid of FIG. 7.

CT40 peptide is a PmpG fragment that lacks both an N-terminus and a transmembrane domain. In one embodiment of the invention, CT40 consists essentially of a peptide with at least about 70%, 75%, 80%, 85%, 90%, 95%, 96%, 97%, 98% or 99% identity to the peptide of FIG. 16. The invention includes CT40 encoded by a polynucleotide with at least about 70%, 75%, 80%, 85%, 90%, 95%, 96%, 97%, 98% or 99% identity to the polynucleotide comprising the nucleic acid of FIG. 16. In one embodiment of the invention, CT40 is encoded by a polynucleotide codon-optimized for expression in *E. coli* or *Salmonella*.

The invention includes additional PmpG peptides, for instance, protein fragments corresponding to SEQ ID NOS: 3, 17, 25 and 27 of U.S. Pat. Nos. 7,459,524; 7,419,807; 6,887,843; and 6,642,023. In one embodiment, the attenuated Salmonella of the invention is capable of expressing a PmpG peptide comprising or consisting essentially of a peptide with at least about 70%, 75%, 80%, 85%, 90%, 95%, 96%, 97%, 98% or 99% identity to the peptide of SEQ ID NOS: 3, 17, 25 and 27 of U.S. Pat. Nos. 7,459,524; 7,419,807; 6,887,843; and 6,642,023.

In one embodiment of the invention, the PmpG peptide comprises a peptide with at least about 70%, 75%, 80%, 85%, 90%, 95%, 96%, 97%, 98% or 99% identity to at least about 20, 25, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390 or 400 or more contiguous amino acids of the peptide of FIGS. 11, 13 and 15.

In one embodiment of the invention, the immunogenic peptide is a PmpE peptide. For instance, the invention includes full length PmpE, mature PmpE and immunogenic PmpE protein fragments. In another embodiment of the invention, the immunogenic peptide is a PmpI peptide. For instance, the invention includes full length PmpI, mature PmpI and immunogenic PmpI protein fragments. PmpE and PmpI peptides include, but are not limited to those peptides disclosed, for instance, in U.S. application Ser. No. 09/677, 752, filed Oct. 2, 2000 and PCT/US01/30345, filed Sep. 28, 2001.

In one embodiment of the invention, the immunogenic peptide is a PmpD, PmpH, OmcB, OmpH or HtrA peptide. For instance, the invention includes PmpD, PmpH, OmcB, OmpH and HtrA peptides disclosed in PCT/US08/006656, filed May 23, 2008 and PCT/US08/007490, filed Jun. 16, 2008;

In one embodiment of the invention, the Chlamydial antigen is a *C. trachomatis* antigen. In another embodiment of the invention, the Chlamydial antigen is a *C. pneumoniae* antigen. In another embodiment of the invention, the Chlamydial antigen is a *C. muridarum* antigen. In yet another embodiment, the Chlamydial antigen is both a *C. trachomatis* and *C. pneumoniae* antigen.

*C. trachomatis* antigens can be from any of the at least 18 known *C. trachomatis* serovars. In one embodiment of the invention, the *C. trachomatis* antigen is from a *C. trachomatis* serovar A, B, or C. *C. trachomatis* serovars A, B and C are most commonly associated with trachoma although other serovars may cause trachoma. In another embodiment of the invention, the *C. trachomatis* antigen is from a *C. trachomatis* serovar D, E, F, G, H, I or K. *C. trachomatis* serovars D, E, F, G, H, I and K are most commonly associated with genital infections.

In one embodiment, the attenuated microorganism and/or immunogenic peptide may be constructed so as to secrete or express on the surface of the attenuated *Salmonella* cell one or more immunogenic peptides, each immunogenic peptide comprising portions of one or more *Chlamydia* antigens, for instance, PmpG, PmpE, Pmpl, PmpD, PmpH, OmcB, OmpH and/or HtrA. By secretion of the immunogenic peptide, a strong antibody response to the antigen, e.g., systemic and/or mucosal, may be elicited. In one embodiment of the invention, a plurality of attenuated *Salmonella* cells of the invention are administered to a subject, wherein some of the attenuated *Salmonella* cells secrete or express on the cell surface one or more *Chlamydia* antigens (i.e., by a secretion tag) and some of the attenuated *Salmonella* cells do not secrete or express on the cell surface *Chlamydia* antigens (i.e., no secretion tag) so as to elicit both a cell mediated and humoral immune response.

In certain embodiments, the immunogenic peptide is designed for secretion or cell surface expression by a bacterial export system. In one embodiment, the immunogenic peptide is secreted by a ClyA export system, e.g., by engineering the expressed immunogenic peptide to include a ClyA secretion tag. ClyA and its use for secretion of proteins from host cells is described in U.S. Pat. No. 7,056,700, which is hereby incorporated by reference in its entirety. Generally, the ClyA export system secretes the immunogenic peptide in close association with membranous vesicles, which may increase the potency of the immune response.

Other secretion systems that may find use with the invention include other members of the HlyE family of proteins. The HlyE family consists of HlyE and its close homologs from *E. coli, Shigella flexneri, S. typhi*, and other bacteria. *E. coli* HlyE is a functionally well characterized, pore-forming, chromosomally-encoded hemolysin. It consist of 303 amino acid residues (34 kDa). HlyE forms stable, moderately cation-selective transmembrane pores with a diameter of 2.5-3.0 nm in lipid bilayers. The crystal structure of *E. coli* HlyE has been solved to 2.0 angstrom resolution, and visualization of the lipid-associated form of the toxin at low resolution has been achieved by electron microscopy. The structure exhibits an elaborate helical bundle about 100 angstroms long. It oligomerizes in the presence of lipid to form transmembrane pores.

This haemolysin family of proteins (of which ClyA is a member), typically cause haemolysis in eukaryotic target cells. Thus, the tag may be modified in some embodiments so as to be non-hemolytic or have reduced hemolytic activity. Such modifications may include modifications at one or more, or all of, positions 180, 185, 187, and 193 of the ClyA encoding polynucleotide. In certain embodiments, the ClyA export tag has one or more or all the following modifications: G180V, V185S, A187S, and I193S. However, alternative modifications to the wild-type sequence may be made, so long as the ClyA tag is substantially non-hemolytic. Such modifications may be guided by the structure of the protein, reported in Wallace et al., *E. coli Hemolysin E (HlyE, ClyA, SheA): X-Ray Crystal Structure of the Toxin and Observation of Membrane Pores by Electron Microscopy, Cell* 100:265-276 (2000), which is hereby incorporated by reference in its entirety. For example, modifications may include modification of outward-facing hydrophobic amino acids in the head domain to amino acids having hydrophilic side chains.

ClyA sequences that may be used and/or modified to export the immunogenic peptide include *S. typhi* clyA (available under GENBANK Accession No. AJ313034); *Salmonella paratyphi* clyA (available under GENBANK Accession No. AJ313033); *Shigella flexneri* truncated HlyE (hlyE), the complete coding sequence available under GENBANK Accession No. AF200955; and the *Escherichia coli* hlyE, available under GENBANK Accession No. AJ001829.

Other secretion sequences may be used to secrete the immunogenic peptide(s) from the bacterial host cell or express the immunogenic peptide(s) on the *Salmonella* cell surface, including, but not limited to secretion sequences involved in the Sec-dependent (general secretory apparatus) and Tat-dependent (twin-arginine translocation) export systems. For instance, a leader sequence from *S. typhi* sufI can be used (msfsrrqflqasgialcagaiplranaagqqqpIpvppllesrrgqpIfm (SEQ ID NO.: 1)) to export the immunogenic peptide. Additional export system sequences comprising the consensus sequence s/strrxfl (SEQ ID NO.: 32) plus a hydrophobic domain can be used to export the immunogenic peptide from the bacterial host cell.

Another secretion sequence of the invention is *E. coli* CS3 as is disclosed in U.S. provisional application 61/107,113, filed Oct. 21, 2008, which is hereby incorporated by reference in its entirety. The invention includes an attenuated *Salmonella* cell wherein the Chlamydial peptide is secreted or expressed on the cell surface. This can be accomplished by cloning a CS3 export signal nucleic acid (atgttaaaaataaaatact-tattaataggtctttcactgtcagctatgagttcatactcactagct (SEQ ID NO.: 2)) upstream and in frame with the heterologous polynucleotide encoding the Chlamydial peptide. The amino acid CS3 export signal sequence (MLKIKYLLIGLSLSAMSSYSLA (SEQ ID NO.: 3)) may be completely or partially removed during the cell surface expression or export of the Chlamydial peptide.

It is envisioned that signal sequences and secretion sequences known in the art can be used to export the immunogenic peptide out of the live, attenuated microorganism and into the host, including the host gastrointestinal tract. Such sequences can be derived, for instance, from virus, eukaryotic organisms and heterologous prokaryotic organisms. See, for instance, U.S. Pat. Nos. 5,037,743; 5,143,830 and 6,025,197 and US Patent Application 20040029281, for disclosure of additional signal sequences and secretion sequences.

In one embodiment of the invention, the secretion sequence is cleaved from the exported immunogenic peptide. In other embodiment of the invention, the bacterial secretion sequence is not cleaved from the exported or cell surface expressed immunogenic peptide, but, rather, remains fused so as to create a secretion tag and immunogenic peptide fusion protein. For instance, the invention includes a fusion protein comprising a ClyA export peptide fused to one or more immunogenic peptides. In other embodiment of the invention, the bacterial export sequence maintains the conformation of the immunogenic peptide.

In another embodiment of the invention, the secretion sequence causes the exported immunogenic peptide to "bleb off" the bacterial cell, i.e., a bacterial outer-membrane vesicle containing the immunogenic peptide is released from the bacterial host cell. See Wai et al., *Vesicle-Mediated Export and Assembly of Pore-Forming Oligomers of the Enterobacterial ClyA Cytotoxin, Cell* 115:25-35 (2003), which is hereby incorporated by reference in its entirety. The invention includes avirulent bacterial vesicles comprising one or more immunogenic peptides of the invention. In one embodiment, avirulent bacterial vesicles comprise a secretion sequence fused to the one or more immunogenic peptides and, optionally, one or more linker peptides. For instance, the invention includes a *S. enterica* vesicle comprising a ClyA export sequence fused to a *C. trachomatis* PmpG peptide (e.g., full length or mature PmpG, CT110, CT84 or CT40).

Secretion tag, export tag, export sequence and secretion sequence are used interchangeably herein and refer to a sequence that directs export of an immunogenic peptide out of a cell or express an immunogenic peptide on the surface of the attenuated *Salmonella* cell.

In one embodiment, a peptide linker is used to separate a secretion tag from an immunogenic peptide. In another embodiment, a peptide linker is used to separate two immunogenic peptides, for instance, a PmpG peptide and HtrA peptide. In yet another embodiment, the peptide linker is used to separate an immunogenic peptide from immunostimulatory therapeutic antigen such as a chemokine or cytokine (e.g., IFN-alpha, IFN-beta, IFN-gamma, IL-2, IL-3, IL-4, IL-5, IL-6, IL-7, IL-8, IL-9, IL-10, IL-11, IL-12, IL-13, IL-14, IL-15 or IL-16).

Accordingly, the present invention includes an attenuated *Salmonella* bacterium capable of expressing (a) a fusion protein comprising a secretion tag+linker+*Chlamydia* immunogenic peptide (e.g., PmpG full length protein, PmpG mature protein, CT110 peptide, CT84 peptide, CT40 peptide and fragments and variants thereof), (b) a fusion protein comprising a first *Chlamydia* immunogenic peptide+linker+a second *Chlamydia* immunogenic peptide, (c) a fusion protein comprising a *Chlamydia* immunogenic peptide (e.g., PmpG full length protein, PmpG mature protein, CT110 peptide, CT84 peptide, CT40 peptide and fragments and variants thereof)+linker+an immunostimulatory therapeutic antigen (e.g., IFN-alpha, IFN-beta, IFN-gamma, IL-2, IL-3, IL-4, IL-5, IL-6, IL-7, IL-8, IL-9, IL-10, IL-11, IL-12, IL-13, IL-14, IL-15 or IL-16) and (d) a fusion protein comprising an immunostimulatory therapeutic antigen (e.g., IFN-alpha, IFN-beta, IFN-gamma, IL-2, IL-3, IL-4, IL-5, IL-6, IL-7, IL-8, IL-9, IL-10, IL-11, IL-12, IL-13, IL-14, IL-15 or IL-16)+linker+a Chlamydia immunogenic peptide (e.g., PmpG full length protein, PmpG mature protein, CT110 peptide, CT84 peptide, CT40 peptide and fragments and variants thereof).

In yet another embodiment, the invention includes a vaccine comprising or expressing (a) a fusion protein comprising a secretion tag+linker+*Chlamydia* immunogenic peptide (e.g., PmpG full length protein, PmpG mature protein, CT110 peptide, CT84 peptide, CT40 peptide and fragments and variants thereof), (b) a fusion protein comprising a first *Chlamydia* immunogenic peptide+linker+a second *Chlamydia* immunogenic peptide, (c) a fusion protein comprising a *Chlamydia* immunogenic peptide (e.g., PmpG full length protein, PmpG mature protein, CT110 peptide, CT84 peptide, CT40 peptide and fragments and variants thereof)+linker+an immunostimulatory therapeutic antigen (e.g., IFN-alpha, IFN-beta, IFN-gamma, IL-2, IL-3, IL-4, IL-5, IL-6, IL-7, IL-8, IL-9, IL-10, IL-11, IL-12, IL-13, IL-14, IL-15 or IL-16) and (d) a fusion protein comprising an immunostimulatory therapeutic antigen (e.g., IFN-alpha, IFN-beta, IFN-gamma, IL-2, IL-3, IL-4, IL-5, IL-6, IL-7, IL-8, IL-9, IL-10, IL-11, IL-12, IL-13, IL-14, IL-15 or IL-16)+linker+a Chlamydia immunogenic peptide (e.g., PmpG full length protein, PmpG mature protein, CT110 peptide, CT84 peptide, CT40 peptide and fragments and variants thereof). The vaccine can be a live, attenuated bacterial vector vaccine or a polypeptide vaccine. In one embodiment, the polypeptide is contained within a bacterial membrane that is lacking genomic DNA.

Without wishing to be bound by a particular theory, it is believed that the peptide linker allows the *C. trachomatis*, *C. pneumoniae* and/or *C. muridarum* immunogenic peptide to maintain correct folding. The linker peptide may also assist with the effective presentation of the Chlamydial immunogenic, in particular by providing spatial separation from the secretion tag and/or other *C. trachomatis* immunogenic peptide and/or immunostimulatory therapeutic antigen. For example, the peptide linker may allow for rotation of two *C. trachomatis* immunogenic peptides relative to each other.

In one embodiment of the invention, the live, attenuated *Salmonella* comprises a nucleic acid sequence encoding a peptide linker about 1, 2, 3, 4, 5, 6, 7, 8, 9, 10, 11, 12, 13, 14 or 15 amino acids in length.

In one embodiment, the linker comprises or consists essentially of glycine, proline, serine, alanine, threonine, and/or asparagine amino acid residues. In one embodiment of the invention, the peptide linker comprises or consists essentially of glycine and/or proline amino acids. For instance, in one embodiment, the peptide linker comprises the amino acid sequence GC. In another embodiment, the peptide linker comprises the amino acid sequence CG.

In one embodiment, the peptide linker comprises or consists essentially of glycine and/or serine amino acids. In one embodiment, the peptide linker comprises or consists essentially of proline amino acids. In one embodiment, the peptide linker comprises or consists essentially of glycine amino acids.

In other aspects, the invention provides recombinant antigens and polynucleotides encoding the same. The recombinant antigens of the invention comprise immunogenic portions of *C. trachomatis*, *C. pneumonia* or *C. muridarum* peptides (as described herein), and may be designed for secretion from a bacterial vector such as *Salmonella*. The recombinant antigens of the invention are useful for inducing an effective immune response, such as a cell mediated immune response or a mucosal immune response, against *C. trachomatis* or *C. pneumoniae* in a human patient.

The recombinant antigens of the invention further comprise a ClyA export tag or CS3 export tag, as described. For example, the recombinant antigen may comprise a ClyA export tag fused to a *Chlamydia* peptide (e.g., PmpG full length protein, PmpG mature protein, CT110, CT84 or CT40). In another embodiment, the recombinant antigen may comprise a *Chlamydia* peptide (e.g., PmpG full length protein, PmpG mature protein, CT110, CT84 or CT40) fused to an immunostimulatory therapeutic peptide such as IL-2. Such recombinant antigens may further comprise a linker between the secretion signal and the *Chlamydia* peptide, between two *Chlamydia* peptides, and/or between the *Chlamydia* peptide and immunostimulatory therapeutic antigen.

The invention includes an isolated recombinant antigen. The recombinant antigen can be isolated by methods known in the art. An isolated recombinant antigen can purified, for instance, substantially purified. An isolated recombinant antigen can be purified by methods generally known in the art, for instance, by electrophoresis (e.g., SDS-PAGE), filtration, chromatography, centrifugation, and the like. A substantially purified recombinant antigen can be at least about 60% purified, 65% purified, 70% purified, 75% purified, 80% purified, 85% purified, 90% purified or 95% or greater purified.

The invention further provides a polynucleotide encoding the recombinant antigens of the invention. Such recombinant antigens may be under the control of an inducible promoter as described, such as a *Salmonella* ssaG promoter, for example. The polynucleotide may be designed for integration at, or integrated at, an aroC and/or ssaV gene deletion site of a

*Salmonella* host cell. In some embodiments, the polynucleotide of the invention is a suicide vector for constructing a microorganism of the invention, as exemplified in FIGS. 2 and 3. The invention includes an isolated and/or purified polynucleotide. By "isolated," it is meant that the polynucleotide is substantially free of other nucleic acids, e.g., at least about 20% pure, preferably at least about 40% pure, more preferably about 60% pure, even more preferably about 80% pure, most preferably about 90% pure, and even most preferably about 95% pure, as determined by agarose gel electrophoresis. A polynucleotide can be isolated or purified by methods generally known in the art.

The invention includes antisera and antibodies to the recombinant antigens, attenuated microorganisms and compositions of the invention. Antisera and antibodies can be raised by methods known in the art. In one embodiment, the antibodies are isolated. In another embodiment, the antibodies are substantially purified using methods known in the art.

The microorganism may be formulated as a composition for delivery to a subject, such as for oral delivery to a human patient. In addition, the invention also includes the formulation of the recombinant antigen as a composition for delivery to a subject, such as oral delivery to a human patient. In one embodiment, the recombinant antigen may be In one embodiment of the invention, the vaccine comprises an attenuated *Salmonella* capable of expressing one or more *C. trachomatis, C. pneumoniae* or *C. muridarum* immunogenic peptides in a subject. In another embodiment, attenuated *Salmonella* is capable of expressing one or more immunogenic peptides from a second pathogenic organism. For instance, the *Salmonella* vaccine vector of the invention can be engineered to additionally express an immunogenic peptide from a second, third or fourth pathogen. In one embodiment, the second, third and/or fourth pathogen is a pathogen that is associated with a sexually transmitted disease such as syphilis, gonorrhea, human papilloma virus or herpes virus. In another embodiment of the invention, the second, third or fourth pathogen is a pathogen that is associated with diseases and conditions of the eyes. In another embodiment of the invention, the second, third or fourth pathogen is associated with a cardiac, vascular or lung disease or condition.

The composition may comprise the microorganism as described, and a pharmaceutically acceptable carrier, for instance, a pharmaceutically acceptable vehicle, excipient and/or diluent. The pharmaceutically acceptable carrier can be any solvent, solid or encapsulating material in which the vaccine can be suspended or dissolved. The pharmaceutically acceptable carrier is non-toxic to the inoculated individual and compatible with the live, attenuated microorganism.

Suitable pharmaceutical carriers are known in the art, and include, but are not limited to, liquid carriers such as saline and other non-toxic salts at or near physiological concentrations. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. Examples of suitable pharmaceutical vehicles, excipients and diluents are described in "Remington's Pharmaceutical Sciences" by E. W. Martin, which is hereby incorporated by reference in its entirety.

In one embodiment of the invention, the composition comprises one or more of the following carriers: disodium hydrogen phosphate, soya peptone, potassium dihydrogen phosphate, ammonium chloride, sodium chloride, magnesium sulphate, calcium chloride, sucrose, sterile saline and sterile water. In one embodiment of the invention, the composition comprises an attenuated *Salmonella enterica* serovar (e.g., Typhi or Typhimurium or Enteritidis) with deleted or inactivated SPI2 (e.g., ssaV) and aroC genes and one or more gene expression cassettes comprising a nucleic acid encoding a *C. trachomatis C. pneumoniae* and/or *C. muridarum* immunogenic peptide (e.g., PmpG full length protein, PmpG mature protein, CT110, CT84, CT40 and fragments and variants thereof) under the control of an in vivo inducible promoter (e.g., ssaG promoter) and a carrier comprising disodium hydrogen phosphate, soya peptone, potassium dihydrogen phosphate, ammonium chloride, sodium chloride, magnesium sulphate, calcium chloride, sucrose and sterile water.

In certain embodiments, the compositions further comprise at least one adjuvant or other substance useful for enhancing an immune response. For instance, the invention includes a composition comprising a live, attenuated *Salmonella* bacterium of the invention with a CpG oligodeoxynucleotide adjuvant. Adjuvants with a CpG motif are described, for instance, in US Patent Application 20060019239, which is herein incorporated by reference in its entirety.

Other adjuvants that can be used in a vaccine composition with the attenuated microorganism of the invention, include, but are not limited to, aluminium salts such as aluminium hydroxide, aluminum oxide and aluminium phosphate, oil-based adjuvants such as Freund's Complete Adjuvant and Freund's Incomplete Adjuvant, mycolate-based adjuvants (e.g., trehalose dimycolate), bacterial lipopolysaccharide (LPS), peptidoglycans (e.g., mureins, mucopeptides, or glycoproteins such as N-Opaca, muramyl dipeptide [MDP], or MDP analogs), proteoglycans (e.g., extracted from *Klebsiella pneumoniae*), streptococcal preparations (e.g., OK432), muramyldipeptides, Immune Stimulating Complexes (the "Iscoms" as disclosed in EP 109 942, EP 180 564 and EP 231 039), saponins, DEAE-dextran, neutral oils (such as miglyol), vegetable oils (such as arachis oil), liposomes, polyols, the Ribi adjuvant system (see, for instance, GB-A-2 189 141), vitamin E, Carbopol, interferons (e.g., IFN-alpha, IFN-gamma, or IFN-beta) or interleukins, particularly those that stimulate cell mediated immunity (e.g., IL-2, IL-3, IL-4, IL-5, IL-6, IL-7, IL-8, IL-9, IL-10, IL-11, IL-12, IL-13, IL-14, IL-15, IL-16 and IL-17).

In certain embodiments, the compositions may comprise a carrier useful for protecting the microorganism from the stomach acid or other chemicals, such as chlorine from tap water, that may be present at the time of administration. For example, the microorganism may be administered as a suspension in a solution containing sodium bicarbonate and ascorbic acid (plus aspartame as sweetener).

Suitable formulations for oral administration include hard or soft gelatin capsules, pills, tablets, including coated tablets, elixirs, suspensions, syrups or inhalations and controlled release forms thereof. Gelatin capsules can serve as carriers for lypholized vaccines.

The compositions of the present invention can be administered via parenteral, subcutaneous, intravenous, intramuscular, intraperitoneal, transdermal, mucosal and buccal routes. Alternatively, or concurrently, administration may be noninvasive by either the oral, inhalation, nasal, or pulmonary route. In one embodiment, the compositions are administered orally. In another embodiment, the compositions of the invention are administered to the eye. In another embodiment, the compositions of the invention are administered vaginally.

Suspensions of the active compounds as appropriate oily injection suspensions may be administered. Suitable lipophilic solvents or vehicles include fatty oils, for example, sesame oil, or synthetic fatty acid esters, for example, ethyl oleate or triglycerides. Aqueous injection suspensions may contain substances which increase the viscosity of the suspension include, for example, sodium carboxymethyl cellulose, sorbitol and dextran. Optionally, the suspension may also contain stabilizers. Liposomes can also be used to encapsulate the agent for delivery into the cell.

In certain embodiments, the vaccine dosage is $1.0\times10^5$ to $1.0\times10^{15}$ CFU/ml or cells/ml. For instance, the invention includes a vaccine with about $1.0\times10^5$, $1.5\times10^5$, $1.0\times10^6$, $1.5\times10^6$, $1.0\times10^7$, $1.5\times10^7$, $1.0\times10^8$, $1.5\times10^8$, $1.0\times10^9$, $1.5\times10^9$, $1.0\times10^{10}$, $1.5\times10^{10}$, $1.0\times10^{11}$, $1.5\times10^{11}$, $1.0\times10^{12}$, $1.5\times10^{12}$, $1.0\times10^{13}$, $1.5\times10^{13}$, $1.0\times10^{14}$, $1.5\times10^{14}$ or about $1.0\times10^{15}$ CFU/ml or cells/ml. In certain embodiments, the dosage administered will be dependent upon the age, health, and weight of the recipient, kind of concurrent treatment, if any, frequency of treatment, and the nature of the effect desired.

In certain embodiments, the compositions of this invention may be co-administered along with other compounds typically prescribed for the prevention or treatment of a *C. trachomatis* or *C. pneumoniae* infection or related condition according to generally accepted medical practice.

Recent studies have indicated that a prime-boost protocol is often a suitable method of administering vaccines. In a prime-boost protocol, one or more compositions of the present invention can be utilized in a "prime boost" regimen. An example of a "prime boost" regimen may be found in Yang, Z. et al. *J. Virol.* 77:799-803 (2002), which is incorporated herein by reference in its entirety. In a non-limiting example, one or more vaccine compositions of the present invention are delivered to an animal, thereby priming the immune response of the animal to a *Chlamydia* polypeptide of the invention, and then a second immunogenic composition is utilized as a boost vaccination. One or more compositions of the present invention are used to prime immunity, and then a second immunogenic composition, e.g., an attenuated bacteria vectored *Chlamydia* vaccine or vaccines or one or more purified subunits of the immunogenic *Chlamydia* peptides or fragments, variants or derivatives thereof is used to boost the anti-*Chlamydia* immune response.

In another embodiment, the priming composition may be administered simultaneously with the boosting composition, but in separate formulations where the priming component and the boosting component are separated.

In one aspect, the invention provides a method for vaccinating a subject against *C. trachomatis* by administering an attenuated *Salmonella* of the invention, or composition comprising the same, to a patient. For example, the microorganism may be orally administered to a patient, such as a patient at risk of acquiring a *C. trachomatis* infection, or a patient having a *C. trachomatis* infection, including a patient having a recurrent infection. Accordingly, the present invention includes methods of preventing and/or treating a *C. trachomatis* infection or related condition comprising administering a composition comprising an attenuated *Salmonella* of the invention. For instance, the invention includes methods of preventing and/or treating a *C. trachomatis* infection or related condition comprising administering a composition comprising an attenuated *Salmonella* capable of expressing a PmpG peptide (e.g., full length protein, mature protein, CT110, CT84, CT40 and fragments and variants thereof) to a subject.

The method of the invention induces an effective immune response in the patient, which may include a cell mediated immune response and/or a mucosal IgA immune response against a *C. trachomatis* peptide (e.g., PmpG full length protein, PmpG mature protein, CT110, CT84, CT40 and fragments and variants thereof). In certain embodiments, the method of the invention may reduce the incidence of (or probability of) recurrent *C. trachomatis* infection. In other embodiments, the vaccine or composition of the invention is administered to a patient post-infection, thereby ameliorating the symptoms and/or course of the illness, as well as preventing recurrence. Symptoms of *C. trachomatis* infection and/or *C. trachomatis*-related conditions that can be prevented, reduced or ameliorated by administering the composition of the invention include, for instance, urethritis, prostatis, proctitis, epididymitis, cervicitis, salpingitis, endometritis, pelvic inflammatory disease, tubal factor infertility, chronic pelvic pain, cervical dysplasia, ectopic pregnancy, lymphogranuloma venereum (LGV), newborn eye infection, newborn lung infection, trachoma and reactive arthritis.

In one embodiment of the invention, administration of an attenuated *Salmonella* of the invention capable of expressing a *C. trachomatis* peptide (e.g., PmpG full length protein, PmpG mature protein, CT110, CT84, CT40 and fragments and variants thereof) reduces the risk of HIV infection.

In another aspect, the invention provides a method for vaccinating a subject against *C. pneumoniae* by administering an attenuated *Salmonella* of the invention, or composition comprising the same, to a patient. For example, the microorganism may be orally administered to a patient, such as a patient at risk of acquiring a *C. pneumoniae* infection, or a patient having a *C. pneumoniae* infection, including a patient having a recurrent infection. Accordingly, the present invention includes methods of preventing and treating a *C. pneumoniae* infection or related condition comprising administering a composition comprising an attenuated microorganism of the invention.

The method of the invention induces an effective immune response in the patient, which may include a cell mediated immune response and/or a mucosal IgA immune response against a *C. pneumoniae* peptide (e.g., PmpG, PmpE, Pmpl, PmpH, PmpD, MOMP, OmcB, OmpH and HtrA full length proteins, mature proteins, fragments and variants thereof). In certain embodiments, the method of the invention may reduce the incidence of (or probability of) recurrent *C. pneumoniae* infection. In other embodiments, the vaccine or composition of the invention is administered to a patient post-infection, thereby ameliorating the symptoms and/or course of the illness, as well as preventing recurrence. Symptoms of *C. pneumoniae* infection and/or *C. pneumoniae*-related conditions that can be prevented, reduced or ameliorated by administering the composition of the invention include, for instance, pneumonia, acute respiratory disease, atherosclerosis, coronary artery disease, myocardial infarction, carotid artery disease, cerebrovascular disease, coronary heart disease, carotid artery stenosis, aortic aneurysm, claudication, stroke, chronic obstructive pulmonary disease, asthma, reactive airway disease, Reiter's syndrome and sarcoidosis.

In another aspect, the invention provides a method for vaccinating a murine subject against *C. muridarum* by administering an attenuated Salmonella of the invention, or composition comprising the same, to a subject. For example, the microorganism may be orally administered to a subject. Accordingly, the present invention includes methods of preventing and treating a *C. muridarum* infection or related condition comprising administering a composition comprising an attenuated microorganism of the invention.

The method of the invention induces an effective immune response in the murine subject, which may include a cell mediated immune response and/or a mucosal IgA immune response against a *C. muridarum* peptide (e.g., PmpG, PmpE, Pmpl, PmpH, PmpD, MOMP, OmcB, OmpH and HtrA full length proteins, mature proteins, fragments and variants thereof). In certain embodiments, the method of the invention may reduce the incidence of (or probability of) recurrent *C. muridarum* infection. In other embodiments, the vaccine or composition of the invention is administered to a subject post-infection, thereby ameliorating the symptoms and/or course of the illness, as well as preventing recurrence.

The vaccine may be administered to the patient once, or may be administered a plurality of times, such as one, two, three, four or five times.

The practice of the present invention will employ, unless otherwise indicated, conventional techniques of cell biology, cell culture, molecular biology, transgenic biology, microbiology, recombinant DNA, and immunology, which are within the skill of the art. Such techniques are explained fully in the literature. See, for example, Molecular Cloning A Laboratory Manual, 2nd Ed., Sambrook et al., ed., Cold Spring Harbor Laboratory Press: (1989); Molecular Cloning: A Laboratory Manual, Sambrook et al., ed., Cold Springs Harbor Laboratory, New York (1992), DNA Cloning, D. N. Glover ed., Volumes I and II (1985); Oligonucleotide Synthesis, M. J. Gait ed., (1984); Mullis et al. U.S. Pat. No: 4,683,195; Nucleic Acid Hybridization, B. D. Hames & S. J. Higgins eds. (1984); Transcription And Translation, B. D. Hames & S. J. Higgins eds. (1984); Culture Of Animal Cells, R. I. Freshney, Alan R. Liss, Inc., (1987); Immobilized Cells And Enzymes, IRL Press, (1986); B. Perbal, A Practical Guide To Molecular Cloning (1984); the treatise, Methods In Enzymology, Academic Press, Inc., N.Y.; Gene Transfer Vectors For Mammalian Cells, J. H. Miller and M. P. Calos eds., Cold Spring Harbor Laboratory (1987); Methods In Enzymology, Vols. 154 and 155 (Wu et al. eds.); Immunochemical Methods In Cell And Molecular Biology, Mayer and Walker, eds., Academic Press, London (1987); Handbook Of Experimental Immunology, Volumes I-IV, D. M. Weir and C. C. Blackwell, eds., (1986); Manipulating the Mouse Embryo, Cold Spring Harbor Laboratory Press, Cold Spring Harbor, N.Y., (1986); and in Ausubel et al., Current Protocols in Molecular Biology, John Wiley and Sons, Baltimore, Maryland (1989).

General principles of antibody engineering are set forth in Antibody Engineering, 2nd edition, C. A. K. Borrebaeck, Ed., Oxford Univ. Press (1995). General principles of protein engineering are set forth in Protein Engineering, A Practical Approach, Rickwood, D., et al., Eds., IRL Press at Oxford Univ. Press, Oxford, Eng. (1995). General principles of antibodies are set forth in: Nisonoff, A., Molecular Immunology, 2nd ed., Sinauer Associates, Sunderland, Mass. (1984); and Steward, M. W., Antibodies, Their Structure and Function, Chapman and Hall, New York, N.Y. (1984). Additionally, standard methods in immunology known in the art and not specifically described are generally followed as in Current Protocols in Immunology, John Wiley & Sons, New York; Stites et al. (eds), Basic and Clinical-Immunology (8th ed.), Appleton & Lange, Norwalk, Conn. (1994) and Mishell and Shiigi (eds), Selected Methods in Cellular Immunology, W. H. Freeman and Co., New York (1980).

Standard reference works setting forth general principles of immunology include Current Protocols in Immunology, John Wiley & Sons, New York; Klein, J., Immunology: The Science of Self-Nonself Discrimination, John Wiley & Sons, New York (1982); Kennett, R., et al., eds., Monoclonal Antibodies, Hybridoma: A New Dimension in Biological Analyses, Plenum Press, New York (1980); Campbell, A., "Monoclonal Antibody Technology" in Burden, R., et al., eds., Laboratory Techniques in Biochemistry and Molecular Biology, Vol. 13, Elsevere, Amsterdam (1984), Kuby Immunology $4^{th}$ ed. Ed. Richard A. Goldsby, Thomas J. Kindt and Barbara A. Osborne, H. Freemand & Co. (2000); Roitt, I., Brostoff, J. and Male D., Immunology, $6^{th}$ ed. London: Mosby (2001); Abbas A., Abul, A. and Lichtman, A., Cellular and Molecular Immunology, Ed. 5, Elsevier Health Sciences Division (2005); Kontermann and Dubel, Antibody Engineering, Springer Verlan (2001); Sambrook and Russell, Molecular Cloning: A Laboratory Manual, Cold Spring Harbor Press (2001); Lewin, Genes VIII, Prentice Hall (2003); Harlow and Lane, Antibodies: A Laboratory Manual, Cold Spring Harbor Press (1988); Dieffenbach and Dveksler, PCR Primer, Cold Spring Harbor Press (2003).

All publications, patents and patent applications herein are incorporated by reference to the same extent as if each individual publication or patent application was specifically and individually indicated to be incorporated by reference.

EXAMPLES

Example 1

Construction of a *Salmonella* ssaV and aroC Double Mutant

A Salmonella ssaV and aroC double mutant was constructed as provided in Hindle et al., *Infect. Immun.*,70(7): 3457-3467 (2002). Briefly, wild type *S. typhi* Ty2 was originally isolated from an individual with typhoid fever in 1916 and has been used for the derivation of all licensed typhoid vaccines. The strain was obtained from the National Collection of Type Cultures (NCTC) (a part of the Public Health Laboratory Service (PHLS) at Colindale, UK). The NCTC prepared the freeze-dried culture in 1982 using nutrient broth as the culture medium. Emergent Product Development UK Limited (then Microscience Ltd) received the strain from NCTC on 3 Jul. 1998 with a certificate of analysis. A vial was re-suspended in liquid broth and streaked onto an agar plate. Inoculum was taken from the plate and cultured in liquid medium overnight. The resulting culture was used for the first step in the construction of the parent strain *S. typhi* (Ty2 aroC$^-$ ssaV$^-$) ZH9.

The wild type aroC gene, derived from the mutant strain *S. typhi* (Ty2 aroA$^-$ purA$^-$) MD9, is contained on plasmid pTAC2. A defined deletion of 600 by was created within the aroC gene in pTAC2 by amplifying DNA fragments, flanking the aroC gene, from the pTAC2 by PCR and cloning them into the vector pUC18 to give plasmid pMIAC23. The 4.8 kb fragment containing the mutated aroC gene was isolated from pMIAC23 and cloned into the suicide vector pCVD442 to give plasmid pYCVC21. The mutated aroC gene was then introduced into wild-type *S. typhi* Ty2 by transformation with the suicide construct pYCVC21. The plasmid was able to integrate into the *S. typhi* genome following recombination between homologous regions on the plasmid and the genome to give ampicillin resistant transformants. The transformants, termed merodiploids, contained in the genome a copy of both the original wild type aroC gene and the mutated aroC gene separated by vector DNA sequences. A merodiploid was grown in the absence of ampicillin to allow for a second recombination event to occur which would result in loss of the pCVD442 vector DNA sequences and one copy of the aroC gene, either the wild-type aroC or the mutated aroC. Plating onto sucrose-containing media allowed for the selection of derivatives of the merodiploids that had undergone the second recombination event and lost the vector DNA sequences, as pCVD442 (and therefore pYCVC21) carries the sacB gene that when expressed results in a sucrose sensitive phenotype. Loss of the vector sequences was confirmed by testing the ampicillin sensitive phenotype, strains that had lost the vector DNA sequences were also ampicillin sensitive as the ampicillin resistance gene is carried on pCVD442. The ampicillin sensitive strains were then tested to determine whether they had retained a copy of the wild-type or mutated aroC gene. Ampicillin sensitive colonies that were unable to grow in the absence of the supplement of aromatic compounds were identified as those that had undergone recombination to lose the vector DNA sequences plus the copy of the wild-type aroC gene. The aroC genotype was confirmed by colony PCR analysis using a primer pair that gives a product of 995 by for the wild type aroC and 401 by for the mutated aroC gene. Sequence analysis of the resulting PCR products confirmed the presence of the required deletion in 5 individual isolates DTY6, DTY7, DTY8, DTY9 and DTY10. These strains are stored in Microbank vials at −80° C. for long-term storage. Strain DTY8 was selected for further use and was denoted *S. typhi* (Ty2 aroC⁻) DTY8.

The construct pTYSV21 carries the wild-type ssaV gene derived from the mutant strain *S. typhi* (aroA⁻ purA⁻) MD9. A defined deletion of 1.909 kb was created within the cloned ssaV gene on plasmid pTYSV21 using inverse PCR to give the plasmid pYDSV1. The 5.5 kb DNA fragment containing the mutated ssaV gene plus flanking regions was isolated from pYDSV1 and cloned into the suicide plasmid pCVD422 to give plasmid pYDSV214. The mutated ssaV gene was then introduced into *S. typhi* (Ty2 aroC⁻) DTY8 by transformation with the suicide construct pYDSV214. A number of ampicillin resistant merodiploids were obtained and one, termed MD120, was selected for further manipulations. MD120 was grown in the absence of ampicillin to allow for loss of the pCVD442 DNA sequences and one copy of the ssaV gene, either the wild-type copy or the mutated copy, and then plated onto sucrose containing plates. Single colonies from these plates were assessed for sensitivity to ampicillin and derivatives of MD120 that had undergone a second recombination event were identified as sucrose resistant and ampicillin resistant. These strains were subjected to colony PCR analysis to identify those that had retained only the deleted ssaV gene, using primers that gave a product of 2486 by for the wild type ssaV and 592 by for the deleted ssaV gene. The resulting PCR products were sequenced and the presence of the desired deletion was confirmed in 5 individual isolates, ZH2, ZH4, ZH6, ZH7 and ZH9. Serological analysis was performed on each of the strains. Strain ZH9 tested positive for the O9 and Vi antigens and was chosen for further use. This strain was denoted *S. typhi* (Ty2 aroC⁻ ssaV⁻)ZH9.

Example 2

Introduction of the ssaG-*Chlamydia* Antigen Promoter-Gene Fusion into the aroC Deletion of *S. typhi* (Ty2 aroC⁻ ssaV⁻) ZH9

A ssaG-*Chlamydia* antigen gene expression cassette was then inserted in the aroC deletion site. Although constructs were made comprising *E. coli* codon optimized polynucleotides encoding CT110 and CT84, the cloning strategy can be used with other polynucleotides disclosed herein that encode immunogenic *Chlamydia* peptides as well as the *Chlamydia* polynucleotides disclosed in PCT/US08/006656, filed May 23, 2008; PCT/US08/007490, filed Jun. 16, 2008; U.S. Pat. No. 7,731,980, filed Aug. 1, 2003; U.S. Pat. No. 7,803,388, filed Jul. 20, 2007; U.S. Pat. No. 7,851,609, filed July 20, 2007; U.S. Pat. No. 7,537,772, filed Oct. 2, 2000; U.S. Pat. No. 7,459,524, filed Oct. 2, 1997; U.S. Pat. No. 7,534,445, filed Jan. 27, 2004; PCT/US98/20737 (WO 99/17741), filed Oct. 1, 1998; U.S. Pat. No. 6,887,843, filed Apr. 3, 2000; U.S. Pat. No. 6,642,023, filed Jul. 6, 2000; U.S. Pat. No. 7,419,807, filed Nov. 4, 2004; and U.S. Pat. No. 7,655,246, filed Sep. 1, 2004, each of which is herein incorporated by reference in its entirety.

*E. coli* codon optimized polynucleotides encoding CT84 and CT110 were cloned into a pMBS intermediate plasmid which contains the ssaG promoter (see for instance, FIG. 1 which was used for cloning CT84). The antigen gene was cloned downstream of the promoter using NdeI and AvrII restriction enzyme sites present in the vector.

In the case of CT110 and CT84, the gene had previously been cloned into a protein expression vector. The restriction enzyme sites in the vector needed to be modified to allow the gene to be cloned into pMBS. The available restriction sites at the 5' end of the gene required modifying to insert an XbaI and AvrII restriction enzyme site. This was added by creating a piece of linker DNA from two custom synthesized oligonucleotides. The plasmid backbone was cut using a unique cutting enzyme (BamHI for CT110 and SalI for CT84) and the custom linker (carrying compatible cohesive ends and the sequence for the additional enzyme sites) was inserted, as shown below:

Addition of a linker (using CT110 as an example):

```
Initial 5' layout
CT110                  BamHI
Stop codons         ~~~~~~~
    TAATAAGGA TCC  (SEQ ID NO.: 4)
    ATTATTCCT AGG Linker
Final site layout-CT110
CT110                     XbaI    AvrII
Stop codons             ~~~~~~   ~~~~~~
    TAATAAGGA TCTCTAGACT AGCCTAGGGG ATCC  (SEQ ID
    NO.: 5)
    ATTATTCCT AGAGATCTGA TCGGATCCCC TAGG
Inserted linker (bold face)
BamHI site (italics)

Final site layout-CT84
                SalI
              ~~~~~~
        XbaI            AvrII
    ~~~~~~~~            ~~~~~~~
TTCA CCTAATCTAG AGTCGACTAG CCTAGGTCGA C  (SEQ ID
NO.: 6)
AAGT GGATTAGATC TCAGCTGATC GGATCCAGCT G
Inserted linker (bold face)
SalI site (italics)
```

Following modification of the antigen source DNA, the antigens were able to be cut from the protein expression vector using NdeI and AvrII. The resulting fragment was then purified and cloned downstream of the ssaG promoter in pMBS resulting in the constructs shown in FIGS. 19 and 20.

Once the promoter-antigen fusion was made the final step was to move the fusions into the suicide vector for insertion into the *S. typhi* chromosome. The promoter-antigen fusion was cut from the pMBS backbone using XhoI and AvrII restriction enzymes. This fragment was then cloned directly into the replicated aroC deletion site present in the pCVD-based suicide vector. The suicide vector used for cloning the CT84 construct is provided in FIG. 2. The suicide vector used for cloning the CT110 construct is provided in FIG. 3.

The mutated aroC gene containing the promoter-antigen fusion was then introduced into wild-type *S. typhi* Ty2 by transformation with the suicide constructs. The plasmid was able to integrate into the *S. typhi* genome following recombination between homologous regions on the plasmid and the genome to give ampicillin resistant transformants. The transformants, termed merodiploids, contained in the genome a copy of both the original deleted aroC gene and the promoter-antigen construct flanked by the aroC gene separated by vector DNA sequences. A merodiploid was grown in the absence of ampicillin to allow for a second recombination event to occur which would result in loss of the pCVD442 vector DNA sequences and one copy of the aroC gene, either the deleted parental aroC or the deleted aroC containing the promoter-antigen. Plating onto sucrose-containing media allowed for the selection of derivatives of the merodiploids that had undergone the second recombination event and lost the vector DNA sequences, as pCVD442 (and therefore any pCVD derivative) carries the sacB gene that when expressed results in a sucrose sensitive phenotype. Loss of the vector sequences was confirmed by testing the ampicillin sensitive phenotype, strains that had lost the vector DNA sequences were also ampicillin sensitive as the ampicillin resistance gene is carried on pCVD442. The ampicillin sensitive strains were then tested using PCR to determine whether they had retained a copy of the parent mutated aroC gene or the mutated aroC gene carrying our promoter-antigen construct.

Although the present invention has been described in detail with reference to examples above, it is understood that various modifications can be made without departing from the spirit of the invention. Accordingly, the invention is limited only by the following claims. All cited patents, patent applications and publications referred to in this application are herein incorporated by reference in their entirety.

Example 3

Mouse Genital Infectivity Model

The modified *Salmonella* of the invention that express one or more *Chlamydia trachomatis* antigens (e.g., CT84 or CT110) can be evaluated as immunogens and vaccinogens using the generally accepted mouse *C. trachomatis* genital infectivity model. For instance, the model can be used to evaluate the constructs as immunogens and for the ability to protect BALB/c mice against challenge with various *C. trachomatis* serovars (e.g., $L_2$, B, E). The modified *Salmonella* can be administered to groups of *Chlamydia*-free animals by three different immunization routes: oral, nasal or subcutaneous. For each route, the immunogenicity of the *Salmonella* can be determined, either alone or in combination with an appropriate adjuvant. After the first immunization, animals are periodically sacrified and serum IgG and mucosal (cervix/vagina and intestinal sIgA levels determined using known methodologies.

Six to eight week old (sexually mature), specific-pathogen free, female mice can be administered the modified *Salmonella* as described below. For oral immunization, animals would be withdrawn from rations 4 hours before dosing. The modified *Salmonella* is administered intragastrically to unanesthetized mice. Intragastrically vaccinated mice are returned to solid rations approximately 3-4 hours after immunization. For nasal immunization, animals are sedated lightly, placed on their backs and administered modified *Salmonella*. For subcutaneous administration, modified *Salmonella* are administered subcutaneously to unanesthetized mice.

Beginning immediately after the first immunization and continuing at 7 day intervals thereafter, animals from each vaccination group can be anesthetized, the abdominal cavity opened, and the animal exasanguinated by cardiac punction. Immediately thereafter, the lower reproductive tract (cervix and vagina) and small intestine can be surgically removed. Mucosal secretions can be collected from the intestine and cervix/vagina by gently scrapping prewashed and dissected organs with a sterile scalpel blade. Sera and mucosal secretions can be stored in PBS at −70° C. until the end of the experiment and analyzed as a group.

Chlamydial IgG and secretory IgA levels in serum and mucosal secretions can be determined by ELISA. Titers to both whole EB lysates and Chlamydial protein can be determined. Briefly, intact purified *C. trachomatis* $L_2$ EBs or Chlamydial protein can be diluted in 0.05 M sodium carbonate buffer and used to coat Immulon-3 (DynaTech) 96 well microtiter plates. After blocking with 1% BSA/PBS/0.05% Tween-20 and extensive washing (3×; PBS/0/05% Tween-20) serum or mucosal secretion samples, serially diluted in PBS, can be added and the plate incubated at 37° C. for 1 hour. All samples can be tested in duplicate. Unbound material can be removed by washing. Affinity-purified HRP-conjugated to either goat anti-mouse IgA (alpha chain) or goat anti-mouse IgG (Vector Labs), diluted 1/5,000 in PBS, can then be added and the plate reincubated at 37° C. for 1 hour. Secondary antibody is removed, the plate washed again and substrate (TMB) added.

The color change can be measured in a microplate spectrophotometer at 450 nm after a 30 minute incubation at room temperature and quenching with $H_2SO_4$. Readings >25D of 10 the mean negative control value (pooled prebleed sera, pooled mucosal secretions from unvaccinated animals) would be defined as positive. Reaction specificity can be monitored by preabsorbing the primary antibody with antigen (antibody-blocking) and the secondary antibody with purified mouse IgG/IgA (conjugate blocking). Antibody titers for each data point (e.g., 5 animals/point) can be presented as the geometric mean ±S.D. of the last positive dilution.

Two weeks after the last (e.g., third) immunization, animals can be challenged intravaginally, while under mild anesthesia, with a single dose of 0.1 ml endotoxin-free PBS containing 108IFU of purified, pretitered *C. trachomatis* EBs. Progesterone can be administered (about 2.0 mg per dose, i.m.) one week prior to and the time of challenge to block estrous and ensure infection of mouse cervical epithelial cells with human *C. trachomatis* strains. The presence and persistence of *C. trachomatis* in the lower reproductive tract of vaccinated animals can be assessed using both a commercial *Chlamydia*-specific ELISA (Chlamydiazyme, Abbott Diagnostics) and by in vitro cultivation.

At 7, 14 and 21 days post-challenge, animals can be sacrificed as above and their lower reproductive tracts (cervix/vagina) and small intestine surgically removed. Tissue homogenates can be prepared by macerating and homogenizing identical amounts of tissue in 1.0 ml SPG buffer. Clarified samples can be serially diluted and tested for *Chlamydia*-specific antigen by commercial ELISA and used to infect McCoy cells grown to about 90% confluency in 24-well tissue culture plates. Each dilution can be assayed in duplicate. After a 24 hour cultivation period, infected monolayers can be fixed with methanol and inclusion bodies visualized by indirect fluorescence antibody staining using an anti-*Chlamydia* LPS antibody. Fluorescent inclusions can be counted at 40× magnification and the resulting titer expressed as the mean number of inclusions per 20 fields. *Chlamydia* IgG and sIgA levels in the serum and intestine can also be determined for these animals as detailed above. Protection is defined as the ability to eliminate or reduce the level of *C. trachomatis* in the lower genital tract.

To determine whether vaccination with modified *Salmonella* protect mice against heterotypic challenge, equivalent groups of mice can be immunized with the modified *Salmo-* nella expressing a $L_2$ serotype antigen (e.g., $L_2$ CT84 or L2 CT110) and subsequently challenged with either *C. trachomatis* serovar B or E.

Example 4

Mouse Model of Salpingitis and Fertility

The Tuffrey murine infertility model can be employed to evaluate the efficacy of the modified *Salmonella* of the invention to protect animals against *Chlamydia* trachomatis-induced salpingitis and infertility. Groups of female C3H HeOuJ mice (about 6 weeks of age) can be employed for this evaluation. The test group of animals can be immunized at, for instance, weeks 0, 2, and 3 by intranasal administration of modified *Salmonella*. Prior to immunization mice can be sedated using an anesthesia cocktail consisting of, for instance, 16% Ketaject and 16% Xylaject in 68% pyrogen-free PBS (100 μl i.p./animal). Sedated animals can be placed on their backs and using a standard laboratory pipette administered the vaccine formulation; about 10 μl of the vaccine solution per nostril with a 5-10 minute wait period between applications.

Briefly at week 4, all animals can be administered a single i.p. dose of progesterone (2.5 mg in pyrogen-free PBS, Depo-Provera, Upjohn) to stabilize the uterine epithelium. At week 5, animals can be immunized and animals in the negative control group can be infected by bilateral intrauterine inoculation with about 5 x $10^5$ inclusion forming units (I FU) of *C. trachomatis* in 100 μl of sucrose phosphate glutamate buffer (SPG). To mimic the manipulations to the reproductive tract experienced by the other two groups, animals in the positive control can be bilaterally inoculated with 100 μl of a McCoy cell extract that contains no *C. trachomatis*. At week 7, animals from each group can be sacrificed by $CO_2$ asphyxiation and the complete genital tract (both upper and lower reproductive tracts) removed for histopathological analysis. At week 9, the remaining females from each group can be caged with 8-10 week old male C3H mice for a 2 month breeding period to assess fertility (1 male for every 2 females per cage with weekly rotation of the males within each group, animals from different experimental groups would not be mixed). Palpation and periodic weighing can be used to determine when animals in each pair became pregnant. The parameters used to estimate group fertility can be: F, the number of mice which littered at least once during the mating period divided by the total number of mice in that study group; M, the number of newborn mice (born dead or alive) divided by the number of litters produced in that group during the mating period; and N, the number of newborn mice (born dead or alive) divided by the total number of mice in that group.

Genital tracts can be treated for >24 hrs in Bouin's fixative, progressively dehydrated in 50%, 70%, and 100% methanol, soaked in toluol, and either paraffin embedded or directly embedded in OCT compound (Tissue-TEK, Miles) and subsequently snap frozen in liquid nitrogen. Tissue sections (about 6 μm) can be stained with hematoxylin and eosin (after deparaffinization of the Bouin fixed samples). Inflammatory changes in the oviducts and ovaries can be graded as follows: 0, no apparent inflammatory reaction; 1, a few mononuclear cells infiltrating the periovarial space or the submucosa of the oviduct; 2, same as 1 but to a greater extent; 3, same as 2 but with a thickened oviductal submucosa and the presence of inflammatory cells in the oviductal lumen; 4, same as 3 but to a greater extent. Inflammation in the cervix/vagina can be scored based on the level of the intraepithelial infiltrate observed.

Blood samples can be collected periodically during the immunization and challenge phases by retroorbital bleeding and serum prepared by centrifugation. Vaginal secretions can be collected by repeated injection of 50 μl of sterile PBS into the vagina with a standard laboratory pipettor and immediately withdrawing the solution. Two-to-three injection/withdrawal cycles can be performed.

Quantitation of antibody (Ab) responses by ELISA can be performed as previously described. Microwell ELISA plates (Maxisorb, NUNC) for determining Ab levels can be coated overnight at 4° C. with about 0.5-1.0 μg of gel-purified antigen per well in 10 mM carbonate/bicarbonate buffer (pH 9.6), washed with PBS containing 0.1% Tween-20 (washing buffer) and blocked for about 1 hr at 37° C. with a PBS solution containing 3% BSA. For the determination of antigen-specific serum IgG levels, test sera can be serially diluted in washing buffer containing 0.5% BSA and aliquots (100 μl ) incubated in the antigen-coated wells for about 2 hr at 37° C. The plates can then be washed and incubated for about 1 hr at 37° C. with a horseradish peroxidase (HRP)-conjugated goat anti-mouse IgG second antibody (Sigma). A HRP-conjugated goat anti-mouse IgA secondary antibody can be used to detect the presence of Chlamydial antigen-specific IgA in vaginal secretions. After incubation with the appropriate secondary Ab, the plates can be washed and incubated for about 20-30 minutes at room temperature with TMB substrate (Sigma). Reactions can be stopped by the addition of 2M $H_2SO_4$ and the absorbance determined at 450 nm on a spectrophotometer (Molecular Devices SpectroMax microplate reader). Titers can be determined as the reciprocal of the sample dilution corresponding to an optical density of 1.0 at 450 nm.

For determination of Chlamydial antigen-specific cellular responses, groups of female C3H HeOuJ mice (Jackson Labs) can be sedated and immunized at weeks 0, 2 and 3 by intranasal administration with the vaccine as described above. At weeks 4 and 5 immediately prior to progesterone treatment and intrauterine challenge, respectively, animals (e.g., 3) from each group can be sacrificed by CO2 asphyxiation and spleens aseptically removed and single cell suspensions prepared using conventional methodologies. Spleen cells from immunized animals can be analyzed separately. For both the positive control group (sham immunized and sham infected) and the negative control group (sham immunized, infected) spleen cells can be pooled and tested for restimulation.

For the measurement of spleen cell proliferation, spleens can be ground (5 to 10 rounds) in 5 ml of RPMI 1640 Glutamax I supplemented with 10% fetal calf serum, 25 mM HEPES, 50 U/ml penicillin, 50 μg/ml streptomycin, 1 mm sodium pyruvate, nonessential amino acids, and 50 μM 2-mercaptoethanol (Gibco-BRL). Live cells can be counted by Trypan Blue staining and diluted in the same media to reach a density of 1.0-2.0×$10^6$ cells/ml (Falcon 2063 polypropylene tubes). Triplicate cultures can be set-up in round bottom 96-well culture plates (Nunclon, Nunc) using about 5×$10^5$ responder cells per well in 200 μl of media Cells were stimulated with either 1.0 μg/ml of antigen (antigen-specific proliferation) or with 4 μg/ml concanavalin A (Boerhinger Mannheim) as a positive stimulation control; unrestimulated cell cultures were used as a negative control of cellular activation. After 72-96 hours of incubation at 37° C. in 5% $CO^2$ cells can be pulsed labelled for about 18 hrs with 1.0 μCi $^3$H-thymidine (Amersham) per well. Pulsed cells can be harvested onto glass-fiber sheets using a Tomtec Cell Harvester (Mk III) and counted for beta-emission in a 3-channel Wallac 1450 Trilux Liquid Scintillation Counter. The stimulation index (SI) for a sample (individual or pooled) can be defined as the mean of the antigen or ConA-stimulated T-cell uptake of ³H-thymidine for triplicate wells divided by the mean of the unstimulated uptake for triplicate wells. SIs for both antigen-specific (rHMWP-specific) and ConA-specific proliferation can be determined.

Example 5

Mouse Pneumonitis Model

The modified *Salmonella* of the invention containing *C. muridarum* inserts (e.g., CT84 and CT110 analogs) can be analyzed using a mouse pneumonitis model. Briefly, the mouse model of female urogenital tract infection with *Chlamydia muridarum* (the mouse pneumonitis strain of *Chlamydia* trachomatis, MoPn) has been used for some time to study immunological protection related to chlamydial infections (Barron AL, et al., *J Infect Dis.* 1981; 143:63-66 and Rank RG, Stephens RS, editors. *Chlamydia: Intracellular Biology, Pathogenesis, and Immunity, American Society for Microbiology*. Washington, D.C.: 1999. p. 295). More recently, it has been used to study pathological immune responses during chlamydia infection. Hydrosalpinx formation, infertility and fibrotic oviduct occlusion are routine consequences of infection following a single intravaginal inoculation of *Chlamydia muridarum* in susceptible mouse strains (Swenson CE, et al., *J Infect Dis.* 1983; 148:1101-1107; Swenson CE and Schachter J., *Sex Trans Dis.* 1984;11:64-67; De La Maza LM et al., *Infect Immun.* 1994;62:2094-2097; Darville T et al., *Inject Immun.* 1997;65:3065-3073 and Shah AA et al., *Sex Trans Dis.* 2005;32:49-56). These sequelae also serve to make the mouse:MoPn infection model a legitimate model to study chlamydia-induced host response-mediated pathology.

Although the present invention has been described in detail with reference to examples above, it is understood that various modifications can be made without departing from the spirit of the invention. Accordingly, the invention is limited only by the following claims. All cited patents, patent applications and publications referred to in this application are herein incorporated by reference in their entirety.

---

```

The invention claimed is:

1. An attenuated *Salmonella* microorganism comprising i) an attenuating mutation in a *Salmonella* Pathogenicity Island 2 (SPI-2) gene; ii) an attenuating mutation in a second gene; and iii) one or more gene expression cassettes, each gene expression cassette comprising a heterologous nucleic acid under the control of an inducible promoter, wherein at least one of said heterologous nucleic acid encodes an immunogenic Chlamydial peptide and Wherein the Chlamydial peptide is secreted from the attenuated *Salmonella* microogranism via a secretion signal.

2. The attenuated *Salmonella* microorganism of claim 1, wherein said attenuated *Salmonella* microorganism induces an effective immune response when administered to a human patient.

3. The attenuated *Salmonella* microorganism of claim 1, wherein the second gene is a *Salmonella* gene involved in the biosynthesis of aromatic compounds.

4. The attenuated *Salmonella* microorganism of claim 3, wherein the gene involved in the biosynthesis of aromatic compounds is aroC.

5. The attenuated *Salmonella* microorganism of claim 1, wherein the SPI-2 gene is selected from the group consisting of a ssa, sse, ssc or ssr gene.

6. The attenuated *Salmonella* microorganism of claim 5, wherein said SPI-2 gene is an ssa gene.

7. The attenuated *Salmonella* microorganism of claim 6, wherein said ssa gene is selected from the group consisting of ssaV, ssaJ, ssaU, ssaK, ssaL, ssaM, ssaO, ssaP, ssaQ, ssaR, ssaS, ssaT, ssaU, ssaD, ssaE, ssaG, ssaI, ssaC (spiA) and ssaH.

8. The attenuated *Salmonella* microorganism of claim 7, wherein said ssa gene is ssaV.

9. The attenuated *Salmonella* microorganism of claim 7, wherein said ssa gene is ssaJ.

10. The attenuated *Salmonella* microorganism of claim 1, wherein the attenuating mutation in the SPI-2 gene is a deletion or inactivation of the SPI-2 gene, and wherein the attenuating mutation in the second gene is a deletion or inactivation of the second gene.

11. The attenuated *Salmonella* microorganism of claim 10, wherein the gene expression cassette is inserted at the SPI-2 gene deletion site and/or the second gene deletion site.

12. The attenuated *Salmonella* microorganism of claim 11, wherein the SPI-2 deletion site is an ssaV gene deletion site and the second gene deletion site is an aroC deletion site.

13. The attenuated *Salmonella* microorganism of claim 1, wherein said inducible promoter is a *Salmonella* -ssaG promoter.

14. The attunuated *Salmonella* microorganism of claim 1, wherein the immunogenic Chlamydial peptide is selected from the group consisting of PmpG, PmpI, PmpE, MOMP, PmpD, PmpH, OmcB, OmpH, and HtrA or an immunogenic fragment thereof.

15. The attenuated *Salmonella* microorganism of claim 14, wherein said immunogenic Chlamydial peptide is PmpG or an immunogenic fragment thereof.

16. The attenuated *Salmonella* microorganism of chum 15, wherein said PmpG or an immunogenic fragment thereof binds to an antibody to PmpG.

17. The attenuated *Salmonella* microorganism of claim 15, wherein said PmpG or immunogenic fragment thereof is CT84, CT110 or CT40.

18. The attenuated *Salmonella* microorganism of claim 1, wherein the Chlamydial peptide is a *C. trachomatis* peptide, *C. pneumoniae* peptide or a *C. muridarum* peptide.

19. The attenuated *Salmonella* microorganism of claim 1, wherein the gene expression cassette further comprises a nucleic acid encoding a linker peptide.

20. A composition for the treatment or prevention of a Chlamydial infection or related condition comprising the attenuated *Salmonella* microorganism of claim 1, and a pharmaceutically acceptable carrier and/or diluent.

21. The composition of claim 20 further comprising at least one adjuvant.

22. A method for vaccinating a subject against a Chlamydial infection, comprising: administering the composition of claim 20 to said subject.

23. A method for preventing or ameliorating a condition associated with a Chlamydial infection, comprising: administering the composition of claim 20 to said subject.

* * * * *

UNITED STATES PATENT AND TRADEMARK OFFICE
CERTIFICATE OF CORRECTION

| | | |
|---|---|---|
| PATENT NO. | : 8,703,153 B2 | Page 1 of 1 |
| APPLICATION NO. | : 12/999246 | |
| DATED | : April 22, 2014 | |
| INVENTOR(S) | : Telfer et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 170 days.

Signed and Sealed this
Thirtieth Day of September, 2014

Michelle K. Lee
*Deputy Director of the United States Patent and Trademark Office*

                        SEQUENCE LISTING

<160> NUMBER OF SEQ ID NOS: 32

<210> SEQ ID NO 1
<211> LENGTH: 50
<212> TYPE: PRT
<213> ORGANISM: Salmonella typhi

<400> SEQUENCE: 1

Met Ser Phe Ser Arg Arg Gln Phe Leu Gln Ala Ser Gly Ile Ala Leu
1               5                   10                  15

Cys Ala Gly Ala Ile Pro Leu Arg Ala Asn Ala Ala Gly Gln Gln Gln
            20                  25                  30

Pro Leu Pro Val Pro Pro Leu Leu Glu Ser Arg Arg Gly Gln Pro Leu
        35                  40                  45

Phe Met
    50

<210> SEQ ID NO 2
<211> LENGTH: 66
<212> TYPE: DNA
<213> ORGANISM: Escherichia coli

<400> SEQUENCE: 2
atgttaaaaa taaaatactt attaataggt ctttcactgt cagctatgag ttcatactca      60
ctagct                                                                 66

<210> SEQ ID NO 3
<211> LENGTH: 22
<212> TYPE: PRT
<213> ORGANISM: Escherichia coli

<400> SEQUENCE: 3

Met Leu Lys Ile Lys Tyr Leu Leu Ile Gly Leu Ser Leu Ser Ala Met
1               5                   10                  15

Ser Ser Tyr Ser Leu Ala
            20

<210> SEQ ID NO 4
<211> LENGTH: 12
<212> TYPE: DNA
```

```
<213> ORGANISM: Artificial Sequence
<220> FEATURE:
<223> OTHER INFORMATION: CT110 linker sequence

<400> SEQUENCE: 4
taataaggat cc                                                           12

<210> SEQ ID NO 5
<211> LENGTH: 33
<212> TYPE: DNA
<213> ORGANISM: Artificial Sequence
<220> FEATURE:
<223> OTHER INFORMATION: CT110 linker sequence

<400> SEQUENCE: 5
taataaggat ctctagacta gcctagggga tcc                                    33

<210> SEQ ID NO 6
<211> LENGTH: 35
<212> TYPE: DNA
<213> ORGANISM: Artificial Sequence
<220> FEATURE:
<223> OTHER INFORMATION: CT84 linker sequence

<400> SEQUENCE: 6
ttcacctaat ctagagtcga ctagcctagg tcgac                                  35

<210> SEQ ID NO 7
<211> LENGTH: 5694
<212> TYPE: DNA
<213> ORGANISM: Artificial Sequence
<220> FEATURE:
<223> OTHER INFORMATION: pMBSssaGCT84linker

<400> SEQUENCE: 7
aaattaaaaa tgaagtttta aatcaatcta agtatatat gagtaaactt ggtctgacag        60
ttaccaatgc ttaatcagtg aggcacctat ctcagcgatc tgtctatttc gttcatccat      120
agttgcctga ctccccgtcg tgtagataac tacgatacgg gagggcttac catctggccc     180
cagtgctgca atgataccgc gagacccacg ctcaccggct ccagatttat cagcaataaa     240
ccagccagcc ggaagggccg agcgcagaag tggtcctgca actttatccg cctccatcca     300
gtctattaat tgttgccggg aagctagagt aagtagttcg ccagttaata gtttgcgcaa     360
cgttgttgcc attgctacag gcatcgtggt gtcacgctcg tcgtttggta tggcttcatt     420
cagctccggt tcccaacgat caaggcgagt tacatgatcc cccatgttgt gcaaaaaagc     480
ggttagctcc ttcggtcctc cgatcgttgt cagaagtaag ttggccgcag tgttatcact     540
catggttatg gcagcactgc ataattctct tactgtcatg ccatccgtaa gatgcttttc     600
tgtgactggt gagtactcaa ccaagtcatt ctgagaatag tgtatgcggc gaccgagttg     660
ctcttgcccg gcgtcaatac gggataatac cgcgccacat agcagaactt taaaagtgct     720
catcattgga aaacgttctt cggggcgaaa actctcaagg atcttaccgc tgttgagatc     780
cagttcgatg taacccactc gtgcacccaa ctgatcttca gcatctttta ctttcaccag     840
cgtttctggg tgagcaaaaa caggaaggca aaatgccgca aaaagggaa taagggcgac     900
acggaaatgt tgaatactca tactcttcct ttttcaatat tattgaagca tttatcaggg     960
ttattgtctc atgagcggat acatatttga atgtatttag aaaaataaac aatagggt    1020
tccgcgcaca tttccccgaa aagtgccacc taaattgtaa gcgttaatat tttgttaaaa    1080
ttcgcgttaa attttgtta atcagctca tttttaacc ataggccga aatcggcaaa      1140
```

```
atcccttata aatcaaaaga atagaccgag atagggttga gtgttgttcc agtttggaac    1200
aagagtccac tattaaagaa cgtggactcc aacgtcaaag ggcgaaaaac cgtctatcag    1260
ggcgatggcc cactacgtga accatcaccc taatcaagtt ttttggggtc gaggtgccgt    1320
aaagcactaa atcggaaccc taaagggagc ccccgattta gagcttgacg gggaaagccg    1380
gcgaacgtgg cgagaaagga agggaagaaa gcgaaggag cgggcgctag gcgctggca     1440 agtgtagcgg tcacgctgcg cgtaaccacc acacccgccg cgcttaatgc gccgctacag    1500
ggcgcgtccc attcgccatt caggctgcgc aactgttggg aagggcgatc ggtgcgggcc    1560
tcttcgctat tacgccagct ggcgaaaggg ggatgtgctg caaggcgatt aagttgggta    1620
acgccagggt tttcccagtc acgacgttgt aaaacgacgg ccagtgaatt gtaatacgac    1680
tcactatagg gcgaattgga gctccaccgc ggtggcggcc gctctagaac tagtggatcc    1740
cccatcaagc ttatcgatac cgtcgacctc gagattgcca tcgcggatgt cgcctgtctt    1800
atctaccatc ataaacatca tttgcctatg gctcacgaca gtataggcaa tgccgttttt    1860
tatattgcta attgtttcgc caatcaacgc aaaagtatgg cgattgctaa agccgtctcc    1920
ctgggcggta gattagcctt aaccgcgacg gtaatgactc attcatactg gagtggtagt    1980
ttgggactac agcctcattt attagagcgt cttaatgata ttacctatgg actaatgagt    2040
tttactcgct tcggtatgga tgggatggca atgaccggta tgcaggtcag cagcccatta    2100
tatcgtttgc tggctcaggt aacgccagaa caacgtgcgc cggagtaatc gttttcaggt    2160
atataccgga tgttcattgc tttctaaatt ttgctatgtt gccagtatcc ttacgatgta    2220 tttatttta ggaaaagcca tatggaaatt atggttccgc agggtatcta cgatggtgaa    2280
accctgaccg tgtctttccc gtataccgtt atcggtgatc cgagcggtac gaccgttttc    2340
agcgccggtg aactgaccct gaaaaacctg gataatagca ttgcggcgct gccgctgtct    2400
tgcttcggta acctgctggg ttcttttcacc gttctgggtc gtggccatag cctgaccttt    2460
gaaaacattc gtaccagcac caatggtgcg gcgctgtcta atagcgcggc ggatggtctg    2520
ttcaccattg aaggttttcaa agaactgtct ttctctaact gcaatagcct gctggcggtt    2580
ctgccggcgg cgaccaccaa caaaggcagc cagaccccga ccaccacgag cacccccgtct    2640 aacggcacca tctacagcaa aaccgatctg ctgctgctga caacgaaaa attctctttt    2700 tatagcaacc tggtttctgg tgatggtggt gcgattgatg cgaaaagcct gaccgttcag    2760
ggtatctcta aactgtgcgt tttccaggaa acaccgcgc aggcggatgg cggtgcgtgc    2820
caggttgtta cctctttcag cgcgatggcc aatgaagcgc cgattgcgtt tgttgccaac    2880
gtggcgggtg ttcgtggtgg tggtatcgcg gcggtgcagg atggtcagca gggtgtgagc    2940
tcttctacct ctaccgaaga tccggtggtg agcttcagcc gtaacaccgc ggtggaattt    3000
gatggtaacg tggcgcgcgt tggtggtggt atctacagct acggtaacgt ggcgttcctg    3060
aacaatggta aaaccctgtt cctgaataac gttgcgagcc cggtgtatat tgcggccaaa    3120
cagccgacct ctggtcaggc gtctaacacc agcaataact acggcgatgg tggcgccatt    3180
ttctgcaaaa acgtgcgca ggcgggcagc aacaactctg gcagcgtgag cttcgatggc    3240
gaaggcgtgg tgttttttcag ctctaatgtg gcggcgggta aggcggcgc gatttatgcg    3300 aaaaaactgt ctgttgcgaa ctgcggcccg gtgcagttcc tgcgtaacat tgcgaacgat    3360
ggtggtgcga tctacctggg tgaaagcggc gaactgtctc tgagcgcgga ttatggcgat    3420
attatcttcg atggtaacat taaacgtacc gcgaaagaaa acgcggcgga tgtgaacggt    3480
gtgaccgtgt cttctcaggc gattagcatg ggtagcggcg gcaaaattac caccctgcgt    3540
```

```
gcgaaagcgg gtcatcagat cctgttcaac gatccgatcg aaatggcgaa cggtaataac    3600
cagccggcgc agtcttctaa actgctgaaa attaacgatg gtgaaggtta caccggtgat    3660
attgtgttcg cgaacggttc tagcaccctg tatcagaacg ttaccatcga cagggccgt    3720 atcgttctgc gtgaaaaagc gaaactgtct gttaacagcc tgagccagac cggtggtagc    3780
ctgtatatgg aagcgggttc taccctggat ttcgttaccc cgcagccgcc gcagcagccg    3840
ccggcggcga atcagctgat cacccctgagc aacctgcatc tgtctctgtc ttctctgctg    3900
gcgaacaacg cggttaccaa cccgccgacc aacccgccgg cgcaggattc tcatccggcg    3960
gtgattggta gcaccaccgc gggtagcgtt accatttctg gtccgatttt ctttgaagat    4020
ctggatgata ccgcgtacga tcgctacgat tggctgggta gcaaccagaa aatcaacgtt    4080
ctgaaactgc aactgggcac caaaccgccg gcgaacgcgc cgtctgatct gaccctgggt    4140
aacgaaatgc cgaaatatgg ctaccagggt tcttggaaac tggcgtggga cccgaacacc    4200
gcgaacaacg gtccgtacac cctgaaagcg acctggacca aaccggtta caatccgggc    4260 ccggaacgtg ttgcgtctct ggttccgaac tctctgtggg gcagcattct ggatattcgc    4320
agcgcgcatt ctgcgatcca ggcgagcgtg atggtcgta gctattgccg cggtctgtgg    4380
gttagcggtg tttctaactt cttctatcat gatcgcgatg cgctgggcca gggctatcgc    4440
tatattagcg gtggttatag cctgggtgcg aacagctatt tcggtagcag catgttcggc    4500
ctggcgttca cctaatctag agtcgactag cctagggta cccagctttt gttcccttta    4560
gtgagggtta atttcgagct tggcgtaatc atggtcatag ctgtttcctg tgtgaaattg    4620
ttatccgctc acaattccac acaacatacg agccggaagc ataaagtgta aagcctgggg    4680
tgcctaatga gtgagctaac tcacattaat tgcgttgcgc tcactgcccg ctttccagtc    4740
gggaaacctg tcgtgccagc tgcattaatg aatcggccaa cgcgcgggga gaggcggttt    4800
gcgtattggg cgctcttccg cttcctcgct cactgactcg ctgcgctcgg tcgttcggct    4860
gcggcgagcg gtatcagctc actcaaaggc ggtaatacgg ttatccacag aatcagggga    4920
taacgcagga agaacatgt gagcaaaagg ccagcaaaag gccaggaacc gtaaaaaggc    4980
cgcgttgctg gcgtttttcc ataggctccg ccccctgac gagcatcaca aaaatcgacg    5040
ctcaagtcag aggtggcgaa acccgacagg actataaaga taccaggcgt ttccccctgg    5100
aagctccctc gtgcgctctc ctgttccgac cctgccgctt accggatacc tgtccgcctt    5160
tctcccttcg ggaagcgtgg cgctttctca tagctcacgc tgtaggtatc tcagttcggt    5220
gtaggtcgtt cgctccaagc tgggctgtgt gcacgaaccc ccgttcagc ccgaccgctg    5280 cgccttatcc ggtaactatc gtcttgagtc aacccggta agacacgact tatcgccact    5340
ggcagcagcc actggtaaca ggattagcag agcgaggtat gtaggcggtg ctacagagtt    5400
cttgaagtgg tggcctaact acggctacac tagaaggaca gtatttggta tctgcgctct    5460
gctgaagcca gttaccttcg gaaaaagagt tggtagctct tgatccggca acaaaccac    5520 cgctggtagc ggtggttttt tgtttgcaa gcagcagatt acgcgcagaa aaaaggatc    5580 tcaagaagat cctttgatct tttctacggg gtctgacgct cagtggaacg aaaactcacg    5640
ttaagggatt ttggtcatga gattatcaaa aaggatcttc acctagatcc tttt          5694
```

<210> SEQ ID NO 8
<211> LENGTH: 12072
<212> TYPE: DNA
<213> ORGANISM: Artificial Sequence
<220> FEATURE:
<223> OTHER INFORMATION: pCVD aro CT84

```
<400> SEQUENCE: 8
tcgagattgc catcgcggat gtcgcctgtc ttatctacca tcataaacat catttgccta      60
tggctcacga cagtataggc aatgccgttt tttatattgc taattgtttc gccaatcaac     120
gcaaaagtat ggcgattgct aaagccgtct ccctgggcgg tagattagcc ttaaccgcga     180
cggtaatgac tcattcatac tggagtggta gtttgggact acagcctcat ttattagagc     240
gtcttaatga tattacctat ggactaatga gttttactcg cttcggtatg gatgggatgg     300
caatgaccgg tatgcaggtc agcagcccat tatatcgttt gctggctcag gtaacgccag     360
aacaacgtgc gccggagtaa tcgttttcag gtatataccg gatgttcatt gctttctaaa     420
ttttgctatg ttgccagtat ccttacgatg tatttatttt aaggaaaagc catatggaaa     480
ttatggttcc gcagggtatc tacgatggtg aaaccctgac cgtgtctttc ccgtataccg     540
ttatcggtga tccgagcggt acgaccgttt tcagcgccgg tgaactgacc ctgaaaaacc     600
tggataatag cattgcggcg ctgccgctgt cttgcttcgg taacctgctg ggttctttca     660
ccgttctggg tcgtggccat agcctgacct ttgaaaacat tcgtaccagc accaatggtg     720
cggcgctgtc taatagcgcg gcggatggtc tgttcaccat tgaaggtttc aaagaactgt     780 cttttctctaa ctgcaatagc ctgctggcgg ttctgccggc ggcgaccacc aacaaaggca     840
gccagacccc gaccaccacg agcacccccgt ctaacggcac catctacagc aaaaccgatc     900
tgctgctgct gaacaacgaa aaattctctt tttatagcaa cctggtttct ggtgatggtg     960
gtgcgattga tgccgaaaagc ctgaccgttc agggtatctc taaactgtgc gttttccagg    1020
aaaacaccgc gcaggcggat ggcggtgcgt gccaggttgt tacctctttc agcgcgatgg    1080
ccaatgaagc gccgattgcg tttgttgcca acgtggcggg tgttcgtggt ggtggtatcg    1140
cggcggtgca ggatggtcag cagggtgtga gctcttctac ctctaccgaa gatccggtgg    1200
tgagcttcag ccgtaacacc gcggtggaat tgatggtaa cgtggcgcgc gttggtggtg    1260
gtatctacag ctacggtaac gtggcgttcc tgaacaatgg taaaaccctg ttcctgaata    1320
acgttgcgag cccggtgtat attgcggcca aacagccgac ctctggtcag gcgtctaaca    1380
ccagcaataa ctacgcgat ggtggcgcca ttttctgcaa aaacggtgcg caggcgggca    1440
gcaacaactc tggcagcgtg agcttcgatg gcgaaggcgt ggtgtttttc agctctaatg    1500
tggcggcggg taaaggcggc gcgatttatg cgaaaaaact gtctgttgcg aactgcggcc    1560
cggtgcagtt cctgcgtaac attgcgaacg atggtggtgc gatctacctg ggtgaaagcg    1620
gcgaactgtc tctgagcgcg gattatgcg atattatctt cgatggtaac attaaacgta    1680
ccgcgaaaga aaacgcggcg gatgtgaacg tgtgaccgt gtcttctcag gcgattagca    1740
tgggtagcgc cggcaaaatt accacccctgc gtgcgaaagc gggtcatcag atcctgttca    1800
acgatccgat cgaaatggcg aacggtaata accagccggc gcagtcttct aaactgctga    1860
aaattaacga tggtgaaggt tacaccggtg atattgtgtt cgcgaacggt tctagcaccc    1920
tgtatcagaa cgttaccatc gaacagggcc gtatcgttct gcgtgaaaaa gcgaaactgt    1980
ctgttaacag cctgagccag accggtggta gcctgtatat ggaagcgggt tctaccctgg    2040
atttcgttac cccgcagccg ccgcagcagc cgccggcggc gaatcagctg atcaccctga    2100
gcaacctgca tctgtctctg tcttctctgc tggcgaacaa cgcggttacc aacccgccga    2160
ccaacccgcc ggcgcaggat tctcatccgg cggtgattgg tagcaccacc gcgggtagcg    2220
ttaccatttc tggtccgatt ttctttgaag atctggatga taccgcgtac gatcgctacg    2280
attggctggg tagcaaccag aaaatcaacg ttctgaaact gcaactgggc accaaaccgc    2340
```

-continued

```
cggcgaacgc gccgtctgat ctgaccctgg gtaacgaaat gccgaaatat ggctaccagg   2400
gttcttggaa actggcgtgg gacccgaaca ccgcgaacaa cggtccgtac accctgaaag   2460
cgacctggac caaaaccggt tacaatccgg gcccggaacg tgttgcgtct ctggttccga   2520
actctctgtg gggcagcatt ctggatattc gcagcgcgca ttctgcgatc caggcgagcg   2580
tggatggtcg tagctattgc cgcggtctgt gggttagcgg tgtttctaac ttcttctatc   2640
atgatcgcga tgcgctgggc cagggctatc gctatattag cggtggttat agcctgggtg   2700
cgaacagcta tttcggtagc agcatgttcg gcctggcgtt cacctaatct agagtcgact   2760
agcctaggtc cagcattacc gtgccgggac gtacgatcaa ccggatgggt gaagaggtcg   2820
agatgatcac caaagggcgc cacgatccgt gtgtgggat tcgcgcagtg ccgatcgcag   2880
aagccatgct ggcgatcgta ctgatggatc acctgctgcg ccatcgggca cagaatgcgg   2940
atgtaaagac agagattcca cgctggtaag aaatgaaaaa aaccgcgatt gcgctgctgg   3000
catggtttgt cagtagcgcc agcctggcgg cgacgccgtg gcagaaaata acccatcctg   3060
tccccggcgc cgcccagtct atcggtagct ttgccaacgg atgcatcatt ggcgccgaca   3120
cgttgccggt acagtccgat aattatcagg tgatgcgcac cgatcagcgc cgttatttcg   3180
gccacccgga tctggtcatg tttatccagc ggttgagtca tcaggcgcag caacgggggc   3240
tcggaaccgt cctgataggc gacatgggga tgcctgccgg aggccgcttt aatggcggac   3300
acgccagtca tcagaccggg cttgatgtgg atattttctt gcagttgccg aaaacgcgct   3360
ggagccaggc gcagctattg cgcccgcagg cgttagatct ggtgtcccgc gacggtaaac   3420
atgtcgtgcc gtcgcgctgg tcgtcggata tcgccagtct gatcaaactg gcggcacaag   3480
acaatgacgt cacccgtatt ttcgtcaatc cggctattaa acaacagctt gcctcgatg    3540 ccggaagcga tcgtgactgg ctacgtaaag tacgcccctg gttccagcat cgcgcgcata   3600
tgcacgtgcg tttacgctgc cctgccgaca gcctggagtg cgaagatcaa cctttacccc   3660
cgccgggcga tggatgcggc gctgaactgc aaagctggtt cgaaccgcca aaacctggca   3720
ccacaaagcc tgagaagaag acaccgccgc cgttgccgct ttcctgccag gcgctactgg   3780
atgagcatgt actctgatgg acaatttta tgatctgttt atggtctccc cgctgctgct    3840
ggtggtgctg ttttttgtcg ccgtactggc aggatttatc gattctatcg ccggaggcgg   3900
agggctgctc actatccctg cgctgatggc cgccgggatg tcgccggcaa acgcgttggc   3960
gaccaataaa ttacaggcgt gcggcggctc cctctcgtct tcgctctatt ttattcgccg   4020
taaagtggta aacctggccg agcaaaagct caatattctg atgacgttca ttggctcgat   4080
gagcggcgcg ctgctggtgc agcacgtgca ggcggatatt ttgcgccaga tcttgcccat   4140
cctggtgatt ttcatcggcc tctatttttt attgatgccg aagctgggcg aggaagatcg   4200
ccagcgccgc ctgtatggat taccgttcgc gctgatagcc gggggatgcg tcgggtttta   4260
cgacggcttt tcgggcctg ccgcaggtc gttttacgct ctggcgtttg tcaccttatg     4320
tggctataac ctggcgaaat ccacggcaca tgccaaagtg cttaacgcta cctccaacgt   4380
tggcggcctg ctgttatta tcatcggcgg caaagtgatc tgggcgacgg ctttgtgat     4440 gctggttggt cagttttag gggcgcgaat ggggtcgcgt ctggtgttga gcaaaggcca    4500
aaagcttgca tgcggtacct ctagaagaag cttgggatcc gtcgacctgc agatccgtcg   4560
acctgcaggt cgactctaga ggatcgatcc ttttaaccc atcacatata cctgccgttc    4620
actattattt agtgaaatga gatattatga tattttctga attgtgatta aaaaggcaac   4680
tttatgccca tgcaacagaa actataaaaa atacagagaa tgaaaagaaa cagatagatt   4740
```

```
ttttagttct ttaggcccgt agtctgcaaa tccttttatg attttctatc aaacaaaaga    4800
ggaaaataga ccagttgcaa tccaaacgag agtctaatag aatgaggtcg aaaagtaaat    4860
cgcgcgggtt tgttactgat aaagcaggca agacctaaaa tgtgtaaagg caaagtgta     4920 tactttggcg tcacccctta catattttag gtcttttttt attgtgcgta actaacttgc    4980
catcttcaaa caggagggct ggaagaagca gaccgctaac acagtacata aaaaaggaga    5040
catgaacgat gaacatcaaa aagtttgcaa acaagcaac agtattaacc tttactaccg     5100
cactgctggc aggaggcgca actcaagcgt ttgcgaaaga acgaaccaa agccatata     5160 aggaaacata cggcatttcc catattacac gccatgatat gctgcaaatc cctgaacagc    5220
aaaaaaatga aaatatcaa gttcctgaat tcgattcgtc cacaattaaa aatatctctt     5280
ctgcaaaagg cctggacgtt tgggacagct ggccattaca aaacgctgac ggcactgtcg    5340
caaactatca cggctaccac atcgtctttg cattagccgg agatcctaaa aatgcggatg    5400
acacatcgat ttacatgttc tatcaaaaag tcggcgaaac ttctattgac agctggaaaa    5460
acgctggccg cgtctttaaa gacagcgaca aattcgatgc aaatgattct atcctaaaag    5520
accaaacaca agaatggtca ggttcagcca catttacatc tgacggaaaa atccgtttat    5580
tctacactga tttctccggt aaacattacg gcaaacaaac actgacaact gcacaagtta    5640
acgtatcagc atcagacagc tctttgaaca tcaacggtgt agaggattat aaatcaatct    5700 tgacggtga cggaaaaacg tatcaaaatg tacagcagtt catcgatgaa ggcaactaca    5760
gctcaggcga caaccatacg ctgagagatc ctcactacgt agaagataaa ggccacaaat    5820
acttagtatt tgaagcaaac actggaactg aagatggcta ccaaggcgaa gaatctttat    5880
ttaacaaagc atactatggc aaaagcacat cattcttccg tcaagaaagt caaaaacttc    5940
tgcaaagcga taaaaaacgc acggctgagt tagcaaacgg cgctctcggt atgattgagc    6000
taaacgatga ttcacactg aaaaaagtga tgaaaccgct gattgcatct aacacagtaa     6060
cagatgaaat tgaacgcgcg aacgtcttta aaatgaacgg caaatggtac ctgttcactg    6120
actcccgcgg atcaaaaatg acgattgacg gcattacgtc taacgatatt tacatgcttg    6180
gttatgtttc taattctta actggcccat acaagccgct gaacaaaact ggccttgtgt     6240
taaaaatgga tcttgatcct aacgatgtaa cctttactta ctcacacttc gctgtacctc    6300
aagcgaaagg aaacaatgtc gtgattacaa gctatatgac aaacagagga ttctacgcag    6360
acaaacaatc aacgtttgcg ccaagcttcc tgctgaacat caaaggcaag aaaacatctg    6420
ttgtcaaaga cagcatcctt gaacaaggac aattaacagt taacaaataa aaacgcaaaa    6480
gaaaatgccg atatcctatt ggcatttttct tttatttctt atcaacataa aggtgaatcc    6540
catatgaact atataaaagc aggcaaatgg ctaaccgtat tcctaacctt ttggtaatga    6600
ctccaactta ttgatagtgt tttatgttca gataatgccc gatgactttg tcatgcagct    6660
ccaccgattt tgagaacgac agcgacttcc gtcccagccg tgccaggtgc tgcctcagat    6720
tcaggttatg ccgctcaatt cgctgcgtat atcgcttgct gattacgtgc agctttccct    6780
tcaggcggga ttcatacagc ggccagccat ccgtcatcca tatcaccacg tcaaagggtg    6840
acagcaggct cataagacgc cccagcgtcg ccatagtgcg ttaccgaat acgtgcgcaa     6900 caaccgtctt ccggagactg tcatacgcgt aaaacagcca gcgctggcgc gatttagccc    6960
cgacatagcc ccactgttcg tccatttccg cgcagacgat gacgtcactg cccggctgta    7020
tgcgcgaggt taccgactgc ggcctgagtt ttttaagtga cgtaaaatcg tgttgaggcc    7080
aacgcccata tgcgggctg ttgcccggca tccaacgcca ttcatggcca tatcaatgat     7140
```

```
tttctggtgc gtaccgggtt gagaagcggt gtaagtgaac tgcaggtggc acttttcggg    7200
gaaatgtgcg cggaacccct atttgtttat ttttctaaat acattcaaat atgtatccgc    7260
tcatgagaca taaccctga taaatgcttc aataatattg aaaaaggaag agtatgagta    7320
ttcaacattt ccgtgtcgcc cttattccct tttttgcggc attttgcctt cctgtttttg    7380
ctcacccaga aacgctggtg aaagtaaaag atgctgaaga tcagttgggt gcacgagtgg    7440
gttacatcga actggatctc aacagcggta agatccttga gttttcgc cccgaagaac     7500
gttttccaat gatgagcact tttaaagttc tgctatgtgg cgcggtatta tcccgtgttg    7560
acgccgggca agagcaactc ggtcgccgca tacactattc tcagaatgac ttggttgagt    7620
actcaccagt cacagaaaag catcttacgg atggcatgac agtaagagaa ttatgcagtg    7680
ctgccataac catgagtgat aacactgcgg ccaacttact tctgacaacg atcggaggac    7740
cgaaggagct aaccgctttt ttgcacaaca tgggggatca tgtaactcgc cttgatcgtt    7800
gggaaccgga gctgaatgaa gccataccaa acgacgagcg tgacaccacg atgcctgcag    7860
caatggcaac aacgttgcgc aaactattaa ctggcgaact acttactcta gcttcccggc    7920
aacaattaat agactggatg gaggcggata aagttgcagg accacttctg cgctcggccc    7980
ttccggctgg ctggtttatt gctgataaat ctggagccgg tgagcgtggg tctcgcggta    8040
tcattgcagc actggggcca gatggtaagc cctcccgtat cgtagttatc tacacgacgg    8100
ggagtcaggc aactatggat gaacgaaata gacagatcgc tgagataggt gcctcactga    8160
ttaagcattg gtaactgtca gaccaagttt actcatatat actttagatt gatttatggt    8220
gcactctcag tacaatctgc tctgatgccg catagttaag ccagtataca ctccgctatc    8280
gctacgtgac tgggtcatgg ctgcgccccg acacccgcca acaccgctg acgcgccctg     8340
acgggcttgt ctgctcccgg catccgctta cagacaagct gtgaccgtct ccgggagctg    8400
catgtgtcag aggttttcac cgtcatcacc gaaacgcgcg aggcagcaag gagatggcgc    8460
ccaacagtcc cccggccacg gggcctgcca ccatacccac gccgaaacaa gcgctcatga    8520
gcccgaagtg gcgagcccga tcttccccat cggtgatgtc ggcgatatag gcgccagcaa    8580
ccgcacctgt ggcgccggtg atgccggcca cgatgcgtcc ggcgtagagg atccttttg     8640
tccggtgttg ggttgaaggt gaagccggtc ggggccgcag cggggccgg cttttcagcc     8700
ttgccccct gcttcggccg ccgtggctcc ggcgtcttgg gtgccggcgc gggttccgca     8760
gccttggcct gcggtgcggg cacatcggcg ggcttggcct tgatgtgccg cctggcgtgc    8820
gagcggaacg tctcgtagga gaacttgacc ttccccgttt cccgcatgtg ctcccaaatg    8880
gtgacgagcg catagccgga cgctaacgcc gcctcgacat ccgccctcac cgccaggaac    8940
gcaaccgcag cctcatcacg ccggcgcttc ttggccgcgc gggattcaac ccactcggcc    9000
agctcgtcgg tgtagctctt tggcatcgtc tctcgcctgt cccctcagtt cagtaatttc    9060
ctgcatttgc ctgtttccag tcggtagata ttccacaaaa cagcagggaa gcagcgcttt    9120
tccgctgcat aaccctgctt cggggtcatt atagcgattt tttcggtata tccatccttt    9180
ttcgcacgat atacaggatt ttgccaaagg gttcgtgtag actttccttg gtgtatccaa    9240
cggcgtcagc cgggcaggat aggtgaagta gcccacccg cgagcgggtg ttccttcttc     9300
actgtccctt attcgcacct ggcggtgctc aacgggaatc ctgctctgcg aggctggccg    9360
gctaccgccg gcgtaacaga tgagggcaag cggatggctg atgaaaccaa gccaaccagg    9420
aagggcagcc cacctatcaa ggtgtactgc cttccagacg aacgaagagc gattgaggaa    9480
aaggcggcgg cggccggcat gagcctgtcg gcctacctgc tggccgtcgg ccagggctac    9540
```

-continued

```
aaaatcacgg gcgtcgtgga ctatgagcac gtccgcgagc tggcccgcat caatggcgac    9600
ctgggccgcc tgggcggcct gctgaaactc tggctcaccg acgacccgcg cacggcgcgg    9660
ttcggtgatg ccacgatcct cgccctgctg gcgaagatcg aagagaagca ggacgagctt    9720
ggcaaggtca tgatgggcgt ggtccgcccg agggcagagc catgactttt ttagccgcta    9780
aaacggccgg ggggtgcgcg tgattgccaa gcacgtcccc atgcgctcca tcaagaagag    9840
cgacttcgcg gagctggtga agtacatcac cgacgagcaa ggcaagaccg agcgcctggg    9900
tcacgtgcgc gtcacgaact gcgaggcaaa caccctgccc gctgtcatgg ccgaggtgat    9960
ggcgacccag cacggcaaca cccgttccga ggccgacaag acctatcacc tgctggttag   10020
cttccgcgcg ggagagaagc ccgacgcgga cgttgcgc gcgattgagg accgcatctg   10080
cgctgggctt ggcttcgccg agcatcagcg cgtcagtgcc gtgcatcacg acaccgacaa   10140
cctgcacatc catatcgcca tcaacaagat tcacccgacc cgaaacacca tccatgagcc   10200
gtatcgggcc taccgcgccc tcgctgacct ctgcgcgacg ctcgaacggg actacgggct   10260
tgagcgtgac aatcacgaaa cgcggcagcg cgtttccgag aaccgcgcga acgacatgga   10320
gcggcacgcg ggcgtggaaa gcctggtcgg ctggatccgg ccacgatgcg tccgcgtag   10380 aggatctgaa gatcagcagt tcaacctgtt gatagtacgt actaagctct catgtttcac   10440
gtactaagct ctcatgttta acgtactaag ctctcatgtt taacgaacta aaccctcatg   10500
gctaacgtac taagctctca tggctaacgt actaagctct catgtttcac gtactaagct   10560
ctcatgtttg aacaataaaa ttaatataaa tcagcaactt aaatagcctc taaggtttta   10620
agttttataa gaaaaaaaag aatatataag gctttaaagc ttttaaggtt taacggttgt   10680
ggacaacaag ccagggatgt aacgcactga gaagcccta gagcctctca aagcaatttt   10740
gagtgacaca ggaacactta acggctgaca tgggaattcc acatgtggaa ttccacatgt   10800
ggaattgtga gcggataaca atttgtggaa ttcccgggag agctcgatat cgcatgccct   10860
ggaggaatac gtggataaaa ttttcgtcga tgaagcagta agtgaactgc ataccattca   10920
ggacatgttg cgctgggcgg taagccgctt tagcgcggcg aatatctggt atggacacgg   10980
taccgataac ccgtgggatg aagcggtaca actggtgttg ccgtctcttt atctgccgct   11040
ggatattccg gaggatatgc ggaccgcgcg gctgacgtcc agcgaaagac accgcattgt   11100
cgagcgagtg attcgtcgca ttaacgagcg tatcccggta gcctacctga ccaataaagc   11160
ctggttctgc ggccacgaat tttatgttga tgagcgcgtg ctggtgccgc gttcaccgat   11220
tggcgagctg attaataacc acttcgctgg cctattagc caacagccga aatatattct   11280
ggatatgtgt accggcagcg gctgcatcgc catcgcctgt gcttatgctt ccccggacgc   11340
agaggttgat gcgtcgata tttcgccgga tgcgctggct gtcgccgagc ataacattga   11400
agaacacggt cttatccatc acgtgacgcc aatccgttcc gatctgttcc gcgatctgcc   11460
gaaagttcag tacgatctga ttgtcactaa cccgccttat gtcgatgcgg aggatatgtc   11520
cgatctgccg aacgaatatc gccacgaacc tgagctgggg ctggcgtccg cactgacgg   11580 cctcaaattg acccgccgta tcctgggaaa tgcgccggat tatctgtccg atgatggcgt   11640
tctgatttgt gaagtcggaa acagcatggt acatctgatg gagcagtatc cggatgtgcc   11700
gttcacctgg ctggagtttg acaacggcgg cgatggcgtc tttatgttga ccaaagcgca   11760
gttgctcgcg gcccgtgaac atttcaatat ttataaagat taaaacacgc aaacgacaac   11820
aacgataacg gagccgtgat ggcaggaaac acaattggac aactctttcg cgtaaccact   11880
ttcggcgaat cacacgggct ggcgcttggg ggtatcgtcg atggcgtgcc gcccggcatc   11940
```

```
ccgttgacgg aggccgatct gcagcacgat ctcgacagac gccgccctgg cacctcgcgc    12000
tatactactc agcgccgcga accggaccag gtaaaaattc tctccggcgt gtttgatggc    12060
gtaacgaccg gc                                                        12072
```

<210> SEQ ID NO 9
<211> LENGTH: 12855
<212> TYPE: DNA
<213> ORGANISM: Artificial Sequence
<220> FEATURE:
<223> OTHER INFORMATION: pCVDssaGCT110linker

<400> SEQUENCE: 9

```
tcgagattgc catcgcggat gtcgcctgtc ttatctacca tcataaacat catttgccta      60
tggctcacga cagtataggc aatgccgttt tttatattgc taattgtttc gccaatcaac     120
gcaaaagtat ggcgattgct aaagccgtct ccctgggcgg tagattagcc ttaaccgcga     180
cggtaatgac tcattcatac tggagtggta gtttgggact acagcctcat ttattagagc     240
gtcttaatga tattacctat ggactaatga gttttactcg cttcggtatg gatgggatgg     300
caatgaccgg tatgcaggtc agcagcccat tatatcgttt gctggctcag gtaacgccag     360
aacaacgtgc gccggagtaa tcgttttcag gtatataccg gatgttcatt gctttctaaa     420
ttttgctatg ttgccagtat ccttacgatg tattttatttt aaggaaaagc catatggaaa    480
ccagcttcca taaattcttc ctgtctatga tcctggcgta cagctgctgt tctctgaacg     540
gtggtggtta tgcggcggaa attatggttc cgcagggtat ctacgatggt gaaaccctga     600
ccgtgtcttt cccgtatacc gttatcggtg atccgagcgg tacgaccgtt tcagcgccg      660 gtgaactgac cctgaaaaac ctggataata gcattgcggc gctgccgctg tcttgcttcg     720
gtaacctgct gggttctttc accgttctgg gtcgtggcca tagcctgacc tttgaaaaca     780
ttcgtaccag caccaatggt gcggcgctgt ctaatagcgc ggcggatggt ctgttcacca     840
ttgaaggttt caaagaactg tctttctcta actgcaatag cctgctggcg gttctgccgg     900
cggcgaccac caacaaaggc agccagaccc cgaccaccac gagcaccccg tctaacggca     960
ccatctacag caaaaccgat ctgctgctgc tgaacaacga aaaattctct ttttatagca    1020
acctggtttc tggtgatggt ggtgcgattg atgcgaaaag cctgaccgtt cagggtatct    1080
ctaaactgtg cgttttccag gaaaacaccg cgcaggcgga tggcggtgcg tgccaggttg    1140
ttacctcttt cagcgcgatg gccaatgaag cgccgattgc gtttgttgcc aacgtggcgg    1200
gtgttcgtgg tggtggtatc gcggcggtgc aggatggtca gcagggtgtg agctcttcta    1260
cctctaccga agatccggtg gtgagcttca gccgtaacac cgcggtggaa tttgatggta    1320
acgtggcgcg cgttggtggt ggtatctaca gctacggtaa cgtggcgttc ctgaacaatg    1380
gtaaaaccct gttcctgaat aacgttgcga gcccggtgta tattgcggcc aaacagccga    1440
cctctggtca ggcgtctaac accagcaata actacgcgca tggtgcgcc attttctgca    1500 aaaacggtgc gcaggcgggc agcaacaact ctggcagcgt gagcttcgat ggcgaaggcg    1560
tggtgttttt cagctctaat gtggcggcgg gtaaggcgg cgcgatttat gcgaaaaaac    1620
tgtctgttgc gaactgcggc ccggtgcagt tcctgcgtaa cattgcgaac gatggtggtg    1680
cgatctacct gggtgaaagc ggcgaactgt ctctgagcgc ggattatggc gatattatct    1740
tcgatggtaa cattaaacgt accgcgaaag aaaacgcggc ggatgtgaac ggtgtgaccg    1800
tgtcttctca ggcgattagc atgggtagcg cggcaaaat taccaccctg cgtgcgaaag    1860
cgggtcatca gatcctgttc aacgatccga tcgaaatggc gaacggtaat aaccagccgg    1920
```

```
cgcagtcttc taaactgctg aaaattaacg atggtgaagg ttacaccggt gatattgtgt    1980
tcgcgaacgg ttctagcacc ctgtatcaga acgttaccat cgaacagggc cgtatcgttc    2040
tgcgtgaaaa agcgaaactg tctgttaaca gcctgagcca gaccggtggt agcctgtata    2100
tggaagcggg ttctaccctg gatttcgtta ccccgcagcc gccgcagcag ccgccggcgg    2160
cgaatcagct gatcacccty agcaacctgc atctgtctct gtcttctctg ctggcgaaca    2220
acgcggttac caacccgccg accaacccgc cggcgcagga ttctcatccg gcggtgattg    2280
gtagcaccac cgcgggtagc gttaccattt ctggtccgat tttctttgaa gatctggatg    2340
ataccgcgta cgatcgctac gattggctgg gtagcaacca gaaaatcaac gttctgaaac    2400
tgcaactggg caccaaaccg ccggcgaacg cgccgtctga tctgaccctg ggtaacgaaa    2460
tgccgaaata tggctaccag ggttcttgga actggcgtg ggacccgaac accgcgaaca    2520
acggtccgta caccctgaaa gcgacctgga ccaaaaccgg ttacaatccg ggcccggaac    2580
gtgttgcgtc tctggttccg aactctctgt ggggcagcat tctggatatt cgcagcgcgc    2640
attctgcgat ccaggcgagc gtggatggtc gtagctattg ccgcggtctg tgggttagcg    2700 gtgttctaa cttcttctat catgatcgcg atgcgctggg ccagggctat cgctatatta    2760
gcggtggtta tagcctgggt gcgaacagct atttcggtag cagcatgttc ggcctggcgt    2820
tcaccgaagt ttttggtcgt tctaaagatt atgttgtgtg ccgtagcaac catcatgcgt    2880
gcattggttc tgtttatctg agcacccagc aggcgctgtg cggttcttat ctgtttggcg    2940
atgcgttcat ccgtgcgtct tatggtttcg gcaaccagca catgaaaacc agctatacct    3000
ttgcggaaga aagcgatgtt cgttgggata caaactgcct ggcgggtgaa attggtgcgg    3060
gcctgccgat cgttatcacc ccgagcaaac tgtatctgaa cgaactgcgc ccgtttgtgc    3120
aggcggaatt ttcttacgcg aaccatgaat ctttaccga agaaggtgat caggcgcgtg    3180
cgttcaaaag cggtcatctg ctgaacctga gcgtgccggt tggcgtgaaa tttgatcgtt    3240
gcagctctac ccatccgaac aaatacagct ttatggcggc gtatatctgt gatgcgtatc    3300
gtaccattag cggcaccgaa accaccctgc tgagccatca gggcacctgg accaccgatg    3360
cgtttcatct ggcgcgtcat ggcgttgtgg ttcgtggcag catgtatgcg agcctgacca    3420
gcaacattga agtgtatggt catggtcgtt atgaatatcg tgatgcgagc cgtggttatg    3480
gtctgagcgc gggtagccgc gttcgttttt aataaggatc tctagactag cctaggtcca    3540
gcattaccgt gccgggacgt acgatcaacc ggatgggtga agaggtcgag atgatcacca    3600
aagggcgcca cgatccgtgt gtggggattc gcgcagtgcc gatcgcagaa gtcatgctgg    3660
cgatcgtact gatggatcac ctgctgcgcc atcgggcaca gaatgcggat gtaaagacag    3720
agattccacg ctggtaagaa atgaaaaaaa ccgcgattgc gctgctggca tggtttgtca    3780
gtagcgccag cctggcggcg acgtcgtggc agaaaataac ccatcctgtc cccggcgccg    3840
cccagtctat cggtagcttt gccaacggat gcatcattgg cgccgacacg ttgccggtac    3900
agtccgataa ttatcaggtg atgcgcaccg atcagcgccg ttatttcggc cacccggatc    3960
tggtcatgtt tatccagcgg ttgagtcatc aggcgcagca acgggggctc ggaaccgtcc    4020
tgataggcga catggggatg cctgccggag gccgctttaa tggcggacac gccagtcatc    4080
agaccgggct tgatgtggat attttcttgc agttgccgaa aacgcgctgg agccaggcgc    4140
agctattgcg cccgcaggcg ttagatctgg tgtcccgcga cggtaaacat gtcgtgccgt    4200
cgcgctggtc gtcggatatc gccagtcga tcaaactggc ggcacaagac aatgacgtca    4260
cccgtatttt cgtcaatccg gctattaaac aacagctttg cctcgatgcc ggaagcgatc    4320
```

```
gtgactggct acgtaaagta cgcccctggt tccagcatcg cgcgcatatg cacgtgcgtt    4380
tacgctgccc tgccgacagc ctggagtgcg aagatcaacc tttaccccg ccgggcgatg     4440 gatgcggcgc tgaactgcaa agctggttcg aaccgccaaa acctggcacc acaaagcctg    4500
agaagaagac accgccgccg ttgccgcttt cctgccaggc gctactggat gagcatgtac    4560
tctgatggac aattttatg atctgtttat ggtctccccg ctgctgctgg tggtgctgtt     4620
ttttgtcgcc gtactggcag gatttatcga ttctatcgcc ggaggcggag ggctgctcac    4680
tatccctgcg ctgatggccg ccgggatgtc gccggcaaac gcgttggcga ccaataaatt    4740
acaggcgtgc ggcggctccc tctcgtcttc gctctatttt attcgccgta aagtggtaaa    4800
cctggccgag caaaagctca atattctgat gacgttcatt ggctcgatga gcggcgcgct    4860
gctggtgcag cacgtgcagg cggatatttt gcgccagatc ttgcccatcc tggtgatttt    4920
catcggcctc tattttttat tgatgccgaa gctgggcgag aagatcgcc agcgccgcct     4980 gtatggatta ccgttcgcgc tgatagccgg gggatgcgtc gggttttacg acggcttttt    5040
cgggcctgcc gcagggtcgt tttacgctct ggcgtttgtc accttatgtg gctataacct    5100
ggcgaaatcc acggcacatg ccaaagtgct taacgctacc tccaacgttg gcggcctgct    5160
gttatttatc atcggcggca aagtgatctg ggcgacgggc tttgtgatgc tggttggtca    5220
gtttttaggg gcgcgaatgg ggtcgcgtct ggtgttgagc aaaggccaaa agctgggaga    5280
gctcgatatc gcatgcgata tcgagctctc ccgggaattc cacaaattgt tatccgctca    5340
caattccaca tgtggaattc cacatgtgga attcccatgt cagccgttaa gtgttcctgt    5400
gtcactcaaa attgctttga gaggctctaa gggcttctca gtgcgttaca tccctggctt    5460
gttgtccaca accgttaaac cttaaaagct ttaaagcctt atatattctt tttttctta    5520 taaaacttaa aaccttagag gctatttaag ttgctgattt atattaattt tattgttcaa    5580
acatgagagc ttagtacgtg aaacatgaga gcttagtacg ttagccatga gcttagta     5640 cgttagccat gagggtttag ttcgttaaac atgagagctt agtacgttaa acatgagagc    5700
ttagtacgtg aaacatgaga gcttagtacg tactatcaac aggttgaact gctgatcttc    5760
agatcctcta cgccggacgc atcgtggccg gatccagccg accaggcttt ccacgcccgc    5820
gtgccgctcc atgtcgttcg cgcggttctc ggaaacgcgc tgccgcgttt cgtgattgtc    5880
acgctcaagc ccgtagtccc gttcgagcgt cgcgcagagg tcagcgaggg gcggtaggc     5940 ccgatacggc tcatggatgg tgtttcgggt cgggtgaatc ttgttgatgg cgatatggat    6000
gtgcaggttg tcgtgtcgt gatgcacggc actgacgcgc tgatgctcgg cgaagccaag    6060
cccagcgcag atgcggtcct caatcgcgcg caacgtctcc gcgtcgggct tctctcccgc    6120
gcggaagcta accagcaggt gataggtctt gtcggcctcg gaacgggtgt tgccgtgctg    6180
ggtcgccatc acctcggcca tgacagcggg cagggtgttt gcctcgcagt tcgtgacgcg    6240
cacgtgaccc aggcgctcgg tcttgccttg ctcgtcggtg atgtacttca ccagctccgc    6300
gaagtcgctc ttcttgatgg agcgcatggg gacgtgcttg gcaatcacgc gcaccccccg    6360
gccgttttag cggctaaaaa agtcatggct ctgccctcgg gcggaccacg cccatcatga    6420
ccttgccaag ctcgtcctgc ttctcttcga tcttcgccag cagggcgagg atcgtggcat    6480
caccgaaccg cgccgtgcgc gggtcgtcgg tgagccagag tttcagcagg ccgcccaggc    6540
ggcccaggtc gccattgatg cgggccagct cgcggacgtg ctcatagtcc acgacgcccg    6600
tgattttgta gccctggccg acggccagca ggtaggccga caggctcatg ccggccgccg    6660 ccgcctttc ctcaatcgct cttcgttcgt ctggaaggca gtacaccttg ataggtgggc    6720
```

```
tgcccttcct ggttggcttg gtttcatcag ccatccgctt gccctcatct gttacgccgg   6780
cggtagccgg ccagcctcgc agagcaggat tcccgttgag caccgccagg tgcgaataag   6840
ggacagtgaa gaaggaacac ccgctcgcgg gtgggcctac ttcacctatc ctgcccggct   6900
gacgccgttg gatacaccaa ggaaagtcta cacgaaccct ttggcaaaat cctgtatatc   6960
gtgcgaaaaa ggatggatat accgaaaaaa tcgctataat gaccccgaag cagggttatg   7020
cagcggaaaa gcgctgcttc cctgctgttt tgtggaatat ctaccgactg gaaacaggca   7080
aatgcaggaa attactgaac tgaggggaca ggcgagagac gatgccaaag agctacaccg   7140
acgagctggc cgagtgggtt gaatcccgcg cggccaagaa gcgccggcgt gatgaggctg   7200
cggttgcgtt cctggcggtg agggcggatg tcgaggcggc gttagcgtcc ggctatgcgc   7260
tcgtcaccat ttgggagcac atgcgggaaa cgggaaggt caagttctcc tacgagacgt   7320
tccgctcgca cgccaggcgg cacatcaagg ccaagcccgc cgatgtgccc gcaccgcagg   7380
ccaaggctgc ggaacccgcg ccggcaccca agacgccgga ccacggcgg ccgaagcagg   7440 ggggcaaggc tgaaaagccg gcccccgctg cggccccgac cggcttcacc ttcaacccaa   7500
caccggacaa aaaggatcct ctacgccgga cgcatcgtgg ccggcatcac cggcgccaca   7560
ggtgcggttg ctggcgccta tatcgccgac atcaccgatg gggaagatcg ggctcgccac   7620
ttcgggctca tgagcgcttg tttcggcgtg ggtatggtgg caggccccgt ggccggggga   7680
ctgttgggcg ccatctcctt gctgcctcgc gcgtttcggt gatgacggtg aaaacctctg   7740
acacatgcag ctcccggaga cggtcacagc ttgtctgtaa gcggatgccg ggagcagaca   7800
agcccgtcag ggcgcgtcag cgggtgttgg cgggtgtcgg ggcgcagcca tgacccagtc   7860
acgtagcgat agcggagtgt atactggctt aactatgcgg catcagagca gattgtactg   7920
agagtgcacc ataaatcaat ctaaagtata tatgagtaaa cttggtctga cagttaccaa   7980
tgcttaatca gtgaggcacc tatctcagcg atctgtctat ttcgttcatc catagttgcc   8040
tgactccccg tcgtgtagat aactacgata cgggagggct taccatctgg ccccagtgct   8100
gcaatgatac cgcgagaccc acgctcaccg gctccagatt tatcagcaat aaaccagcca   8160
gccggaaggg ccgagcgcag aagtggtcct gcaactttat ccgcctccat ccagtctatt   8220
aattgttgcc gggaagctag agtaagtagt tcgccagtta atagtttgcg caacgttgtt   8280
gccattgctg caggcatcgt ggtgtcacgc tcgtcgtttg gtatggcttc attcagctcc   8340
ggttcccaac gatcaaggcg agttacatga tcccccatgt tgtgcaaaaa agcggttagc   8400
tccttcggtc ctccgatcgt tgtcagaagt aagttggccg cagtgttatc actcatggtt   8460
atggcagcac tgcataattc tcttactgtc atgccatccg taagatgctt ttctgtgact   8520
ggtgagtact caaccaagtc attctgagaa tagtgtatgc ggcgaccgag ttgctcttgc   8580
ccggcgtcaa cacgggataa taccgcgcca catagcagaa ctttaaaagt gctcatcatt   8640
ggaaaacgtt cttcggggcg aaaactctca aggatcttac cgctgttgag atccagttcg   8700
atgtaaccca ctcgtgcacc caactgatct tcagcatctt ttactttcac cagcgtttct   8760
gggtgagcaa aaacaggaag gcaaaatgcc gcaaaaaagg gaataagggc gacacggaaa   8820
tgttgaatac tcatactctt cctttttcaa tattattgaa gcatttatca gggttattgt   8880
ctcatgagcg gatacatatt tgaatgtatt tagaaaaata aacaaatagg ggttccgcgc   8940
acatttcccc gaaaagtgcc acctgcagtt cacttacacc gcttctcaac ccggtacgca   9000
ccagaaaatc attgatatgg ccatgaatgg cgttggatgc cggcaacag cccgcattat   9060 gggcgttggc ctcaacacga ttttacgtca cttaaaaaac tcaggccgca gtcggtaacc   9120
```

```
tcgcgcatac agccgggcag tgacgtcatc gtctgcgcgg aaatggacga acagtggggc    9180
tatgtcgggg ctaaatcgcg ccagcgctgg ctgttttacg cgtatgacag tctccggaag    9240
acggttgttg cgcacgtatt cggtgaacgc actatggcga cgctggggcg tcttatgagc    9300
ctgctgtcac cctttgacgt ggtgatatgg atgacggatg gctggccgct gtatgaatcc    9360
cgcctgaagg gaaagctgca cgtaatcagc aagcgatata cgcagcgaat tgagcggcat    9420
aacctgaatc tgaggcagca cctggcacgg ctgggacgga agtcgctgtc gttctcaaaa    9480
tcggtggagc tgcatgacaa agtcatcggg cattatctga acataaaaca ctatcaataa    9540
gttggagtca ttaccaaaag gttaggaata cggttagcca tttgcctgct tttatatagt    9600
tcatatggga ttcacccttta tgttgataag aaataaaaga aatgccaat aggatatcgg    9660
catttctttt tgcgttttta tttgttaact gttaattgtc cttgttcaag gatgctgtct    9720
ttgacaacag atgttttctt gcctttgatg ttcagcagga agcttggcgc aaacgttgat    9780
tgtttgtctg cgtagaatcc tctgtttgtc atatagcttg taatcacgac attgtttcct    9840
ttcgcttgag gtacagcgaa gtgtgagtaa gtaaaggtta catcgttagg atcaagatcc    9900
attttttaaca caaggccagt tttgttcagc ggcttgtatg ggccagttaa agaattagaa    9960
acataaccaa gcatgtaaat atcgttagac gtaatgccgt caatcgtcat ttttgatccg   10020
cgggagtcag tgaacaggta ccatttgccg ttcattttaa agacgttcgc gcgttcaatt   10080
tcatctgtta ctgtgttaga tgcaatcagc ggtttcatca ctttttttcag tgtgtaatca   10140
tcgtttagct caatcatacc gagagcgccg tttgctaact cagccgtgcg ttttttatcg   10200
ctttgcagaa gttttttgact ttcttgacgg aagaatgatg tgcttttgcc atagtatgct   10260
ttgttaaata aagattcttc gccttggtag ccatcttcag ttccagtgtt tgcttcaaat   10320
actaagtatt tgtggccttt atcttctacg tagtgaggat ctctcagcgt atggttgtcg   10380
cctgagctgt agttgccttc atcgatgaac tgctgtacat tttgatacgt ttttccgtca   10440
ccgtcaaaga ttgatttata atcctctaca ccgttgatgt tcaaagagct gtctgatgct   10500
gatacgttaa cttgtgcagt tgtcagtgtt tgtttgccgt aatgtttacc ggagaaatca   10560
gtgtagaata aacggatttt tccgtcagat gtaaatgtgg ctgaacctga ccattcttgt   10620
gtttggtctt ttaggataga atcatttgca tcgaatttgt cgctgtcttt aaagacgcgg   10680
ccagcgtttt tccagctgtc aatagaagtt tcgccgactt tttgatagaa catgtaaatc   10740
gatgtgtcat ccgcattttt aggatctccg gctaatgcaa agacgatgtg gtagccgtga   10800
tagtttgcga cagtgccgtc agcgttttgt aatggccagc tgtcccaaac gtccaggcct   10860
tttgcagaag agatattttt aattgtggac gaatcgaatt caggaacttg atattttttca   10920
ttttttttgct gttcagggat ttgcagcata tcatggcgtg taatatggga aatgccgtat   10980
gtttccttat atggcttttg gttcgtttct ttcgcaaacg cttgagttgc gcctcctgcc   11040
agcagtgcgg tagtaaaggt taatactgtt gcttgttttg caaactttt gatgttcatc   11100
gttcatgtct ccttttttat gtactgtgtt agcggtctgc ttcttccagc cctcctgttt   11160
gaagatggca agttagttac gcacaataaa aaaagaccta aaatatgtaa ggggtgacgc   11220
caaagtatac actttgccct ttacacattt taggtcttgc ctgctttatc agtaacaaac   11280
ccgcgcgatt tacttttcga cctcattcta ttagactctc gtttggattg caactggtct   11340
attttcctct tttgtttgat agaaaatcat aaaaggattt gcagactacg ggcctaaaga   11400
actaaaaaat ctatctgttt cttttcattc tctgtatttt ttatagtttc tgttgcatgg   11460
gcataaagtt gccttttaa tcacaattca gaaaatatca taatatctca tttcactaaa   11520
```

```
taatagtgaa cggcaggtat atgtgatggg ttaaaaagga tcgatcctct agagtcgacc  11580
tgcaggtcga cggatctgca ggtcgacgga tcccaagctt cttctagagg taccgcatgc  11640
cctggaggaa tacgtggata aaattttcgt cgatgaagca gtaagtgaac tgcataccat  11700
tcaggacatg ttgcgctggg cggtaagccg ctttagcgcg cgaatatct ggtatggaca  11760 cggtaccgat aacccgtggg atgaagcggt acaactggtg ttgccgtctc tttatctgcc  11820
gctggatatt ccgaggata tgcggaccgc gcggctgacg tccagcgaaa gacaccgcat  11880
tgtcgagcga gtgattcgtc gcattaacga gcgtatcccg gtagcctacc tgaccaataa  11940
agcctggttc tgcggccacg aattttatgt tgatgagcgc gtgctggtgc cgcgttcacc  12000
gattggcgag ctgattaata accacttcgc tggccttatt agccaacagc gaaatatat  12060 tctggatatg tgtaccggcg gcggctgcat cgccatcgcc tgtgcttatg ctttcccgga  12120
cgcagaggtt gatgcggtcg atatttcgcc ggatgcgctg gctgtcgccg agcataacat  12180
tgaagaacac ggtcttatcc atcacgtgac gccaatccgt tccgatctgt tccgcgatct  12240
gccgaaagtt cagtacgatc tgattgtcac taacccgcct tatgtcgatg cggaggatat  12300
gtccgatctg ccgaacgaat atcgccacga acctgagctg gggctggcgt ccggcactga  12360
cggcctcaaa ttgacccgcc gtatcctggg aaatgcgccg gattatctgt ccgatgatgg  12420
cgttctgatt tgtgaagtcg gaaacagcat ggtacatctg atggagcagt atccggatgt  12480
gccgttcacc tggctggagt ttgacaacgg cggcgatggc gtctttatgt tgaccaaagc  12540
gcagttgctc gcggcccgtg aacatttcaa tatttataaa gattaaaaca cgcaaacgac  12600
aacaacgata acggagccgt gatggcagga aacacaattg gacaactctt tcgcgtaacc  12660
actttcggcg aatcacacgg gctggcgctt ggggtatcg tcgatggcgt gccgcccggc  12720
atcccgttga cggaggccga tctgcagcac gatctcgaca gacgccgccc tggcacctcg  12780
cgctatacta ctcagcgccg cgaaccggac caggtaaaaa ttctctccgg cgtgtttgat  12840
ggcgtaacga ccggc                                                 12855
```

<210> SEQ ID NO 10
<211> LENGTH: 3075
<212> TYPE: DNA
<213> ORGANISM: Artificial Sequence
<220> FEATURE:
<223> OTHER INFORMATION: CT110 E. coli codon optimized sequence

<400> SEQUENCE: 10

```
catatggaaa ccagcttcca taaattcttc ctgtctatga tcctggcgta cagctgctgt   60
tctctgaacg gtggtggtta tgcggcggaa attatggttc gcagggtat ctacgatggt  120 gaaaccctga ccgtgtcttt cccgtatacc gttatcggtg atccgagcgg tacgaccgtt  180
ttcagcgccg gtgaactgac cctgaaaaac ctggataata gcattgcggc gctgccgctg  240
tcttgcttcg gtaaccctgct gggttctttc accgttctgg gtcgtggcca tagcctgacc  300
tttgaaaaca ttcgtaccag caccaatggt gcggcgctgt ctaatagcgc ggcggatggt  360
ctgttcacca ttgaaggttt caagaactg tctttctcta actgcaatag cctgctggcg  420
gttctgccgg cggcgaccac caacaaaggc agccagaccc cgaccaccac gagcaccccg  480
tctaacggca ccatctacag caaaaccgat ctgctgctgc tgaacaacga aaaattctct  540
ttttatagca acctggtttc tggtgatggt ggtgcgattg atgcgaaaag cctgaccgtt  600
cagggtatct ctaaactgtg cgttttccag gaaacaccg cgcaggcgga tggcggtgcg  660
tgccaggttg ttacctcttt cagcgcgatg gccaatgaag cgccgattgc gtttgttgcc  720
```

```
aacgtggcgg gtgttcgtgg tggtggtatc gcggcggtgc aggatggtca gcagggtgtg      780
agctcttcta cctctaccga agatccggtg gtgagcttca gccgtaacac cgcggtggaa      840
tttgatggta acgtggcgcg cgttggtggt ggtatctaca gctacggtaa cgtggcgttc      900
ctgaacaatg gtaaaaccct gttcctgaat aacgttgcga gcccggtgta tattgcggcc      960
aaacagccga cctctggtca ggcgtctaac accagcaata actacggcga tggtggcgcc     1020
attttctgca aaaacggtgc gcaggcgggc agcaacaact ctggcagcgt gagcttcgat     1080
ggcgaaggcg tggtgttttt cagctctaat gtggcggcgg gtaaaggcgg cgcgatttat     1140
gcgaaaaaac tgtctgttgc gaactgcggc ccggtgcagt tcctgcgtaa cattgcgaac     1200
gatggtggtg cgatctacct gggtgaaagc ggcgaactgt ctctgagcgc ggattatggc     1260
gatattatct tcgatggtaa cattaaacgt accgcgaaag aaaacgcggc ggatgtgaac     1320
ggtgtgaccg tgtcttctca ggcgattagc atgggtagcg gcggcaaaat taccaccctg     1380
cgtgcgaaag cgggtcatca gatcctgttc aacgatccga tcgaaatggc gaacggtaat     1440
aaccagccgg cgcagtcttc taaactgctg aaaattaacg atggtgaagg ttacaccggt     1500
gatattgtgt tcgcgaacgg ttctagcacc ctgtatcaga acgttaccat cgaacagggc     1560
cgtatcgttc tgcgtgaaaa agcgaaactg tctgttaaca gcctgagcca gaccggtggt     1620
agcctgtata tggaagcggg ttctaccctg gatttcgtta ccccgcagcc gccgcagcag     1680
ccgccggcgg cgaatcagct gatcaccctg agcaacctgc atctgtctct gtcttctctg     1740
ctggcgaaca acgcggttac caacccgccg accaacccgc cggcgcagga ttctcatccg     1800
gcggtgattg gtagcaccac cgcgggtagc gttaccattt ctggtccgat tttctttgaa     1860
gatctggatg ataccgcgta cgatcgctac gattggctgg gtagcaacca gaaaatcaac     1920
gttctgaaac tgcaactggg caccaaaccg ccggcgaacg cgccgtctga tctgaccctg     1980
ggtaacgaaa tgccgaaata tggctaccag ggttcttgga aactggcgtg ggaccccgaac     2040 accgcgaaca acggtccgta cacccctgaaa gcgacctgga ccaaaaccgg ttacaatccg     2100
ggcccggaac gtgttgcgtc tctggttccg aactctctgt ggggcagcat tctggatatt     2160
cgcagcgcgc attctgcgat ccaggcgagc gtggatggtc gtagctattg ccgcggtctg     2220
tgggttagcg gtgtttctaa cttcttctat catgatcgcg atgcgctggg ccagggctat     2280
cgctatatta gcggtggtta tagcctgggt gcgaacagct atttcggtag cagcatgttc     2340
ggcctggcgt tcaccgaagt ttttggtcgt tctaaagatt atgttgtgtg ccgtagcaac     2400
catcatgcgt gcattggttc tgtttatctg agcacccagc aggcgctgtg cggttcttat     2460
ctgtttggcg atgcgttcat ccgtgcgtct tatggtttcg gcaaccagca catgaaaacc     2520 agctataccct ttgcggaaga aagcgatgtt cgttgggata caactgcct ggcgggtgaa     2580 attggtgcgg gcctgccgat cgttatcacc ccgagcaaac tgtatctgaa cgaactgcgc     2640
ccgtttgtgc aggcggaatt ttcttacgcg aaccatgaat ctttaccga agaaggtgat     2700 caggcgcgtg cgttcaaaag cggtcatctg ctgaacctga gcgtgccggt tggcgtgaaa     2760
tttgatcgtt gcagctctac ccatccgaac aaatacagct ttatggcggc gtatatctgt     2820
gatgcgtatc gtaccattag cggcaccgaa accacccctgc tgagccatca gggcacctgg     2880
accaccgatg cgtttcatct ggcgcgtcat ggcgttgtgg ttcgtggcag catgtatgcg     2940
agcctgacca gcaacattga agtgtatggt catggtcgtt atgaatatcg tgatgcgagc     3000
cgtggttatg gtctgagcgc gggtagccgc gttcgttttt aataaggatc cactagttct     3060
agagtcgacc tgcag                                                      3075
```

<210> SEQ ID NO 11
<211> LENGTH: 3039
<212> TYPE: DNA
<213> ORGANISM: Artificial Sequence
<220> FEATURE:
<223> OTHER INFORMATION: CT110 E. coli codon optimized coding region

<400> SEQUENCE: 11

| | | | | | |
|---|---|---|---|---|---|
| atggaaacca | gcttccataa | attcttcctg | tctatgatcc | tggcgtacag | ctgctgttct   60 |
| ctgaacggtg | gtggttatgc | ggcggaaatt | atggttccgc | agggtatcta | cgatggtgaa  120 |
| accctgaccg | tgtcttttcc | gtataccgtt | atcggtgatc | cgagcggtac | gaccgttttc  180 |
| agcgccggtg | aactgaccct | gaaaaacctg | ataatagca  | ttgcggcgct | gccgctgtct  240 |
| tgcttcggta | acctgctggg | ttcttttcacc | gttctgggtc | gtggccatag | cctgaccttt  300 |
| gaaaacattc | gtaccagcac | caatggtgcg | cgctgtcta  | atagcgcggc | ggatggtctg  360 |
| ttcaccattg | aaggtttcaa | agaactgtct | ttctctaact | gcaatagcct | gctggcggtt  420 |
| ctgccggcgg | cgaccaccaa | caaaggcagc | cagaccccga | ccaccacgag | caccccgtct  480 |
| aacggcacca | tctacagcaa | aaccgatctg | ctgctgctga | caacgaaaa  | attctctttt  540 |
| tatagcaacc | tggtttctgg | tgatggtggt | gcgattgatg | cgaaaagcct | gaccgttcag  600 |
| ggtatctcta | aactgtgcgt | tttccaggaa | aacaccgcgc | aggcggatgg | cggtgcgtgc  660 |
| caggttgtta | cctctttcag | cgccgatggc | aatgaagcgc | cgattgcgtt | tgttgccaac  720 |
| gtggcgggtg | ttcgtggtgg | tggtatcgcg | cggtgcagg  | atggtcagca | gggtgtgagc  780 |
| tcttctacct | ctaccgaaga | tccggtggtg | agcttcagcc | gtaacaccgc | ggtggaattt  840 |
| gatggtaacg | tggcgcgcgt | tggtggtggt | atctacagct | acggtaacgt | ggcgttcctg  900 |
| aacaatggta | aaccctgtt  | cctgaataac | gttgcgagcc | cggtgtatat | tgcggccaaa  960 |
| cagccgacct | ctggtcaggc | gtctaacacc | agcaataact | acggcgatgg | tggcgccatt 1020 |
| ttctgcaaaa | acggtgcgca | ggcgggcagc | aacaactctg | gcagcgtgag | cttcgatggc 1080 |
| gaaggcgtgg | tgttttttcag | ctctaatgtg | gcggcgggta | aggcggcgc  | gatttatgcg 1140 |
| aaaaaactgt | ctgttgcgaa | ctgcggcccg | gtgcagttcc | tgcgtaacat | tgcgaacgat 1200 |
| ggtggtgcga | tctacctggg | tgaaagcggc | gaactgtctc | tgagcgcgga | ttatggcgat 1260 |
| attatcttcg | atggtaacat | taaacgtacc | gcgaaagaaa | acgcggcgga | tgtgaacggt 1320 |
| gtgaccgtgt | cttctcaggc | gattagcatg | ggtagcggcg | gcaaaattac | caccctgcgt 1380 |
| gcgaaagcgg | tcatcagat  | cctgttcaac | gatccgatcg | aaatggcgaa | cggtaataac 1440 |
| cagccggcgc | agtcttctaa | actgctgaaa | attaacgatg | gtgaaggtta | caccggtgat 1500 |
| attgtgttcg | cgaacggttc | tagcaccctg | tatcagaacg | ttaccatcga | acagggccgt 1560 |
| atcgttctgc | gtgaaaaagc | gaaactgtct | gttaacagcc | tgagccagac | cggtggtagc 1620 |
| ctgtatatgg | aagcgggttc | taccctggat | ttcgttaccc | cgcagccgcc | gcagcagccg 1680 |
| ccggcggcga | atcagctgat | caccctgagc | aacctgcatc | tgtctctgtc | ttctctgctg 1740 |
| gcgaacaacg | cggttaccaa | cccgccgacc | aacccgccgg | cgcaggattc | tcatccggcg 1800 |
| gtgattggta | gcaccaccgc | gggtagcgtt | accatttctg | gtccgatttt | ctttgaagat 1860 |
| ctggatgata | ccgcgtacga | tcgctacgat | tggctgggta | gcaaccagaa | aatcaacgtt 1920 |
| ctgaaactgc | aactgggcac | caaaccgccg | gcgaacgcgc | cgtctgatct | gaccctgggt 1980 |
| aacgaaatgc | cgaaatatgg | ctaccagggt | tcttggaaac | tggcgtggga | cccgaacacc 2040 |
| gcgaacaacg | gtccgtacac | cctgaaagcg | acctggacca | aaaccggtta | caatccgggc 2100 |

-continued

```
ccggaacgtg ttgcgtctct ggttccgaac tctctgtggg gcagcattct ggatattcgc    2160
agcgcgcatt ctgcgatcca ggcgagcgtg gatggtcgta gctattgccg cggtctgtgg    2220
gttagcggtg tttctaactt cttctatcat gatcgcgatg cgctgggcca gggctatcgc    2280
tatattagcg gtggttatag cctgggtgcg aacagctatt tcggtagcag catgttcggc    2340
ctggcgttca ccgaagtttt tggtcgttct aaagattatg ttgtgtgccg tagcaaccat    2400
catgcgtgca ttggttctgt ttatctgagc acccagcagg cgctgtgcgg ttcttatctg    2460
tttggcgatg cgttcatccg tgcgtcttat ggtttcggca accagcacat gaaaaccagc    2520
tatacctttg cggaagaaag cgatgttcgt tgggataaca actgcctggc gggtgaaatt    2580
ggtgcgggcc tgccgatcgt tatcaccccg agcaaactgt atctgaacga actgcgcccg    2640
tttgtgcagg cggaattttc ttacgcgaac catgaatctt ttaccgaaga aggtgatcag    2700
gcgcgtgcgt tcaaaagcgg tcatctgctg aacctgagcg tgccggttgg cgtgaaattt    2760
gatcgttgca gctctaccca tccgaacaaa tacagcttta tggcggcgta tatctgtgat    2820
gcgtatcgta ccattagcgg caccgaaacc accctgctga gccatcaggg cacctggacc    2880
accgatgcgt tcatctggc gcgtcatggc gttgtggttc gtggcagcat gtatgcgagc    2940
ctgaccagca acattgaagt gtatggtcat ggtcgttatg aatatcgtga tgcgagccgt    3000
ggttatggtc tgagcgcggg tagccgcgtt cgttttttaa                         3039
```

<210> SEQ ID NO 12
<211> LENGTH: 1012
<212> TYPE: PRT
<213> ORGANISM: Chlamydia muridarum

<400> SEQUENCE: 12

```
Met Glu Thr Ser Phe His Lys Phe Phe Leu Ser Met Ile Leu Ala Tyr
  1               5                  10                  15

Ser Cys Cys Ser Leu Asn Gly Gly Gly Tyr Ala Ala Glu Ile Met Val
                 20                  25                  30

Pro Gln Gly Ile Tyr Asp Gly Glu Thr Leu Thr Val Ser Phe Pro Tyr
             35                  40                  45

Thr Val Ile Gly Asp Pro Ser Gly Thr Thr Val Phe Ser Ala Gly Glu
         50                  55                  60

Leu Thr Leu Lys Asn Leu Asp Asn Ser Ile Ala Ala Leu Pro Leu Ser
 65                  70                  75                  80

Cys Phe Gly Asn Leu Leu Gly Ser Phe Thr Val Leu Gly Arg Gly His
                 85                  90                  95

Ser Leu Thr Phe Glu Asn Ile Arg Thr Ser Asn Gly Ala Ala Leu
                100                 105                 110

Ser Asn Ser Ala Ala Asp Gly Leu Phe Thr Ile Glu Gly Phe Lys Glu
            115                 120                 125

Leu Ser Phe Ser Asn Cys Asn Ser Leu Leu Ala Val Leu Pro Ala Ala
        130                 135                 140

Thr Thr Asn Lys Gly Ser Gln Thr Pro Thr Thr Thr Ser Thr Pro Ser
145                 150                 155                 160

Asn Gly Thr Ile Tyr Ser Lys Thr Asp Leu Leu Leu Asn Asn Glu
                165                 170                 175

Lys Phe Ser Phe Tyr Ser Asn Leu Val Ser Gly Asp Gly Ala Ile
            180                 185                 190

Asp Ala Lys Ser Leu Thr Val Gln Gly Ile Ser Lys Leu Cys Val Phe
        195                 200                 205

Gln Glu Asn Thr Ala Gln Ala Asp Gly Gly Ala Cys Gln Val Val Thr
```

```
              210                 215                 220
Ser Phe Ser Ala Met Ala Asn Glu Ala Pro Ile Ala Phe Val Ala Asn
225                 230                 235                 240

Val Ala Gly Val Arg Gly Gly Ile Ala Ala Val Gln Asp Gly Gln
                245                 250                 255

Gln Gly Val Ser Ser Thr Ser Thr Glu Asp Pro Val Val Ser Phe
                260                 265                 270

Ser Arg Asn Thr Ala Val Glu Phe Asp Gly Asn Val Ala Arg Val Gly
                275                 280                 285

Gly Gly Ile Tyr Ser Tyr Gly Asn Val Ala Phe Leu Asn Asn Gly Lys
                290                 295                 300

Thr Leu Phe Leu Asn Asn Val Ala Ser Pro Val Tyr Ile Ala Ala Lys
305                 310                 315                 320

Gln Pro Thr Ser Gly Gln Ala Ser Asn Thr Ser Asn Asn Tyr Gly Asp
                325                 330                 335

Gly Gly Ala Ile Phe Cys Lys Asn Gly Ala Gln Ala Gly Ser Asn Asn
                340                 345                 350

Ser Gly Ser Val Ser Phe Asp Gly Glu Gly Val Val Phe Phe Ser Ser
                355                 360                 365

Asn Val Ala Ala Gly Lys Gly Gly Ala Ile Tyr Ala Lys Lys Leu Ser
                370                 375                 380

Val Ala Asn Cys Gly Pro Val Gln Phe Leu Arg Asn Ile Ala Asn Asp
385                 390                 395                 400

Gly Gly Ala Ile Tyr Leu Gly Glu Ser Gly Glu Leu Ser Leu Ser Ala
                405                 410                 415

Asp Tyr Gly Asp Ile Ile Phe Asp Gly Asn Ile Lys Arg Thr Ala Lys
                420                 425                 430

Glu Asn Ala Ala Asp Val Asn Gly Val Thr Val Ser Ser Gln Ala Ile
                435                 440                 445

Ser Met Gly Ser Gly Gly Lys Ile Thr Thr Leu Arg Ala Lys Ala Gly
                450                 455                 460

His Gln Ile Leu Phe Asn Asp Pro Ile Glu Met Ala Asn Gly Asn Asn
465                 470                 475                 480

Gln Pro Ala Gln Ser Ser Lys Leu Leu Lys Ile Asn Asp Gly Glu Gly
                485                 490                 495

Tyr Thr Gly Asp Ile Val Phe Ala Asn Gly Ser Ser Thr Leu Tyr Gln
                500                 505                 510

Asn Val Thr Ile Glu Gln Gly Arg Ile Val Leu Arg Glu Lys Ala Lys
                515                 520                 525

Leu Ser Val Asn Ser Leu Ser Gln Thr Gly Gly Ser Leu Tyr Met Glu
530                 535                 540

Ala Gly Ser Thr Leu Asp Phe Val Thr Pro Gln Pro Gln Gln Pro
545                 550                 555                 560

Pro Ala Asn Gln Leu Ile Thr Leu Ser Asn Leu His Leu Ser Leu
                565                 570                 575

Ser Ser Leu Leu Ala Asn Asn Ala Val Thr Asn Pro Pro Thr Asn Pro
                580                 585                 590

Pro Ala Gln Asp Ser His Pro Ala Val Ile Gly Ser Thr Thr Ala Gly
                595                 600                 605

Ser Val Thr Ile Ser Gly Pro Ile Phe Phe Glu Asp Leu Asp Asp Thr
                610                 615                 620

Ala Tyr Asp Arg Tyr Asp Trp Leu Gly Ser Asn Gln Lys Ile Asn Val
625                 630                 635                 640
```

```
Leu Lys Leu Gln Leu Gly Thr Lys Pro Pro Ala Asn Ala Pro Ser Asp
                645                 650                 655

Leu Thr Leu Gly Asn Glu Met Pro Lys Tyr Gly Tyr Gln Gly Ser Trp
            660                 665                 670

Lys Leu Ala Trp Asp Pro Asn Thr Ala Asn Asn Gly Pro Tyr Thr Leu
        675                 680                 685

Lys Ala Thr Trp Thr Lys Thr Gly Tyr Asn Pro Gly Pro Glu Arg Val
    690                 695                 700

Ala Ser Leu Val Pro Asn Ser Leu Trp Gly Ser Ile Leu Asp Ile Arg
705                 710                 715                 720

Ser Ala His Ser Ala Ile Gln Ala Val Asp Gly Arg Ser Tyr Cys
                725                 730                 735

Arg Gly Leu Trp Val Ser Gly Val Ser Asn Phe Phe Tyr His Asp Arg
            740                 745                 750

Asp Ala Leu Gly Gln Gly Tyr Arg Tyr Ile Ser Gly Tyr Ser Leu
        755                 760                 765

Gly Ala Asn Ser Tyr Phe Gly Ser Ser Met Phe Gly Leu Ala Phe Thr
    770                 775                 780

Glu Val Phe Gly Arg Ser Lys Asp Tyr Val Val Cys Arg Ser Asn His
785                 790                 795                 800

His Ala Cys Ile Gly Ser Val Tyr Leu Ser Thr Gln Ala Leu Cys
                805                 810                 815

Gly Ser Tyr Leu Phe Gly Asp Ala Phe Ile Arg Ala Ser Tyr Gly Phe
            820                 825                 830

Gly Asn Gln His Met Lys Thr Ser Tyr Thr Phe Ala Glu Glu Ser Asp
        835                 840                 845

Val Arg Trp Asp Asn Asn Cys Leu Ala Gly Glu Ile Gly Ala Gly Leu
    850                 855                 860

Pro Ile Val Ile Thr Pro Ser Lys Leu Tyr Leu Asn Glu Leu Arg Pro
865                 870                 875                 880

Phe Val Gln Ala Glu Phe Ser Tyr Ala Asn His Glu Ser Phe Thr Glu
                885                 890                 895

Glu Gly Asp Gln Ala Arg Ala Phe Lys Ser Gly His Leu Leu Asn Leu
            900                 905                 910

Ser Val Pro Val Gly Val Lys Phe Asp Arg Cys Ser Ser Thr His Pro
        915                 920                 925

Asn Lys Tyr Ser Phe Met Ala Ala Tyr Ile Cys Asp Ala Tyr Arg Thr
    930                 935                 940

Ile Ser Gly Thr Glu Thr Thr Leu Leu Ser His Gln Gly Thr Trp Thr
945                 950                 955                 960

Thr Asp Ala Phe His Leu Ala Arg His Gly Val Val Val Arg Gly Ser
                965                 970                 975

Met Tyr Ala Ser Leu Thr Ser Asn Ile Glu Val Tyr Gly His Gly Arg
            980                 985                 990

Tyr Glu Tyr Arg Asp Ala Ser Arg  Gly Tyr Gly Leu Ser  Ala Gly Ser
        995                 1000                 1005

Arg Val  Arg Phe
    1010

<210> SEQ ID NO 13
<211> LENGTH: 2295
<212> TYPE: DNA
<213> ORGANISM: Artificial Sequence
<220> FEATURE:
<223> OTHER INFORMATION: CT84 E. coli codon optimized sequence
```

<400> SEQUENCE: 13

```
catatggaaa ttatggttcc gcagggtatc tacgatggtg aaaccctgac cgtgtctttc      60
ccgtataccg ttatcggtga tccgagcggt acgaccgttt tcagcgccgg tgaactgacc     120
ctgaaaaacc tggataatag cattgcggcg ctgccgctgt cttgcttcgg taacctgctg     180
ggttctttca ccgttctggg tcgtggccat agcctgacct ttgaaaacat tcgtaccagc     240
accaatggtg cggcgctgtc taatagcgcg cggatggtc tgttcaccat tgaaggtttc     300
aaagaactgt ctttctctaa ctgcaatagc ctgctggcgg ttctgccggc ggcgaccacc     360
aacaaaggca gccagacccc gaccaccacg agcaccccgt ctaacggcac catctacagc     420
aaaaccgatc tgctgctgct gaacaacgaa aaattctctt tttatagcaa cctggtttct     480
ggtgatggtg gtgcgattga tgcgaaaagc ctgaccgttc agggtatctc taaactgtgc     540
gttttccagg aaaacaccgc gcaggcggat ggcggtgcgt gccaggttgt tacctctttc     600
agcgcgatgg ccaatgaagc gccgattgcg tttgttgcca acgtggcggg tgttcgtggt     660
ggtggtatcg cggcggtgca ggatggtcag cagggtgtga gctcttctac ctctaccgaa     720
gatccggtgg tgagcttcag ccgtaacacc gcggtggaat tgatggtaa cgtgcgcgc     780
gttggtggtg gtatctacag ctacggtaac gtggcgttcc tgaacaatgg taaaaccctg     840
ttcctgaata cgttgcgag cccggtgtat attgcggcca acagccgac ctctggtcag     900
gcgtctaaca ccagcaataa ctacggcgat ggtggcgcca ttttctgcaa aaacggtgcg     960
caggcgggca gcaacaactc tggcagcgtg agcttcgatg gcgaaggcgt ggtgttttc    1020
agctctaatg tggcggcggg taaaggcggc gcgatttatg cgaaaaaact gtctgttgcg    1080
aactgcggcc cggtgcagtt cctgcgtaac attgcgaacg atggtggtgc gatctacctg    1140
ggtgaaagcg gcgaactgtc tctgagcgcg gattatggcg atattatctt cgatggtaac    1200
attaaacgta ccgcgaaaga aaacgcggcg gatgtgaacg tgtgaccgt gtcttctcag    1260
gcgattagca tgggtagcgg cggcaaaatt accaccctgc gtgcgaaagc gggtcatcag    1320
atcctgttca cgatccgat cgaaatggcg aacggtaata accagccggc gcagtcttct    1380
aaactgctga aaattaacga tggtgaaggt tacaccggtg atattgtgtt cgcgaacggt    1440
tctagcaccc tgtatcagaa cgttaccatc gaacagggcc gtatcgttct gcgtgaaaaa    1500
gcgaaactgt ctgttaacag cctgagccag accggtggta gcctgtatat ggaagcgggt    1560
tctacccctgg atttcgttac cccgcagccg ccgcagcagc cgccggcggc gaatcagctg    1620
atcaccctga gcaacctgca tctgtctctg tcttctctgc tggcgaacaa cgcggttacc    1680
aacccgccga ccaacccgcc ggcgcaggat tctcatccgg cggtgattgg tagcaccacc    1740
gcgggtagcg ttaccatttc tggtccgatt ttctttgaag atctggatga taccgcgtac    1800
gatcgctacg attggctggg tagcaaccag aaaatcaacg ttctgaaact gcaactgggc    1860
accaaaccgc cggcgaacgc gccgtctgat ctgaccctgg gtaacgaaat gccgaaatat    1920
ggctaccagg gttcttggaa actggcgtgg gacccgaaca ccgcgaacaa cggtccgtac    1980
accctgaaag cgacctggac caaaaccggt tacaatccgg gccgaacg tgttgcgtct    2040
ctggttccga actctctgtg gggcagcatt ctggatattc gcagcgcgca ttctgcgatc    2100
caggcgagcg tggatggtcg tagctattgc cgcggtctgt gggttagcgg tgtttctaac    2160
ttcttctatc atgatcgcga tgcgctgggc cagggctatc gctatattag cggtggttat    2220
agcctgggtg cgaacagcta tttcggtagc agcatgttcg gcctggcgtt cacctaatct    2280
agagtcgacc tgcag                                                     2295
```

<210> SEQ ID NO 14
<211> LENGTH: 2274
<212> TYPE: DNA
<213> ORGANISM: Artificial Sequence
<220> FEATURE:
<223> OTHER INFORMATION: CT84 E. coli codon optimized coding region

<400> SEQUENCE: 14

| | | | | | |
|---|---|---|---|---|---|
| atggaaatta | tggttccgca | gggtatctac | gatggtgaaa | ccctgaccgt | gtctttcccg | 60 |
| tataccgtta | tcggtgatcc | gagcggtacg | accgttttca | gcgccggtga | actgaccctg | 120 |
| aaaaacctgg | ataatagcat | tgcggcgctg | ccgctgtctt | gcttcggtaa | cctgctgggt | 180 |
| tctttcaccg | ttctgggtcg | tggccatagc | ctgacctttg | aaaacattcg | taccagcacc | 240 |
| aatggtgcgg | cgctgtctaa | tagcgcgcg | atggtctgt | tcaccattga | aggtttcaaa | 300 |
| gaactgtctt | tctctaactg | caatagcctg | ctggcggttc | tgccggcggc | gaccaccaac | 360 |
| aaaggcagcc | agaccccgac | caccacgagc | accccgtcta | acggcaccat | ctacagcaaa | 420 |
| accgatctgc | tgctgctgaa | caacgaaaaa | ttctcttttt | atagcaacct | ggtttctggt | 480 |
| gatggtggtg | cgattgatgc | gaaaagcctg | accgttcagg | gtatctctaa | actgtgcgtt | 540 |
| ttccaggaaa | acaccgcgca | ggcggatggc | ggtgcgtgcc | aggttgttac | ctcttttcagc | 600 |
| gcgatggcca | tgaagcgcc | gattgcgttt | gttgccaacg | tggcgggtgt | tcgtggtggt | 660 |
| ggtatcgcgg | cggtgcagga | tggtcagcag | ggtgtgagct | cttctacctc | taccgaagat | 720 |
| ccggtggtga | gcttcagccg | taacaccgcg | gtggaatttg | atggtaacgt | ggcgcgcgtt | 780 |
| ggtggtggta | tctacagcta | cggtaacgtg | gcgttcctga | caatggtaa | aaccctgttc | 840 |
| ctgaataacg | ttgcgagccc | ggtgtatatt | gcggccaaac | agccgacctc | tggtcaggcg | 900 |
| tctaacacca | gcaataacta | cggcgatggt | ggcgccattt | tctgcaaaaa | cggtgcgcag | 960 |
| gcggcagca | acaactctgg | cagcgtgagc | ttcgatggcg | aaggcgtggt | gttttttcagc | 1020 |
| tctaatgtgg | cggcgggtaa | aggcggcgcg | atttatgcga | aaaaactgtc | tgttgcgaac | 1080 |
| tgcggcccgg | tgcagttcct | gcgtaacatt | gcgaacgatg | tggtgcgat | ctacctgggt | 1140 |
| gaaagcggcg | aactgtctct | gagcgcgat | tatggcgata | ttatcttcga | tggtaacatt | 1200 |
| aaacgtaccg | cgaaagaaaa | cgcggcggat | gtgaacggtg | tgaccgtgtc | ttctcaggcg | 1260 |
| attagcatgg | tagcggcgg | caaaattacc | accctgcgtg | cgaaagcggg | tcatcagatc | 1320 |
| ctgttcaacg | atccgatcga | atggcgaac | ggtaataacc | agccggcgca | gtcttctaaa | 1380 |
| ctgctgaaaa | ttaacgatgg | tgaaggttac | accggtgata | ttgtgttcgc | gaacggttct | 1440 |
| agcaccctgt | atcagaacgt | taccatcgaa | cagggccgta | tcgttctgcg | tgaaaaagcg | 1500 |
| aaactgtctg | ttaacagcct | gagccagacc | ggtggtagcc | tgtatatgga | agcgggttct | 1560 |
| accctggatt | tcgttacccc | gcagccgccg | cagcagccgc | cggcggcgaa | tcagctgatc | 1620 |
| accctgagca | acctgcatct | gtctctgtct | tctctgctgg | caacaacgc | ggttaccaac | 1680 |
| ccgccgacca | acccgccggc | gcaggattct | catccggcgg | tgattggtag | caccaccgcg | 1740 |
| ggtagcgtta | ccatttctgg | tccgattttc | tttgaagatc | tggatgatac | cgcgtacgat | 1800 |
| cgctacgatt | ggctgggtag | caaccagaaa | atcaacgttc | tgaaactgca | actgggcacc | 1860 |
| aaaccgccgg | cgaacgcgcc | gtctgatctg | accctgggta | cgaaatgcc | gaaatatggc | 1920 |
| taccagggtt | cttggaaact | ggcgtgggac | ccgaacaccg | cgaacaacgg | tccgtacacc | 1980 |
| ctgaaagcga | cctggaccaa | aaccggttac | aatccgggcc | cggaacgtgt | tgcgtctctg | 2040 |
| gttccgaact | ctctgtgggg | cagcattctg | gatattcgca | gcgcgcattc | tgcgatccag | 2100 |

```
gcgagcgtgg atggtcgtag ctattgccgc ggtctgtggg ttagcggtgt ttctaacttc   2160
ttctatcatg atcgcgatgc gctgggccag ggctatcgct atattagcgg tggttatagc   2220
ctgggtgcga acagctattt cggtagcagc atgttcggcc tggcgttcac ctaa         2274
```

<210> SEQ ID NO 15
<211> LENGTH: 757
<212> TYPE: PRT
<213> ORGANISM: Chlamydia muridarum

<400> SEQUENCE: 15

```
Met Glu Ile Met Val Pro Gln Gly Ile Tyr Asp Gly Glu Thr Leu Thr
1               5                   10                  15

Val Ser Phe Pro Tyr Thr Val Ile Gly Asp Pro Ser Gly Thr Thr Val
            20                  25                  30

Phe Ser Ala Gly Glu Leu Thr Leu Lys Asn Leu Asp Asn Ser Ile Ala
        35                  40                  45

Ala Leu Pro Leu Ser Cys Phe Gly Asn Leu Gly Ser Phe Thr Val
    50                  55                  60

Leu Gly Arg Gly His Ser Leu Thr Phe Glu Asn Ile Arg Thr Ser Thr
65                  70                  75                  80

Asn Gly Ala Ala Leu Ser Asn Ser Ala Ala Asp Gly Leu Phe Thr Ile
                85                  90                  95

Glu Gly Phe Lys Glu Leu Ser Phe Ser Asn Cys Asn Ser Leu Leu Ala
            100                 105                 110

Val Leu Pro Ala Ala Thr Thr Asn Lys Gly Ser Gln Thr Pro Thr Thr
        115                 120                 125

Thr Ser Thr Pro Ser Asn Gly Thr Ile Tyr Ser Lys Thr Asp Leu Leu
    130                 135                 140

Leu Leu Asn Asn Glu Lys Phe Ser Phe Tyr Ser Asn Leu Val Ser Gly
145                 150                 155                 160

Asp Gly Gly Ala Ile Asp Ala Lys Ser Leu Thr Val Gln Gly Ile Ser
                165                 170                 175

Lys Leu Cys Val Phe Gln Glu Asn Thr Ala Gln Ala Asp Gly Gly Ala
            180                 185                 190

Cys Gln Val Val Thr Ser Phe Ser Ala Met Ala Asn Glu Ala Pro Ile
        195                 200                 205

Ala Phe Val Ala Asn Val Ala Gly Val Arg Gly Gly Ile Ala Ala
    210                 215                 220

Val Gln Asp Gly Gln Gln Gly Val Ser Ser Thr Ser Thr Glu Asp
225                 230                 235                 240

Pro Val Val Ser Phe Ser Arg Asn Thr Ala Val Glu Phe Asp Gly Asn
                245                 250                 255

Val Ala Arg Val Gly Gly Gly Ile Tyr Ser Tyr Gly Asn Val Ala Phe
            260                 265                 270

Leu Asn Asn Gly Lys Thr Leu Phe Leu Asn Asn Val Ala Ser Pro Val
        275                 280                 285

Tyr Ile Ala Ala Lys Gln Pro Thr Ser Gly Gln Ala Ser Asn Thr Ser
    290                 295                 300

Asn Asn Tyr Gly Asp Gly Gly Ala Ile Phe Cys Lys Asn Gly Ala Gln
305                 310                 315                 320

Ala Gly Ser Asn Asn Ser Gly Ser Val Ser Phe Asp Gly Glu Gly Val
                325                 330                 335

Val Phe Ser Ser Asn Val Ala Gly Lys Gly Gly Ala Ile Tyr
            340                 345                 350
```

```
Ala Lys Lys Leu Ser Val Ala Asn Cys Gly Pro Val Gln Phe Leu Arg
        355                 360                 365

Asn Ile Ala Asn Asp Gly Gly Ala Ile Tyr Leu Gly Glu Ser Gly Glu
370             375                 380

Leu Ser Leu Ser Ala Asp Tyr Gly Asp Ile Ile Phe Asp Gly Asn Ile
385                 390                 395                 400

Lys Arg Thr Ala Lys Glu Asn Ala Ala Asp Val Asn Gly Val Thr Val
                405                 410                 415

Ser Ser Gln Ala Ile Ser Met Gly Ser Gly Gly Lys Ile Thr Thr Leu
            420                 425                 430

Arg Ala Lys Ala Gly His Gln Ile Leu Phe Asn Asp Pro Ile Glu Met
        435                 440                 445

Ala Asn Gly Asn Asn Gln Pro Ala Gln Ser Ser Lys Leu Leu Lys Ile
450                 455                 460

Asn Asp Gly Glu Gly Tyr Thr Gly Asp Ile Val Phe Ala Asn Gly Ser
465                 470                 475                 480

Ser Thr Leu Tyr Gln Asn Val Thr Ile Glu Gln Gly Arg Ile Val Leu
                485                 490                 495

Arg Glu Lys Ala Lys Leu Ser Val Asn Ser Leu Ser Gln Thr Gly Gly
            500                 505                 510

Ser Leu Tyr Met Glu Ala Gly Ser Thr Leu Asp Phe Val Thr Pro Gln
        515                 520                 525

Pro Pro Gln Gln Pro Pro Ala Ala Asn Gln Leu Ile Thr Leu Ser Asn
530                 535                 540

Leu His Leu Ser Leu Ser Ser Leu Leu Ala Asn Asn Ala Val Thr Asn
545                 550                 555                 560

Pro Pro Thr Asn Pro Pro Ala Gln Asp Ser His Pro Ala Val Ile Gly
                565                 570                 575

Ser Thr Thr Ala Gly Ser Val Thr Ile Ser Gly Pro Ile Phe Phe Glu
            580                 585                 590

Asp Leu Asp Asp Thr Ala Tyr Asp Arg Tyr Asp Trp Leu Gly Ser Asn
        595                 600                 605

Gln Lys Ile Asn Val Leu Lys Leu Gln Leu Gly Thr Lys Pro Pro Ala
610                 615                 620

Asn Ala Pro Ser Asp Leu Thr Leu Gly Asn Glu Met Pro Lys Tyr Gly
625                 630                 635                 640

Tyr Gln Gly Ser Trp Lys Leu Ala Trp Asp Pro Asn Thr Ala Asn Asn
                645                 650                 655

Gly Pro Tyr Thr Leu Lys Ala Thr Trp Thr Lys Thr Gly Tyr Asn Pro
            660                 665                 670

Gly Pro Glu Arg Val Ala Ser Leu Val Pro Asn Ser Leu Trp Gly Ser
        675                 680                 685

Ile Leu Asp Ile Arg Ser Ala His Ser Ala Ile Gln Ala Ser Val Asp
690                 695                 700

Gly Arg Ser Tyr Cys Arg Gly Leu Trp Val Ser Gly Val Ser Asn Phe
705                 710                 715                 720

Phe Tyr His Asp Arg Asp Ala Leu Gly Gln Tyr Arg Tyr Ile Ser
                725                 730                 735

Gly Gly Tyr Ser Leu Gly Ala Asn Ser Tyr Phe Gly Ser Ser Met Phe
            740                 745                 750

Gly Leu Ala Phe Thr
        755
```

<210> SEQ ID NO 16

```
<211> LENGTH: 4435
<212> TYPE: DNA
<213> ORGANISM: Chlamydia trachomatis serovar L2
<220> FEATURE:
<221> NAME/KEY: CDS
<222> LOCATION: (382)..(3420)

<400> SEQUENCE: 16
gggcaaaact cttccccccg ggatttatat gggaaagggg aaactttggc ccgtattcaa      60
gcgccacggg ttttggggcg aatgaatttt tttcgttccg gaaaaagtaa ttccccggga     120
acgtagggta tcggtttcat aggctcgcca aatgggatat aggtggaaag gtaaaaaaaa     180
ctgagccaag caaaggatag agaagtcttg taatcatcgc aggttaaagg ggggatgtta     240
ttttagcctg caaatagtgt aattattgga tcctgtaaag agaaaaggac gaatgcgctg     300
aagataagaa catttattga tattaaatta ttaattttt atgaagcgga gtaattaatt     360
```

| | | | |
|---|---|---|---|
| ttatctctca gcttttgtgt g atg caa acg tct ttc cat aag ttc ttt ctt | | | 411 |
| Met Gln Thr Ser Phe His Lys Phe Phe Leu | | | |
| 1 5 10 | | | | tca atg att cta gct tat tct tgc tgc tct tta aat ggg ggg gga tat      459
Ser Met Ile Leu Ala Tyr Ser Cys Cys Ser Leu Asn Gly Gly Gly Tyr
         15                  20                  25 gca gca gaa atc atg gtt cct caa gga att tac gat ggg gag acg tta      507
Ala Ala Glu Ile Met Val Pro Gln Gly Ile Tyr Asp Gly Glu Thr Leu
     30                  35                  40 act gta tca ttt ccc tat act gtt ata gga gat ccg agt ggg act act      555
Thr Val Ser Phe Pro Tyr Thr Val Ile Gly Asp Pro Ser Gly Thr Thr
 45                  50                  55 gtt ttt tct gca gga gag tta aca tta aaa aat ctt gac aat tct att      603
Val Phe Ser Ala Gly Glu Leu Thr Leu Lys Asn Leu Asp Asn Ser Ile
 60                  65                  70 gca gct ttg cct tta agt tgt ttt ggg aac tta tta ggg agt ttt act      651
Ala Ala Leu Pro Leu Ser Cys Phe Gly Asn Leu Leu Gly Ser Phe Thr
75                  80                  85                  90 gtt tta ggg aga gga cac tcg ttg act ttc gag aac ata cgg act tct      699
Val Leu Gly Arg Gly His Ser Leu Thr Phe Glu Asn Ile Arg Thr Ser
             95                 100                 105 aca aat ggg gca gct cta agt aat agc gct gct gat gga ctg ttt act      747
Thr Asn Gly Ala Ala Leu Ser Asn Ser Ala Ala Asp Gly Leu Phe Thr
         110                 115                 120 att gag ggt ttt aaa gaa tta tcc ttt tcc aat tgc aat tca tta ctt      795
Ile Glu Gly Phe Lys Glu Leu Ser Phe Ser Asn Cys Asn Ser Leu Leu
     125                 130                 135 gcc gta ctg cct gct gca acg act aat aag ggt agc cag act ccg acg      843
Ala Val Leu Pro Ala Ala Thr Thr Asn Lys Gly Ser Gln Thr Pro Thr
 140                 145                 150 aca aca tct aca ccg tct aat ggt act att tat tct aaa aca gat ctt      891
Thr Thr Ser Thr Pro Ser Asn Gly Thr Ile Tyr Ser Lys Thr Asp Leu
155                 160                 165                 170 ttg tta ctc aat aat gag aag ttc tca ttc tat agt aat tta gtc tct      939
Leu Leu Leu Asn Asn Glu Lys Phe Ser Phe Tyr Ser Asn Leu Val Ser
             175                 180                 185 gga gat ggg gga gct ata gat gct aag agc tta acg gtt caa gga att      987
Gly Asp Gly Gly Ala Ile Asp Ala Lys Ser Leu Thr Val Gln Gly Ile
         190                 195                 200 agc aag ctt tgt gtc ttc caa gaa aat act gct caa gct gat ggg gga     1035
Ser Lys Leu Cys Val Phe Gln Glu Asn Thr Ala Gln Ala Asp Gly Gly
     205                 210                 215 gct tgt caa gta gtc acc agt ttc tct gct atg gct aac gag gct cct     1083
Ala Cys Gln Val Val Thr Ser Phe Ser Ala Met Ala Asn Glu Ala Pro
 220                 225                 230

-continued

| | | |
|---|---|---|
| att gcc ttt gta gcg aat gtt gca gga gta aga ggg gga ggg att gct<br>Ile Ala Phe Val Ala Asn Val Ala Gly Val Arg Gly Gly Gly Ile Ala<br>235                240                245                250 | 1131 |
| gct gtt cag gat ggg cag cag gga gtg tca tca tct act tca aca gaa<br>Ala Val Gln Asp Gly Gln Gln Gly Val Ser Ser Ser Thr Ser Thr Glu<br>                255                260                265 | 1179 |
| gat cca gta gta agt ttt tcc aga aat act gcg gta gag ttt gat ggg<br>Asp Pro Val Val Ser Phe Ser Arg Asn Thr Ala Val Glu Phe Asp Gly<br>            270                275                280 | 1227 |
| aac gta gcc cga gta gga gga ggg att tac tcc tac ggg aac gtt gct<br>Asn Val Ala Arg Val Gly Gly Gly Ile Tyr Ser Tyr Gly Asn Val Ala<br>                285                290                295 | 1275 |
| ttc ctg aat aat gga aaa acc ttg ttt ctc aac aat gtt gct tct cct<br>Phe Leu Asn Asn Gly Lys Thr Leu Phe Leu Asn Asn Val Ala Ser Pro<br>300                305                310 | 1323 |
| gtt tac att gct gct aag caa cca aca agt gga cag gct tct aat acg<br>Val Tyr Ile Ala Ala Lys Gln Pro Thr Ser Gly Gln Ala Ser Asn Thr<br>315                320                325                330 | 1371 |
| agt aat aat tac gga gat gga gga gct atc ttc tgt aag aat ggt gcg<br>Ser Asn Asn Tyr Gly Asp Gly Gly Ala Ile Phe Cys Lys Asn Gly Ala<br>                335                340                345 | 1419 |
| caa gca gga tcc aat aac tct gga tca gtt tcc ttt gat gga gag gga<br>Gln Ala Gly Ser Asn Asn Ser Gly Ser Val Ser Phe Asp Gly Glu Gly<br>            350                355                360 | 1467 |
| gta gtt ttc ttt agt agc aat gta gct gct ggg aaa ggg gga gct att<br>Val Val Phe Phe Ser Ser Asn Val Ala Ala Gly Lys Gly Gly Ala Ile<br>                365                370                375 | 1515 |
| tat gcc aaa aag ctc tcg gtt gct aac tgt ggc cct gta caa ttt tta<br>Tyr Ala Lys Lys Leu Ser Val Ala Asn Cys Gly Pro Val Gln Phe Leu<br>380                385                390 | 1563 |
| agg aat atc gct aat gat ggt gga gcg att tat tta gga gaa tct gga<br>Arg Asn Ile Ala Asn Asp Gly Gly Ala Ile Tyr Leu Gly Glu Ser Gly<br>395                400                405                410 | 1611 |
| gag ctc agt tta tct gct gat tat gga gat att att ttc gat ggg aat<br>Glu Leu Ser Leu Ser Ala Asp Tyr Gly Asp Ile Ile Phe Asp Gly Asn<br>                415                420                425 | 1659 |
| ctt aaa aga aca gcc aaa gag aat gct gcc gat gtt aat ggc gta act<br>Leu Lys Arg Thr Ala Lys Glu Asn Ala Ala Asp Val Asn Gly Val Thr<br>            430                435                440 | 1707 |
| gtg tcc tca caa gcc att tcg atg gga tcg gga ggg aaa ata acg aca<br>Val Ser Ser Gln Ala Ile Ser Met Gly Ser Gly Gly Lys Ile Thr Thr<br>            445                450                455 | 1755 |
| tta aga gct aaa gca ggg cat cag att ctc ttt aat gat ccc atc gag<br>Leu Arg Ala Lys Ala Gly His Gln Ile Leu Phe Asn Asp Pro Ile Glu<br>460                465                470 | 1803 |
| atg gca aac gga aat aac cag cca gcg cag tct tcc aaa ctt cta aaa<br>Met Ala Asn Gly Asn Asn Gln Pro Ala Gln Ser Ser Lys Leu Leu Lys<br>475                480                485                490 | 1851 |
| att aac gat ggt gaa gga tac aca ggg gat att gtt ttt gct aat gga<br>Ile Asn Asp Gly Glu Gly Tyr Thr Gly Asp Ile Val Phe Ala Asn Gly<br>                495                500                505 | 1899 |
| agc agt act ttg tac caa aat gtt acg ata gag caa gga agg att gtt<br>Ser Ser Thr Leu Tyr Gln Asn Val Thr Ile Glu Gln Gly Arg Ile Val<br>            510                515                520 | 1947 |
| ctt cgt gaa aag gca aaa tta tca gtg aat tct cta agt cag aca ggt<br>Leu Arg Glu Lys Ala Lys Leu Ser Val Asn Ser Leu Ser Gln Thr Gly<br>525                530                535 | 1995 |
| ggg agt ctg tat atg gaa gct ggg agt aca tgg gat ttt gta act cca<br>Gly Ser Leu Tyr Met Glu Ala Gly Ser Thr Trp Asp Phe Val Thr Pro<br>540                545                550 | 2043 |

```
caa cca cca caa cag cct cct gcc gct aat cag ttg atc acg ctt tcc    2091
Gln Pro Pro Gln Gln Pro Pro Ala Ala Asn Gln Leu Ile Thr Leu Ser
555                 560                 565                 570 aat ctg cat ttg tct ctt tct tct ttg tta gca aac aat gca gtt acg    2139
Asn Leu His Leu Ser Leu Ser Ser Leu Leu Ala Asn Asn Ala Val Thr
            575                 580                 585 aat cct cct acc aat cct cca gcg caa gat tct cat cct gca gtc att    2187
Asn Pro Pro Thr Asn Pro Pro Ala Gln Asp Ser His Pro Ala Val Ile
            590                 595                 600 ggt agc aca act gct ggt tct gtt aca att agt ggg cct atc ttt ttt    2235
Gly Ser Thr Thr Ala Gly Ser Val Thr Ile Ser Gly Pro Ile Phe Phe
            605                 610                 615 gag gat ttg gat gat aca gct tat gat agg tat gat tgg cta ggt tct    2283
Glu Asp Leu Asp Asp Thr Ala Tyr Asp Arg Tyr Asp Trp Leu Gly Ser
620                 625                 630 aat caa aaa atc aat gtc ctg aaa tta cag tta ggg act aag ccc cca    2331
Asn Gln Lys Ile Asn Val Leu Lys Leu Gln Leu Gly Thr Lys Pro Pro
635                 640                 645                 650 gct aat gcc cca tca gat ttg act cta ggg aat gag atg cct aag tat    2379
Ala Asn Ala Pro Ser Asp Leu Thr Leu Gly Asn Glu Met Pro Lys Tyr
            655                 660                 665 ggc tat caa gga agc tgg aag ctt gcg tgg gat cct aat aca gca aat    2427
Gly Tyr Gln Gly Ser Trp Lys Leu Ala Trp Asp Pro Asn Thr Ala Asn
            670                 675                 680 aat ggt cct tat act ctg aaa gct aca tgg act aaa act ggg tat aat    2475
Asn Gly Pro Tyr Thr Leu Lys Ala Thr Trp Thr Lys Thr Gly Tyr Asn
            685                 690                 695 cct ggg cct gag cga gta gct tct ttg gtt cca aat agt tta tgg gga    2523
Pro Gly Pro Glu Arg Val Ala Ser Leu Val Pro Asn Ser Leu Trp Gly
700                 705                 710 tcc att tta gat ata cga tct gcg cat tca gca att caa gca agt gtg    2571
Ser Ile Leu Asp Ile Arg Ser Ala His Ser Ala Ile Gln Ala Ser Val
715                 720                 725                 730 gat ggg cgc tct tat tgt cga gga tta tgg gtt tct gga gtt tcg aat    2619
Asp Gly Arg Ser Tyr Cys Arg Gly Leu Trp Val Ser Gly Val Ser Asn
            735                 740                 745 ttc ttc tat cat gac cgc gat gct tta ggt cag gga tat cgg tat att    2667
Phe Phe Tyr His Asp Arg Asp Ala Leu Gly Gln Gly Tyr Arg Tyr Ile
            750                 755                 760 agt ggg ggt tat tcc tta gga gca aac tcc tac ttt gga tca tcg atg    2715
Ser Gly Gly Tyr Ser Leu Gly Ala Asn Ser Tyr Phe Gly Ser Ser Met
            765                 770                 775 ttt ggt cta gca ttt acc gaa gta ttt ggt aga tct aaa gat tat gta    2763
Phe Gly Leu Ala Phe Thr Glu Val Phe Gly Arg Ser Lys Asp Tyr Val
780                 785                 790 gtg tgt cgt tcc aat cat cat gct tgc ata gga tcc gtt tat cta tct    2811
Val Cys Arg Ser Asn His His Ala Cys Ile Gly Ser Val Tyr Leu Ser
795                 800                 805                 810 acc caa caa gct tta tgt gga tcc tat ttg ttc gga gat gcg ttt atc    2859
Thr Gln Gln Ala Leu Cys Gly Ser Tyr Leu Phe Gly Asp Ala Phe Ile
            815                 820                 825 cgt gct agc tac ggg ttt ggg aat cag cat atg aaa acc tca tat aca    2907
Arg Ala Ser Tyr Gly Phe Gly Asn Gln His Met Lys Thr Ser Tyr Thr
            830                 835                 840 ttt gca gag gag agc gat gtt cgt tgg gat aat aac tgt ctg gct gga    2955
Phe Ala Glu Glu Ser Asp Val Arg Trp Asp Asn Asn Cys Leu Ala Gly
            845                 850                 855 gag att gga gcg gga tta ccg att gtg att act cca tct aag ctc tat    3003
Glu Ile Gly Ala Gly Leu Pro Ile Val Ile Thr Pro Ser Lys Leu Tyr
860                 865                 870
```

```
ttg aat gag ttg cgt cct ttc gtg caa gct gag ttt tct tat gcc gat         3051
Leu Asn Glu Leu Arg Pro Phe Val Gln Ala Glu Phe Ser Tyr Ala Asp
875                 880                 885                 890 cat gaa tct ttt aca gag gaa ggc gat caa gct cgg gca ttc aag agc         3099
His Glu Ser Phe Thr Glu Glu Gly Asp Gln Ala Arg Ala Phe Lys Ser
            895                 900                 905 gga cat ctc cta aat cta tca gtt cct gtt gga gtg aag ttt gat cga         3147
Gly His Leu Leu Asn Leu Ser Val Pro Val Gly Val Lys Phe Asp Arg
        910                 915                 920 tgt tct agt aca cat cct aat aaa tat agc ttt atg gcg gct tat atc         3195
Cys Ser Ser Thr His Pro Asn Lys Tyr Ser Phe Met Ala Ala Tyr Ile
    925                 930                 935 tgt gat gct tat cgc acc atc tct ggt act gag aca acg ctc cta tcc         3243
Cys Asp Ala Tyr Arg Thr Ile Ser Gly Thr Glu Thr Thr Leu Leu Ser
940                 945                 950 cat caa gag aca tgg aca aca gat gcc ttt cat tta gca aga cat gga         3291
His Gln Glu Thr Trp Thr Thr Asp Ala Phe His Leu Ala Arg His Gly
955                 960                 965                 970 gtt gtg gtt aga gga tct atg tat gct tct cta aca agt aat ata gaa         3339
Val Val Val Arg Gly Ser Met Tyr Ala Ser Leu Thr Ser Asn Ile Glu
            975                 980                 985 gta tat ggc cat gga aga tat gag tat cga gat gct tct cga  ggc tat        3387
Val Tyr Gly His Gly Arg Tyr Glu Tyr Arg Asp Ala Ser Arg  Gly Tyr
        990                 995                 1000 ggt ttg agt  gca gga agt aga gtc  cgg ttc taa aaatattggt                3430
Gly Leu Ser  Ala Gly Ser Arg Val  Arg Phe
        1005                1010 tagatagtta agtgttagcg atgcctttt cttgagatc tacatcattt tgttttttag         3490
cttgtttgtg ttcctattcg tatggattcg cgagctctcc tcaagtgtta acgcctaatg       3550
taaccactcc ttttaaggga gacgatgttt acttgaatgg agactgcgct tttgtcaatg       3610
tctatgcagg agctgaagaa ggttcgatta tctcagctaa tggcgacaat ttaacgatta       3670
ccggacaaaa ccatacatta tcatttacag attctcaagg gccagttctt caaaattatg       3730
ccttcatttc agcaggagag acacttactc tgagagattt ttcgagtctg atgttctcga       3790
aaaatgtttc ttgcggagaa aagggaatga tctccgggaa aaccgtgagt atttccggag       3850
caggcgaagt gattttctgg gataactccg tggggtattc tccttttatct actgtgccaa      3910
cctcatcatc aactccgcct gctccaacag ttagtgatgc tcggaaaggg tctattttt        3970
ctgtagagac tagtttggag atctcaggcg tcaaaaaagg ggtcatgttc gataataatg       4030
ccgggaattt cggaacagtt tttcgaggta agaataataa taatgctggt ggtggaggca       4090
gtgggttccg ctacaccatc aagtacgact tttacagtta aaaactgtaa agggaaagtt       4150
tctttcacag ataacgtagc ctcttgcgga ggcggagtgg tttataaagg cattgtgctt       4210
ttcaaagaca atgaaggagg catattcttc cgagggaaca cagcatacga tgatttaagg       4270
attcttgctg ctactaatca ggatcagaat acggagacag gaggcggtgg aggagttatt       4330
tgctctccag atgattctgt aaagtttgaa ggcaataaag gttctattgt ttttgattac       4390
aactttgcaa aaggcagagg cggaagcatc ctaacgaaag aattc                       4435

<210> SEQ ID NO 17
<211> LENGTH: 1012
<212> TYPE: PRT
<213> ORGANISM: Chlamydia trachomatis serovar L2

<400> SEQUENCE: 17

Met Gln Thr Ser Phe His Lys Phe Phe Leu Ser Met Ile Leu Ala Tyr
```

-continued

```
1               5                   10                  15
Ser Cys Cys Ser Leu Asn Gly Gly Tyr Ala Ala Glu Ile Met Val
            20                  25                  30

Pro Gln Gly Ile Tyr Asp Gly Glu Thr Leu Thr Val Ser Phe Pro Tyr
            35                  40                  45

Thr Val Ile Gly Asp Pro Ser Gly Thr Thr Val Phe Ser Ala Gly Glu
50                  55                  60

Leu Thr Leu Lys Asn Leu Asp Asn Ser Ile Ala Ala Leu Pro Leu Ser
65                  70                  75                  80

Cys Phe Gly Asn Leu Leu Gly Ser Phe Thr Val Leu Gly Arg Gly His
                85                  90                  95

Ser Leu Thr Phe Glu Asn Ile Arg Thr Ser Thr Asn Gly Ala Ala Leu
                100                 105                 110

Ser Asn Ser Ala Ala Asp Gly Leu Phe Thr Ile Glu Gly Phe Lys Glu
                115                 120                 125

Leu Ser Phe Ser Asn Cys Asn Ser Leu Leu Ala Val Leu Pro Ala Ala
                130                 135                 140

Thr Thr Asn Lys Gly Ser Gln Thr Pro Thr Thr Thr Ser Thr Pro Ser
145                 150                 155                 160

Asn Gly Thr Ile Tyr Ser Lys Thr Asp Leu Leu Leu Asn Asn Glu
                165                 170                 175

Lys Phe Ser Phe Tyr Ser Asn Leu Val Ser Gly Asp Gly Ala Ile
                180                 185                 190

Asp Ala Lys Ser Leu Thr Val Gln Gly Ile Ser Lys Leu Cys Val Phe
                195                 200                 205

Gln Glu Asn Thr Ala Gln Ala Asp Gly Gly Ala Cys Gln Val Val Thr
                210                 215                 220

Ser Phe Ser Ala Met Ala Asn Glu Ala Pro Ile Ala Phe Val Ala Asn
225                 230                 235                 240

Val Ala Gly Val Arg Gly Gly Gly Ile Ala Ala Val Gln Asp Gly Gln
                245                 250                 255

Gln Gly Val Ser Ser Ser Thr Ser Thr Glu Asp Pro Val Val Ser Phe
                260                 265                 270

Ser Arg Asn Thr Ala Val Glu Phe Asp Gly Asn Val Ala Arg Val Gly
                275                 280                 285

Gly Gly Ile Tyr Ser Tyr Gly Asn Val Ala Phe Leu Asn Asn Gly Lys
                290                 295                 300

Thr Leu Phe Leu Asn Asn Val Ala Ser Pro Val Tyr Ile Ala Ala Lys
305                 310                 315                 320

Gln Pro Thr Ser Gly Gln Ala Ser Asn Thr Ser Asn Asn Tyr Gly Asp
                325                 330                 335

Gly Gly Ala Ile Phe Cys Lys Asn Gly Ala Gln Ala Gly Ser Asn Asn
                340                 345                 350

Ser Gly Ser Val Ser Phe Asp Gly Glu Gly Val Val Phe Phe Ser Ser
                355                 360                 365

Asn Val Ala Ala Gly Lys Gly Gly Ala Ile Tyr Ala Lys Lys Leu Ser
                370                 375                 380

Val Ala Asn Cys Gly Pro Val Gln Phe Leu Arg Asn Ile Ala Asn Asp
385                 390                 395                 400

Gly Gly Ala Ile Tyr Leu Gly Glu Ser Gly Glu Leu Ser Leu Ser Ala
                405                 410                 415

Asp Tyr Gly Asp Ile Ile Phe Ser Gly Asn Leu Lys Arg Thr Ala Lys
                420                 425                 430
```

```
Glu Asn Ala Ala Asp Val Asn Gly Val Thr Val Ser Ser Gln Ala Ile
        435                 440                 445

Ser Met Gly Ser Gly Gly Lys Ile Thr Thr Leu Arg Ala Lys Ala Gly
    450                 455                 460

His Gln Ile Leu Phe Asn Asp Pro Ile Glu Met Ala Asn Gly Asn Asn
465                 470                 475                 480

Gln Pro Ala Gln Ser Ser Lys Leu Leu Lys Ile Asn Asp Gly Glu Gly
                485                 490                 495

Tyr Thr Gly Asp Ile Val Phe Ala Asn Gly Ser Ser Thr Leu Tyr Gln
            500                 505                 510

Asn Val Thr Ile Glu Gln Gly Arg Ile Val Leu Arg Glu Lys Ala Lys
        515                 520                 525

Leu Ser Val Asn Ser Leu Ser Gln Thr Gly Gly Ser Leu Tyr Met Glu
    530                 535                 540

Ala Gly Ser Thr Trp Asp Phe Val Thr Pro Gln Pro Pro Gln Gln Pro
545                 550                 555                 560

Pro Ala Ala Asn Gln Leu Ile Thr Leu Ser Asn Leu His Leu Ser Leu
                565                 570                 575

Ser Ser Leu Leu Ala Asn Asn Ala Val Thr Asn Pro Pro Thr Asn Pro
            580                 585                 590

Pro Ala Gln Asp Ser His Pro Ala Val Ile Gly Ser Thr Thr Ala Gly
        595                 600                 605

Ser Val Thr Ile Ser Gly Pro Ile Phe Phe Glu Asp Leu Asp Asp Thr
    610                 615                 620

Ala Tyr Asp Arg Tyr Asp Trp Leu Gly Ser Asn Gln Lys Ile Asn Val
625                 630                 635                 640

Leu Lys Leu Gln Leu Gly Thr Lys Pro Pro Ala Asn Ala Pro Ser Asp
                645                 650                 655

Leu Thr Leu Gly Asn Glu Met Pro Lys Tyr Gly Tyr Gln Gly Ser Trp
            660                 665                 670

Lys Leu Ala Trp Asp Pro Asn Thr Ala Asn Asn Gly Pro Tyr Thr Leu
        675                 680                 685

Lys Ala Thr Trp Thr Lys Thr Gly Tyr Asn Pro Gly Pro Glu Arg Val
    690                 695                 700

Ala Ser Leu Val Pro Asn Ser Leu Trp Gly Ser Ile Leu Asp Ile Arg
705                 710                 715                 720

Ser Ala His Ser Ala Ile Gln Ala Ser Val Asp Gly Arg Ser Tyr Cys
                725                 730                 735

Arg Gly Leu Trp Val Ser Gly Val Ser Asn Phe Phe Tyr His Asp Arg
            740                 745                 750

Asp Ala Leu Gly Gln Gly Tyr Arg Tyr Ile Ser Gly Gly Tyr Ser Leu
        755                 760                 765

Gly Ala Asn Ser Tyr Phe Gly Ser Ser Met Phe Gly Leu Ala Phe Thr
    770                 775                 780

Glu Val Phe Gly Arg Ser Lys Asp Tyr Val Val Cys Arg Ser Asn His
785                 790                 795                 800

His Ala Cys Ile Gly Ser Val Tyr Leu Ser Thr Gln Gln Ala Leu Cys
                805                 810                 815

Gly Ser Tyr Leu Phe Gly Asp Ala Phe Ile Arg Ala Ser Tyr Gly Phe
            820                 825                 830

Gly Asn Gln His Met Lys Thr Ser Tyr Thr Phe Ala Glu Glu Ser Asp
        835                 840                 845

Val Arg Trp Asp Asn Asn Cys Leu Ala Gly Glu Ile Gly Ala Gly Leu
    850                 855                 860
```

```
Pro Ile Val Ile Thr Pro Ser Lys Leu Tyr Leu Asn Glu Leu Arg Pro
865 870 875 880

Phe Val Gln Ala Glu Phe Ser Tyr Ala Asp His Glu Ser Phe Thr Glu
885 890 895

Glu Gly Asp Gln Ala Arg Ala Phe Lys Ser Gly His Leu Leu Asn Leu
900 905 910

Ser Val Pro Val Gly Val Lys Phe Asp Arg Cys Ser Ser Thr His Pro
915 920 925

Asn Lys Tyr Ser Phe Met Ala Ala Tyr Ile Cys Asp Ala Tyr Arg Thr
930 935 940

Ile Ser Gly Thr Glu Thr Thr Leu Leu Ser His Gln Glu Thr Trp Thr
945 950 955 960

Thr Asp Ala Phe His Leu Ala Arg His Gly Val Val Val Arg Gly Ser
965 970 975

Met Tyr Ala Ser Leu Thr Ser Asn Ile Glu Val Tyr Gly His Gly Arg
980 985 990

Tyr Glu Tyr Arg Asp Ala Ser Arg Gly Tyr Gly Leu Ser Ala Gly Ser
995 1000 1005

Arg Val Arg Phe
1010
```

```
<210> SEQ ID NO 18
<211> LENGTH: 3354
<212> TYPE: DNA
<213> ORGANISM: Chlamydia trachomatis serovar B
<400> SEQUENCE: 18
atgcaaacgt ctttccataa gttctttctt tcaatgattc tagcttattc ttgctgctct 60
ttaaatgggg gggggtatgc agaaatcatg gttcctcaag gaatttacga tggggagacg 120
ttaactgtat catttcccta tactgttata ggagatccga gtgggactac tgtttttct 180
gcaggagagt taacgttaaa aaatcttgac aattctattg cagctttgcc tttaagttgt 240
tttgggaact tattagggag ttttactgtt ttagggagag gacactcgtt gactttcgag 300
aacatacgga cttctacaaa tggagctgca ctaagtgaca gcgctaatag cgggttattt 360
actattgagg gttttaaaga attatctttt tccaattgca acccattact tgccgtactg 420
cctgctgcaa cgactaataa tggtagccag actccgtcga caacatctac accgtctaat 480
ggtactattt attctaaaac agatcttttg ttactcaata atgagaagtt ctcattctat 540
agtaattcag tctctggaga tgggggagct atagatgcta agagcttaac ggttcaagga 600
attagcaagc tttgtgtctt ccaagaaaat actgctcaag ctgatggggg agcttgtcaa 660
gtagtcacca gtttctctgc tatggctaac gaggctccta ttgcctttgt agcgaatgtt 720
gcaggagtaa gagggggagg gattgctgct gttcaggatg ggcagcaggg agtgtcatca 780
tctacttcaa cagaagatcc agtagtaagt tttccagaa atactgcggt agagtttgat 840
gggaacgtag cccgagtagg aggagggatt tactcctacg ggaacgttgc tttcctgaat 900
aatggaaaaa ccttgtttct caacaatgtt gcttctcctg tttacattgc tgctgagcaa 960
ccaacaaatg gacaggcttc taatacgagt gataattacg gagatggagg agctatcttc 1020
tgtaagaatg gtgcgcaagc agcaggatcc aataactctg gatcagtttc ctttgatgga 1080
gagggagtag ttttctttag tagcaatgta gctgctggga aagggggagc tatttatgcc 1140
aaaaagctct cggttgctaa ctgtggccct gtacaactct tagggaatat cgctaatgat 1200
ggtggagcga tttatttagg agaatctgga gagctcagtt tatctgctga ttatggagat 1260

-continued

```
atgattttcg atgggaatct taaaagaaca gccaaagaga atgctgccga tgttaatggc    1320
gtaactgtgt cctcacaagc catttcgatg ggatcgggag ggaaaataac gacattaaga    1380
gctaaagcag ggcatcagat tctctttaat gatcccatcg agatggcaaa cggaaataac    1440
cagccagcgc agtcttccga acctctaaaa attaacgatg gtgaaggata cacaggggat    1500 attgttttg ctaatggaaa cagtactttg taccaaaatg ttacgataga gcaaggaagg     1560
attgttcttc gtgaaaaggc aaaattatca gtgaattctc taagtcagac aggtgggagt    1620
ctgtatatgg aagctgggag tacattggat tttgtaactc cacaaccacc acaacagcct    1680
cctgccgcta atcagtcgat cacgctttcc aatctgcatt tgtctctttc ttctttgtta    1740
gcaaacaatg cagttacgaa tcctcctacc aatcctccag cgcaagattc tcatcctgca    1800
gtcattggta gcacaactgc tggttctgtt acaattagtg ggcctatctt ttttgaggat    1860
ttggatgata cagcttatga taggtatgat tggctaggtt ctaatcaaaa aatcgatgtc    1920
ctgaaattac agttagggac tcagccccca gctaatgccc catcagattt gactctaggg    1980
aatgagatgc taagtatgg ctatcaagga agctggaagc ttgcgtggga tcctaataca     2040
gcaaataatg gtccttatac tctgaaagct acatggacta aaactgggta taatcctggg    2100
cctgagcgag tagcttcttt ggttccaaat agtttatggg gatccatttt agatatacga    2160
tctgcgcatt cagcaattca agcaagtgtg gatgggcgct cttattgtcg aggattatgg    2220
gtttctggag tttcgaattt cttctatcat gaccgcgatg ctttaggtca gggatatcgg    2280
tatattagtg ggggttattc cttaggagca aactcctact ttggatcatc gatgtttggt    2340
ctagcattta ctgaagtatt tggtagatct aaagattatg tagtgtgtcg ttccaatcat    2400
catgcttgca taggatccgt ttatctatct accaaacagg ctttatgtgg atcttatgtg    2460
tttggagatg cgtttattcg tgctagctac gggtttggga atcagcatat gaaaacctca    2520
tatacatttg cagaggagag cgatgttgt tgggataata actgtctggt tggagagatt     2580
ggagtgggat taccgattgt gattactcca tctaagctct atttgaatga gttgcgtcct    2640
ttcgtgcaag ctgagttttc ttatgccgat catgaatctt ttacagagga aggcgatcaa    2700
gctcgggcat tcaggagtgg acatctcatg aatctatcag ttcctgttgg agtaaaattt    2760
gatcgatgtt ctagtacaca ccctaataaa tatagctta tgggggctta tatctgtgat      2820
gcttatcgca ccatctctgg gactcagaca acactcctat cccatcaaga gacatggaca    2880
acagatgcct tcatttggc aagacatgga gtcatagtta gagggtctat gtatgcttct     2940
ctaacaagca atatagaagt atatggccat ggaagatatg agtatcgaga tacttctcga    3000
ggttatggtt tgagtgcagg aagtaaagtc cggttctaaa aatattggtt agatagttaa    3060
gtgttagcga tgccttttc tttgagatct acatcatttt gtttttagc ttgtttgtgt       3120 tcctattcgt atggattcgc gagctctcct caagtgttaa cacctaatgt aaccactcct    3180
tttaaggggg acgatgttta cttgaatgga gactgcgctt ttgtcaatgt ctatgcaggg    3240
gcagagaacg gctcaattat ctcagctaat ggcgacaatt taacgattac cggacaaaac    3300
catacattat catttacaca ttctcaaggg ccagttcttc aaaattagcc ttca          3354
```

<210> SEQ ID NO 19
<211> LENGTH: 1013
<212> TYPE: PRT
<213> ORGANISM: Chlamydia trachomatis serovar B

<400> SEQUENCE: 19

Met Gln Thr Ser Phe His Lys Phe Phe Leu Ser Met Ile Leu Ala Tyr

-continued

```
1               5               10              15
Ser Cys Cys Ser Leu Asn Gly Gly Tyr Ala Ala Glu Ile Met Val
            20              25              30

Pro Gln Gly Ile Tyr Asp Gly Glu Thr Leu Thr Val Ser Phe Pro Tyr
            35              40              45

Thr Val Ile Gly Asp Pro Ser Gly Thr Thr Val Phe Ser Ala Gly Glu
50              55              60

Leu Thr Leu Lys Asn Leu Asp Asn Ser Ile Ala Ala Leu Pro Leu Ser
65              70              75              80

Cys Phe Gly Asn Leu Leu Gly Ser Phe Thr Val Leu Gly Arg Gly His
            85              90              95

Ser Leu Thr Phe Glu Asn Ile Arg Thr Ser Thr Asn Gly Ala Ala Leu
            100             105             110

Ser Asp Ser Ala Asn Ser Gly Leu Phe Thr Ile Glu Gly Phe Lys Glu
            115             120             125

Leu Ser Phe Ser Asn Cys Asn Pro Leu Leu Ala Val Leu Pro Ala Ala
            130             135             140

Thr Thr Asn Asn Gly Ser Gln Thr Pro Ser Thr Thr Ser Thr Pro Ser
145             150             155             160

Asn Gly Thr Ile Tyr Ser Lys Thr Asp Leu Leu Leu Asn Asn Glu
            165             170             175

Lys Phe Ser Phe Tyr Ser Asn Ser Val Ser Gly Asp Gly Ala Ile
            180             185             190

Asp Ala Lys Ser Leu Thr Val Gln Gly Ile Ser Lys Leu Cys Val Phe
            195             200             205

Gln Glu Asn Thr Ala Gln Ala Asp Gly Gly Ala Cys Gln Val Val Thr
            210             215             220

Ser Phe Ser Ala Met Ala Asn Glu Ala Pro Ile Ala Phe Val Ala Asn
225             230             235             240

Val Ala Gly Val Arg Gly Gly Ile Ala Ala Val Gln Asp Gly Gln
            245             250             255

Gln Gly Val Ser Ser Thr Ser Thr Glu Asp Pro Val Val Ser Phe
            260             265             270

Ser Arg Asn Thr Ala Val Glu Phe Asp Gly Asn Val Ala Arg Val Gly
            275             280             285

Gly Gly Ile Tyr Ser Tyr Gly Asn Val Ala Phe Leu Asn Asn Gly Lys
            290             295             300

Thr Leu Phe Leu Asn Asn Val Ala Ser Pro Val Tyr Ile Ala Ala Glu
305             310             315             320

Gln Pro Thr Asn Gly Gln Ala Ser Asn Thr Ser Asp Asn Tyr Gly Asp
            325             330             335

Gly Gly Ala Ile Phe Cys Lys Asn Gly Ala Gln Ala Ala Gly Ser Asn
            340             345             350

Asn Ser Gly Ser Val Ser Phe Asp Gly Glu Gly Val Val Phe Phe Ser
            355             360             365

Ser Asn Val Ala Ala Gly Lys Gly Gly Ala Ile Tyr Ala Lys Lys Leu
            370             375             380

Ser Val Ala Asn Cys Gly Pro Val Gln Leu Leu Gly Asn Ile Ala Asn
385             390             395             400

Asp Gly Gly Ala Ile Tyr Leu Gly Glu Ser Gly Glu Leu Ser Leu Ser
            405             410             415

Ala Asp Tyr Gly Asp Met Ile Phe Asp Gly Asn Leu Lys Arg Thr Ala
            420             425             430
```

-continued

```
Lys Glu Asn Ala Ala Asp Val Asn Gly Val Thr Val Ser Ser Gln Ala
        435                 440                 445
Ile Ser Met Gly Ser Gly Lys Ile Thr Thr Leu Arg Ala Lys Ala
    450                 455                 460
Gly His Gln Ile Leu Phe Asn Asp Pro Ile Glu Met Ala Asn Gly Asn
465                 470                 475                 480
Asn Gln Pro Ala Gln Ser Ser Glu Pro Leu Lys Ile Asn Asp Gly Glu
                485                 490                 495
Gly Tyr Thr Gly Asp Ile Val Phe Ala Asn Gly Asn Ser Thr Leu Tyr
            500                 505                 510
Gln Asn Val Thr Ile Glu Gln Gly Arg Ile Val Leu Arg Glu Lys Ala
        515                 520                 525
Lys Leu Ser Val Asn Ser Leu Ser Gln Thr Gly Gly Ser Leu Tyr Met
    530                 535                 540
Glu Ala Gly Ser Thr Leu Asp Phe Val Thr Pro Gln Pro Pro Gln Gln
545                 550                 555                 560
Pro Pro Ala Ala Asn Gln Ser Ile Thr Leu Ser Asn Leu His Leu Ser
                565                 570                 575
Leu Ser Ser Leu Leu Ala Asn Asn Ala Val Thr Asn Pro Pro Thr Asn
            580                 585                 590
Pro Pro Ala Gln Asp Ser His Pro Ala Val Ile Gly Ser Thr Thr Ala
        595                 600                 605
Gly Ser Val Thr Ile Ser Gly Pro Ile Phe Phe Glu Asp Leu Asp Asp
    610                 615                 620
Thr Ala Tyr Asp Arg Tyr Asp Trp Leu Gly Ser Asn Gln Lys Ile Asp
625                 630                 635                 640
Val Leu Lys Leu Gln Leu Gly Thr Gln Pro Pro Ala Asn Ala Pro Ser
                645                 650                 655
Asp Leu Thr Leu Gly Asn Glu Met Pro Lys Tyr Gly Tyr Gln Gly Ser
            660                 665                 670
Trp Lys Leu Ala Trp Asp Pro Asn Thr Ala Asn Asn Gly Pro Tyr Thr
        675                 680                 685
Leu Lys Ala Thr Trp Thr Lys Thr Gly Tyr Asn Pro Gly Pro Glu Arg
    690                 695                 700
Val Ala Ser Leu Val Pro Asn Ser Leu Trp Gly Ser Ile Leu Asp Ile
705                 710                 715                 720
Arg Ser Ala His Ser Ala Ile Gln Ala Ser Val Asp Gly Arg Ser Tyr
                725                 730                 735
Cys Arg Gly Leu Trp Val Ser Gly Val Ser Asn Phe Phe Tyr His Asp
            740                 745                 750
Arg Asp Ala Leu Gly Gln Gly Tyr Arg Tyr Ile Ser Gly Gly Tyr Ser
        755                 760                 765
Leu Gly Ala Asn Ser Tyr Phe Gly Ser Ser Met Phe Gly Leu Ala Phe
    770                 775                 780
Thr Glu Val Phe Gly Arg Ser Lys Asp Tyr Val Val Cys Arg Ser Asn
785                 790                 795                 800
His His Ala Cys Ile Gly Ser Val Tyr Leu Ser Thr Lys Gln Ala Leu
                805                 810                 815
Cys Gly Ser Tyr Val Phe Gly Asp Ala Phe Ile Arg Ala Ser Tyr Gly
            820                 825                 830
Phe Gly Asn Gln His Met Lys Thr Ser Tyr Thr Phe Ala Glu Glu Ser
        835                 840                 845
Asp Val Cys Trp Asp Asn Asn Cys Leu Val Gly Glu Ile Gly Val Gly
    850                 855                 860
```

```
Leu Pro Ile Val Ile Thr Pro Ser Lys Leu Tyr Leu Asn Glu Leu Arg
865                 870                 875                 880

Pro Phe Val Gln Ala Glu Phe Ser Tyr Ala Asp His Glu Ser Phe Thr
            885                 890                 895

Glu Glu Gly Asp Gln Ala Arg Ala Phe Arg Ser Gly His Leu Met Asn
                900                 905                 910

Leu Ser Val Pro Val Gly Val Lys Phe Asp Arg Cys Ser Ser Thr His
            915                 920                 925

Pro Asn Lys Tyr Ser Phe Met Gly Ala Tyr Ile Cys Asp Ala Tyr Arg
        930                 935                 940

Thr Ile Ser Gly Thr Gln Thr Thr Leu Leu Ser His Gln Glu Thr Trp
945                 950                 955                 960

Thr Thr Asp Ala Phe His Leu Ala Arg His Gly Val Ile Val Arg Gly
                965                 970                 975

Ser Met Tyr Ala Ser Leu Thr Ser Asn Ile Glu Val Tyr Gly His Gly
            980                 985                 990

Arg Tyr Glu Tyr Arg Asp Thr Ser  Arg Gly Tyr Gly Leu  Ser Ala Gly
        995                 1000                1005

Ser Lys  Val Arg Phe
    1010

<210> SEQ ID NO 20
<211> LENGTH: 3324
<212> TYPE: DNA
<213> ORGANISM: Chlamydia trachomatis serovar F

<400> SEQUENCE: 20
atgcaaacgt ctttccataa gttctttctt tcaatgattc tagcttattc ttgctgctct      60
ttaagtgggg gggggtatgc agcagaaatc atgattcctc aaggaattta cgatggggag     120
acgttaactg tatcatttcc ctatactgtt ataggagatc cgagtgggac tactgttttt     180
tctgcaggag agttaacgtt aaaaaatctt gacaattcta ttgcagcttt gcctttaagt     240
tgttttggga acttattagg gagttttact gttttaggga aggacactc gttgactttc     300 gagaacatac ggacttctac aaatggagct gcactaagtg acagcgctaa tagcgggtta     360
tttactattg agggttttaa agaattatct ttttccaatt gcaactcatt acttgccgta     420
ctgcctgctg caacgactaa taatggtagc cagactccga cgacaacatc tacaccgtct     480
aatggtacta tttattctaa aacagatctt ttgttactca ataatgagaa gttctcattc     540
tatagtaatt tagtctctgg agatggggga actatagatg ctaagagctt aacggttcaa     600
ggaattagca agctttgtgt cttccaagaa aatactgctc aagctgatgg gggagcttgt     660
caagtagtca ccagtttctc tgctatggct aacgaggctc ctattgcctt tatagcgaat     720
gttgcaggag taagagggg agggattgct gctgttcagg atgggcagca gggagtgtca     780
tcatctactt caacagaaga tccagtagta agttttttcca gaaatactgc ggtagagttt     840
gatgggaacg tagcccgagt aggaggaggg atttactcct acgggaacgt tgctttcctg     900
aataatggaa aaaccttgtt tctcaacaat gttgcttctc ctgtttacat tgctgctgag     960
caaccaacaa atggacaggc ttctaatacg agtgataatt acggagatgg aggagctatc    1020
ttctgtaaga atggtcgcca agcagcagga tccataact ctggatcagt ttccttgat     1080 ggagagggag tagttttctt tagtagcaat gtagctgctg ggaagggggg agctatttat    1140
gccaaaaagc tctcggttgc taactgtggc cctgtacaat tcttagggaa atcgctaat     1200 gatggtggag cgatttattt aggagaatct ggagagctca gtttatctgc tgattatgga    1260
```

-continued

| | |
|---|---|
| gatattattt tcgatgggaa tcttaaaaga acagccaaag agaatgctgc cgatgttaat | 1320 |
| ggcgtaactg tgtcctcaca agccatttcg atgggatcgg gagggaaaat aacgacatta | 1380 |
| agagctaaag cagggcatca gattctcttt aatgatccca tcgagatggc aaacggaaat | 1440 |
| aaccagccag cgcagtcttc cgaacctcta aaaattaacg atggtgaagg atacacaggg | 1500 |
| gatattgttt ttgctaatgg aaacagtact ttgtaccaaa atgttacgat agagcaagga | 1560 |
| aggattgttc ttcgtgaaaa ggcaaaatta tcagtgaatt ctctaagtca gacaggtggg | 1620 |
| agtctgtata tggaagctgg gagtacattg gattttgtaa ctccacaacc accacaacag | 1680 |
| cctcctgccg ctaatcagtt gatcacgctt tccaatctgc atttgtctct ttcttctttg | 1740 |
| ttagcaaaca atgcagttac gaatcctcct accaatcctc cagcgcaaga ttctcatcct | 1800 |
| gcagtcattg gtagcacaac tgctggtcct gtcacaatta gtgggccttt cttttttgag | 1860 |
| gatttggatg atacagctta tgataggtat gattggctag gttctaatca aaaaatcgat | 1920 |
| gtcctgaaat tacagttagg gactcagccc tcagctaatg ccccatcaga tttgactcta | 1980 |
| gggaatgaga tgcctaagta tggctatcaa ggaagctgga agcttgcgtg ggatcctaat | 2040 |
| acagcaaata atggtcctta tactctgaaa gctacatgga ctaaaactgg gtataatcct | 2100 |
| gggcctgagc gagtagcttc tttggttcca aatagtttat ggggatccat tttagatata | 2160 |
| cgatctgcgc attcagcaat tcaagcaagt gtggatgggc gctcttattg tcgaggatta | 2220 |
| tgggtttctg gagtttcgaa tttctcctat catgaccgcg atgctttagg tcagggatat | 2280 |
| cggtatatta gtgggggtta ttccttagga gcaaactcct actttggatc atcgatgttt | 2340 |
| ggtctagcat ttaccgaagt atttggtaga tctaaagatt atgtagtgtg tcgttccaat | 2400 |
| catcatgctt gcataggatc cgtttatcta tctaccaaac aagctttatg tggatcctat | 2460 |
| ttgttcggag atgcgtttat ccgtgctagc tacgggtttg ggaaccagca tatgaaaacc | 2520 |
| tcatacacat ttgcagagga gagcgatgtt cgttgggata taactgtct ggttggagag | 2580 |
| attggagtgg gattaccgat tgtgactact ccatctaagc tctatttgaa tgagttgcgt | 2640 |
| cctttcgtgc aagctgagtt ttcttatgcc gatcatgaat cttttacaga ggaaggcgat | 2700 |
| caagctcggg cattcaggag tggtcatctc atgaatctat cagttcctgt tggagtaaaa | 2760 |
| tttgatcgat gttctagtac acaccctaat aaatatagct ttatgggggc ttatatctgt | 2820 |
| gatgcttatc gcaccatctc tgggactcag acaacactcc tatcccatca agagacatgg | 2880 |
| acaacagatg cctttcattt ggcaagacat ggagtcatag ttagagggtc tatgtatgct | 2940 |
| tctctaacaa gcaatataga agtatatggc catggaagat atgagtatcg agatacttct | 3000 |
| cgaggttatg gtttgagtgc aggaagtaaa gtccggttct aaaaatattg gttagatagt | 3060 |
| taagtgttag cgatgccttt ttctttgaga tctacatcat tttgttttt agcttgtttg | 3120 |
| tgttcctatt cgtatggatt cgcgagctct cctcaagtgt taacacctaa tgtaaccact | 3180 |
| ccttttaagg gggacgatgt ttacttgaat ggagactgcg ctttagtcaa tgtctatgca | 3240 |
| ggggcagaga acggctcaat tatctcagct aatggcgaca atttaacgat taccggacaa | 3300 |
| aaccatgcat tatcatttac agat | 3324 |

<210> SEQ ID NO 21
<211> LENGTH: 1013
<212> TYPE: PRT
<213> ORGANISM: Chlamydia trachomatis serovar F

<400> SEQUENCE: 21

Met Gln Thr Ser Phe His Lys Phe Phe Leu Ser Met Ile Leu Ala Tyr

-continued

```
  1               5              10              15
Ser Cys Cys Ser Leu Thr Gly Gly Tyr Ala Ala Glu Ile Met Val
                20              25              30

Pro Gln Gly Ile Tyr Asp Gly Glu Thr Leu Thr Val Ser Phe Pro Tyr
                35              40              45

Thr Val Ile Gly Asp Pro Ser Gly Thr Thr Val Phe Ser Ala Gly Glu
50              55              60

Leu Thr Leu Lys Asn Leu Asp Asn Ser Ile Ala Ala Leu Pro Leu Ser
65              70              75              80

Cys Phe Gly Asn Leu Leu Gly Ser Phe Thr Val Leu Gly Arg Gly His
                85              90              95

Ser Leu Thr Phe Glu Asn Ile Arg Thr Ser Thr Asn Gly Ala Ala Leu
                100             105             110

Ser Asp Ser Ala Asn Ser Gly Leu Phe Thr Ile Glu Gly Phe Lys Glu
                115             120             125

Leu Ser Phe Ser Asn Cys Asn Ser Leu Leu Ala Val Leu Pro Ala Ala
                130             135             140

Thr Thr Asn Asn Gly Ser Gln Thr Pro Thr Thr Thr Ser Thr Pro Ser
145             150             155             160

Asn Gly Thr Ile Tyr Ser Lys Thr Asp Leu Leu Leu Asn Asn Glu
                165             170             175

Lys Phe Ser Phe Tyr Ser Asn Leu Val Ser Gly Asp Gly Thr Ile
                180             185             190

Asp Ala Lys Ser Leu Thr Val Gln Gly Ile Ser Lys Leu Cys Val Phe
                195             200             205

Gln Glu Asn Thr Ala Gln Ala Asp Gly Gly Ala Cys Gln Val Val Thr
                210             215             220

Ser Phe Ser Ala Met Ala Asn Glu Ala Pro Ile Ala Phe Ile Ala Asn
225             230             235             240

Val Ala Gly Val Arg Gly Gly Ile Ala Ala Val Gln Asp Gly Gln
                245             250             255

Gln Gly Val Ser Ser Thr Ser Thr Glu Asp Pro Val Val Ser Phe
                260             265             270

Ser Arg Asn Thr Ala Val Glu Phe Asp Gly Asn Val Ala Arg Val Gly
                275             280             285

Gly Gly Ile Tyr Ser Tyr Gly Asn Val Ala Phe Leu Asn Asn Gly Lys
                290             295             300

Thr Leu Phe Leu Asn Asn Val Ala Ser Pro Val Tyr Ile Ala Ala Glu
305             310             315             320

Gln Pro Thr Asn Gly Gln Ala Ser Asn Thr Ser Asp Asn Tyr Gly Asp
                325             330             335

Gly Gly Ala Ile Phe Cys Lys Asn Gly Ala Gln Ala Ala Gly Ser Asn
                340             345             350

Asn Ser Gly Ser Val Ser Phe Asp Gly Glu Gly Val Val Phe Ser
                355             360             365

Ser Asn Val Ala Ala Gly Lys Gly Gly Ala Ile Tyr Ala Lys Lys Leu
                370             375             380

Ser Val Ala Asn Cys Gly Pro Val Gln Phe Leu Gly Asn Ile Ala Asn
385             390             395             400

Asp Gly Gly Ala Ile Tyr Leu Gly Glu Ser Gly Glu Leu Ser Leu Ser
                405             410             415

Ala Asp Tyr Gly Asp Ile Ile Phe Asp Gly Asn Leu Lys Arg Thr Ala
                420             425             430
```

```
Lys Glu Asn Ala Ala Asp Val Asn Gly Val Thr Val Ser Ser Gln Ala
            435                 440                 445
Ile Ser Met Gly Ser Gly Lys Ile Thr Thr Leu Arg Ala Lys Ala
450                 455                 460
Gly His Gln Ile Leu Phe Asn Asp Pro Ile Glu Met Ala Asn Gly Asn
465                 470                 475                 480
Asn Gln Pro Ala Gln Ser Ser Glu Pro Leu Lys Ile Asn Asp Gly Glu
                485                 490                 495
Gly Tyr Thr Gly Asp Ile Val Phe Ala Asn Gly Asn Ser Thr Leu Tyr
            500                 505                 510
Gln Asn Val Thr Ile Glu Gln Gly Arg Ile Val Leu Arg Glu Lys Ala
            515                 520                 525
Lys Leu Ser Val Asn Ser Leu Ser Gln Thr Gly Gly Ser Leu Tyr Met
530                 535                 540
Glu Ala Gly Ser Thr Leu Asp Phe Val Thr Pro Gln Pro Pro Gln Gln
545                 550                 555                 560
Pro Pro Ala Ala Asn Gln Leu Ile Thr Leu Ser Asn Leu His Leu Ser
                565                 570                 575
Leu Ser Ser Leu Leu Ala Asn Asn Ala Val Thr Asn Pro Pro Thr Asn
            580                 585                 590
Pro Pro Ala Gln Asp Ser His Pro Ala Val Ile Gly Ser Thr Thr Ala
            595                 600                 605
Gly Pro Val Thr Ile Ser Gly Pro Phe Phe Phe Glu Asp Leu Asp Asp
610                 615                 620
Thr Ala Tyr Asp Arg Tyr Asp Trp Leu Gly Ser Asn Gln Lys Ile Asp
625                 630                 635                 640
Val Leu Lys Leu Gln Leu Gly Thr Gln Pro Ser Ala Asn Ala Pro Ser
                645                 650                 655
Asp Leu Thr Leu Gly Asn Glu Met Pro Lys Tyr Gly Tyr Gln Gly Ser
            660                 665                 670
Trp Lys Leu Ala Trp Asp Pro Asn Thr Ala Asn Asn Gly Pro Tyr Thr
            675                 680                 685
Leu Lys Ala Thr Trp Thr Lys Thr Gly Tyr Asn Pro Gly Pro Glu Arg
            690                 695                 700
Val Ala Ser Leu Val Pro Asn Ser Leu Trp Gly Ser Ile Leu Asp Ile
705                 710                 715                 720
Arg Ser Ala His Ser Ala Ile Gln Ala Ser Val Asp Gly Arg Ser Tyr
                725                 730                 735
Cys Arg Gly Leu Trp Val Ser Gly Val Ser Asn Phe Ser Tyr His Asp
            740                 745                 750
Arg Asp Ala Leu Gly Gln Gly Tyr Arg Tyr Ile Ser Gly Gly Tyr Ser
            755                 760                 765
Leu Gly Ala Asn Ser Tyr Phe Gly Ser Ser Met Phe Gly Leu Ala Phe
770                 775                 780
Thr Glu Val Phe Gly Arg Ser Lys Asp Tyr Val Val Cys Arg Ser Asn
785                 790                 795                 800
His His Ala Cys Ile Gly Ser Val Tyr Leu Ser Thr Lys Gln Ala Leu
                805                 810                 815
Cys Gly Ser Tyr Leu Phe Gly Asp Ala Phe Ile Arg Ala Ser Tyr Gly
            820                 825                 830
Phe Gly Asn Gln His Met Lys Thr Ser Tyr Thr Phe Ala Glu Glu Ser
            835                 840                 845
Asp Val Arg Trp Asp Asn Asn Cys Leu Val Gly Glu Ile Gly Val Gly
850                 855                 860
```

```
Leu Pro Ile Val Thr Thr Pro Ser Lys Leu Tyr Leu Asn Glu Leu Arg
865                 870                 875                 880

Pro Phe Val Gln Ala Glu Phe Ser Tyr Ala Asp His Glu Ser Phe Thr
                885                 890                 895

Glu Glu Gly Asp Gln Ala Arg Ala Phe Arg Ser Gly His Leu Met Asn
            900                 905                 910

Leu Ser Val Pro Val Gly Val Lys Phe Asp Arg Cys Ser Ser Thr His
        915                 920                 925

Pro Asn Lys Tyr Ser Phe Met Gly Ala Tyr Ile Cys Asp Ala Tyr Arg
    930                 935                 940

Thr Ile Ser Gly Thr Gln Thr Thr Leu Leu Ser His Gln Glu Thr Trp
945                 950                 955                 960

Thr Thr Asp Ala Phe His Leu Ala Arg His Gly Val Ile Val Arg Gly
                965                 970                 975

Ser Met Tyr Ala Ser Leu Thr Ser Asn Ile Glu Val Tyr Gly His Gly
            980                 985                 990

Arg Tyr Glu Tyr Arg Asp Thr Ser  Arg Gly Tyr Gly Leu  Ser Ala Gly
        995                 1000                1005

Ser Lys  Val Arg Phe
    1010
```

<210> SEQ ID NO 22
<211> LENGTH: 1098
<212> TYPE: DNA
<213> ORGANISM: Chlamydia muridarum

<400> SEQUENCE: 22

```
atgattttcg atgggaatat taaaagaaca gccaaagaga atgctgccga tgttaatggc     60
gtaactgtgt cctcacaagc catttcgatg ggatcgggag ggaaaataac gacattaaga    120
gctaaagcag ggcatcagat tctctttaat gatcccatcg agatggcaaa cggaaataac    180
cagccagcgc agtcttccaa acttctaaaa attaacgatg gtgaaggata cacaggggat    240
attgtttttg ctaatggaag cagtactttg taccaaaatg ttacgataga gcaaggaagg    300
attgttcttc gtgaaaaggc aaaattatca gtgaattctc taagtcagac aggtgggagt    360
ctgtatatgg aagctgggag tacattggat tttgtaactc cacaaccacc acaacagcct    420
cctgccgcta atcagttgat cacgctttcc aatctgcatt tgtctctttc ttctttgtta    480
gcaaacaatg cagttacgaa tcctcctacc aatcctccag cgcaagattc tcatcctgca    540
gtcattggta gcacaactgc tggttctgtt acaattagtg ggcctatctt ttttgaggat    600
ttggatgata cagcttatga taggtatgat tggctaggtt ctaatcaaaa aatcaatgtc    660
ctgaaattac agttagggac taagccccca gctaatgccc catcagattt gactctaggg    720
aatgagatgc ctaagtatgg ctatcaagga agctggaagc ttgcgtggga tcctaataca    780
gcaaataatg gtccttatac tctgaaagct acatggacta aaactgggta taatcctggg    840
cctgagcgag tagcttcttt ggttccaaat agtttatggg gatccatttt agatatacga    900
tctgcgcatt cagcaattca agcaagtgtg gatgggcgct cttattgtcg aggattatgg    960
gtttctggag tttcgaattt cttctatcat gaccgcgatg ctttaggtca gggatatcgg   1020
tatattagtg gggttattc cttaggagca aactcctact ttggatcatc gatgtttggt   1080
ctagcattta cctaataa                                                 1098
```

<210> SEQ ID NO 23
<211> LENGTH: 364

```
<212> TYPE: PRT
<213> ORGANISM: Chlamydia muridarum

<400> SEQUENCE: 23

Met Ile Phe Asp Gly Asn Ile Lys Arg Thr Ala Lys Glu Asn Ala Ala
1               5                   10                  15

Asp Val Asn Gly Val Thr Val Ser Ser Gln Ala Ile Ser Met Gly Ser
            20                  25                  30

Gly Gly Lys Ile Thr Thr Leu Arg Ala Lys Ala Gly His Gln Ile Leu
        35                  40                  45

Phe Asn Asp Pro Ile Glu Met Ala Asn Gly Asn Asn Gln Pro Ala Gln
    50                  55                  60

Ser Ser Lys Leu Leu Lys Ile Asn Asp Gly Glu Gly Tyr Thr Gly Asp
65                  70                  75                  80

Ile Val Phe Ala Asn Gly Ser Ser Thr Leu Tyr Gln Asn Val Thr Ile
                85                  90                  95

Glu Gln Gly Arg Ile Val Leu Arg Glu Lys Ala Lys Leu Ser Val Asn
            100                 105                 110

Ser Leu Ser Gln Thr Gly Gly Ser Leu Tyr Met Glu Ala Gly Ser Thr
        115                 120                 125

Leu Asp Phe Val Thr Pro Gln Pro Pro Gln Gln Pro Pro Ala Ala Asn
    130                 135                 140

Gln Leu Ile Thr Leu Ser Asn Leu His Leu Ser Leu Ser Ser Leu Leu
145                 150                 155                 160

Ala Asn Asn Ala Val Thr Asn Pro Pro Thr Asn Pro Pro Ala Gln Asp
                165                 170                 175

Ser His Pro Ala Val Ile Gly Ser Thr Thr Ala Gly Ser Val Thr Ile
            180                 185                 190

Ser Gly Pro Ile Phe Phe Glu Asp Leu Asp Asp Thr Ala Tyr Asp Arg
        195                 200                 205

Tyr Asp Trp Leu Gly Ser Asn Gln Lys Ile Asn Val Leu Lys Leu Gln
    210                 215                 220

Leu Gly Thr Lys Pro Pro Ala Asn Ala Pro Ser Asp Leu Thr Leu Gly
225                 230                 235                 240

Asn Glu Met Pro Lys Tyr Gly Tyr Gln Gly Ser Trp Lys Leu Ala Trp
                245                 250                 255

Asp Pro Asn Thr Ala Asn Asn Gly Pro Tyr Thr Leu Lys Ala Thr Trp
            260                 265                 270

Thr Lys Thr Gly Tyr Asn Pro Gly Pro Glu Arg Val Ala Ser Leu Val
        275                 280                 285

Pro Asn Ser Leu Trp Gly Ser Ile Leu Asp Ile Arg Ser Ala His Ser
    290                 295                 300

Ala Ile Gln Ala Ser Val Asp Gly Arg Ser Tyr Cys Arg Gly Leu Trp
305                 310                 315                 320

Val Ser Gly Val Ser Asn Phe Phe Tyr His Asp Arg Asp Ala Leu Gly
                325                 330                 335

Gln Gly Tyr Arg Tyr Ile Ser Gly Gly Tyr Ser Leu Gly Ala Asn Ser
            340                 345                 350

Tyr Phe Gly Ser Ser Met Phe Gly Leu Ala Phe Thr
        355                 360

<210> SEQ ID NO 24
<211> LENGTH: 506
<212> TYPE: DNA
<213> ORGANISM: Artificial Sequence
<220> FEATURE:
```

<223> OTHER INFORMATION: ssaG promoter sequence

<400> SEQUENCE: 24

```
gcgcgccgct cgtagccctg gcagggattg gccttgctat tgccatcgcg gatgtcgcct    60
gtcttatcta ccatcataaa catcatttgc ctatggctca cgacagtata ggcaatgccg   120
ttttttatat tgctaattgt ttcgccaatc aacgcaaaag tatggcgatt gctaaagccg   180
tctccctggg cggtagatta gccttaaccg cgacggtaat gactcattca tactggagtg   240
gtagtttggg actacagcct catttattag agcgtcttaa tgatattacc tatggactaa   300
tgagttttac tcgcttcggt atggatggga tggcaatgac cggtatgcag gtcagcagcc   360
cattatatcg tttgctggct caggtaacgc cagaacaacg tgcgccggag taatcgtttt   420
caggtatata ccggatgttc attgctttct aaatttgct atgttgccag tatccttacg   480
atgtatttat tttaaggaaa agcatt                                        506
```

<210> SEQ ID NO 25
<211> LENGTH: 305
<212> TYPE: PRT
<213> ORGANISM: Salmonella sp.

<400> SEQUENCE: 25

```
Met Thr Ser Ile Phe Ala Glu Gln Thr Val Glu Val Val Lys Ser Ala
 1               5                  10                  15

Ile Glu Thr Ala Asp Gly Ala Leu Asp Leu Tyr Asn Lys Tyr Leu Asp
                20                  25                  30

Gln Val Ile Pro Trp Lys Thr Phe Asp Glu Thr Ile Lys Glu Leu Ser
            35                  40                  45

Arg Phe Lys Gln Glu Tyr Ser Gln Gly Ala Ser Val Leu Val Gly Asp
        50                  55                  60

Ile Lys Val Leu Leu Met Asp Ser Gln Asp Lys Tyr Phe Glu Ala Thr
 65                  70                  75                  80

Gln Thr Val Tyr Glu Trp Cys Gly Val Val Thr Gln Leu Leu Ser Ala
                85                  90                  95

Tyr Ile Leu Leu Phe Asp Glu Tyr Asn Glu Lys Ala Ser Ala Gln
           100                 105                 110

Lys Asp Ile Leu Ile Arg Ile Leu Asp Asp Gly Val Lys Lys Leu Asn
           115                 120                 125

Glu Ala Gln Lys Ser Leu Leu Thr Ser Ser Gln Ser Phe Asn Asn Ala
       130                 135                 140

Ser Gly Lys Leu Leu Ala Leu Asp Ser Gln Leu Thr Asn Asp Phe Ser
145                 150                 155                 160

Glu Lys Ser Ser Tyr Phe Gln Ser Gln Val Asp Arg Ile Arg Lys Glu
               165                 170                 175

Ala Tyr Ala Val Ala Ala Ala Gly Ser Val Ser Gly Pro Phe Gly Leu
           180                 185                 190

Ser Ile Ser Tyr Ser Ile Ala Ala Gly Val Ile Glu Gly Lys Leu Ile
       195                 200                 205

Pro Glu Leu Asn Asn Arg Leu Lys Thr Val Gln Asn Phe Phe Thr Ser
   210                 215                 220

Leu Ser Ala Thr Val Lys Gln Ala Asn Lys Asp Ile Asp Ala Ala Lys
225                 230                 235                 240

Leu Lys Leu Ala Thr Glu Ile Ala Ala Ile Gly Glu Ile Lys Thr Glu
               245                 250                 255

Thr Glu Thr Thr Arg Phe Tyr Val Asp Tyr Asp Asp Leu Met Leu Ser
           260                 265                 270
```

Leu Leu Lys Gly Ala Ala Lys Lys Met Ile Asn Thr Cys Asn Glu Tyr
            275                 280                 285

Gln Gln Arg His Ile Ser Gly Lys Lys Thr Leu Phe Glu Val Pro Asp
        290                 295                 300

Val
305

<210> SEQ ID NO 26
<211> LENGTH: 3410
<212> TYPE: DNA
<213> ORGANISM: Artificial Sequence
<220> FEATURE:
<223> OTHER INFORMATION: CT84-ssaG promoter construct

<400> SEQUENCE: 26

```
tcgcggcccg tgaacatttc aatatttata aagattaaaa cacgcaaacg acaacaacga      60
taacggagcc gtgatggcag gaaacacaat tggacaactc tttcgcgtaa ccactttcgg     120
cgaatcacac gggctggcgc ttgggggtat cgtcgatggc gtgccgcccg gcatcccgtt     180
gacggaggcc gatctgcagc acgatctcga cagacgccgc cctggcacct cgcgctatac     240
tactcagcgc cgcgaaccgg accaggtaaa aattctctcc ggcgtgtttg atggcgtaac     300
gaccggctcg agattgccat cgcggatgtc gcctgtctta tctaccatca taaacatcat     360
ttgcctatgg ctcacgacag tataggcaat gccgtttttt atattgctaa ttgtttcgcc     420
aatcaacgca aaagtatggc gattgctaaa gccgtctccc tgggcggtag attagcctta     480
accgcgacgg taatgactca ttcatactgg agtggtagtt tgggactaca gcctcattta     540
ttagagcgtc ttaatgatat tacctatgga ctaatgagtt ttactcgctt cggtatggat     600
gggatggcaa tgaccggtat gcaggtcagc agcccattat atcgtttgct ggctcaggta     660
acgccagaac aacgtgcgcc ggagtaatcg ttttcaggta tataccggat gttcattgct     720
ttctaaattt tgctatgttg ccagtatcct tacgatgtat ttattttaag gaaaagccat     780
atggaaatta tggttccgca gggtatctac gatggtgaaa ccctgaccgt gtctttcccg     840
tataccgtta tcggtgatcc gagcggtacg accgttttca gcgccggtga actgaccctg     900
aaaaacctgg ataatagcat tgcggcgctg ccgctgtctt gcttcggtaa cctgctgggt     960
tctttcaccg ttctgggtcg tggccatagc ctgacctttg aaaacattcg taccagcacc    1020
aatggtgcgg cgctgtctaa tagcgcggcg gatggtctgt tcaccattga aggtttcaaa    1080
gaactgtctt tctctaactg caatagcctg ctggcggttc tgccggcggc gaccaccaac    1140
aaaggcagcc agaccccgac caccacgagc accccgtcta acggcaccat ctacagcaaa    1200
accgatctgc tgctgctgaa caacgaaaaa ttctcttttt atagcaacct ggtttctggt    1260
gatggtggtg cgattgatgc gaaaagcctg accgttcagg gtatctctaa actgtgcgtt    1320
ttccaggaaa acaccgcgca ggcggatggc ggtgcgtgcc aggttgttac ctctttcagc    1380
gcgatggcca atgaagcgcc gattgcgttt gttgccaacg tggcgggtgt tcgtggtggt    1440
ggtatcgcgg cggtgcagga tggtcagcag ggtgtgagct cttctacctc taccgaagat    1500
ccggtggtga gcttcagccg taacaccgcg gtggaatttg atggtaacgt ggcgcgcgtt    1560
ggtggtggta tctacagcta cggtaacgtg gcgttcctga acaatggtaa aaccctgttc    1620
ctgaataacg ttgcgagccc ggtgtatatt gcggccaaac agccgacctc tggtcaggcg    1680
tctaacacca gcaataacta cggcgatggt ggcgccattt tctgcaaaaa cggtgcgcag    1740
gcgggcagca acaactctgg cagcgtgagc ttcgatggcg aaggcgtggt gttttttcagc    1800
```

```
tctaatgtgg cggcgggtaa aggcggcgcg atttatgcga aaaaactgtc tgttgcgaac   1860
tgcggcccgg tgcagttcct gcgtaacatt gcgaacgatg gtggtgcgat ctacctgggt   1920
gaaagcggcg aactgtctct gagcgcggat tatggcgata ttatcttcga tggtaacatt   1980
aaacgtaccg cgaaagaaaa cgcggcggat gtgaacggtg tgaccgtgtc ttctcaggcg   2040
attagcatgg gtagcggcgg caaaattacc accctgcgtg cgaaagcggg tcatcagatc   2100
ctgttcaacg atccgatcga aatggcgaac ggtaataacc agccggcgca gtcttctaaa   2160
ctgctgaaaa ttaacgatgg tgaaggttac accggtgata ttgtgttcgc gaacggttct   2220
agcaccctgt atcagaacgt taccatcgaa cagggccgta tcgttctgcg tgaaaaagcg   2280
aaactgtctg ttaacagcct gagccagacc ggtggtagcc tgtatatgga agcgggttct   2340
accctggatt tcgttacccc gcagccgccg cagcagccgc cggcggcgaa tcagctgatc   2400
accctgagca acctgcatct gtctctgtct tctctgctgg cgaacaacgc ggttaccaac   2460
ccgccgacca acccgccggc gcaggattct catccggcgg tgattggtag caccaccgcg   2520
ggtagcgtta ccatttctgg tccgattttc tttgaagatc tggatgatac cgcgtacgat   2580
cgctacgatt ggctgggtag caaccagaaa atcaacgttc tgaaactgca actgggcacc   2640
aaaccgccgg cgaacgcgcc gtctgatctg accctgggta acgaaatgcc gaaatatggc   2700
taccagggtt cttggaaact ggcgtgggac ccgaacaccg cgaacaacgg tccgtacacc   2760
ctgaaagcga cctggaccaa aaccggttac aatccgggcc cggaacgtgt tgcgtctctg   2820
gttccgaact ctctgtgggg cagcattctg gatattcgca gcgcgcattc tgcgatccag   2880
gcgagcgtgg atggtcgtag ctattgccgc ggtctgtggg ttagcggtgt ttctaacttc   2940
ttctatcatg atcgcgatgc gctgggccag ggctatcgct atattagcgg tggttatagc   3000
ctgggtgcga acagctattt cggtagcagc atgttcggcc tggcgttcac ctaatctaga   3060
gtcgactagc ctaggtccag cattaccgtg ccgggacgta cgatcaaccg gatgggtgaa   3120
gaggtcgaga tgatcaccaa agggcgccac gatccgtgtg tggggattcg cgcagtgccg   3180
atcgcagaag tcatgctggc gatcgtactg atggatcacc tgctgcgcca tcgggcacag   3240
aatgcggatg taaagacaga gattccacgc tggtaagaaa tgaaaaaaac cgcgattgcg   3300
ctgctggcat ggtttgtcag tagcgccagc ctggcggcga cgtcgtggca gaaaataacc   3360
catcctgtcc ccggcgccgc ccagtctatc ggtagctttg ccaacggatg              3410
```

<210> SEQ ID NO 27
<211> LENGTH: 757
<212> TYPE: PRT
<213> ORGANISM: Chlamydia muridarum

<400> SEQUENCE: 27

```
Met Glu Ile Met Val Pro Gln Gly Ile Tyr Asp Gly Glu Thr Leu Thr
1               5                   10                  15

Val Ser Phe Pro Tyr Thr Val Ile Gly Asp Pro Ser Gly Thr Thr Val
            20                  25                  30

Phe Ser Ala Gly Glu Leu Thr Leu Lys Asn Leu Asp Asn Ser Ile Ala
        35                  40                  45

Ala Leu Pro Leu Ser Cys Phe Gly Asn Leu Leu Gly Ser Phe Thr Val
    50                  55                  60

Leu Gly Arg Gly His Ser Leu Thr Phe Glu Asn Ile Arg Thr Ser Thr
65                  70                  75                  80

Asn Gly Ala Ala Leu Ser Asn Ser Ala Ala Asp Gly Leu Phe Thr Ile
                85                  90                  95
```

```
Glu Gly Phe Lys Glu Leu Ser Phe Ser Asn Cys Asn Ser Leu Leu Ala
            100                 105                 110

Val Leu Pro Ala Ala Thr Thr Asn Lys Gly Ser Gln Thr Pro Thr Thr
        115                 120                 125

Thr Ser Thr Pro Ser Asn Gly Thr Ile Tyr Ser Lys Thr Asp Leu Leu
    130                 135                 140

Leu Leu Asn Asn Glu Lys Phe Ser Phe Tyr Ser Asn Leu Val Ser Gly
145                 150                 155                 160

Asp Gly Gly Ala Ile Asp Ala Lys Ser Leu Thr Val Gln Gly Ile Ser
                165                 170                 175

Lys Leu Cys Val Phe Gln Glu Asn Thr Ala Gln Ala Asp Gly Gly Ala
            180                 185                 190

Cys Gln Val Val Thr Ser Phe Ser Ala Met Ala Asn Glu Ala Pro Ile
        195                 200                 205

Ala Phe Val Ala Asn Val Ala Gly Val Arg Gly Gly Ile Ala Ala
    210                 215                 220

Val Gln Asp Gly Gln Gln Gly Val Ser Ser Thr Ser Thr Glu Asp
225                 230                 235                 240

Pro Val Val Ser Phe Ser Arg Asn Thr Ala Val Glu Phe Asp Gly Asn
            245                 250                 255

Val Ala Arg Val Gly Gly Gly Ile Tyr Ser Tyr Gly Asn Val Ala Phe
        260                 265                 270

Leu Asn Asn Gly Lys Thr Leu Phe Leu Asn Asn Val Ala Ser Pro Val
    275                 280                 285

Tyr Ile Ala Ala Lys Gln Pro Thr Ser Gly Gln Ala Ser Asn Thr Ser
290                 295                 300

Asn Asn Tyr Gly Asp Gly Gly Ala Ile Phe Cys Lys Asn Gly Ala Gln
305                 310                 315                 320

Ala Gly Ser Asn Asn Ser Gly Ser Val Ser Phe Asp Gly Glu Gly Val
            325                 330                 335

Val Phe Phe Ser Ser Asn Val Ala Ala Gly Lys Gly Gly Ala Ile Tyr
        340                 345                 350

Ala Lys Lys Leu Ser Val Ala Asn Cys Gly Pro Val Gln Phe Leu Arg
    355                 360                 365

Asn Ile Ala Asn Asp Gly Gly Ala Ile Tyr Leu Gly Glu Ser Gly Glu
370                 375                 380

Leu Ser Leu Ser Ala Asp Tyr Gly Asp Ile Ile Phe Asp Gly Asn Ile
385                 390                 395                 400

Lys Arg Thr Ala Lys Glu Asn Ala Ala Asp Val Asn Gly Val Thr Val
            405                 410                 415

Ser Ser Gln Ala Ile Ser Met Gly Ser Gly Gly Lys Ile Thr Thr Leu
        420                 425                 430

Arg Ala Lys Ala Gly His Gln Ile Leu Phe Asn Asp Pro Ile Glu Met
    435                 440                 445

Ala Asn Gly Asn Gln Pro Ala Gln Ser Ser Lys Leu Leu Lys Ile
450                 455                 460

Asn Asp Gly Glu Gly Tyr Thr Gly Asp Ile Val Phe Ala Asn Gly Ser
465                 470                 475                 480

Ser Thr Leu Tyr Gln Asn Val Thr Ile Glu Gln Gly Arg Ile Val Leu
            485                 490                 495

Arg Glu Lys Ala Lys Leu Ser Val Asn Ser Leu Ser Gln Thr Gly Gly
        500                 505                 510

Ser Leu Tyr Met Glu Ala Gly Ser Thr Leu Asp Phe Val Thr Pro Gln
    515                 520                 525
```

```
Pro Pro Gln Gln Pro Pro Ala Ala Asn Gln Leu Ile Thr Leu Ser Asn
    530                 535                 540
Leu His Leu Ser Leu Ser Ser Leu Leu Ala Asn Asn Ala Val Thr Asn
545                 550                 555                 560
Pro Pro Thr Asn Pro Pro Ala Gln Asp Ser His Pro Ala Val Ile Gly
                565                 570                 575
Ser Thr Thr Ala Gly Ser Val Thr Ile Ser Gly Pro Ile Phe Phe Glu
            580                 585                 590
Asp Leu Asp Asp Thr Ala Tyr Asp Arg Tyr Asp Trp Leu Gly Ser Asn
        595                 600                 605
Gln Lys Ile Asn Val Leu Lys Leu Gln Leu Gly Thr Lys Pro Pro Ala
    610                 615                 620
Asn Ala Pro Ser Asp Leu Thr Leu Gly Asn Glu Met Pro Lys Tyr Gly
625                 630                 635                 640
Tyr Gln Gly Ser Trp Lys Leu Ala Trp Asp Pro Asn Thr Ala Asn Asn
                645                 650                 655
Gly Pro Tyr Thr Leu Lys Ala Thr Trp Thr Lys Thr Gly Tyr Asn Pro
            660                 665                 670
Gly Pro Glu Arg Val Ala Ser Leu Val Pro Asn Ser Leu Trp Gly Ser
        675                 680                 685
Ile Leu Asp Ile Arg Ser Ala His Ser Ala Ile Gln Ala Ser Val Asp
    690                 695                 700
Gly Arg Ser Tyr Cys Arg Gly Leu Trp Val Ser Gly Val Ser Asn Phe
705                 710                 715                 720
Phe Tyr His Asp Arg Asp Ala Leu Gly Gln Gly Tyr Arg Tyr Ile Ser
                725                 730                 735
Gly Gly Tyr Ser Leu Gly Ala Asn Ser Tyr Phe Gly Ser Ser Met Phe
            740                 745                 750
Gly Leu Ala Phe Thr
            755

<210> SEQ ID NO 28
<211> LENGTH: 3934
<212> TYPE: DNA
<213> ORGANISM: Artificial Sequence
<220> FEATURE:
<223> OTHER INFORMATION: CT84-ssaG promoter construct

<400> SEQUENCE: 28
aaagggggat gtgctgcaag gcgattaagt tgggtaacgc cagggttttc ccagtcacga      60
cgttgtaaaa cgacggccag tgaattgtaa tacgactcac tatagggcga attggagctc    120
caccgcggtg gcggccgctc tagaactagt ggatcccccg gctgcagga attcgatatc     180
aagcttatcg ataccgtcga cctcgagatt gccatcgcgg atgtcgcctg tcttatctac    240
catcataaac atcatttgcc tatggctcac gacagtatag gcaatgccgt ttttatatt    300
gctaattgtt tcgccaatca acgcaaaagt atggcgattg ctaaagccgt ctccctgggc    360
ggtagattag ccttaaccgc gacggtaatg actcattcat actggagtgg tagtttggga    420
ctacagcctc atttattaga gcgtcttaat gatattacct atggactaat gagtttact    480
cgcttcggta tggatgggat ggcaatgacc ggtatgcagg tcagcagccc attatatcgt    540
ttgctggctc aggtaacgcc agaacaacgt gcgccggagt aatcgttttc aggtatatac    600
cggatgttca ttgctttcta aattttgcta tgttgccagt atccttacga tgtatttatt    660
ttaaggaaaa gccatatgga aaccagcttc cataaattct tcctgtctat gatcctggcg    720
```

```
tacagctgct gttctctgaa cggtggtggt tatgcggcgg aaattatggt tccgcagggt    780
atctacgatg gtgaaaccct gaccgtgtct ttcccgtata ccgttatcgg tgatccgagc    840
ggtacgaccg ttttcagcgc cggtgaactg accctgaaaa acctggataa tagcattgcg    900
gcgctgccgc tgtcttgctt cggtaacctg ctgggttctt tcaccgttct gggtcgtggc    960
catagcctga cctttgaaaa cattcgtacc agcaccaatg gtgcggcgct gtctaatagc   1020
gcggcggatg gtctgttcac cattgaaggt ttcaaagaac tgtctttctc taactgcaat   1080
agcctgctgg cggttctgcc ggcggcgacc accaacaaag gcagccagac cccgaccacc   1140
acgagcaccc cgtctaacgg caccatctac agcaaaaccg atctgctgct gctgaacaac   1200
gaaaaattct cttttttatag caacctggtt tctggtgatg gtggtgcgat tgatgcgaaa   1260
agcctgaccg ttcagggtat ctctaaactg tgcgttttcc aggaaaacac cgcgcaggcg   1320
gatggcggtg cgtgccaggt tgttacctct ttcagcgcga tggccaatga agcgccgatt   1380
gcgtttgttg ccaacgtggc gggtgttcgt ggtggtggta tcgcggcggt gcaggatggt   1440
cagcagggtg tgagctcttc tacctctacc gaagatccgg tggtgagctt cagccgtaac   1500
accgcggtga aatttgatgg taacgttgcg cgcgttggtg gtggtatcta cagctacggt   1560
aacgtggcgt tcctgaacaa tggtaaaaacc ctgttcctga ataacgttgc gagcccggtg   1620
tatattgcgg ccaaacagcc gacctctggt caggcgtcta acaccagcaa taactacggc   1680
gatggtggcg ccattttctg caaaaacggt gcgcaggcgg gcagcaacaa ctctggcagc   1740
gtgagcttcg atggcgaagg cgtggtgttt ttcagctcta atgtggcggc gggtaaaggc   1800
ggcgcgattt atgcgaaaaa actgtctgtt gcgaactgcg gcccggtgca gttcctgcgt   1860
aacattgcga cgatggtgg tgcgatctac ctgggtgaaa gcggcgaact gtctctgagc   1920
gcggattatg gcgatattat cttcgatggt aacattaaac gtaccgcgaa agaaaacgcg   1980
gcggatgtga acggtgtgac cgtgtcttct caggcgatta gcatgggtag cggcggcaaa   2040
attaccaccc tgcgtgcgaa agcgggtcat cagatcctgt tcaacgatcc gatcgaaatg   2100
gcgaacggta ataaccagcc ggcgcagtct tctaaactgc tgaaaattaa cgatggtgaa   2160
ggttacaccg gtgatattgt gttcgcgaac ggttctagca ccctgtatca gaacgttacc   2220
atcgaacagg gccgtatcgt tctgcgtgaa aaagcgaaac tgtctgttaa cagcctgagc   2280
cagaccggtg gtagcctgta tatggaagcg ggttctaccc tggatttcgt taccccgcag   2340
ccgccgcagc agccgccggc ggcgaatcag ctgatcaccc tgagcaacct gcatctgtct   2400
ctgtcttctc tgctggcgaa caacgcggtt accaacccgc cgaccaaccc gccggcgcag   2460
gattctcatc cggcggtgat tggtagcacc accgcgggta gcgttaccat ttctggtccg   2520
attttctttg aagatctgga tgataccgcg tacgatcgct acgattggct gggtagcaac   2580
cagaaaatca acgttctgaa actgcaactg ggcaccaaac cgccggcgaa cgcgccgtct   2640
gatctgaccc tgggtaacga aatgccgaaa tatggctacc agggttcttg gaaactggcg   2700
tgggacccga acaccgcgaa caacggtccg tacaccctga aagcgacctg gaccaaaacc   2760
ggttacaatc cgggccccga acgtgttgcg tctctggttc cgaactctct gtggggcagc   2820
attctggata ttcgcagcgc gcattctgcg atccaggcga gcgtggatgg tcgtagctat   2880
tgccgcggtc tgtgggttag cggtgttttct aacttcttct atcatgatcg cgatgcgctg   2940
ggccagggct atcgctatat tagcggtggt tatagcctgg gtgcgaacag ctatttcggt   3000
agcagcatgt tcggcctggc gttcaccgaa gttttggtc gttctaaaga ttatgttgtg   3060
tgccgtagca accatcatgc gtgcattggt tctgtttatc tgagcaccca gcaggcgctg   3120
```

-continued

```
tgcggttctt atctgtttgg cgatgcgttc atccgtgcgt cttatggttt cggcaaccag   3180
cacatgaaaa ccagctatac ctttgcggaa gaaagcgatg ttcgttggga taacaactgc   3240
ctggcgggtg aaattggtgc gggcctgccg atcgttatca ccccgagcaa actgtatctg   3300
aacgaactgc gcccgtttgt gcaggcggaa ttttcttacg cgaaccatga atcttttacc   3360
gaagaaggtg atcaggcgcg tgcgttcaaa agcggtcatc tgctgaacct gagcgtgccg   3420
gttggcgtga aatttgatcg ttgcagctct acccatccga acaaatacag ctttatggcg   3480
gcgtatatct gtgatgcgta tcgtaccatt agcggcaccg aaaccaccct gctgagccat   3540
cagggcacct ggaccaccga tgcgtttcat ctggcgcgtc atggcgttgt ggttcgtggc   3600
agcatgtatg cgagcctgac cagcaacatt gaagtgtatg gtcatggtcg ttatgaatat   3660
cgtgatgcga gccgtggtta tggtctgagc gcgggtagcc gcgttcgttt ttaataagga   3720
tctctagact agcctagggg tacccagctt ttgttccctt tagtgagggt taatttcgag   3780
cttggcgtaa tcatggtcat agctgtttcc tgtgtgaaat tgttatccgc tcacaattcc   3840
acacaacata cgagccggaa gcataaagtg taaagcctgg ggtgcctaat gagtgagcta   3900
actcacatta attgcgttgc gctcactgcc cgct                               3934
```

<210> SEQ ID NO 29
<211> LENGTH: 1012
<212> TYPE: PRT
<213> ORGANISM: Chlamydia muridarum

<400> SEQUENCE: 29

```
Met Glu Thr Ser Phe His Lys Phe Phe Leu Ser Met Ile Leu Ala Tyr
1               5                   10                  15

Ser Cys Cys Ser Leu Asn Gly Gly Gly Tyr Ala Ala Glu Ile Met Val
            20                  25                  30

Pro Gln Gly Ile Tyr Asp Gly Glu Thr Leu Thr Val Ser Phe Pro Tyr
        35                  40                  45

Thr Val Ile Gly Asp Pro Ser Gly Thr Thr Val Phe Ser Ala Gly Glu
    50                  55                  60

Leu Thr Leu Lys Asn Leu Asp Asn Ser Ile Ala Ala Leu Pro Leu Ser
65                  70                  75                  80

Cys Phe Gly Asn Leu Leu Gly Ser Phe Thr Val Leu Gly Arg Gly His
                85                  90                  95

Ser Leu Thr Phe Glu Asn Ile Arg Thr Ser Thr Asn Gly Ala Ala Leu
            100                 105                 110

Ser Asn Ser Ala Ala Asp Gly Leu Phe Thr Ile Glu Gly Phe Lys Glu
        115                 120                 125

Leu Ser Phe Ser Asn Cys Asn Ser Leu Leu Ala Val Leu Pro Ala Ala
    130                 135                 140

Thr Thr Asn Lys Gly Ser Gln Thr Pro Thr Thr Thr Ser Thr Pro Ser
145                 150                 155                 160

Asn Gly Thr Ile Tyr Ser Lys Thr Asp Leu Leu Leu Leu Asn Asn Glu
                165                 170                 175

Lys Phe Ser Phe Tyr Ser Asn Leu Val Ser Gly Asp Gly Gly Ala Ile
            180                 185                 190

Asp Ala Lys Ser Leu Thr Val Gln Gly Ile Ser Lys Leu Cys Val Phe
        195                 200                 205

Gln Glu Asn Thr Ala Gln Ala Asp Gly Gly Ala Cys Gln Val Val Thr
    210                 215                 220

Ser Phe Ser Ala Met Ala Asn Glu Ala Pro Ile Ala Phe Val Ala Asn
225                 230                 235                 240
```

```
Val Ala Gly Val Arg Gly Gly Ile Ala Ala Val Gln Asp Gly Gln
            245                 250                 255

Gln Gly Val Ser Ser Thr Ser Thr Glu Asp Pro Val Val Ser Phe
            260                 265                 270

Ser Arg Asn Thr Ala Val Glu Phe Asp Gly Asn Val Ala Arg Val Gly
            275                 280                 285

Gly Gly Ile Tyr Ser Tyr Gly Asn Val Ala Phe Leu Asn Asn Gly Lys
            290                 295                 300

Thr Leu Phe Leu Asn Asn Val Ala Ser Pro Val Tyr Ile Ala Ala Lys
305                 310                 315                 320

Gln Pro Thr Ser Gly Gln Ala Ser Asn Thr Ser Asn Tyr Gly Asp
            325                 330                 335

Gly Gly Ala Ile Phe Cys Lys Asn Gly Ala Gln Ala Gly Ser Asn Asn
            340                 345                 350

Ser Gly Ser Val Ser Phe Asp Gly Glu Gly Val Val Phe Phe Ser Ser
            355                 360                 365

Asn Val Ala Ala Gly Lys Gly Gly Ala Ile Tyr Ala Lys Lys Leu Ser
            370                 375                 380

Val Ala Asn Cys Gly Pro Val Gln Phe Leu Arg Asn Ile Ala Asn Asp
385                 390                 395                 400

Gly Gly Ala Ile Tyr Leu Gly Glu Ser Gly Glu Leu Ser Leu Ser Ala
            405                 410                 415

Asp Tyr Gly Asp Ile Ile Phe Asp Gly Asn Ile Lys Arg Thr Ala Lys
            420                 425                 430

Glu Asn Ala Ala Asp Val Asn Gly Val Thr Val Ser Ser Gln Ala Ile
            435                 440                 445

Ser Met Gly Ser Gly Gly Lys Ile Thr Thr Leu Arg Ala Lys Ala Gly
            450                 455                 460

His Gln Ile Leu Phe Asn Asp Pro Ile Glu Met Ala Asn Gly Asn Asn
465                 470                 475                 480

Gln Pro Ala Gln Ser Ser Lys Leu Leu Lys Ile Asn Asp Gly Glu Gly
            485                 490                 495

Tyr Thr Gly Asp Ile Val Phe Ala Asn Gly Ser Ser Thr Leu Tyr Gln
            500                 505                 510

Asn Val Thr Ile Glu Gln Gly Arg Ile Val Leu Arg Glu Lys Ala Lys
            515                 520                 525

Leu Ser Val Asn Ser Leu Ser Gln Thr Gly Gly Ser Leu Tyr Met Glu
530                 535                 540

Ala Gly Ser Thr Leu Asp Phe Val Thr Pro Gln Pro Gln Gln Pro
545                 550                 555                 560

Pro Ala Ala Asn Gln Leu Ile Thr Leu Ser Asn Leu His Leu Ser Leu
            565                 570                 575

Ser Ser Leu Leu Ala Asn Asn Ala Val Thr Asn Pro Thr Asn Pro
            580                 585                 590

Pro Ala Gln Asp Ser His Pro Ala Val Ile Gly Ser Thr Thr Ala Gly
            595                 600                 605

Ser Val Thr Ile Ser Gly Pro Ile Phe Phe Glu Asp Leu Asp Asp Thr
            610                 615                 620

Ala Tyr Asp Arg Tyr Asp Trp Leu Gly Ser Asn Gln Lys Ile Asn Val
625                 630                 635                 640

Leu Lys Leu Gln Leu Gly Thr Lys Pro Pro Ala Asn Ala Pro Ser Asp
            645                 650                 655

Leu Thr Leu Gly Asn Glu Met Pro Lys Tyr Gly Tyr Gln Gly Ser Trp
```

```
            660                 665                 670

Lys Leu Ala Trp Asp Pro Asn Thr Ala Asn Asn Gly Pro Tyr Thr Leu
        675                 680                 685

Lys Ala Thr Trp Thr Lys Thr Gly Tyr Asn Pro Gly Pro Glu Arg Val
    690                 695                 700

Ala Ser Leu Val Pro Asn Ser Leu Trp Gly Ser Ile Leu Asp Ile Arg
705                 710                 715                 720

Ser Ala His Ser Ala Ile Gln Ala Ser Val Asp Gly Arg Ser Tyr Cys
                725                 730                 735

Arg Gly Leu Trp Val Ser Gly Val Ser Asn Phe Phe Tyr His Asp Arg
            740                 745                 750

Asp Ala Leu Gly Gln Gly Tyr Arg Tyr Ile Ser Gly Gly Tyr Ser Leu
        755                 760                 765

Gly Ala Asn Ser Tyr Phe Gly Ser Ser Met Phe Gly Leu Ala Phe Thr
    770                 775                 780

Glu Val Phe Gly Arg Ser Lys Asp Tyr Val Val Cys Arg Ser Asn His
785                 790                 795                 800

His Ala Cys Ile Gly Ser Val Tyr Leu Ser Thr Gln Gln Ala Leu Cys
                805                 810                 815

Gly Ser Tyr Leu Phe Gly Asp Ala Phe Ile Arg Ala Ser Tyr Gly Phe
            820                 825                 830

Gly Asn Gln His Met Lys Thr Ser Tyr Thr Phe Ala Glu Glu Ser Asp
        835                 840                 845

Val Arg Trp Asp Asn Asn Cys Leu Ala Gly Glu Ile Gly Ala Gly Leu
    850                 855                 860

Pro Ile Val Ile Thr Pro Ser Lys Leu Tyr Leu Asn Glu Leu Arg Pro
865                 870                 875                 880

Phe Val Gln Ala Glu Phe Ser Tyr Ala Asn His Glu Ser Phe Thr Glu
                885                 890                 895

Glu Gly Asp Gln Ala Arg Ala Phe Lys Ser Gly His Leu Leu Asn Leu
            900                 905                 910

Ser Val Pro Val Gly Val Lys Phe Asp Arg Cys Ser Ser Thr His Pro
        915                 920                 925

Asn Lys Tyr Ser Phe Met Ala Ala Tyr Ile Cys Asp Ala Tyr Arg Thr
    930                 935                 940

Ile Ser Gly Thr Glu Thr Thr Leu Leu Ser His Gln Gly Thr Trp Thr
945                 950                 955                 960

Thr Asp Ala Phe His Leu Ala Arg His Gly Val Val Val Arg Gly Ser
                965                 970                 975

Met Tyr Ala Ser Leu Thr Ser Asn Ile Glu Val Tyr Gly His Gly Arg
            980                 985                 990

Tyr Glu Tyr Arg Asp Ala Ser Arg  Gly Tyr Gly Leu Ser  Ala Gly Ser
        995                 1000                 1005

Arg Val  Arg Phe
    1010

<210> SEQ ID NO 30
<211> LENGTH: 985
<212> TYPE: PRT
<213> ORGANISM: Chlamydia muridarum

<400> SEQUENCE: 30

Val Met Gln Thr Pro Phe His Lys Phe Phe Leu Leu Ala Met Leu Ser
1               5                   10                  15

Tyr Ser Leu Leu Gln Gly Gly His Ala Ala Asp Ile Ser Met Pro Pro
```

```
                    20                  25                  30
Gly Ile Tyr Asp Gly Thr Thr Leu Thr Ala Pro Phe Pro Tyr Thr Val
                35                  40                  45

Ile Gly Asp Pro Arg Gly Thr Lys Val Thr Ser Ser Gly Ser Leu Glu
            50                  55                  60

Leu Lys Asn Leu Asp Asn Ser Ile Ala Thr Leu Pro Leu Ser Cys Phe
65                  70                  75                  80

Gly Asn Leu Leu Gly Asn Phe Thr Ile Ala Gly Arg Gly His Ser Leu
                85                  90                  95

Val Phe Glu Asn Ile Arg Thr Ser Thr Asn Gly Ala Ala Leu Ser Asn
            100                 105                 110

His Ala Pro Ser Gly Leu Phe Val Ile Glu Ala Phe Asp Glu Leu Ser
            115                 120                 125

Leu Leu Asn Cys Asn Ser Leu Val Ser Val Val Pro Gln Thr Gly Gly
        130                 135                 140

Thr Thr Thr Ser Val Pro Ser Asn Gly Thr Ile Tyr Ser Arg Thr Asp
145                 150                 155                 160

Leu Val Leu Arg Asp Ile Lys Lys Val Ser Phe Tyr Ser Asn Leu Val
                165                 170                 175

Ser Gly Asp Gly Gly Ala Ile Asp Ala Gln Ser Leu Met Val Asn Gly
                180                 185                 190

Ile Glu Lys Leu Cys Thr Phe Gln Glu Asn Val Ala Gln Ser Asp Gly
            195                 200                 205

Gly Ala Cys Gln Val Thr Lys Thr Phe Ser Ala Val Gly Asn Lys Val
            210                 215                 220

Pro Leu Ser Phe Leu Gly Asn Val Ala Gly Asn Lys Gly Gly Val
225                 230                 235                 240

Ala Ala Val Lys Asp Gly Gln Gly Ala Gly Ala Thr Asp Leu Ser
                245                 250                 255

Val Asn Phe Ala Asn Asn Thr Ala Val Glu Phe Glu Gly Asn Ser Ala
                260                 265                 270

Arg Ile Gly Gly Gly Ile Tyr Ser Asp Gly Asn Ile Ser Phe Leu Gly
            275                 280                 285

Asn Ala Lys Thr Val Phe Leu Ser Asn Val Ala Ser Pro Ile Tyr Val
        290                 295                 300

Asp Pro Ala Ala Ala Gly Gln Pro Pro Ala Asp Lys Asp Asn Tyr
305                 310                 315                 320

Gly Asp Gly Gly Ala Ile Phe Cys Lys Asn Asp Thr Asn Ile Gly Glu
                325                 330                 335

Val Ser Phe Lys Asp Glu Gly Val Val Phe Phe Ser Lys Asn Ile Ala
            340                 345                 350

Ala Gly Lys Gly Gly Ala Ile Tyr Ala Lys Lys Leu Thr Ile Ser Asp
        355                 360                 365

Cys Gly Pro Val Gln Phe Leu Gly Asn Val Ala Asn Asp Gly Gly Ala
        370                 375                 380

Ile Tyr Leu Val Asp Gln Gly Glu Leu Ser Leu Ser Ala Asp Arg Gly
385                 390                 395                 400

Asp Ile Ile Phe Asp Gly Asn Leu Lys Arg Met Ala Thr Gln Gly Ala
                405                 410                 415

Ala Thr Val His Asp Val Met Val Ala Ser Asn Ala Ile Ser Met Ala
                420                 425                 430

Thr Gly Gly Gln Ile Thr Thr Leu Arg Ala Lys Glu Gly Arg Arg Ile
            435                 440                 445
```

```
Leu Phe Asn Asp Pro Ile Glu Met Ala Asn Gly Gln Pro Val Ile Gln
450                 455                 460

Thr Leu Thr Val Asn Glu Gly Glu Gly Tyr Thr Gly Asp Ile Val Phe
465                 470                 475                 480

Ala Lys Gly Asp Asn Val Leu Tyr Ser Ser Ile Glu Leu Ser Gln Gly
                485                 490                 495

Arg Ile Ile Leu Arg Glu Gln Thr Lys Leu Leu Val Asn Ser Leu Thr
                500                 505                 510

Gln Thr Gly Gly Ser Val His Met Glu Gly Gly Ser Thr Leu Asp Phe
                515                 520                 525

Ala Val Thr Thr Pro Pro Ala Ala Asn Ser Met Ala Leu Thr Asn Val
530                 535                 540

His Phe Ser Leu Ala Ser Leu Leu Lys Asn Asn Gly Val Thr Asn Pro
545                 550                 555                 560

Pro Thr Asn Pro Pro Val Gln Val Ser Ser Pro Ala Val Ile Gly Asn
                565                 570                 575

Thr Ala Ala Gly Thr Val Thr Ile Ser Gly Pro Ile Phe Phe Glu Asp
                580                 585                 590

Leu Asp Glu Thr Ala Tyr Asp Asn Asn Gln Trp Leu Gly Ala Asp Gln
                595                 600                 605

Thr Ile Asp Val Leu Gln Leu His Leu Gly Ala Asn Pro Pro Ala Asn
                610                 615                 620

Ala Pro Thr Asp Leu Thr Leu Gly Asn Glu Ser Ser Lys Tyr Gly Tyr
625                 630                 635                 640

Gln Gly Ser Trp Thr Leu Gln Trp Glu Pro Asp Pro Ala Asn Pro Pro
                645                 650                 655

Gln Asn Asn Ser Tyr Met Leu Lys Ala Ser Trp Thr Lys Thr Gly Tyr
                660                 665                 670

Asn Pro Gly Pro Glu Arg Val Ala Ser Leu Val Ser Asn Ser Leu Trp
                675                 680                 685

Gly Ser Ile Leu Asp Val Arg Ser Ala His Ser Ala Ile Gln Ala Ser
                690                 695                 700

Ile Asp Gly Arg Ala Tyr Cys Arg Gly Ile Trp Ile Ser Gly Ile Ser
705                 710                 715                 720

Asn Phe Phe Tyr His Asp Gln Asp Ala Leu Gly Gln Gly Tyr Arg His
                725                 730                 735

Gly Gly Tyr Ser Ile Gly Ala Asn Ser Tyr Phe Gly Ser Met Phe
                740                 745                 750

Gly Leu Ala Phe Thr Glu Thr Phe Gly Arg Ser Lys Asp Tyr Val Val
                755                 760                 765

Cys Arg Ser Asn Asp His Thr Cys Val Gly Ser Val Tyr Leu Ser Thr
                770                 775                 780

Arg Gln Ala Leu Cys Gly Ser Cys Leu Phe Gly Asp Ala Phe Val Arg
785                 790                 795                 800

Ala Ser Tyr Gly Phe Gly Asn Gln His Met Lys Thr Ser Tyr Thr Phe
                805                 810                 815

Ala Glu Glu Ser Asn Val Arg Trp Asp Asn Asn Cys Val Val Gly Glu
                820                 825                 830

Val Gly Ala Gly Leu Pro Ile Met Leu Ala Ala Ser Lys Leu Tyr Leu
                835                 840                 845

Asn Glu Leu Arg Pro Phe Val Gln Ala Glu Phe Ala Tyr Ala Glu His
850                 855                 860
```

```
Glu Ser Phe Thr Glu Arg Gly Asp Gln Ala Arg Glu Phe Lys Ser Gly
865                 870                 875                 880

His Leu Met Asn Leu Ser Ile Pro Val Gly Val Lys Phe Asp Arg Cys
                885                 890                 895

Ser Ser Lys His Pro Asn Lys Tyr Ser Phe Met Gly Ala Tyr Ile Cys
            900                 905                 910

Asp Ala Tyr Arg Ser Ile Ser Gly Thr Glu Thr Thr Leu Leu Ser His
        915                 920                 925

Lys Glu Thr Trp Thr Thr Asp Ala Phe His Leu Ala Arg His Gly Val
    930                 935                 940

Met Val Arg Gly Ser Met Tyr Ala Ser Leu Thr Gly Asn Ile Glu Val
945                 950                 955                 960

Tyr Gly His Gly Lys Tyr Glu Tyr Arg Asp Ala Ser Arg Gly Tyr Gly
                965                 970                 975

Leu Ser Ile Gly Ser Lys Ile Arg Phe
            980                 985

<210> SEQ ID NO 31
<211> LENGTH: 2964
<212> TYPE: DNA
<213> ORGANISM: Chlamydia muridarum

<400> SEQUENCE: 31
gtgatgcaaa cgccttttca taagttcttt cttctagcaa tgctatctta ctctttattg      60
caaggagggc atgcggcaga tatttccatg cctccgggaa tttatgatgg gacaacattg     120
acggcgccat ttccctacac tgtgatcgga gatcccagag ggacaaaggt tacttcatcg     180
ggatcgctag agttgaaaaa cctggacaat tccattgcga ctttacctct aagttgtttt     240
ggtaatttgt tggggaattt cactattgca ggaagagggc attcgttagt atttgagaat     300
atacgaacat ctacaaatgg ggcggcattg agtaatcatg ctccttctgg actgtttgta     360
attgaagctt ttgatgaact ctctcttttg aattgtaatt cattggtatc tgtagttcct     420
caaacagggg gtacgactac ttctgttcct tctaatggga cgatctattc tagaacagat     480
cttgttctaa gagatatcaa gaaggtttct ttctatagta acttagtttc tggagatggg     540
ggagctatag atgcacaaag tttaatggtt aacggaattg aaaaactttg taccttccaa     600
gaaaatgtag cgcagtccga tgggggagcg tgtcaggtaa caaagacctt ctctgctgtg     660
ggcaataagg ttcctttgtc ttttttaggc aatgttgctg gtaataaggg gggaggagtt     720
gctgctgtca aagatggtca gggggcagga ggggcgactg atctatcggt taattttgcc     780
aataatactg ctgtagaatt tgagggaaat agtgctcgaa taggtggagg gatctactcg     840
gacggaaata tttccttttt agggaatgca aagacagttt tcctaagtaa cgtagcttcg     900
cctatttatg ttgaccctgc tgctgcagga ggacagcccc ctgcagataa agataactat     960
ggagatggag gagccatctt ctgcaaaaat gatactaaca taggtgaagt ctctttcaaa    1020
gacgagggtg ttgttttctt tagtaaaaat attgccgcag gaaagggggg cgctatttat    1080
gctaagaaac tgacaatttc tgactgtggt ccggtccagt ttcttggtaa tgtcgcgaat    1140
gacgggggcg ctatttatct agtagatcag ggggaactta gtctatctgc tgatcgcgga    1200
gatattattt ttgatggaaa tttaaagaga atggctacgc aaggcgctgc caccgtccat    1260
gatgtaatgg ttgcatcgaa tgctatctct atggctacag gggggcaaat cacaacatta    1320
agggctaagg aaggtcgccg aattcttttt aatgacccta ttgaaatggc gaatggacaa    1380
```

```
cctgtaatac aaactcttac agtaaacgag ggcgaaggat atacggggga cattgttttt    1440
gctaaaggtg ataatgtttt gtactcaagt attgagctga gtcagggaag aattattctc    1500
cgagagcaaa caaaattatt ggttaactcc ctgactcaga ctggagggag tgtacatatg    1560 gaaggggga gtacactaga ctttgcagta acaacgccac cagctgctaa ttcgatggct    1620
cttactaatg tacacttctc cttagcttct ttactaaaaa ataatggggt tacaaatcct    1680
ccaacgaatc ctccagtaca ggtttctagt ccagctgtaa ttggtaatac agctgctggt    1740
actgttacga tttctggtcc gatctttttt gaagatttag atgaaactgc ttacgataat    1800
aatcagtggt taggtgcgga tcaaactatt gatgtgctgc agttgcattt aggagcgaat    1860
cctccggcta acgctccaac tgatttgact ttagggaacg aaagttctaa atatgggtat    1920
caaggaagtt ggacacttca atgggaacca gatcctgcga atcctccaca gaacaatagc    1980
tacatgttga aggcaagctg gactaaaaca ggttataatc ctggtccgga gcgcgtagct    2040
tctctggtct ctaatagtct ttggggatcc attttagatg tgccgttccgc gcattctgcg    2100 attcaagcaa gtatagatgg acgagcttat tgtcggggta tttggatttc tgggatttcg    2160
aactttttct atcatgatca ggatgcttta ggacaggggt atcgtcatat tagtggggga    2220
tattcgatag gagcaaactc ttatttcggg tcttctatgt ttggacttgc ttttactgaa    2280
acttttggta ggtccaaaga ttatgtggtc tgtcgatcta acgatcacac ttgtgtaggc    2340
tctgtttact tatccactag acaagcgtta tgcggatcct gtttatttgg agatgctttt    2400
gttcgggcga gttacggatt tggaaatcag catatgaaga cctcttatac atttgctgaa    2460
gagagtaatg tgcgttggga taataactgt gtagtgggag aagttggagc tgggctccct    2520
atcatgctcg ctgcatctaa gctttatcta aatgagttgc gtcccttcgt gcaagcagag    2580
tttgcttatg cagagcatga atcttttaca gagagagggg atcaggctag ggagtttaag    2640
agtgggcatc ttatgaatct atctattcca gttggggtga agtttgatcg atgctctagt    2700
aaacatccta acaagtatag ttttatggga gcttatatct gtgatgctta ccggtccatt    2760
tctggaacgg agacaacact cctgtctcat aaagagactt ggacaacaga tgctttccat    2820
ttagcaaggc atggagttat ggtcagagga tctatgtatg cttcttttaac aggtaatata    2880 gaagtctatg gccatggaaa atatgaatac agggatgcct ctcgagggta tggtttaagt    2940
attggaagta aaatccgatt ctaa                                          2964
```

```
<210> SEQ ID NO 32
<211> LENGTH: 8
<212> TYPE: PRT
<213> ORGANISM: Unknown
<220> FEATURE:
<223> OTHER INFORMATION: Export system consensus sequence
<220> FEATURE:
<221> NAME/KEY: misc_feature
<222> LOCATION: (6)..(6)
<223> OTHER INFORMATION: Xaa may be any amino acid

<400> SEQUENCE: 32

Ser Ser Thr Arg Arg Xaa Phe Leu
1               5
```